United States Patent [19]

Demarest et al.

[11] Patent Number: 5,500,991
[45] Date of Patent: Mar. 26, 1996

[54] NEEDLE AND SUTURE SWAGING AND PULL-TESTING METHOD

[75] Inventors: David Demarest, Parsippany; Michael G. Hodulik, Dunellen, both of N.J.

[73] Assignee: Ethicon, Inc., Somerville, N.J.

[21] Appl. No.: 412,751

[22] Filed: Mar. 29, 1995

Related U.S. Application Data

[62] Division of Ser. No. 181,607, Jan. 13, 1994.

[51] Int. Cl.⁶ .................................................. B23Q 17/00
[52] U.S. Cl. ........................................ 29/407.08; 29/517
[58] Field of Search .................................. 606/224, 225, 606/226, 227; 163/1, 5; 53/118, 138.1, 244, 253, 329, 430; 83/151, 153, 950; 206/63.3, 227; 29/243.5, 243.517, 283.5, 407, 515, 516, 517, 564.6, 705, 711, 715, 783, 785, 786, 788, 792, 793, 796, 818; 73/827

[56] References Cited

U.S. PATENT DOCUMENTS

| | | | |
|---|---|---|---|
| 2,928,395 | 3/1960 | Forbes et al. | 606/227 |
| 3,611,551 | 10/1971 | Shave et al. | |
| 3,875,946 | 4/1975 | Duncan | 606/227 |
| 3,980,177 | 9/1976 | McGregor . | |
| 4,072,041 | 2/1978 | Hoffman et al. | |
| 4,424,898 | 1/1984 | Thyen et al. | 206/63.3 |
| 4,672,871 | 6/1987 | Gudmestad . | |
| 4,722,384 | 2/1988 | Matsutani . | |
| 4,806,737 | 2/1989 | Coates . | |
| 4,832,025 | 5/1989 | Coates et al. | |
| 4,922,904 | 5/1990 | Vetake et al. | |
| 5,226,336 | 7/1993 | Coates . | |
| 5,230,424 | 7/1993 | Alpern et al. | 206/63.3 |

FOREIGN PATENT DOCUMENTS 212027  9/1988  Japan ........................... 163/1

*Primary Examiner*—David P. Bryant
*Attorney, Agent, or Firm*—Scully, Scott, Murphy & Presser

[57] ABSTRACT

An method and apparatus for automatically forming a plurality of needle-suture assemblies out of a plurality of unsorted needles and an indefinite length strand of suture material, and, automatically positioning them within a package tray, comprises a first machine located at a first location for sorting a plurality of randomly oriented needles and orienting each needle for automatic handling at a first predetermined location, a second machine located at a second predetermined location for automatically drawing and cutting an indefinite length strand of suture material and automatically inserting a free end thereof into a suture receiving opening of the needle, and swaging the needle about the sutures to form a needle suture assembly, and a first indexing device for sequentially receiving individual oriented needles at the first location and transporting each of the needles from the first location to the second location to form the needle-suture assemblies. A second indexing device is provided for registering an empty package tray at a third location for sequentially receiving one or more of the needle-suture assemblies from the first indexing device. A control system computer enables the first indexing device to sequentially transport the needle-suture assemblies from the second location to the third location, and enables the sequential insertion of the needle-suture assemblies to the package tray while registered at the third location.

18 Claims, 74 Drawing Sheets

EXTEND MAG (RELEASE NEEDLE)

SERVO TOWER SUTURE EXTEND/RETRACT

SUTURE INSERTION

SUTURE PULL TEST (NON-DESTRUCTIVE)

SUTURE PULL TEST (DESTRUCTIVE)

SWAGE/CUT/MONITOR ROUTINE

RETRACT MAG (GRIP NEEDLE)

PACKAGE DETECT

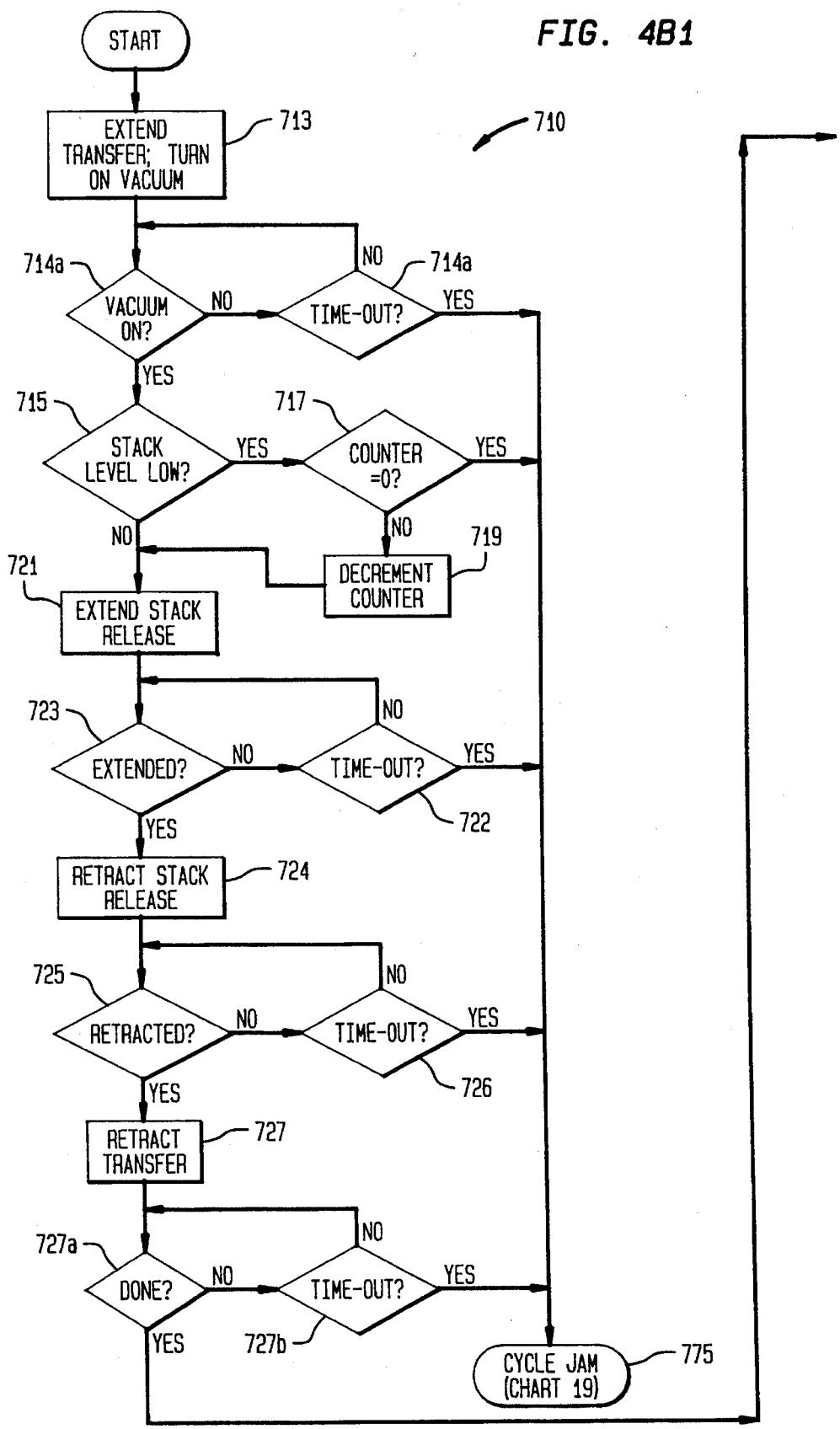
FIG. 4B1

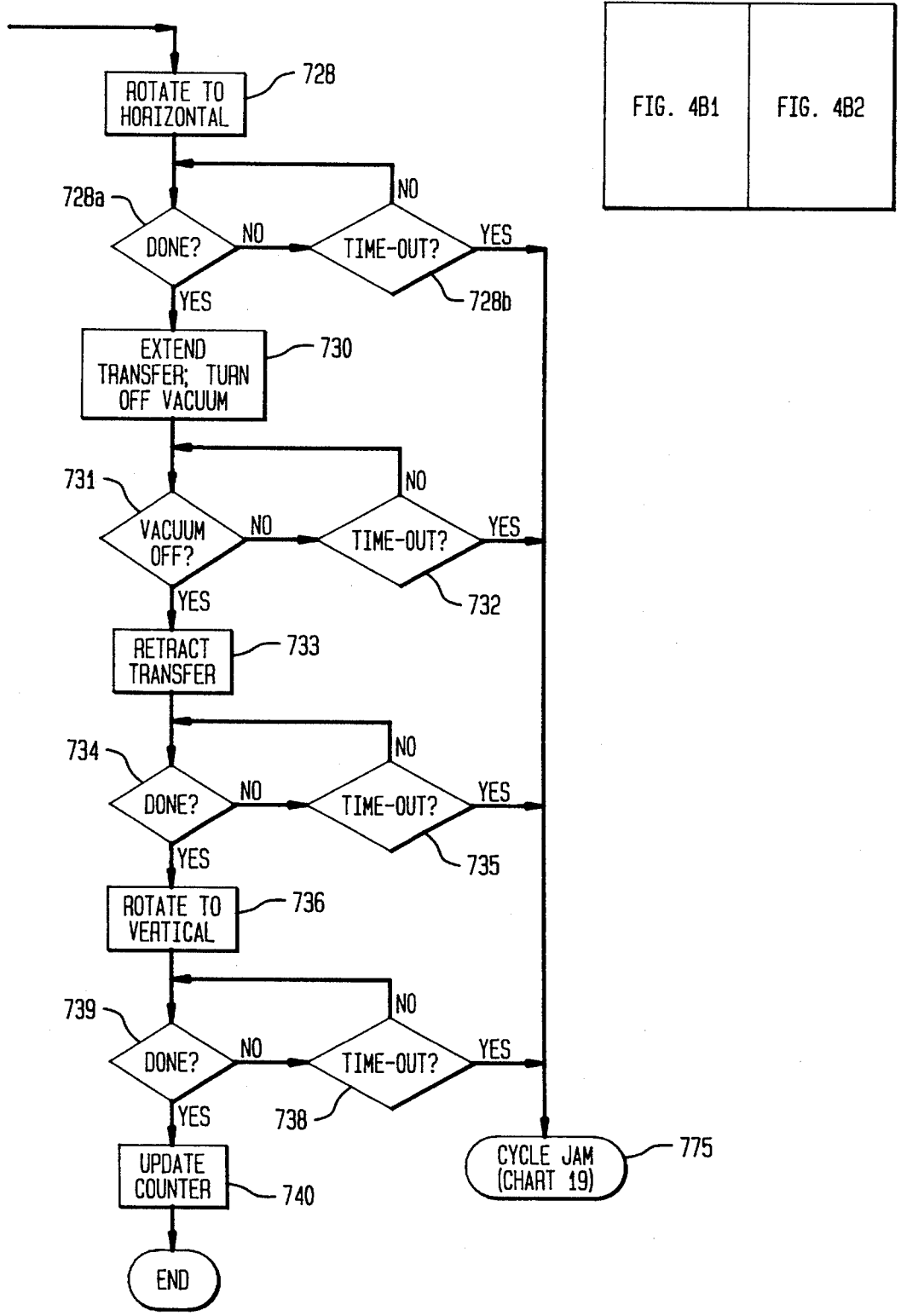

PACKAGE ELEVATOR INDEX

NEEDLE DETECT

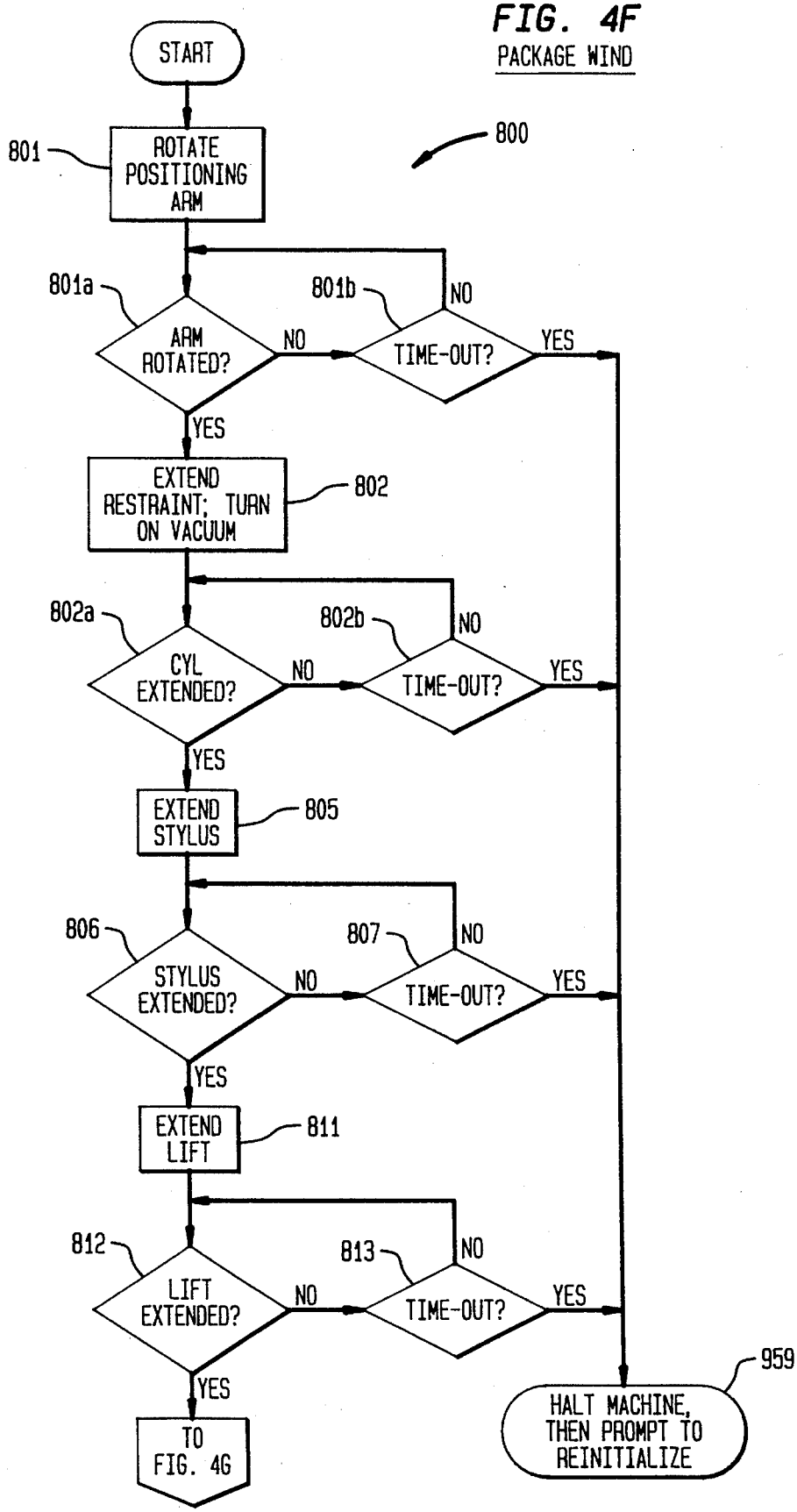

PACKAGE WIND

PACKAGE WIND

PACKAGE WIND

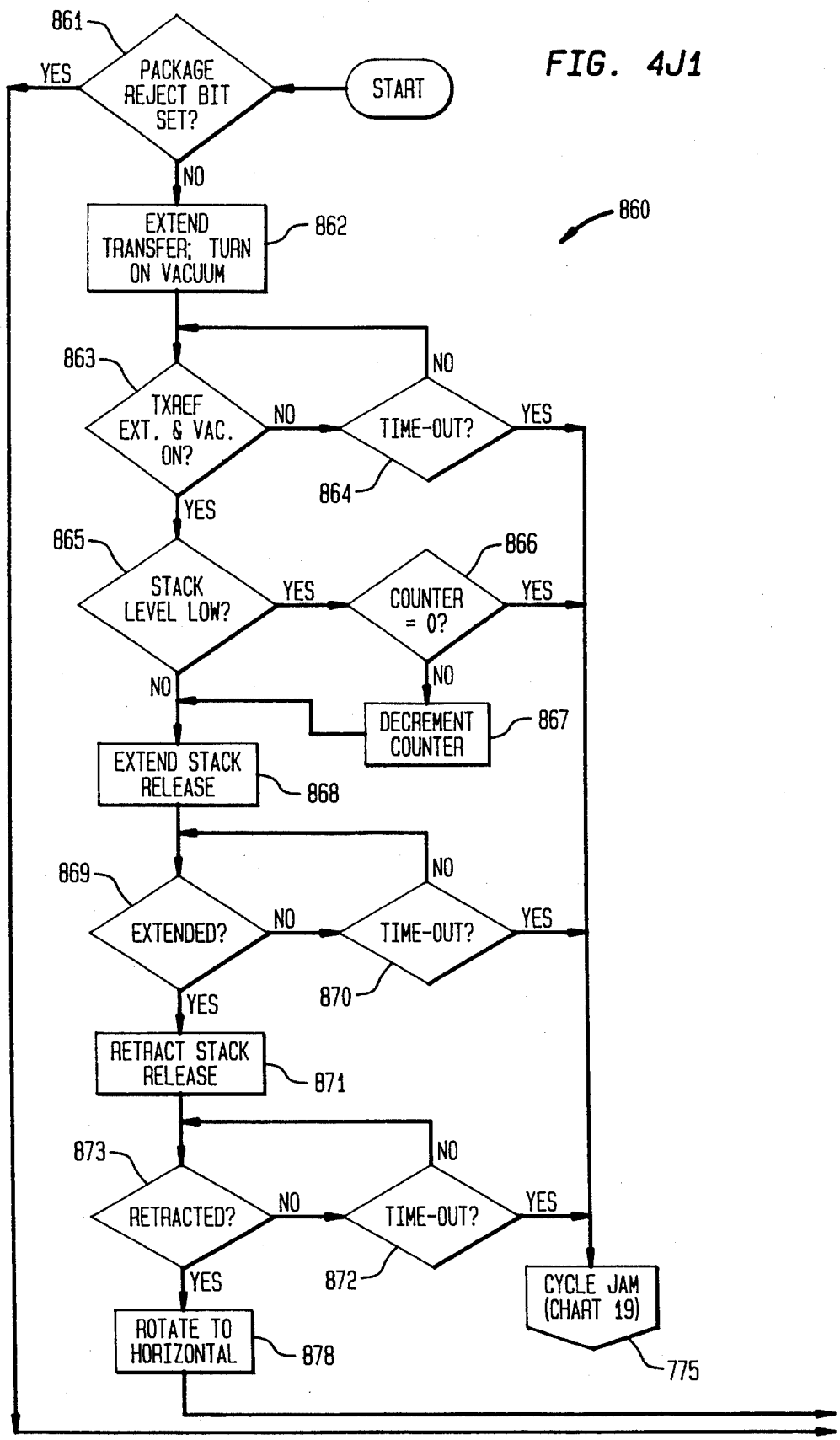
FIG. 4J1

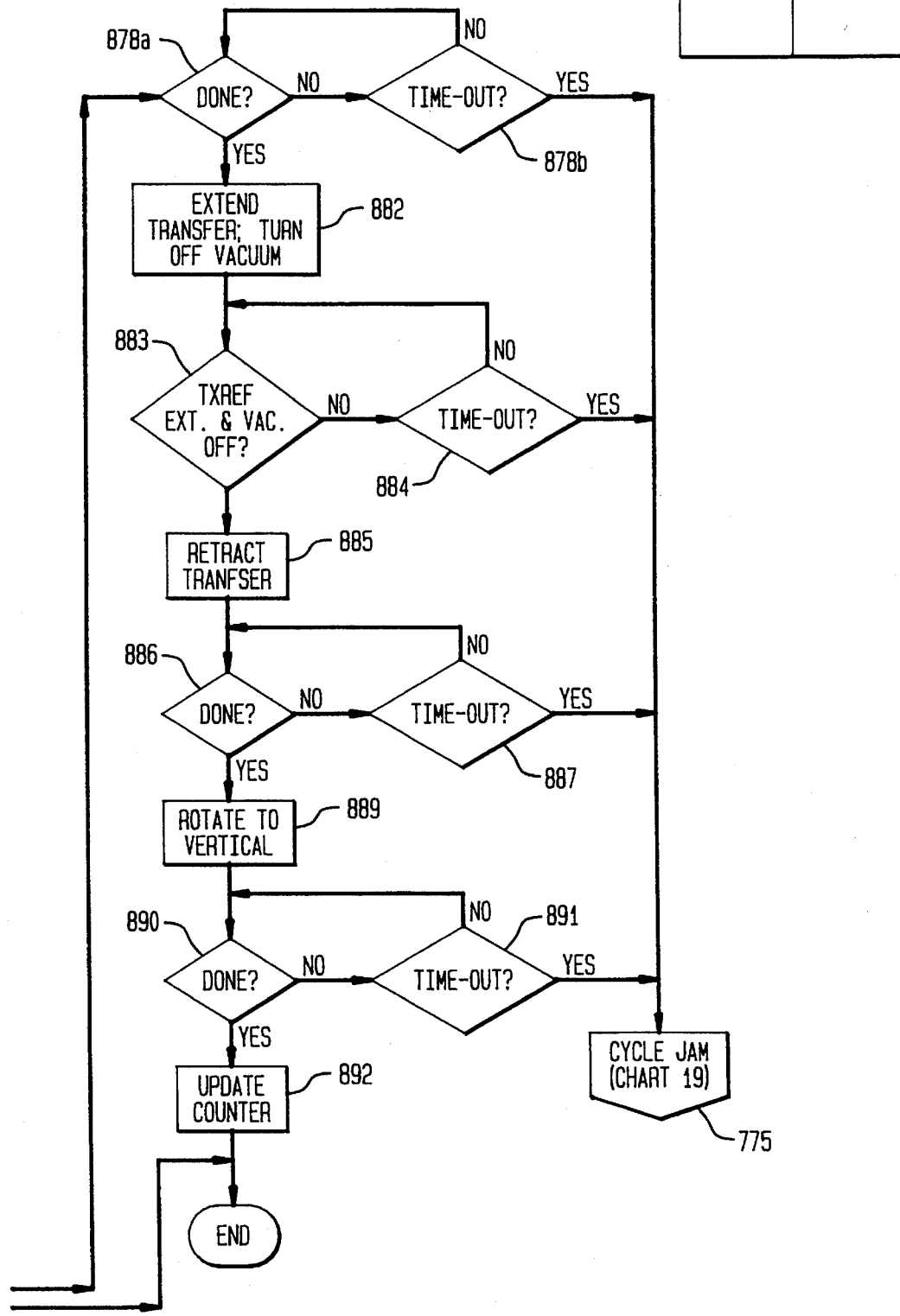

PACKAGE UNLOAD/SCRAP

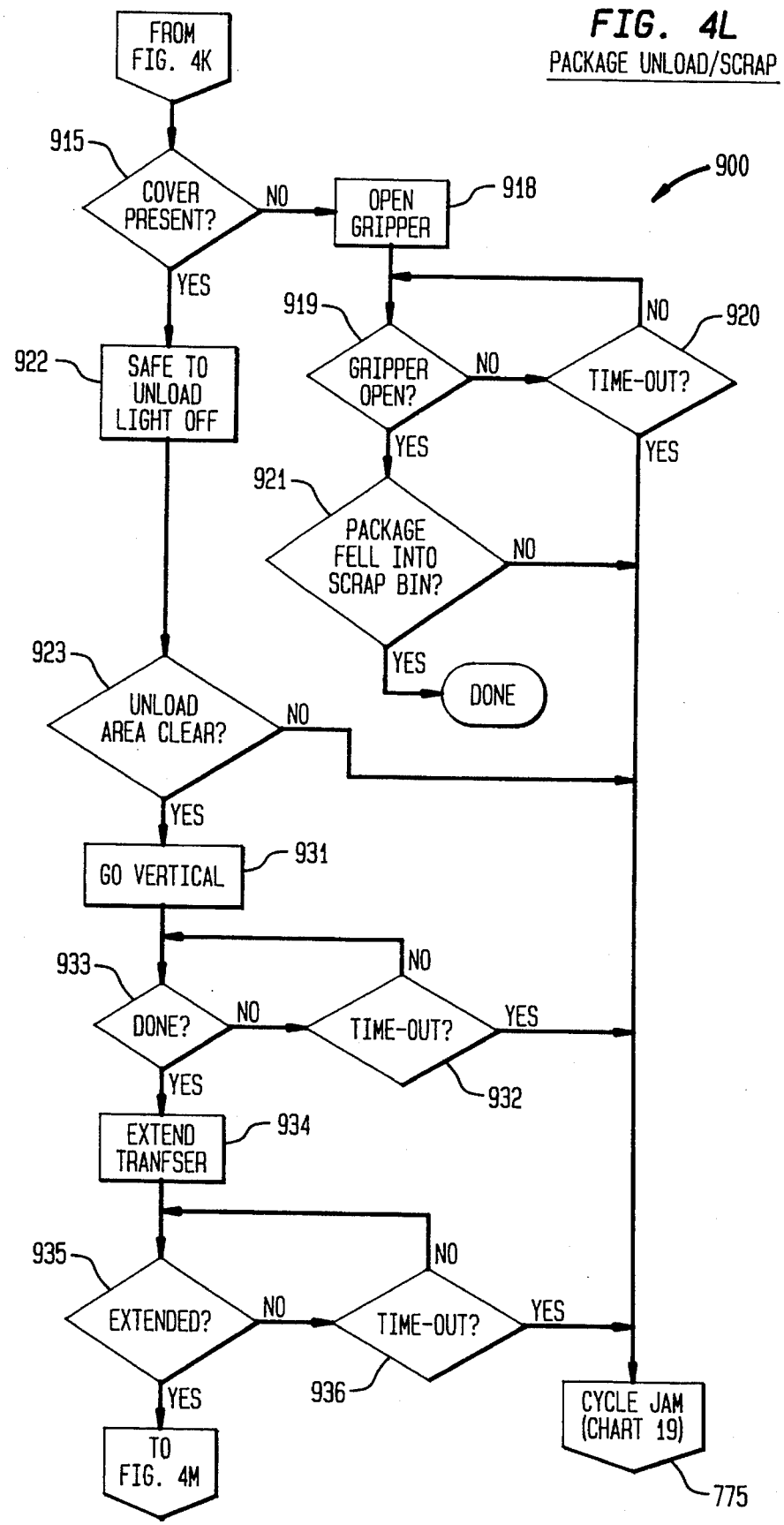

PACKAGE UNLOAD/SCRAP

CYCLE JAM

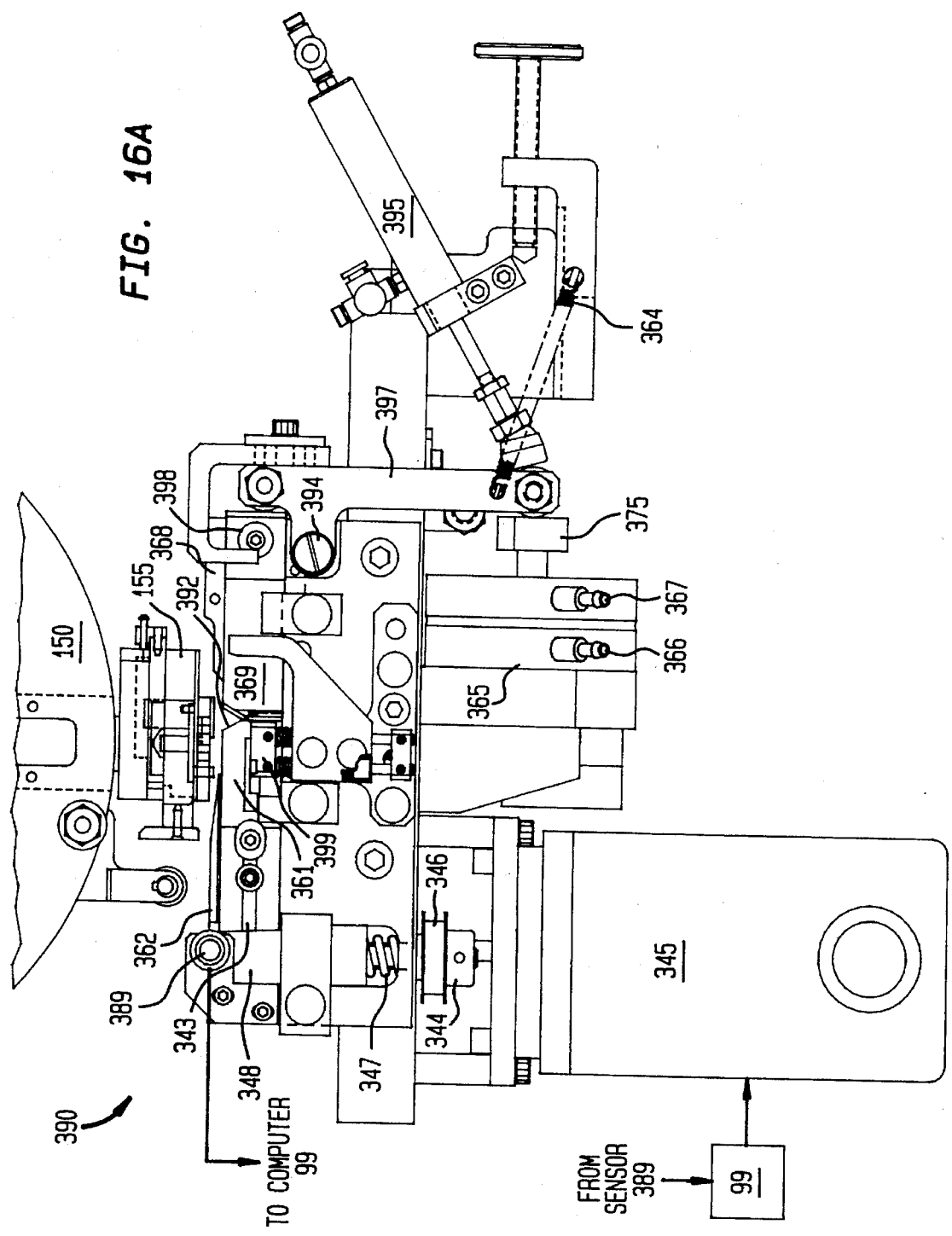

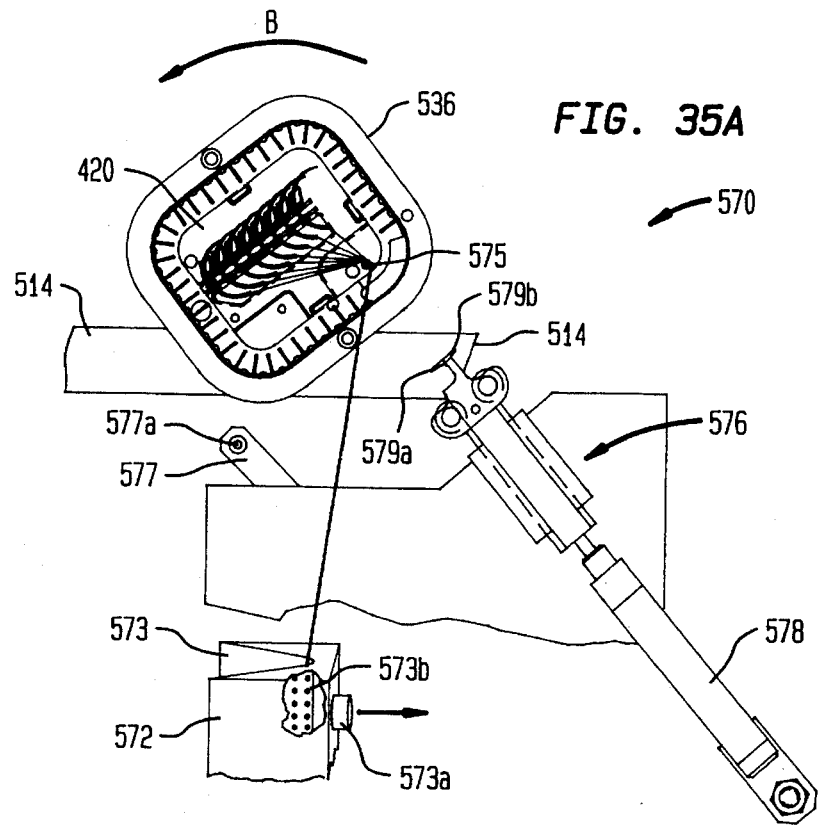
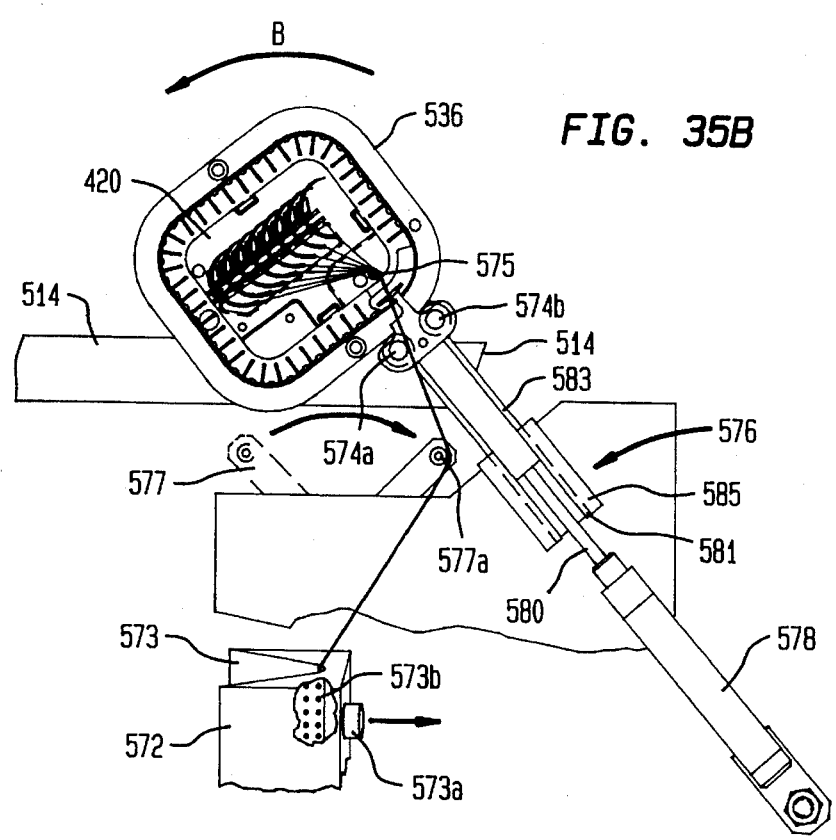

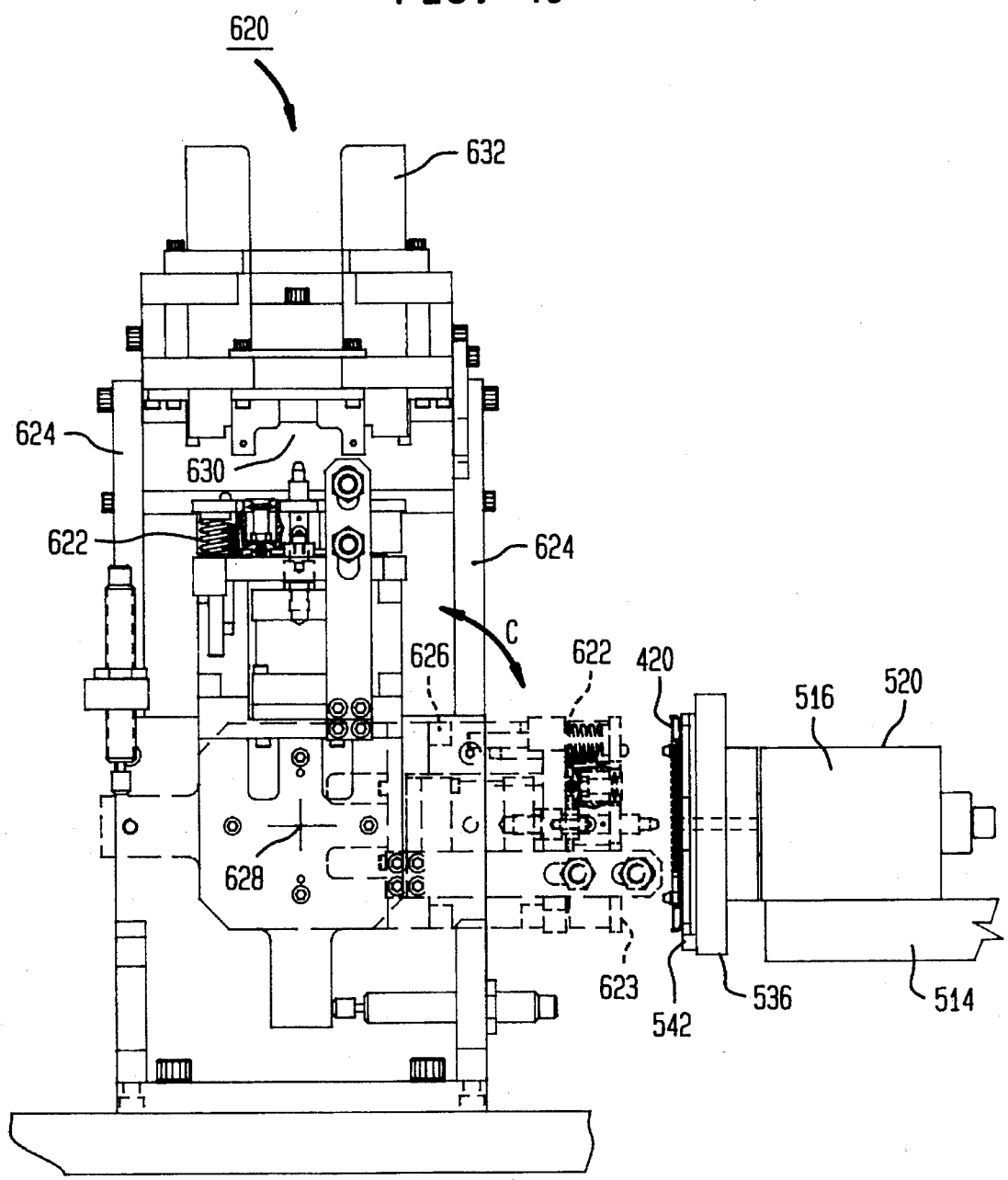

INITIALIZE OR RE-INITIALIZE

INITIALIZE OR RE-INITIALIZE

INITIALIZE OR RE-INITIALIZE

INITIALIZE OR RE-INITIALIZE

INITIALIZE OR RE-INITIALIZE

INITIALIZE OR RE-INITIALIZE

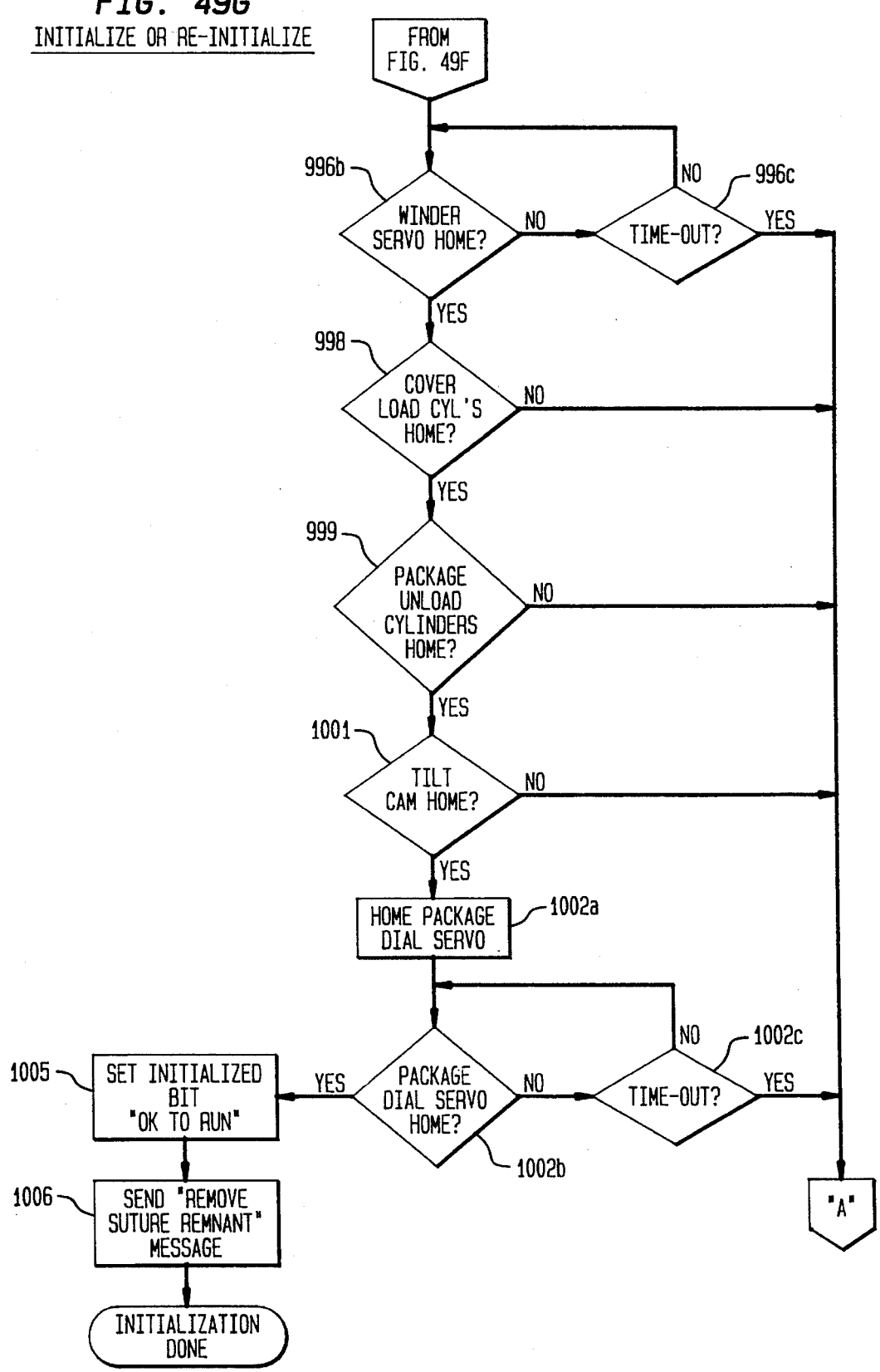

NEEDLE AND SUTURE SWAGING AND PULL-TESTING METHOD

This is a divisional of copending application Ser. No. 08/181,607, filed on Jan. 13, 1994.

1. Field of the Invention

The present invention relates generally to machines for automatically producing armed surgical needles, i.e., needles having a suture strand of predetermined length attached at one end thereof, and automatically packaging the same, and more specifically, to a control system for controlling the processes involved in the automatic production, testing, and packaging of armed surgical needles.

2. Description of the Prior Art

Presently, armed surgical needles used by surgeons and medical personnel are manufactured utilizing manual and semi-automated procedures such as those described in U.S. Pat. Nos. 3,611,551, 3,980,177, and 4,922,904. For instance, as described in U.S. Pat. No. 3,611,551, manual intervention is required by an operator to accurately position a suture tip within a suture receiving opening of a surgical needle to accomplish swaging thereof. This process is costly in terms of man-hour labor and efficiency because of the manual manipulations involved.

Indefinite length of suture material may be supplied wound on a bobbin, or, a king or driven spool before being cut and positioned within the swaging end of a surgical needle. In U.S. Pat. No. 3,980,177 the suture material is fed from a spool and taken up on a rotating tension rack where uniform length strands are subsequently cut. Thus, the length of the suture is determined by the size of the rack and manual intervention is required to prepare the rack for the cutting of the suture material wound thereabout. Moreover, manual intervention is required to change the rack each time a suture strand of different length is desired.

In U.S. Pat. No. 4,922,904, the suture material is supplied wound on a bobbin and is fed through various guide means prior to insertion within the suture receiving end of the surgical needle. In one embodiment shown therein, an elaborate television monitoring means is required for aligning the drawn suture within the suture receiving opening of the surgical needle prior to swaging thereof. In the same embodiment, a rotary encoder device is used to determine the length of suture material unwound from the bobbin prior to cutting. In an alternative embodiment, after swaging of the indefinite length of suture material to the needle, the needle-suture assembly is additionally fed a predetermined distance prior to cutting to obtain a suture strand of predetermined length. Thus, to obtain uniform lengths of suture material every time requires careful manipulations and precise controls, and the processes used to accomplish these tasks are slow and inefficient.

Additionally, at the present time, the introduction of needles with attached sutures into suture packages or molded plastic trays is being implemented in a substantially manual manner. In that instance, the needles are manually placed into the tray so as to be clampingly engaged by means of suitable needle-gripping structure, and thereafter the attached sutures are wound or positioned within the confines of the tray. Subsequently, a suitable cover is superimposed upon and fastened to the filled tray, and the resultant suture package conveyed to a suitable arrangement for possible sterilizing or further overwrapping.

The foregoing essentially manual and relatively basic process for winding the sutures into the tray, and especially the locating thereof into the peripheral channel of the tray during manipulation of the tray, is quite time-consuming, and in conjunction with the manual application of the cover into the tray in a basically individual or piece-by-piece mode, represents a serious hindrance to a high volume mass produced manufacturing output, and adversely affects the economics in attempting to provide such large quantities of suture packages containing multiple surgical needles and attached sutures.

In view of the limitations of the devices described in the aforementioned patents, it would be desirable to provide a needle threading and swaging machine that is fully automated and which can automatically prepare surgical needles having uniform lengths of suture material attached thereto.

Furthermore, it would be desirable to provide a packaging machine facilitating the automated high-speed packaging of surgical needles having sutures attached thereto.

Furthermore, it would be highly desirable to provide an automatic high-speed needle threading and swaging system and automatic high-speed packaging system that is computer controlled and that can provide automatic adjustments to the swage tooling dies when different size sutures are swaged to correspondingly sized surgical needles.

SUMMARY OF THE INVENTION

Accordingly, it is an object of the present invention to provide a control system for a high-speed, automatic needle-suture assembly and packaging system.

It is another object of the instant invention to provide a cost-effective automatic needle threading and swaging system and automatic packaging system that virtually eliminates operator exposure to any repetitive manual operations.

It is still another object of the instant invention to provide an automatic needle-suture assembly and packaging system that incorporates a rotatable swage dial having a plurality of multi-axis grippers that automatically grip surgical needles for indexing to a plurality of processing stations that include: a loading station for transferring individual precisely oriented surgical needles from a conveyor to the multi-axis grippers; a swaging station that automatically draws an indefinite length strand of suture material, cuts the strand, inserts the free end of the definite length strand within the suture receiving end of the needle, and swages the suture strand to the surgical needle; a pull-test station that automatically performs minimum and n-count destructive pull-testing of the needle-suture combination; and finally, a needle-suture load to package station where armed, pull-tested needles are transferred to the automatic packaging station for packaging thereof.

Yet another object of the present invention is to provide an automatic needle-suture assembly and packaging system that incorporates a rotatable suture winding and packaging dial for automatically packaging armed surgical needles with a variety of processing stations that include: a package load station for loading an empty package tray onto a supporting structure of the tool nest; a package detect station for detecting the presence of an empty package tray; a needle-suture load to package station where armed needles are transferred to the package from the rotary swage dial; a needle check station where the presence or absence of the armed needles is checked; a winding station where the sutures that depend from each surgical needle are gathered to a bundle and wound around a peripheral channel located about the periphery of the package tray; a cover loading station where a cover is applied to the package; and finally, a package removal station where the completed package is removed from the machine, or rejected if the package is flawed.

Yet still another object of the present invention is to provide a needle threading and swaging system that can provide continuous on-line tool adjustments without unnecessary interruptions and without manual intervention.

These and other objects of the present invention are attained with an automated system for attaching suture material to a suture receiving opening formed in a surgical needle, and packaging the same, the system comprising a first means located at a first location for sorting a plurality of randomly oriented needles and orienting each needle for automatic handling at a first predetermined location. A second means located at a second location is provided for automatically drawing and cutting an indefinite length strand of suture material and automatically inserting a free end thereof into the suture receiving opening of said needle and swaging the needle about the sutures to form a needle suture assembly. A first indexing means sequentially receives individual oriented needles at the first location and transports each of the needles from the first location to the second location to form the needle-suture assembly. A second indexing means is provided for registering an empty package tray at a third location for sequentially receiving one or more of the needle-suture assemblies from the first indexing means. A control means enables the first indexing means to sequentially transport the one or more needle-suture assemblies from the second location to the third location, and enables the sequential insertion of one or more of the needle-suture assemblies to the package tray while registered at the third location.

Further benefits and advantages of the invention will become apparent from a consideration of the following detailed description given with reference to the accompanying drawings, which specify and show preferred embodiments of the invention.

BRIEF DESCRIPTION OF THE DRAWINGS

FIG. 9(a) is detailed top view of the cam dial assembly 120 having cam dial plate 125 with cam follower 165a in a retracted position within cam track 60a;

FIG. 9(b) is cut away top view of the cam dial plate 125 showing cam follower 165a in an extended position within cam track 160a;

FIG. 16(a) is a top view of the swage assembly 390 of the instant invention with the multi-axis gripper 155 indexed thereat;

FIG. 17 for cutting material in the instant invention;

FIGS. 35(a) through 35(c) schematically illustrate, respectively, various stages in the operation of the suture winding arrangement;

FIG. 40 illustrates a front elevational view of the cover applying device in two operative conditions thereof;

FIG. 45 illustrates, on an enlarged scale a fragmentary view of the encircled portion in FIG. 43;

FIGS. 49(a)–49(g) illustrate the initialization or re-initialization routines utilized in the present invention; and, FIGS. 50(a)–50(e) illustrate the pneumatic control circuitry of the needle-suture assembly and suture wind and packaging systems as controlled by the control system of the present invention.

DETAILED DESCRIPTION OF THE PREFERRED EMBODIMENT

Figure 1:
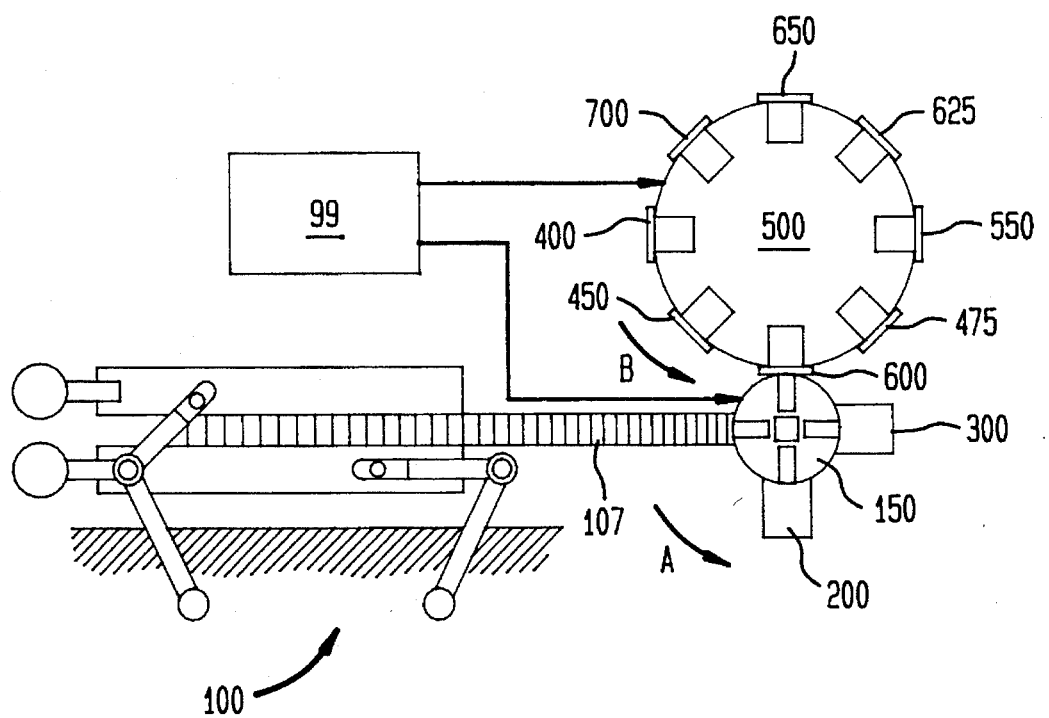
FIG. 1 is a conceptual top view of the needle threading and swaging machine and automatic packaging machine that are operable under the control system of the instant invention.
Figure 2:
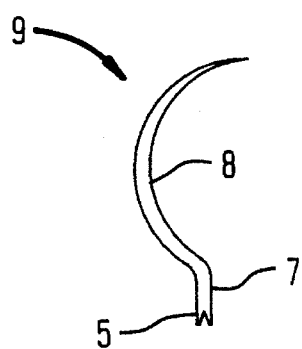
FIG. 2 is a detailed illustration of a typical surgical needle 9 having an arcuate portion 8 and suture receiving end 7.

Generally, as shown in the conceptual plan view of the needle threading and swaging system and needle-suture packaging system of FIG. 1, parallel operations take place simultaneously at four (4) different workstations positioned about a rotary swage dial 150 to enable the assembly, swaging and discharge of approximately sixty (60) surgical needles per minute with sutures attached thereto. Additionally, parallel operations take place simultaneously at eight (8) different workstations positioned about the larger suture winding and packaging dial 500 where the armed surgical needles are automatically parked into a reduced size organizer package of unique construction. FIG. 2 illustrates a typical surgical needle 9 having a suture receiving opening or end 7 for swaging a suture strand thereto, and an arcuate blade portion 8.

The automatic needle threading and swaging apparatus shown in FIG. 1 includes four workstations located about the periphery of the rotary swage dial 150 that are successively utilized to form needle-suture assemblies. These workstations include: a needle sorting station 100 that sorts, singulates, and conveys precisely oriented surgical needles to a plurality of retractable (multi-axis) grippers mounted on the rotary swage dial 150. The rotary swage dial 150 successively rotates counter-clockwise as shown by arrow "A" in FIG. 1, to index each needle to the automatic swaging station 200 where the suture material inserted into the needle, cut, and automatically swaged thereto. Next, the rotary swage dial 150 rotates further to index the armed needle to the automatic pull-test station 300 where each armed needle is pull-tested to ensure that minimum and/or destructive pull-test requirements are met. Then, the rotary swage dial 150 indexes the pull-tested armed needle to a discharge station 600 where the armed surgical needles are handed off to a package tray of unique construction at the suture winding and packaging turret 500 for automatic packaging thereof. Hereinafter, the discharge station 600 will be referred to as the needle-suture load to package station.

Generally, the automatic packaging apparatus shown in FIG. 1, includes eight (8) workstations located about the periphery of the rotary suture wind and packaging dial 500 that are successively utilized to form the completed package of surgical needles. These stations include: a package load station 400 for successively feeding an empty package onto a support plate of a tool nest mounted on the packaging dial; an optional package detect station 450 for checking the presence of the loaded empty package; the needle/suture to package load station 600; an optional needle check station 475 for detecting missing needles; a suture winding station 550 where the trailing sutures of the armed needles are gathered and wound into the package; an optional manual inspection station 625; a paper insert station 650 where a paper cover is applied to the package; and, a package removal station 700 where the completed package is removed from the machine for further processing, or, if the package has been found defective during inspection, is scrapped.

All of the processes performed at the apparatuses mentioned above and described in detail hereinbelow are controlled by the control system of the instant invention and implemented by software program(s) resident in the control system computer 99 as shown in FIG. 1. Alternatively, the control system may be implemented in a plurality of programmable logic controllers or other such suitable control devices (not shown).

Figure 3A:
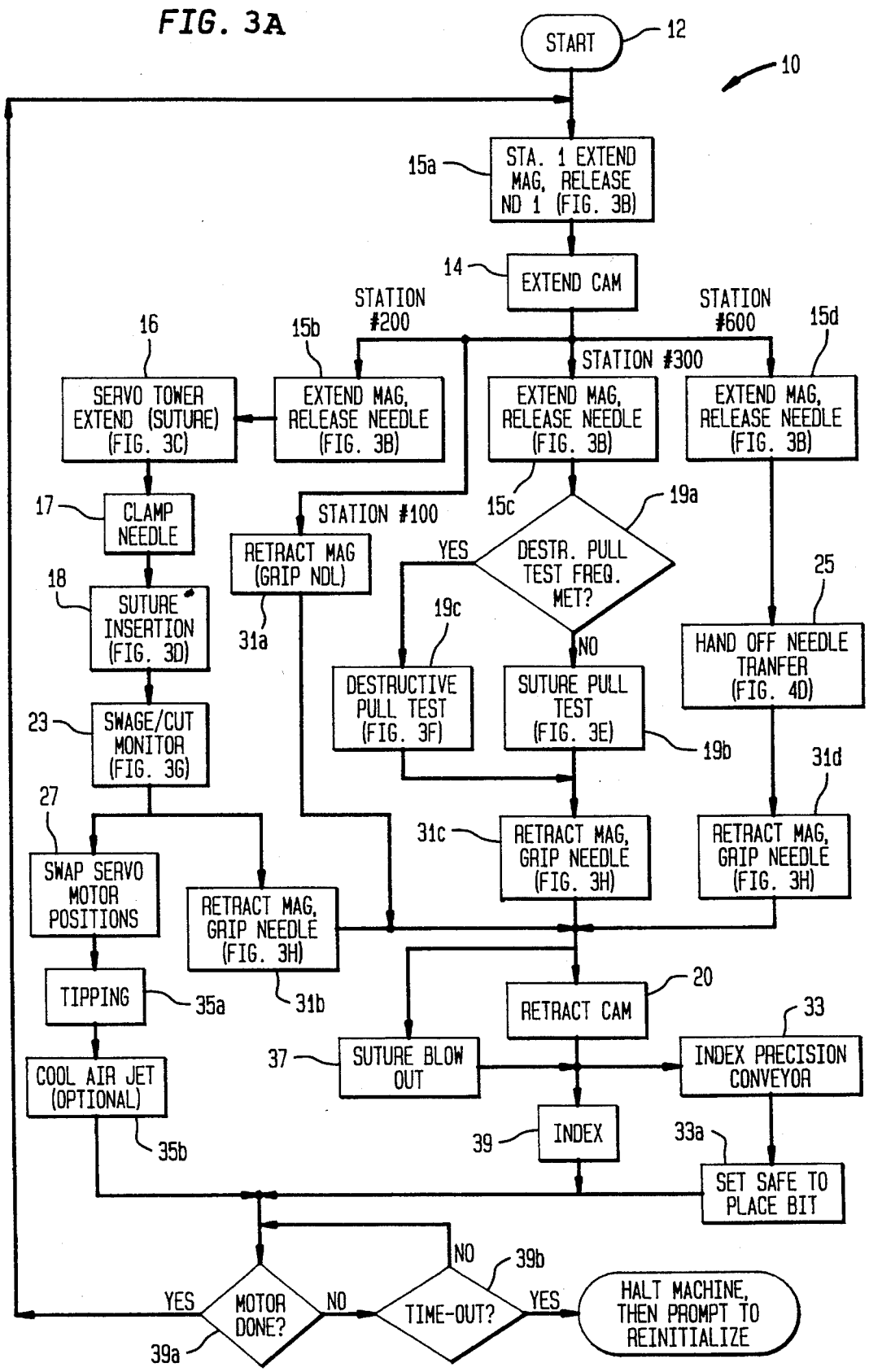
FIGS. 3(a)–3(h) are flow diagrams illustrating the sequential processes taking place at the rotary swage dial and operable under the control system of the instant invention.

FIGS. 3(a)–3(h) illustrate the automatic needle threading and swaging processes 10 operable under the control of the control system of the instant invention. To the extent possible, each process performed at each workstation, as illustrated in FIG. 3(a), will be described below in the sequential manner as illustrated. When the needle threading and swaging system is in steady state operation, the sequence of operative steps as shown in FIG. 3(a) is continually repeated to produce armed surgical needles at a rate of approximately 60/min.

To begin, the control system 99 initiates power up of the various devices utilized in the automatic needle threading and swaging system and the automatic suture winding and packaging system as indicated at step 12 in FIG. 3(a). At this point, an operator may be prompted to set up the dies for the swaging assembly that correspond to the size of the batch of needles to be processed. Additionally, any other necessary adjustments and setups may be performed for each assembly, for e.g., to initialize the Adept® robot assembly at the needle sorting station 100. Also as part of the power up display, an operator may be prompted to choose between operating the system in the normal, fully automatic mode, or, in a single step mode, perhaps for diagnostic troubleshooting purposes. This power up routine may be part of a greater initialization (or reinitialization) routine discussed below with respect to FIGS. 49(a) through 49(g).

Needle Sorting Station

The needle sorting station 100 is activated to sort, singulate, and convey individual and precisely oriented surgical needles to each of four multi-axis grippers mounted on the rotary swage dial assembly indexed at station 100.

Figure 5:
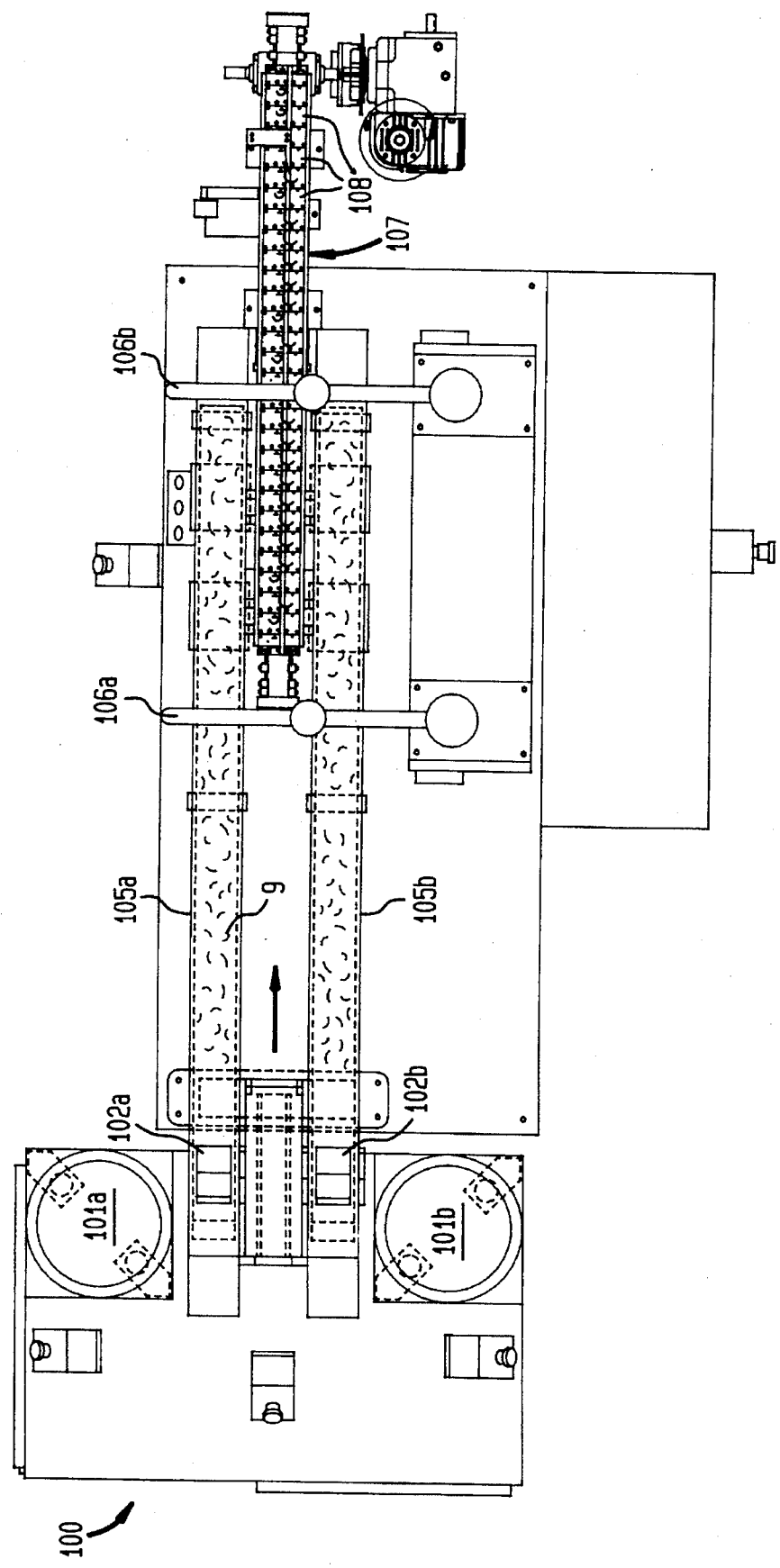
FIG. 5 is a top view of the needle sorting station 100 of the automated needle threading and swaging system.

At the needle sorting station 100 illustrated in FIG. 5, a batch of unoriented needles of uniform size are first loaded into vibratory bowls 101a,b, automatically sorted and linearly fed by singulating devices 102a,b to each of two translucent indexing conveyors 105a,b, evaluated with respect to orientation and position by a vision tracking system (not shown), picked up by either of two robotic apparatuses 106a,b, transferred to individual engagement devices (boats) 108 located on a precision conveyor 107 by each robot apparatus, and finally conveyed to the rotary swage dial assembly where the needles are transferred to a multi-axis gripper at step 15a in FIG. 3(a) for subsequent transfer to the swaging station 200. A detailed explanation of the needle sorting apparatus 100 is explained in further detail in copending U.S. patent application Ser. No. 08/181,600 (attorney docket 8920), and a detailed explanation of the robotic control system utilized therein is described in copending U.S. patent application Ser. No. 08/181,624 (attorney docket 8921) both of which are assigned to the same assignee as the present invention, and incorporated by reference herein.

Figure 6:
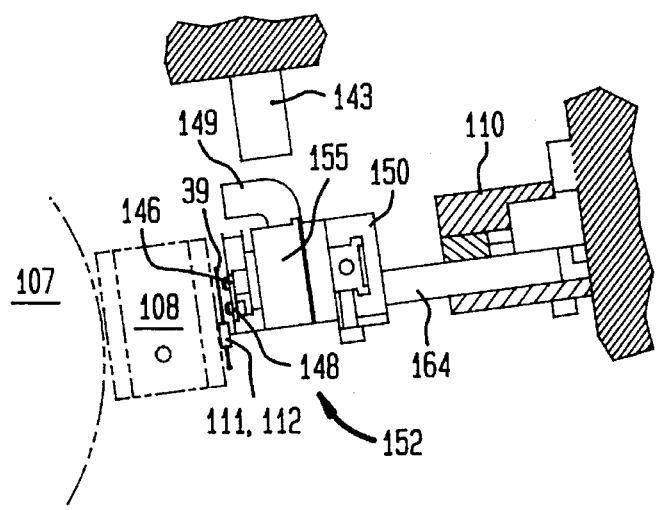
FIG. 6 illustrates the precision conveyor handing off surgical needle 9 to the multi-axis gripper 155.
Figure 4K:
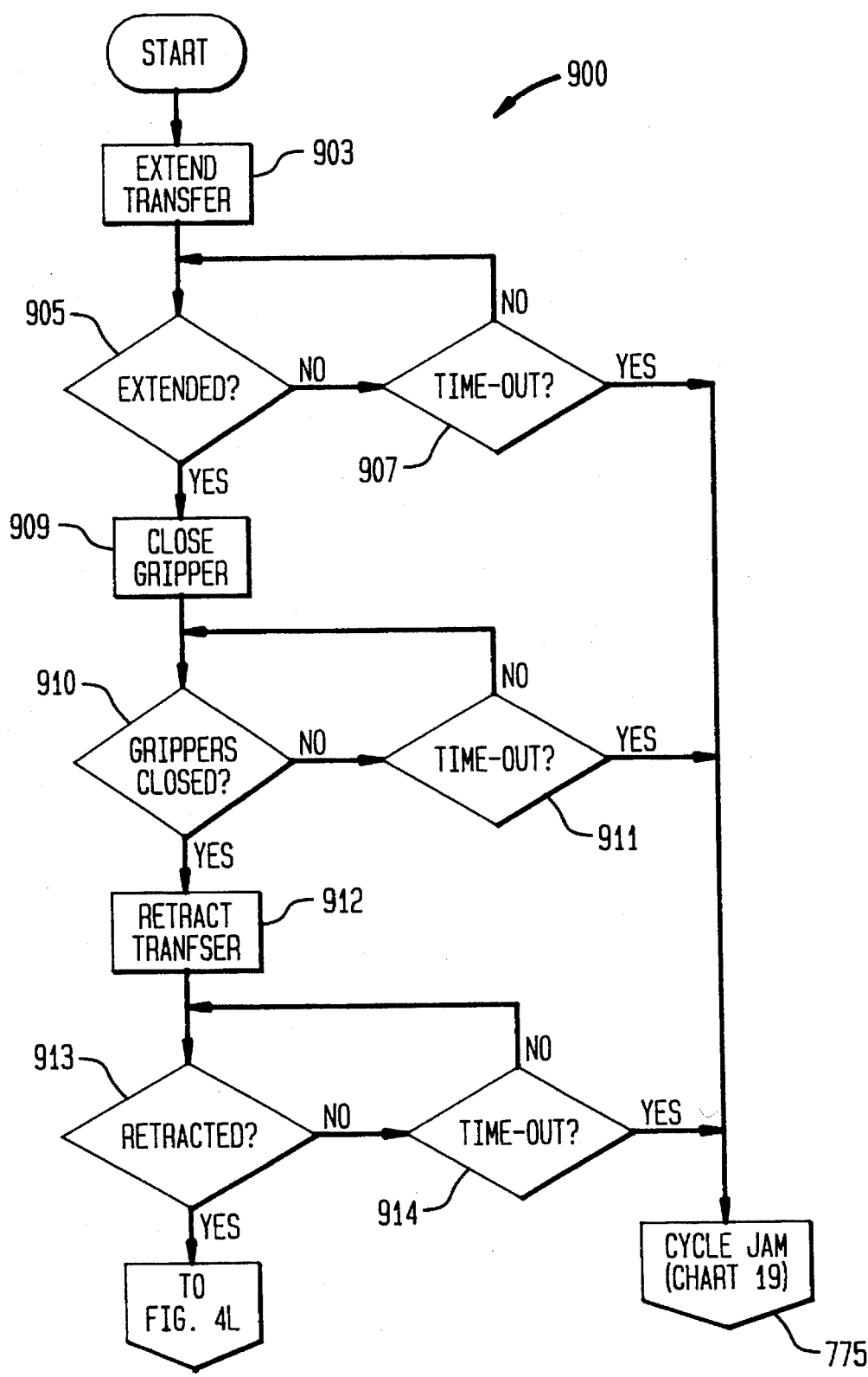
Figure 4M:
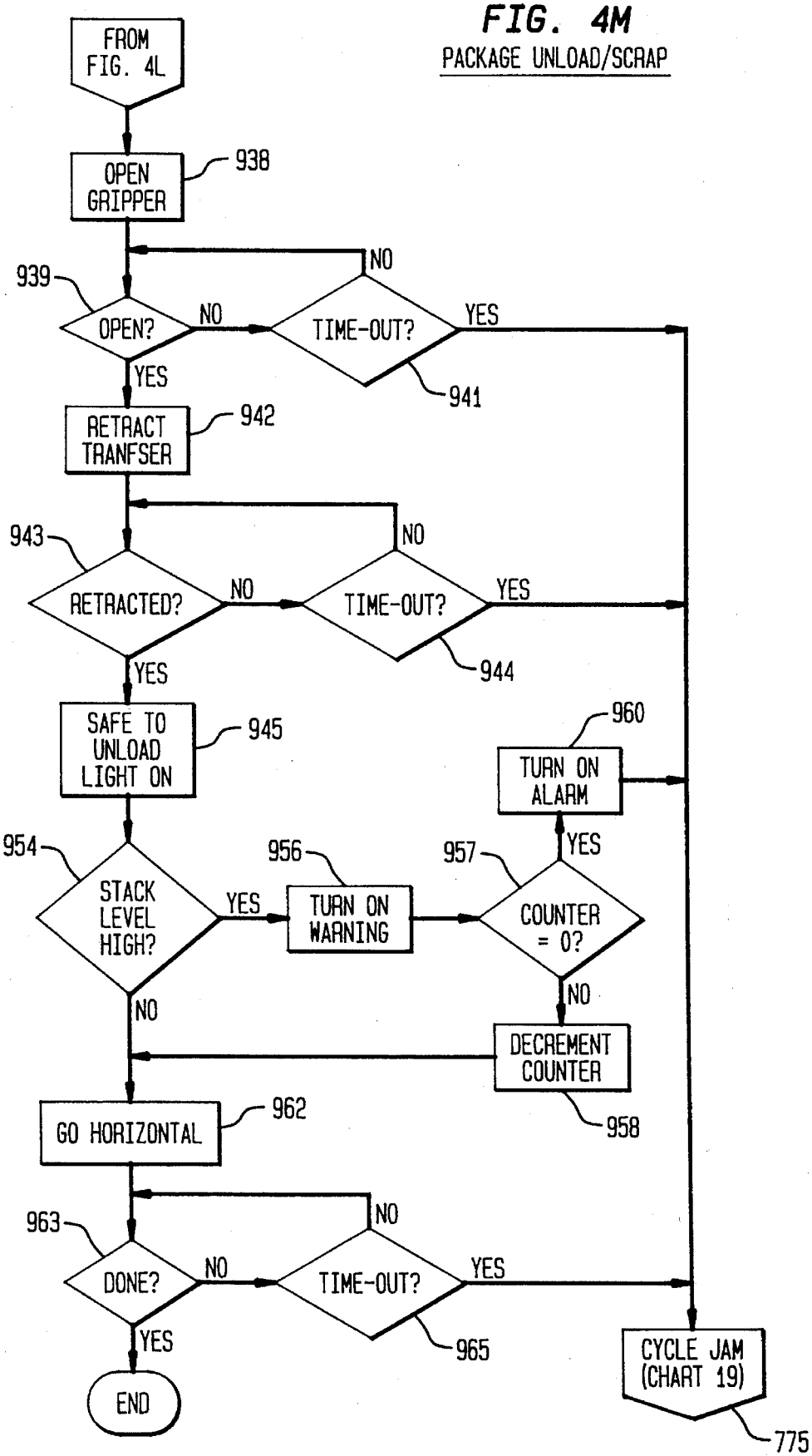
Figure 4N:
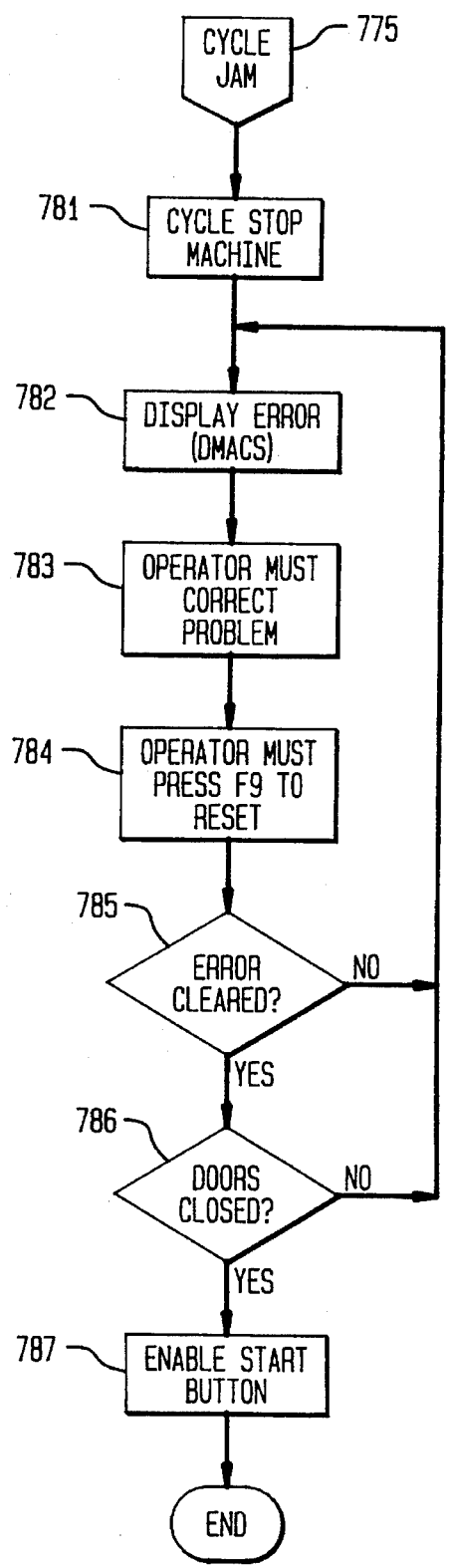
Figure 11A:
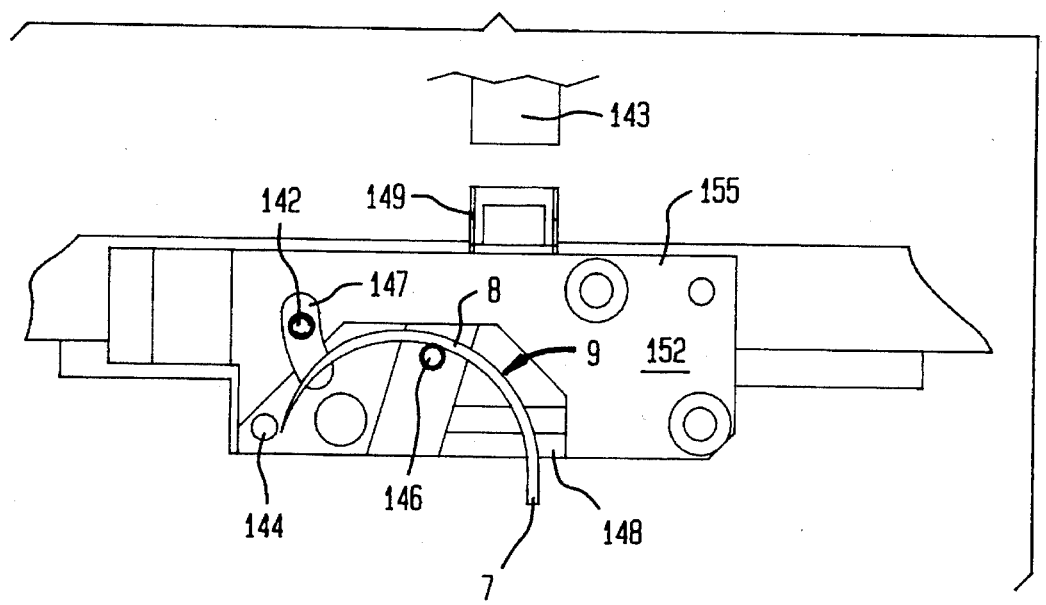
FIG. 11(a) is front face view of the multi-axis gripper 155 showing a surgical needle 9 in a relaxed engagement thereby, and additionally showing pin 142 in a retracted position.
Figure 11B:
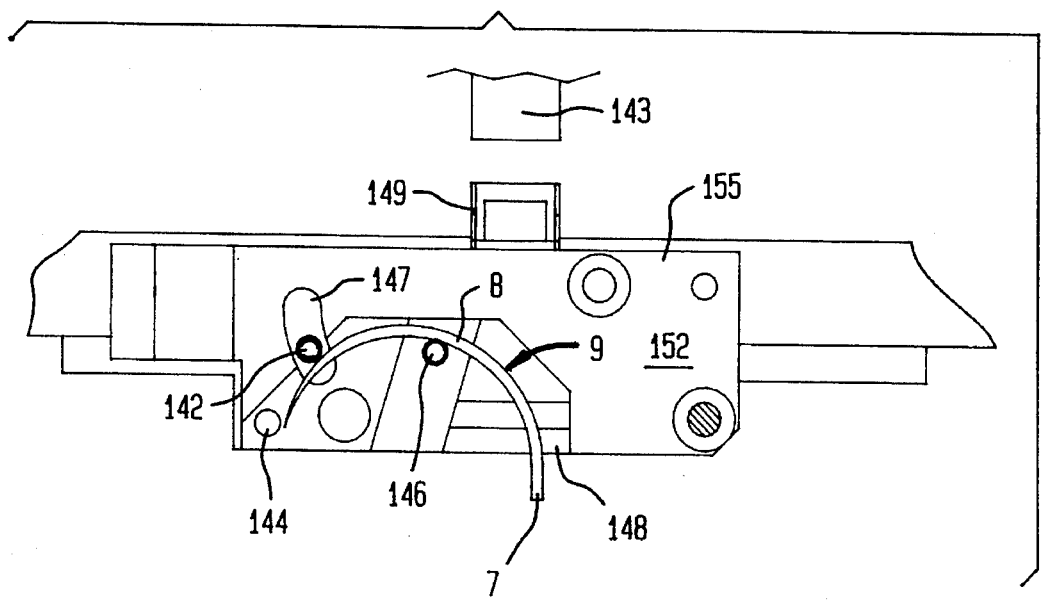
FIG. 11(b) is front face view of the multi-axis gripper 155 showing a surgical needle 9 in an engaged position therein.

Generally, to accomplish the transfer of the needle to the multi-axis gripper at step 15a in FIG. 3(a), the multi-axis gripper 155 is registered at station 100 so that the gripper pin assembly 152 thereof is confronting the needle precision conveyor boat 108 as shown in FIG. 6. As indicated at step 15a and as described in further detail below with respect to FIG. 3(b), the multi-axis gripper pin assembly and pins 146 and 148 thereof are able to penetrate a plane formed by the curvature of needle 9. Then, the control system 99 initiates the command for a solenoid or plunger 143 to depress plunger 149 to retract an engagement pin of the pin assembly 152 and enable the needle to become deposited between pins 146 and 148 of the multi-axis gripper 155. Simultaneously, the control system 99 initiates the command for a solenoid of similar device to open engagement jaws 111,112 of the precision conveyor boat 108 to release the needle 9 and effectuate the transfer of the needle to the pin assembly 152 of the multi-axis gripper. A front view of the multi-axis gripper 155 retaining the needle 9 after transfer from the precision conveyor boat 108 is illustrated in FIG. 11(b).

The description hereinbelow of the sequence of steps shown in FIG. 3(a) assumes steady state operation, i.e., that surgical needles have been transferred from the needle sorting apparatus at workstation 100 onto each of the four multi-axis grippers mounted on the swage dial 150 that have been successively indexed to station 100 at step 39 to receive the needle from the precision conveyor at step 15a. In the preferred embodiment, the control system 99 initiates a needle transfer to the multi-axis gripper once every second to feed the swaging apparatus. Immediately prior to indexing a multi-axis gripper to workstation 100 at step 39, the precision conveyor 107 has been indexed at step 33 and is dwelled for the next hand-off the needle to the multi-axis gripper. Immediately after indexing the precision conveyor at step 33, the control system 99 sets a SAFE TO PLACE flag at step 33a indicating that it is safe for one of the robot apparatuses 106a,b to place a needle on another boat 108 located upstream of the swage dial 150.

Rotary Swage Dial/Multi-axis Gripper

Figure 7:
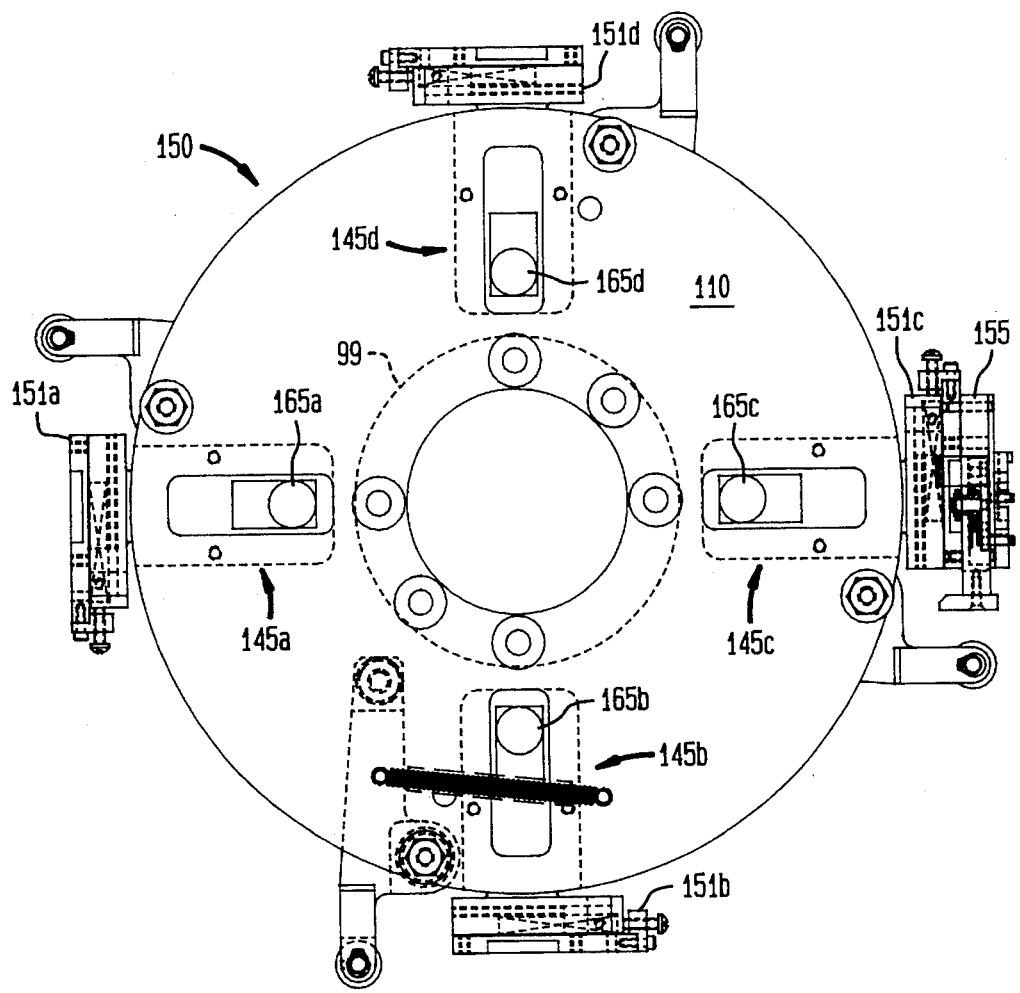
FIG. 7 is a top view of the rotary swage dial assembly 150 comprising a swage dial plate 110 having four multi-axis gripper stations 145a,b,c,d mounted thereon.

Step 14 in FIG. 3(a), involves actuating a cam mechanism to enable each multi-axis gripper, indexed at each respective workstation 200, 300, 600 to extend out from the rotary swage dial 150 and place each precisely oriented surgical needle 9 that is gripped thereby, within each respective workstation for processing thereat. This is explained in detail as follows:

As illustrated in FIGS. 1 and 7, the rotatable swage dial assembly 150 includes four multi-axis grippers each retaining a needle for processing to occur simultaneously at workstations 100, 200, 300, and 600. In the detailed illustration of FIG. 7, the swage dial assembly 150 includes a swage plate 110 having four multi-axis gripper stations 145a, 145b, 145c, 145d spaced equally thereon. The swage plate 110 is rotatably mounted at a central hub 109 and is rotated by suitable drive motors (not shown) operable under the control of the control system computer 99.

As shown in FIG. 7, multi-axis gripper station 145a includes reciprocating carriage 151a, while station 145b includes reciprocating carriage 151b, station 145c includes reciprocating carriage 151c, and station 145d includes reciprocating carriage 151d. Mounted to each reciprocating carriage 151a,b,c,d for reciprocal movement therewith, are multi-axis grippers, one of which 155 is shown connected to gripper carriage 151c in FIG. 7. Each gripper carriage 151a,b,c,d and multi-axis gripper 155 thereof is movable from a retracted position to an extended position. During steady state operation of the system, when each gripper 155 is in its retracted position shown in FIG. 8(a), each needle 9 carried thereby may be indexed to the next successive workstation as the swage plate 110 rotates; when a gripper 155 is in its extended position as shown in FIG. 8(b), a needle 9 is in one of the processing stations, for e.g., the automatic swaging station 200, or, the automatic pull-test station 300 for processing thereof.

Figure 8A:
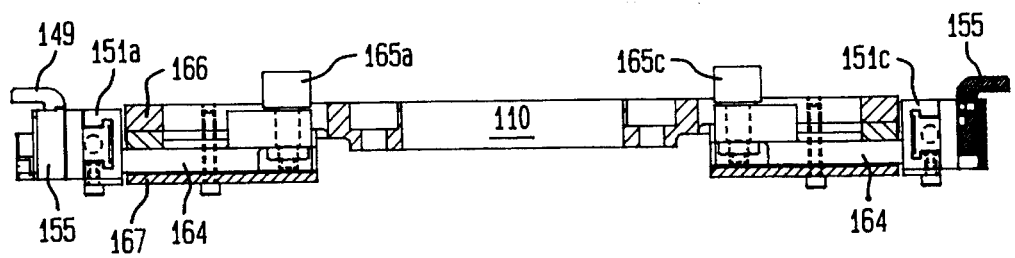
FIG. 8(a) is cross-sectional view of the four station swage dial assembly 150 showing multi-axis gripper 155 in a retracted position.
Figure 8B:
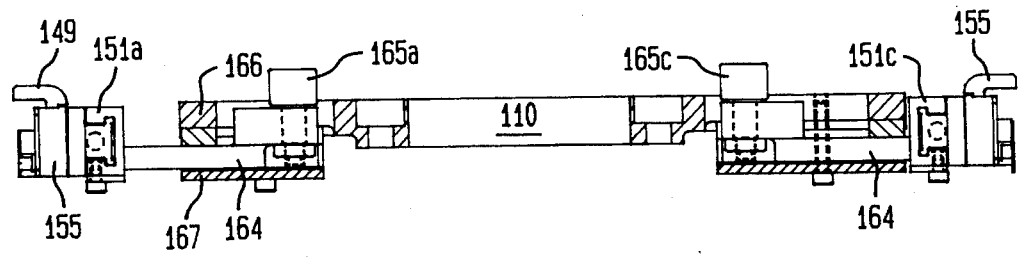
FIG. 8(b) is cross-sectional view of the four station swage dial assembly 150 showing multi-axis gripper 155 in an extended position.
Figure 9A:
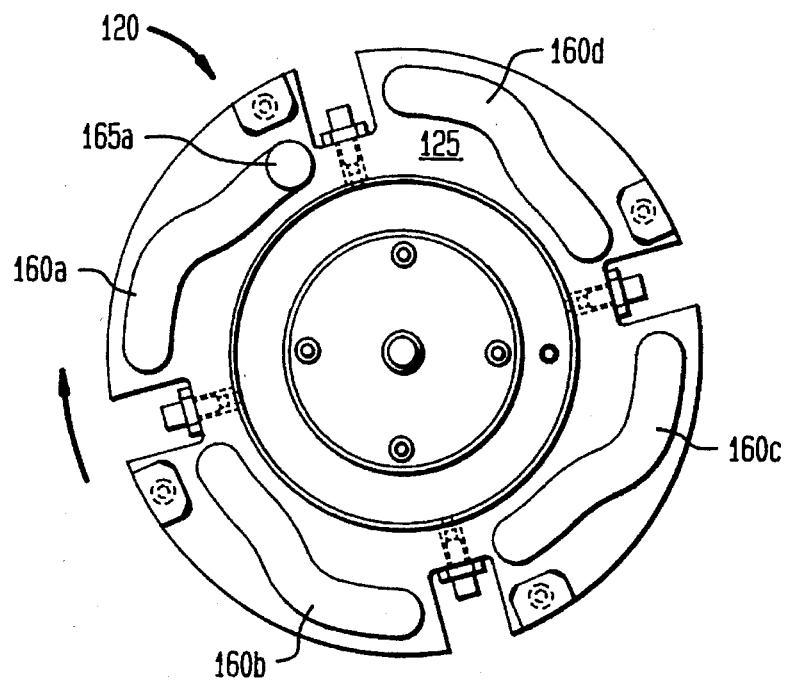
Figure 9B:
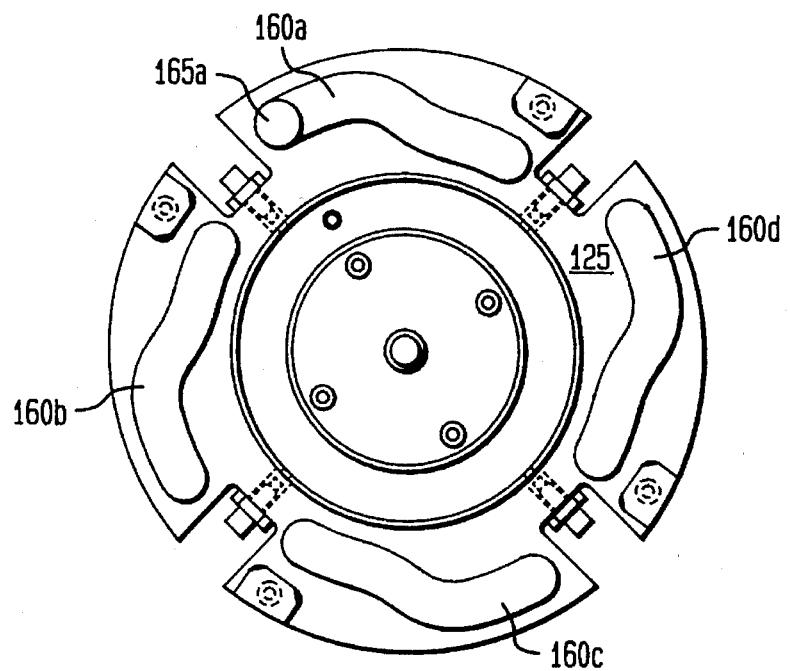
Figure 10:
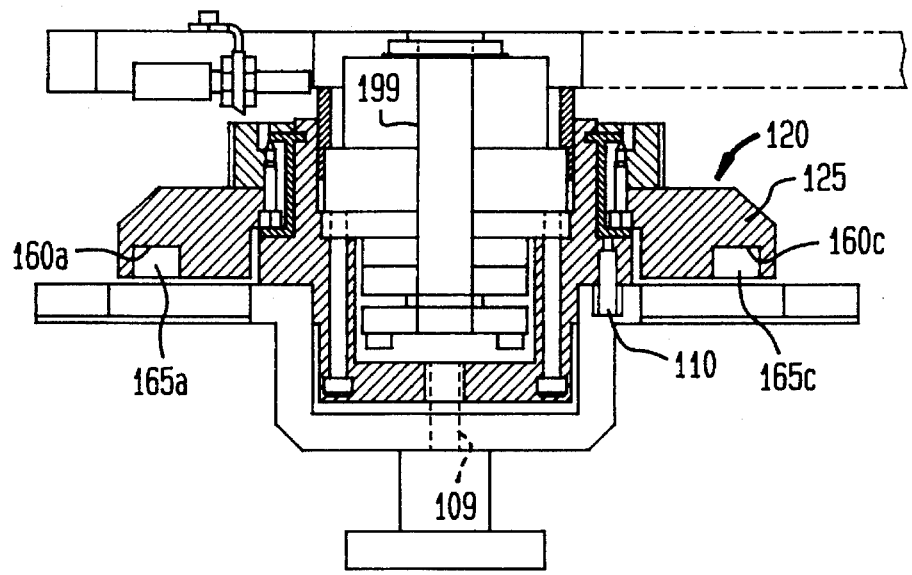
FIG. 10 is a cross-sectional view of the cam dial plate 125 mounted coaxial with the swage dial plate 110 for cooperative rotational movement thereof, and showing cam followers 165a and 165c positioned within their respective cam tracks 160a and 160c.

The mechanism for extending each multi-axis gripper 155 is shown in FIGS. 8(a) and 8(b), 9(a)–9(b) and FIG. 10. In FIG. 8(a), a cam follower 165a(b,c,d) is mounted to a cam slide 164 at one end of each reciprocating carriage 151a(b, c,d), and the multi-axis gripper 155 is connected to the cam slide 164 at the other end. Cam slide 164 is slidable within stationary guides 166,167 and is adapted for reciprocal movement when the cam follower 165a(b,c,d) is actuated by a cam dial assembly. In the preferred embodiment shown in FIG. 9(a), cam follower 165 is a roller that fits within cam tracks of a rotatable cam dial assembly 120. Cam dial assembly 120 is shown in FIG. 9(a) as comprising a cam dial plate 125 having four cam tracks 160a,b,c, and 160d which correspond to respective multi-axis gripper stations 145a,b, c, and 145d. Each cam follower 165 is positioned within each respective cam track at each station for movement therein. For instance, in the cutaway side view shown in FIG. 10, cam follower 165a is positioned within cam track 160a and cam follower 165c is positioned within cam track 160c. Also in FIG. 10, the cam dial plate 125 is positioned within the swage dial assembly 150 and mounted coaxial therewith. The cam dial plate 125 is rotatable about a central shaft 199 and operated by a separate rotary indexing transmission (not shown) under the control of the control system 99, so that it may rotate separately from the swage dial plate 110. FIG. 9(a) shows cam follower 165a in a first retracted position within the cam track 160a. When in this position, reciprocating carriage 151a and consequently multi-axis gripper 155 are in their retracted position as shown in FIG. 8(a) discussed above. To extend each multi-axis gripper 155 in place at its respective station as indicated at step 14 in FIG. 3(a), the cam dial plate 125 is rotated in the clockwise direction indicated by the arrow in FIG. 9(a), for approximately 45–55 degrees with respect to the swage plate 110, forcing cam follower 165a in its cam track 160a to move toward the periphery of the dial as shown in FIG. 9(b). Consequently, the cam slide 164, reciprocating carriage 151a, and the multi-axis gripper 155 move to the extended position as shown in FIG. 8(b) and discussed above.

It should be understood that when cam dial plate 125 rotates clockwise with respect to swage plate 110, each multi-axis gripper 155 is extended within its respective cam track. Thus, during steady state operation, the system is designed so that all processes performed at each workstation occur simultaneously and for approximately the same duration of time when the multi-axis grippers are in their extended positions, for e.g., for needle pickup from the sorting station 100 (step 15a), needle swaging (step 23), for needle pull-testing (steps 19a,b), and for needle-suture hand-off to the suture wind and packaging dial (step 25).

After each multi-axis gripper has been extended at respective stations 200,300, and 600, the control system 99 initiates an extend multi-axis gripper release needle process for releasing each needle from the grip of the multi-axis grippers as indicated in the EXTEND MAG RELEASE NEEDLE steps 15b,c,d in FIG. 3(a). The releasing of the needle 9 from grip of the multi-axis grippers at each workstation is desirable for performing the processes at each station as discussed generally above with respect to step 15a. In the frontal view of the multi-axis gripper 155 shown in FIG. 11(b), pins 142, 146, and 148 of the multi-axis gripper 155 extend perpendicularly from the gripper pin assembly 152 of the gripper to engage the arcuate portion 8 of needle 9. The three pin needle engagement configuration shown in FIG. 11(b) ensures that the needle 9 will not be displaced when the swage dial 150 is rotating, or, when the multi-axis gripper 155 is being retracted or extended. In the preferred embodiment, pin 142 is spring loaded and is retractable within guide 147 to a non-engaging or relaxed position when a plunger 149 is depressed as shown in FIG. 11(a).

Figure 3B:
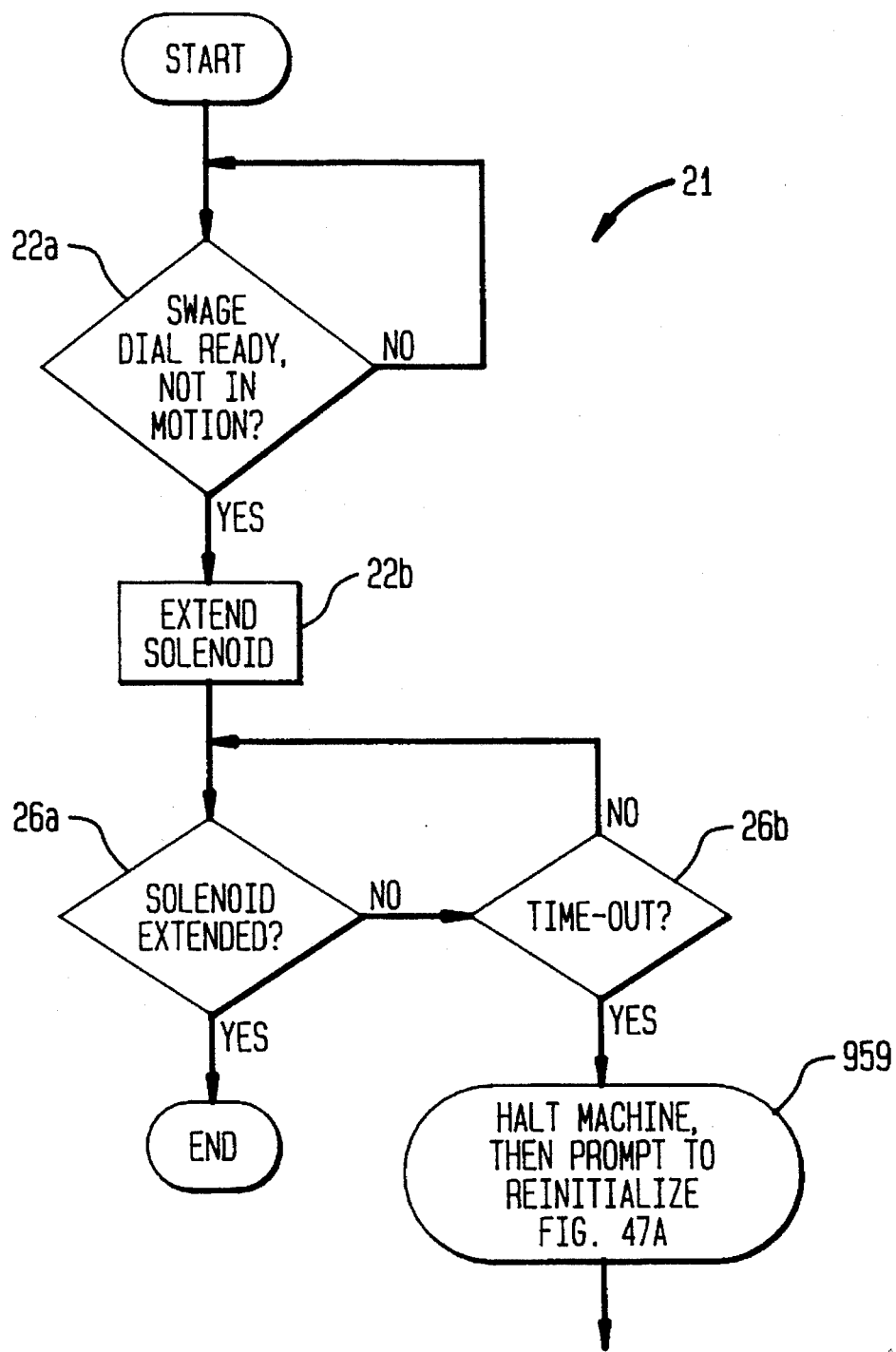

The control process 21 for relaxing each needle retained by each multi-axis gripper at each respective workstation is illustrated in FIG. 3(b). First, the control system performs a check at step 22a to verify that the rotary swage dial 150 is not in motion, i.e., that it has stopped rotating upon reaching its indexed position. If the swage dial has arrived at its indexed position, a cam solenoid 143 is actuated to depress the plunger 149 of the multi-axis gripper as shown in FIG. 11(a). If the swage dial has not been indexed, the system will wait until it is indexed before extending the cam (step 22b). While the cam solenoid is extending, a suitable proximity sensor (not shown) senses its motion at step 26a and will inform the control system accordingly. The system performs a check at step 26b to determine whether a time-out flag has been generated by the control system indicating a time-out error. If a time-out flag had not been generated, then the cam 143 has been fully extended (step 26a) and that the needle has been relaxed from the grip of the multi-axis gripper. If the time-out flag is generated by the control system indicating an error, the process will be terminated and prompted for re-initialization at step 959.

At the same time the cam solenoid 143 is extended to relax the needle for processing as indicated at steps 15b, 15c, and 15d in FIG. 3(a), the indefinite length of suture strand is drawn up a servo tower at workstation 200 as indicated at step 16 in FIG. 3(a). The drawing of the indefinite length of suture strand is described in detail below and in further detail in copending patent application Ser. No. 08/181,599 (attorney docket No. 8937) assigned to the same assignee of the present invention and incorporated by reference herein.

Needle Threading and Swaging Station

As previously mentioned, the automatic swaging station 200 is where the suture of indefinite length is drawn, cut, and inserted within the suture receiving end of a surgical needle for swaging thereof.

Figure 13:
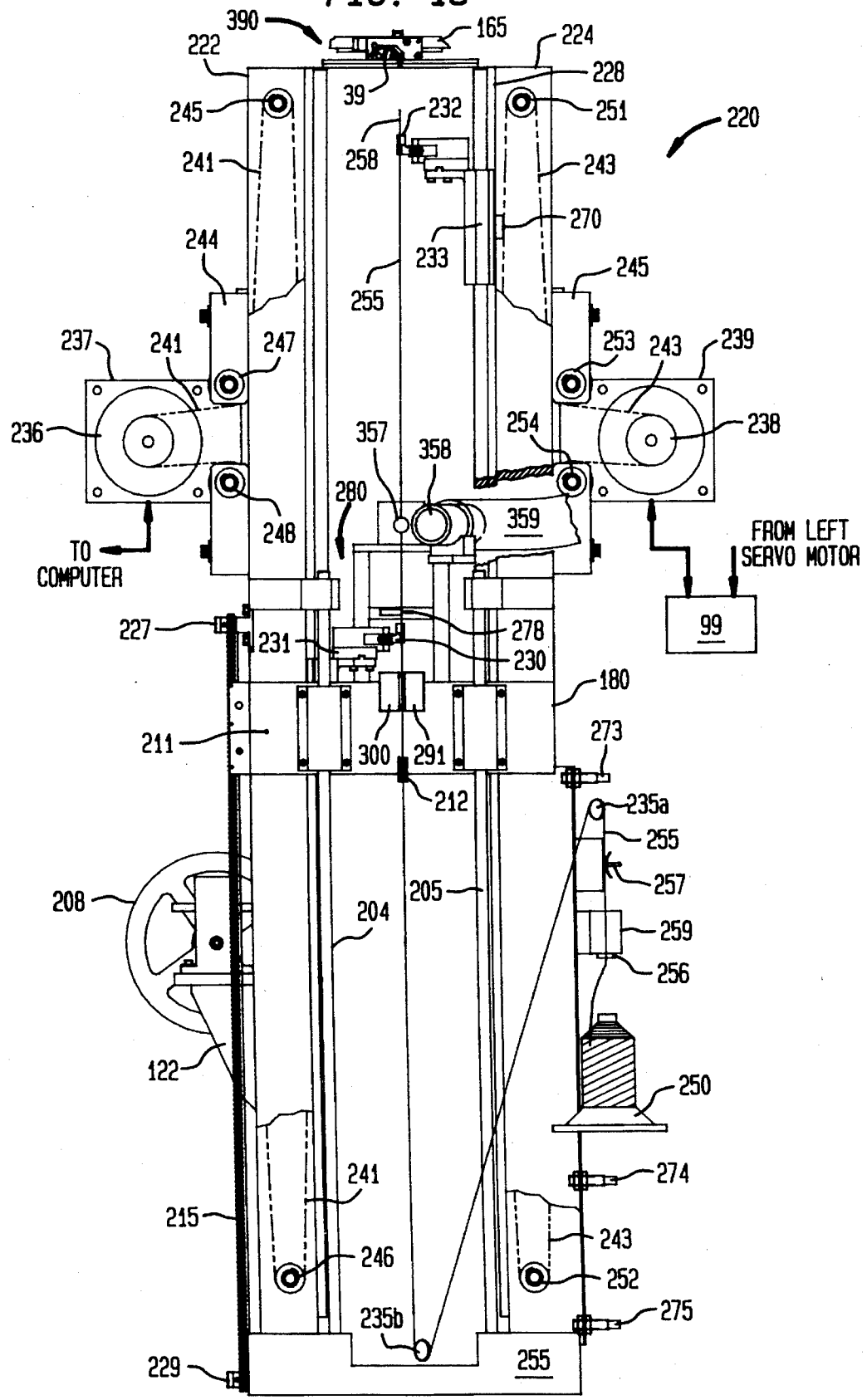
FIG. 13 is a detailed view of the servo (suture drawing) tower including the automatic swaging station 200 with cutter assembly 280 and heater assembly 290 mounted on tip and cut carrier 180, and the right gripper 232 registering indefinite length suture strand tip 258 for insertion within end 7 of surgical needle 9 shown engaged by the multi-axis gripper 155.

The step 16 of drawing the indefinite length of suture material is accomplished at a drawing tower 220 shown in FIG. 13. The drawing tower 220 comprises left side rail 222 and right side rail 224 both mounted on suitable mounting block 225 and defining a drawing bed for drawing an indefinite length of suture material along a drawing axis therebetween. Located parallel to the left and right side rails 222,224 and suitably connected thereto are respective left guide rod 226 and right guide rod 228. The lead gripper means or right gripper 232 reciprocates up and down along right guide rod 228 while the bottom gripper means or left gripper 230 reciprocates up and down the left guide rod 226. Each of the grippers 230,232 grip the suture material that is fed from a spool through pulley 235 located at the bottom of the drawing tower 220, and carries the material to the upper end of the tower. The right gripper 232 is mounted on right gripper carrier 233 for vertical movement along right guide rod 228, and the left gripper 230 is mounted on left gripper carrier 231 for vertical movement along left guide rod 226 as shown in FIG. 13.

Figure 12:
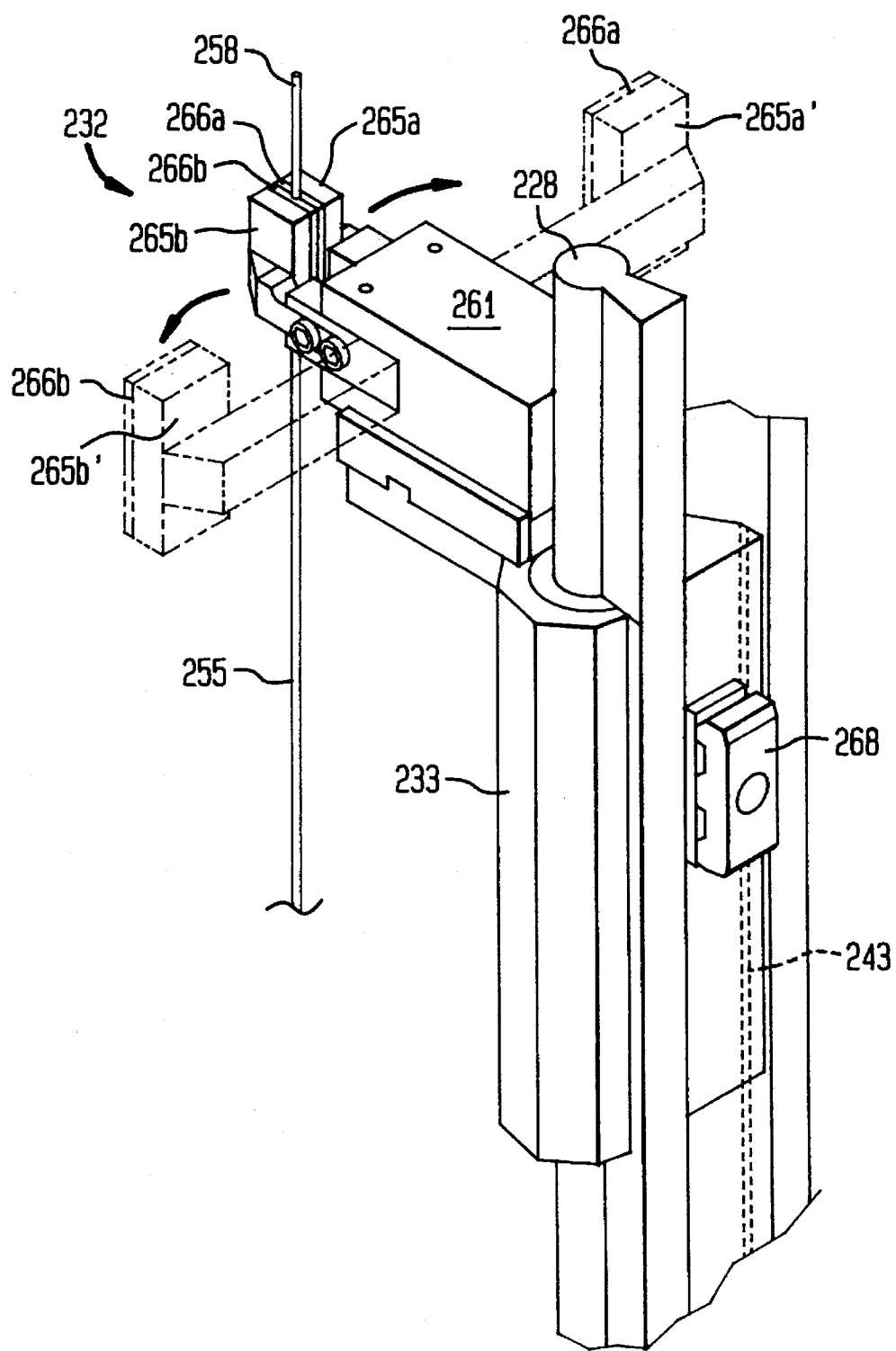
FIG. 12 is an enlarged view of a gripper assembly having gripper arms 265a,265b shown in their closed (suture gripping) and open positions.

FIG. 12 illustrates a gripper 232 (and 230) having a gripper arm drive 261 that is pneumatically operated to drive pair of retractable gripper arms 265a, 265b toward each other to a suture gripping position, or, away from each other to an open position. Each retractable gripper arm is provided with a non-metallic pad 266a, 266b for gripping the suture material 255 at a free end thereof when actuated to the gripping position. To release the grip of the suture, gripper arms 65a,265b are retracted approximately 180 degrees apart in the direction indicated by the arrows of FIG. 18 to the open position. When in the open position the gripper arms 265a', 265b' do not interfere with the motion of the other vertically moving gripper as it reciprocates along the respective left or right rod, nor will it interfere with the retractable cutter assembly 280 that cuts the strand to a predetermined length. The retractable nature of the grippers and of the cutting assembly enables single drawing axis operation.

Figure 50A:
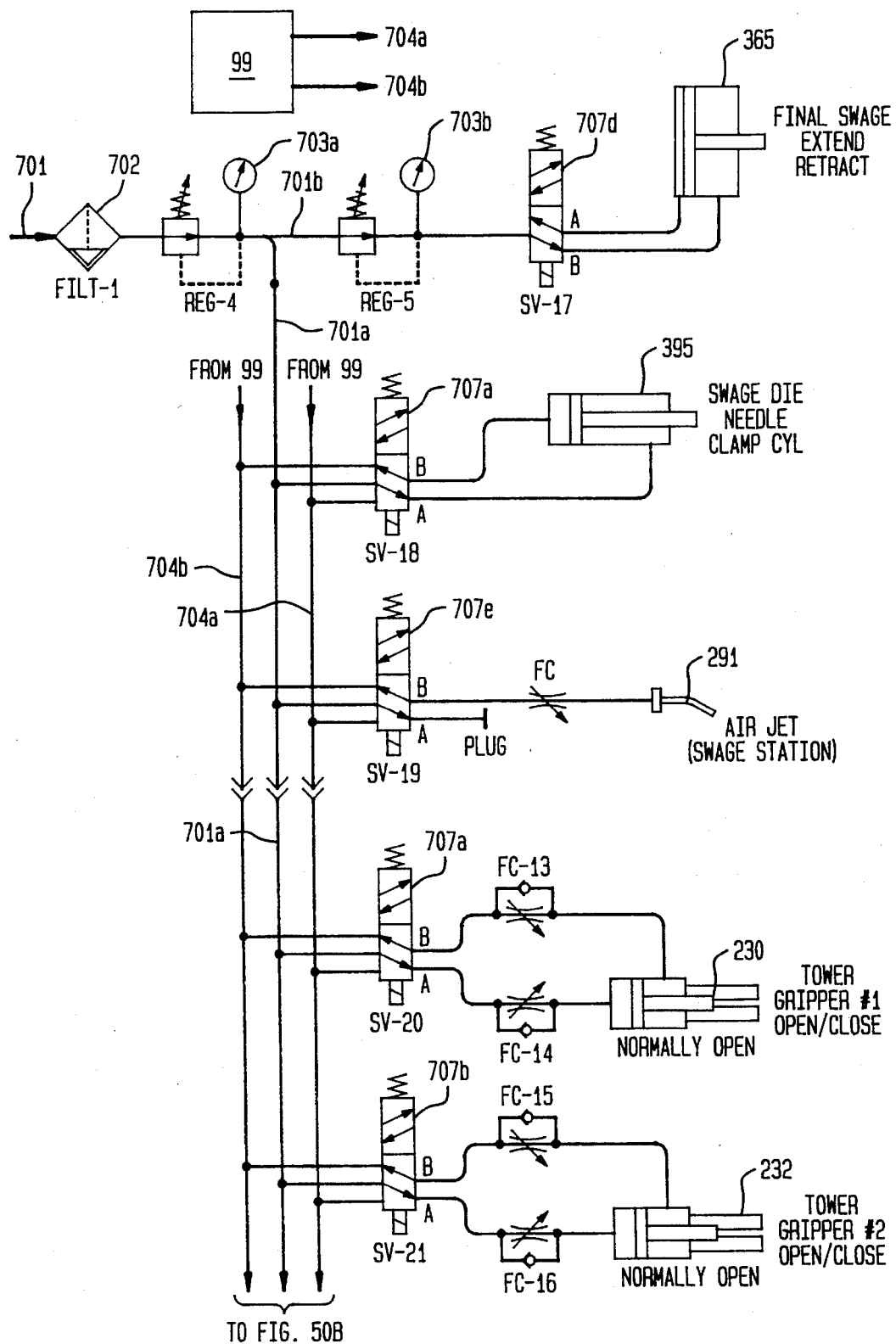

The pneumatic schematic diagram of FIG. 50(a) illustrates supply line 701 that supplies pressurized air through suitable filter 702, through pressure monitoring device 703a and through switching devices 707a and 707b, to provide the pressurized air for controlling the gripper arm drive 261 of each respective gripper 230 and 232. Specifically, the pressurized air supply line 701 is split into the pressure line 701a for supplying air pressure to the top and bottom grippers 232,230, respectively, as shown in FIG. 50(a). Control signal lines 704a,b interface with the control system 99 to control the timing and positioning of each switching device 707a,b. Thus, the pneumatic opening and closing of the gripper arms 265a,b of each retractable gripper 230,232 are controlled by the control system 99.

As mentioned above, each gripper carrier and gripper thereof is designed to advance vertically along the respective left and right rods. As shown in FIG. 13, the right gripper 232 and gripper carrier 233 is driven by right servo motor 238 which is mounted to the right side rail 224 by right motor mounting bracket 239. Similarly, the left gripper 230 and gripper carrier 231 is driven by left servo motor 236 which is mounted to the left side rail 222 by left motor mounting bracket 237. In the preferred embodiment, both left and right servo motors are interfaced with and controlled by the control system computer 99. As shown in FIG. 13, right servo motor 238 drives timing belt 243 which consequently enables vertical positioning of right gripper carrier 233 along right rod 228, while the left servo motor 236 drives timing belt 241 which consequently enables vertical positioning of left gripper carrier 231 along left rod 226. As FIG. 12 illustrates, timing belt 243 is clamped to its respective gripper carrier 233 by a timing belt clamp 268 located on the back of the gripper carrier. A similar timing belt clamp (not shown) is provided on gripper carrier 231 for clamping timing belt 241 to enable vertical movement of gripper 230.

FIG. 13 also shows the tip and cut carrier 180 positioned along shafts 204 and 205 which are located parallel to respective left and right rods 226,228. Tip and cut carrier 180 provides the support for tipping assembly 290 that applies heat to a specific location of the suture material, and also provides support for the cutter assembly 280 that cuts the suture material. Therefor, its vertical positioning is dictated by the length of suture strands desired to be cut in any given batch. The vertical positioning of the tip and cut carrier 180 is accomplished by cranking handwheel 208 shown in FIG. 13. Alternatively, a computer controlled servo motor may vertically register the tip and cut carrier 180 prior to cutting and heat tipping the suture material.

Both the stroke of the grippers 230,232 and the positioning of the tip and cut carrier 180 along drawing tower 220 dictates the length of the material that will be cut. For instance, as shown in FIG. 13, proximity sensors 273,274, and 275 are positioned vertically at different heights along the drawing tower 220 to enable predetermination of the length of suture material to be cut. Specifically, the locations of the proximity sensors 273,274, and 275 sense the positioning of the tip and cut assembly 180 as controlled by handcrank 208 in order to notify the control system 99 to change the reciprocating travel of grippers 230,232. Also as shown in FIG. 13, proximity sensor 270 is mounted at a position along the right side rail 224 to verify that right gripper 232 has reached a desired position at the upper end of the tower 220 and notify the control system 99 accordingly. Likewise, a proximity sensor (not shown) is mounted at the desired height along the left side rail 222 to verify that left gripper 230 has reached its desired position at the upper end of the drawing tower 220.

When loading the indefinite length suture material, the suture material 255 is first manually threaded through eyelet 256 and through optional knot detector 257 which senses any sudden change in the thickness of the suture material. Detection of a knot in suture material 255 during steady state operation will inform the control system 99 to enable the pull-test station to discard that strand of material, in the manner discussed below, as indicated at steps 19a,b of FIG. 3(a). Additionally, the suture material may be threaded within a tensioning (or dancer) assembly 259 which comprises a plurality of vertically spaced apart cones 223 each of which may be positioned laterally to increase or decrease the tension of the suture strand 255 as shown generally in FIG. 14.

The suture material 255 is then advanced over pulleys 235a and 235b located at the bottom of the drawing tower 220, and around pulley 212 which is mounted on the lower portion of tip and cut carrier 180 that is illustrated near the center of the tower as shown in FIG. 13. Note that the lower threading pulley 235b, guide pulley 212, left gripper 230 and right gripper 232 are vertically aligned so that the cutter assembly 280 will always cut horizontally across the strand of material.

Figure 3C:
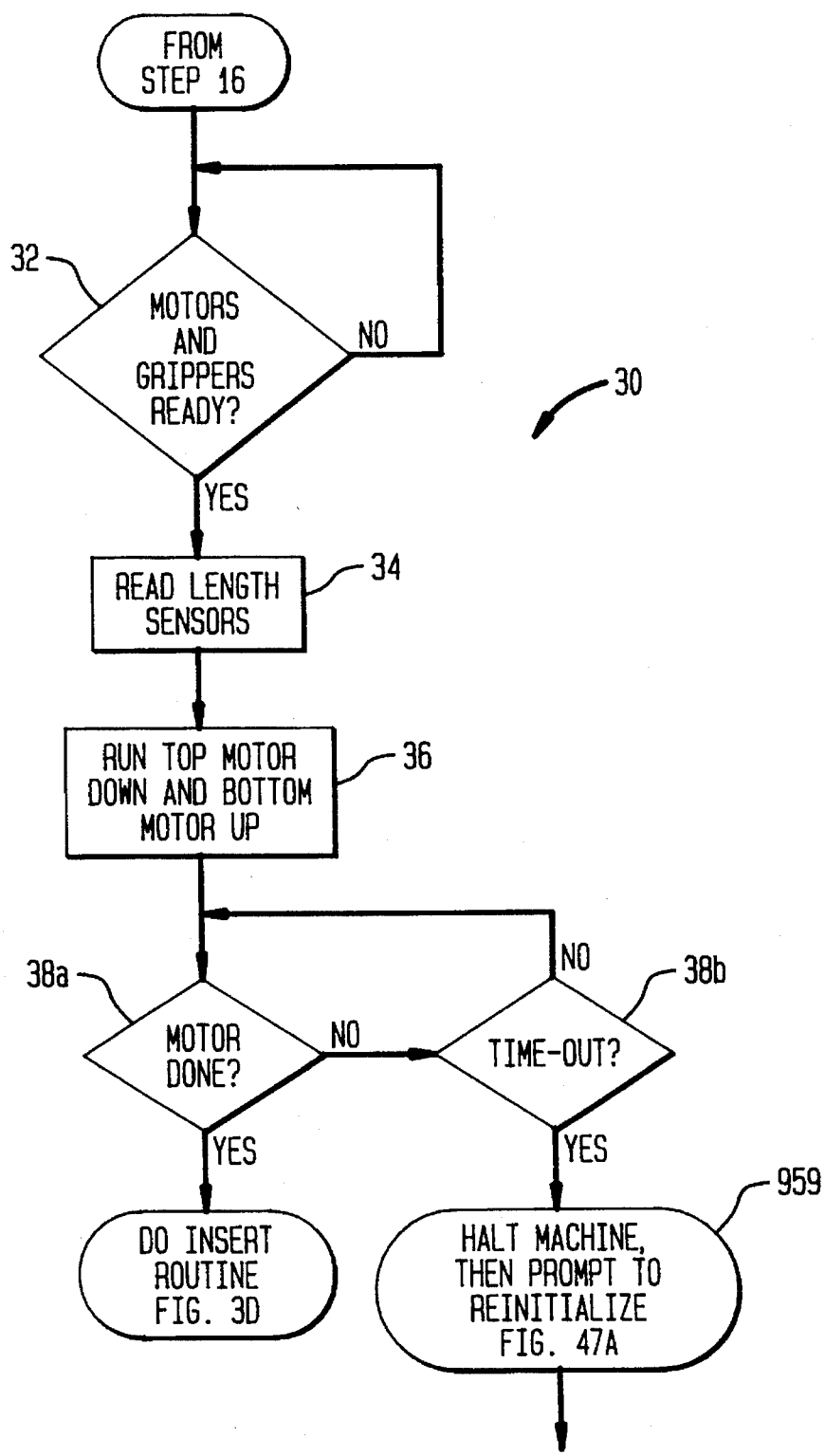

The control process 30 for drawing of the indefinite length suture material up the servo tower at the swaging station, is illustrated in FIG. 3(c). At step 32, a check is made to ensure that the left and right servomotors are operational. Additionally, a check is provided to ensure that the left and right grippers and their corresponding gripper arm drives are operational and able to grip the suture strand. Next, as indicated in FIG. 3(c) at step 34, a check of the proximity sensor locations is provided to determine the length of the suture strand to be cut, i.e., to determine the reciprocating travel of the left (bottom) and right (top) grippers along the respective left and right guide rods. Immediately thereafter, as indicated in FIG. 3(c) at step 36, the right servo motor 238 is enabled to drive the top (right) gripper vertically along right rod 228 to register the tip of the indefinite length suture strand 255 for positioning within the suture receiving end 7 of a precisely oriented surgical needle shown engaged by the multi-axis gripper 155 at the swaging assembly 390 located at the top of the drawing tower 220 as shown in FIG. 13. To accomplish this, the lead gripper servomotor advances the lead gripper for a long stroke distance, which may range from 12 inches to 36 inches depending upon the length of said suture strand desired. The long stroke moves right gripper 232 from a home position just above the tip and cut carrier 180 and below the cutter assembly 280, to the position slightly below swaging assembly 390 as shown in FIG. 13.

Simultaneous with the positioning of the right gripper 232 during the long stroke of step 36, the other servomotor, for e.g., servomotor 236, positions the bottom gripper, for e.g., left gripper 230, along left rod 226 at the home position preferably above the tip and cut carrier 180 and below the position of the cutter assembly 280 as shown in FIG. 13. It is understood that the lead gripper is gripping the material 255 at all times during the long stroke, while the bottom gripper is in its open position and not gripping (FIG. 12). The process of advancing suture material 255 by alternating grippers at each cycle eliminates the recycle or return time for retaining the gripper to the original position. This makes faster machine speeds and hence, higher production rates possible.

Finally, as indicated in FIG. 3(c) at step 38a, a continuous check is provided to ensure that the lead gripper drawing the indefinite length suture strand during the long stroke, has reached its vertical destination along its respective guide rod as detected by proximity sensor 270 as shown in FIG. 13. If the lead gripper has not reached its vertical position along the guide rod, the system will perform a check at step 38b to determine whether a time-out flag has been generated by the control system indicating a time-out error. If a time-out flag has not been generated, then the top or right gripper has reached its vertical position, (step 38a) and the process continues. If the time-out flag is generated by the control system indicating a time-out error, the process will be terminated and prompted for reinitialization at step 959.

Swaging Assembly

The swaging operation taking place at the swaging station will now be described. FIGS. 15(a)–15(f) illustrate the multi-axis needle gripper 155 and swaging and suture alignment dies shown in various stages of the suture insertion and needle swaging sequence. This sequence, and the interaction of the dies in relation to each other, the needle, and the insertion of the suture, accomplish the insert and swage function with minimal parts and simple motions.

Figure 15A:
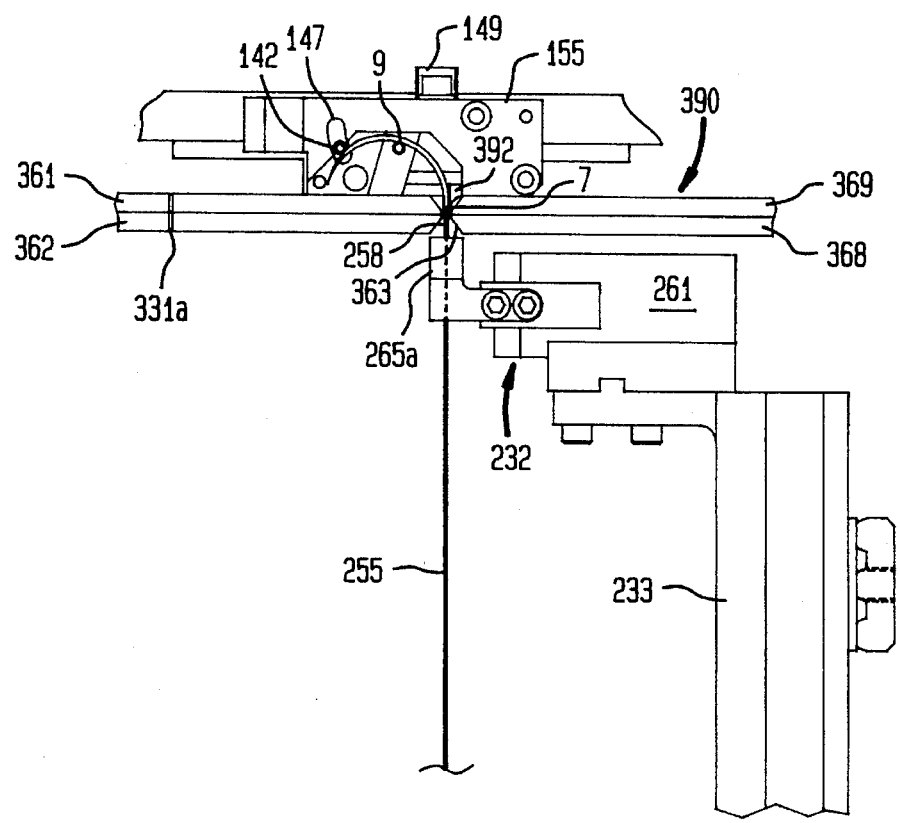
FIG. 15(a) is a detailed view of the gripper 232 shown inserting the suture tip 258 within the confines of the suture receiving end of the surgical needle.
Figure 15B:
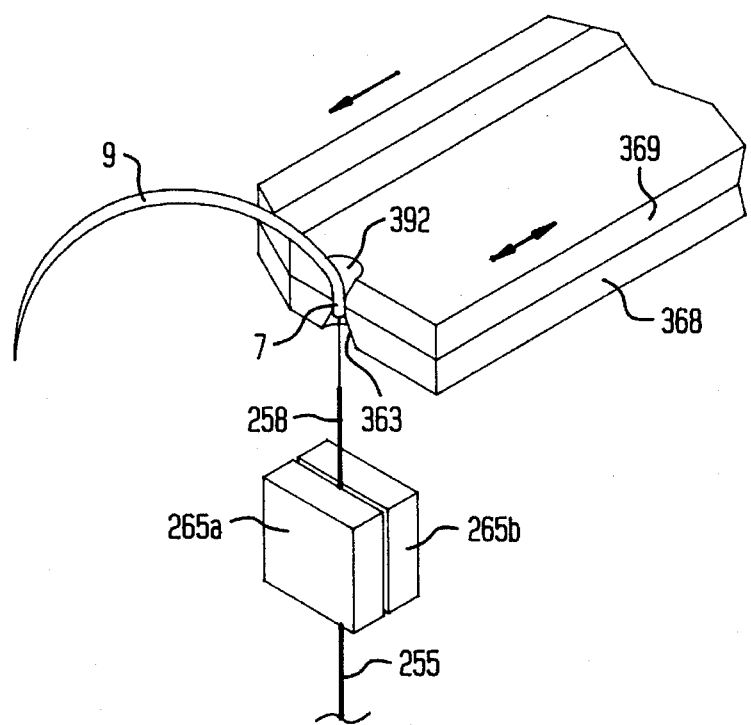
FIGS. 15(b)–15(f) illustrate the multi-axis needle gripper 155 and swaging and suture alignment dies shown in various stages of the suture insertion and needle swaging sequence.

After conveying the needle to swaging assembly 390 shown in FIGS. 15(a) and 16(a), the multi-axis gripper 155 is radially extended (step 14) from the swage dial in the manner described above to position the suture receiving end 7 of needle 9 between the funnel shaped die opening formed at the ends of two swage dies 361,369 as shown in FIG. 15(a) and the partial perspective view of FIG. 15(b). As will be explained, swage die 361 is fixed in position and swage die 369 is movable laterally toward the fixed swage die 361, as indicated by the arrow, to accomplish swaging of the suture receiving end of a needle placed therebetween. A funnel shaped die opening 392 having an exit diameter slightly larger than the diameter of the suture receiving end 37 of the needle is formed when the two swage dies 361,363 are positioned adjacent each other as shown in FIGS. 15(e) through 15(f). In the preferred embodiment the ends of each of the swage dies 361,369 are provided with recesses so that the metal deformation that occurs as a result of the swaging of the needle 9, does not result in metal flash or spurs at the suture receiving end 7 of the needle. Note that different sets of swage dies may be provided, depending upon the size (diameters) of the needles and sutures to be swaged.

To precisely position the sutures receiving end 7 of needle 9 between the swage die opening 392 formed at the ends of two swaging dies 361,369, the movable swage die 369 is temporarily moved apart. In the illustration of the swaging assembly 390 shown in FIG. 16(a), swage die 369 is moved apart from the fixed swage die 361 by actuating air cylinder 395 to provide a force upon cylinder rod 393 to enable swage die operating lever 397 to pivot about screw 394 and pull moveable swage die 368 a predetermined distance away from the fixed swage die 361. In the preferred embodiment, lever 397 is biased by spring 364 so that the movable swage die 369 will return toward the fixed swage die by the spring restoring force when the pressure provided by the air cylinder 395 is terminated as controlled by the control system 99.

As shown in the pneumatic schematic of FIG. 50(a), supply line 701 supplies pressurized air through suitable filter 702, through pressure monitoring device 703a and through switching device 707c to provide the pressurized air for controlling the air cylinder 395 that provides the force necessary for the swage dies to open for clamping of the needle 9 at the swage die opening 392. The operation of the air cylinder 395 is controlled by control lines 704a,b which operate the switch 707c under the timing and control of the control system 99.

Figure 15C:
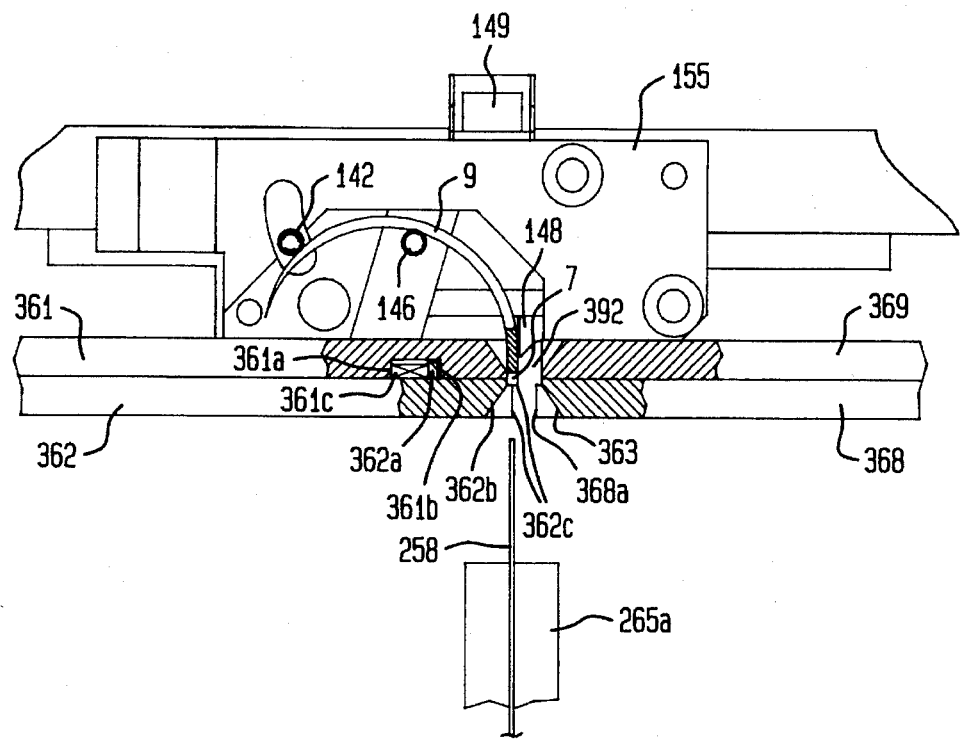

FIG. 15(c) shows die 361 in its fixed position, and moveable die 369 in its spaced apart position prior to receiving the surgical needle 9 presented by multi-axis gripper 155. Suture alignment die 362, containing suture guide funnel half 362b, is positioned under swage die 361, and free to slide laterally within limits. Alignment die 362 has a tang 362a that protrudes into cavity 361a formed within swage die 420. Compression spring 361c bears against the back wall of cavity 361a and tang 362a such that funnel die 362 slides forward until it is constrained by cavity wall 361b. In this position, it is forward of the center axis defined by the suture receiving end of the needle, and serves as a shelf 362c that helps assure suture receiving end 7 of needle 9 is in position for swaging. In this stage of the cycle, the parts are not positioned for suture insertion, and suture clamp 265a gripping suture 255 and stiffened end 258, are in dwell. Suture alignment die 368, containing funnel half 363, is fastened to swage die 369 by suitable fastening means, described in detail below, and travels with it to the open position shown.

Figure 15D:
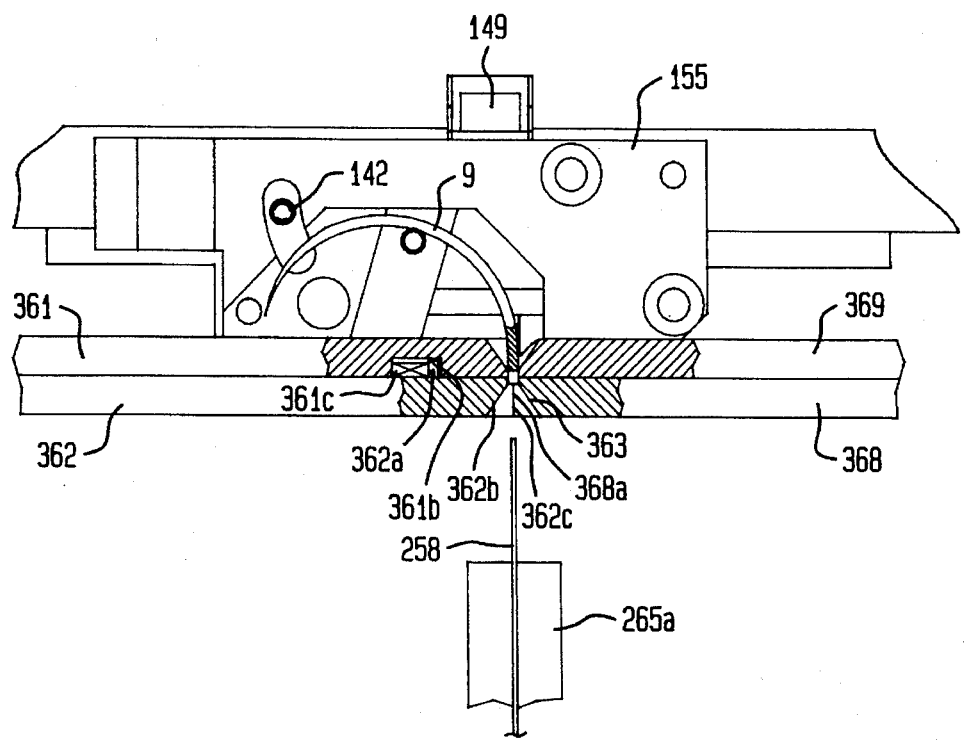
Figure 15E:
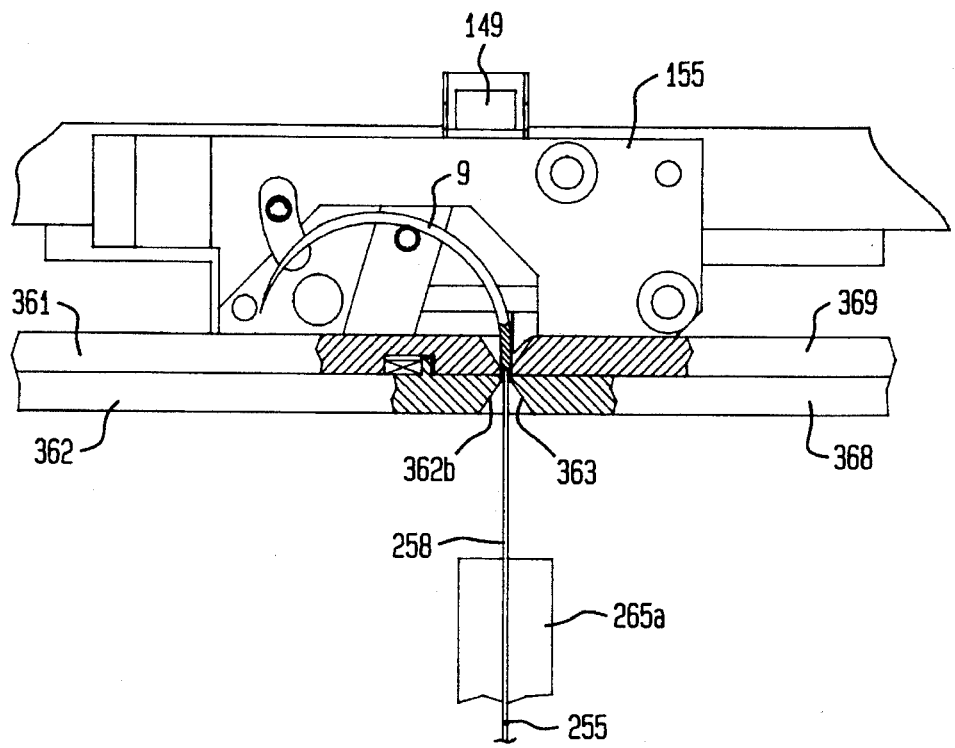
Figure 15F:
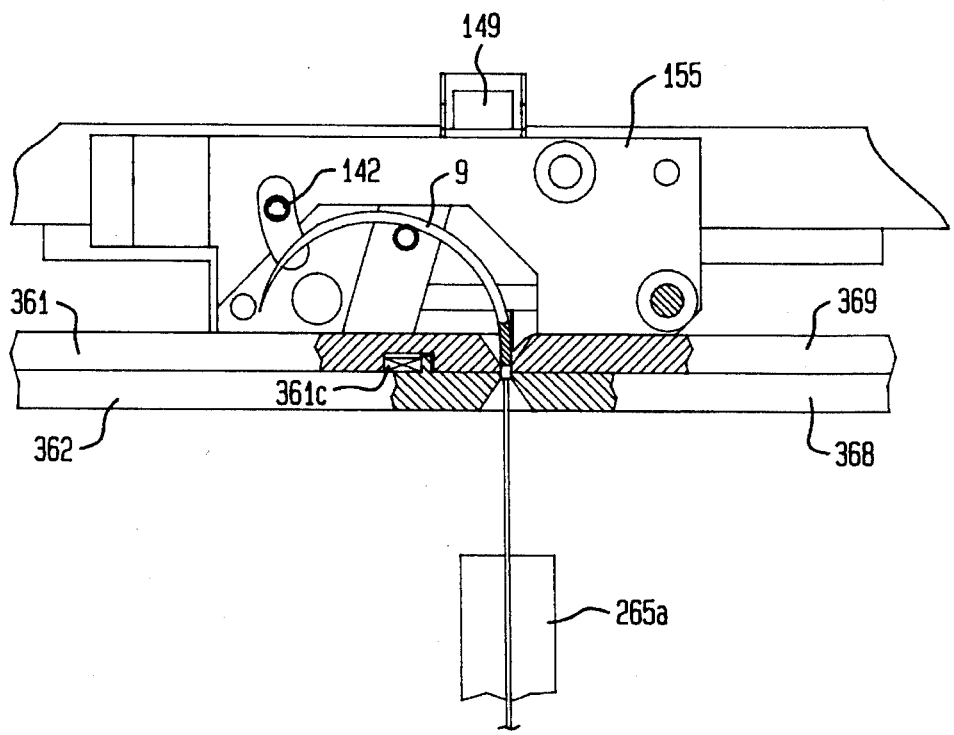

While the swage dies are apart, the multi-axis gripper 155 is extended to position the suture receiving end 7 of needle 9 within the opening 392 as shown in FIG. 15(c) and FIG. 16(a). After positioning the suture receiving opening 7 of needle 9 at the swage die opening 392, the swage die 369, and suture alignment die 368, are moved toward needle 9 with the resilient spring force present in spring 364 (FIG. 16(a)) that is sufficient to enable the die 369 to grip and locate the suture receiving end 7 precisely against fixed swage die 361 without deforming the cavity of the suture receiving opening 7 formed therein. This is indicated at step 17 in FIG. 3(a). Since the needle retaining pin 142 of multi-axis gripper 155 had been raised by downward external force on plunger 149, as described above at step 15b, the position of the needle is determined by the grip of swaging dies 361 and 369. The motion of dies 368 and 369 cause the face 368a of suture alignment die 368 to come in contact with the corresponding face 362c of suture alignment die 362. The resilient force causing this motion is forceful enough to compress spring 361c, and move funnel die 362 to the left, such that tang 362a is no longer in contact with cavity wall 361b. Dimensioning of dies 369 and 368 is such that this motion results in the formation of two funnel halves 362b and 363 defining a smooth conical shape that is coaxial with the suture receiving end 7 of needle 9. FIG. 15(d) shows the suture receiving end 7 being gripped by the swage dies 361,369 prior to suture insertion. Note that the exit diameter of the conically shaped funnel guide formed of funnel halves 362b and 363 is preferably equal to or greater than the diameter of the suture tipped end 258 and smaller than the diameter of the suture receiving end 7 of the needle 9, as shown in FIG. 15(e), so that the tipped end 258 of the suture strand may be easily inserted therein as indicated at step 18 in FIG. 3(a).

Figure 3D:
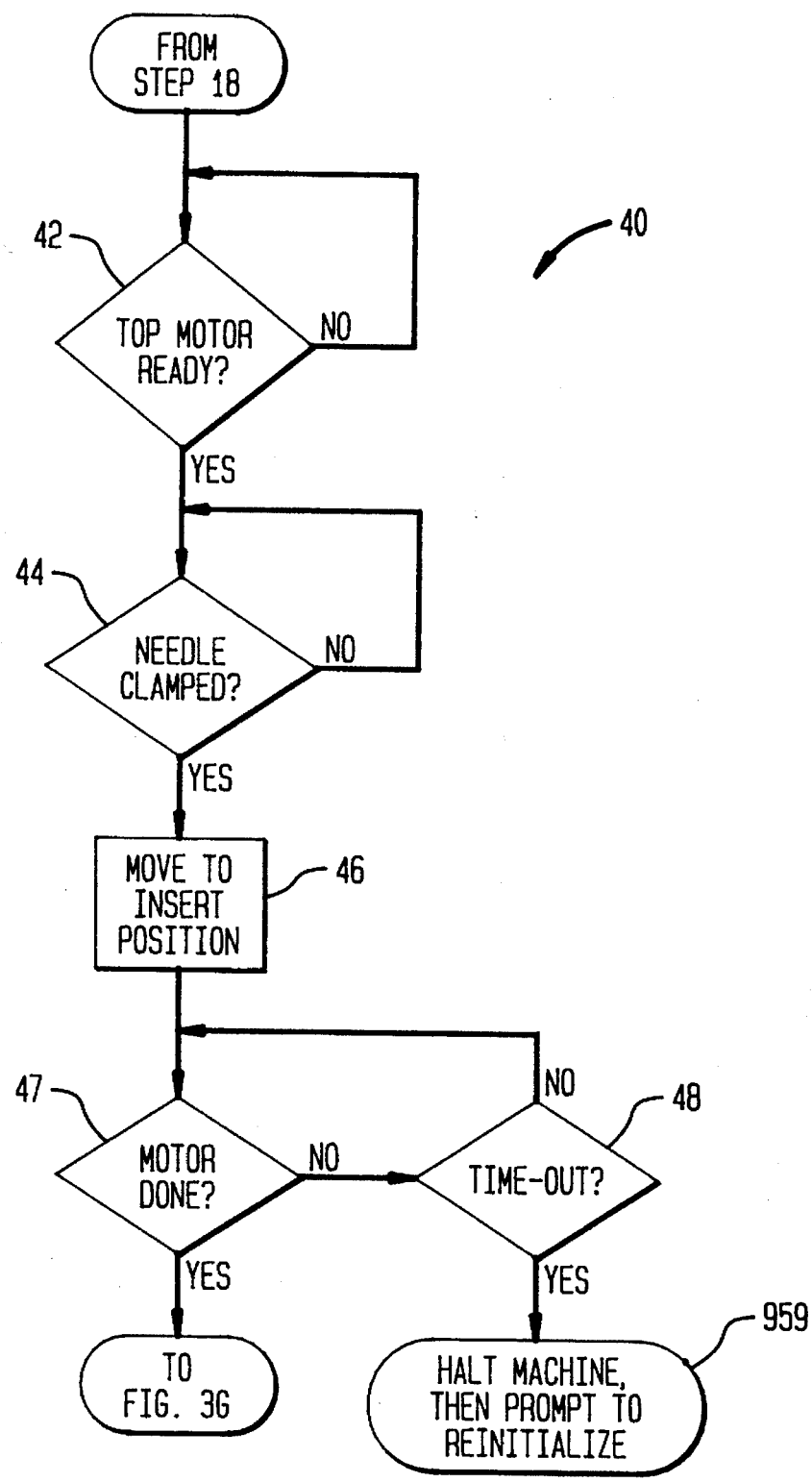

The control process 40 for inserting the free end 258 of the indefinite length suture strand within the suture receiving end 7 of surgical needle 9, is illustrated in FIG. 3(d). First, a check is made to ensure that the top or right gripper is at its predetermined position along its respective vertical guide rod as indicated at step 42 in FIG. 3(d). Next, as indicated as step 44 in FIG. 3(d), a check is made to ensure that the needle 9 has been clamped in position within the swage die opening 392 as described above. Immediately thereafter, the lead gripper 232 is enabled to advance the suture material 255 for a short stroke distance of about 1 to 5 inches, and preferably, 1.9 inches, so that the tip 258 will advance precisely within the suture receiving end 7 for a swaging operation to take place at the swaging assembly 390. This is indicated at step 46 in FIG. 3(d). The status of the lead gripper servomotor that advances the suture material for the short stroke is continuously monitored, as indicated as step 47 in FIG. 3(d), to ensure that the suture has been inserted within the suture receiving end 7 of the needle 9. While the lead gripper is inserting the suture during the short stroke, the system performs a check at step 48 to determine whether a time-out flag has been generated by the control system indicating a time-out error. If a time-out flag has not been generated, the lead gripper has inserted the tipped end of the indefinite length of suture material within the suture receiving end of the needle (step 47) and the process continues. If the time-out flag is generated by the control system as a time-out error, the process will be terminated and prompted for reinitialization at step 959.

FIG. 15(e) shows suture gripper 265a moved vertically to the insertion position, which causes stiffened suture end 258 to enter funnel 362b and 363, and be guided into the suture receiving cavity 7 of needle 9 axially aligned therewith. Once the strand is inserted into the suture receiving end 37 of the needle (step 18) as discussed above, the automatic cutting of the indefinite length suture strand and the automatic swaging of the suture receiving cavity occurs as indicated at step 23 in FIG. 3(a).

The control process 80 for performing the automatic swaging of the needle and the cutting of the indefinite length strand of suture material is described in detail with reference to FIG. 3(g).

As shown in FIG. 16(a), swage air cylinder 365 is extended to provide air pressure sufficient to actuate cam 375 to bear on lever 397 and thrust movable swage die 369 toward the fixed swage die to accomplish the swaging of the suture receiving end of the needle placed therebetween. This step is indicated at step 81 in FIG. 3(g). Air pressure is supplied to the swage cylinder 365 via ports 366,367 under the control of the control system 99. As shown in the pneumatic schematic of FIG. 50(a), supply line 701 supplies pressurized air through suitable filter 702, through pressure monitoring devices 703a and 703b, and, through switching device 707d to provide the pressurized air for controlling the swage cylinder 365 that provides the pressure to accomplish swaging of needle 9 at the swage die opening 392. Note that the pressurized air supply line 701 is split into air supply line 701b that supplies the air pressure for the swage cylinder 365.

The operation of the swage cylinder 365 is controlled by control lines 704a,b which operate the switch 707d under the timing and control of the control system 99. In the preferred embodiment, the moveable swage die 369 comes to an automatic stop by a swage stop mechanism.

Figure 16B:
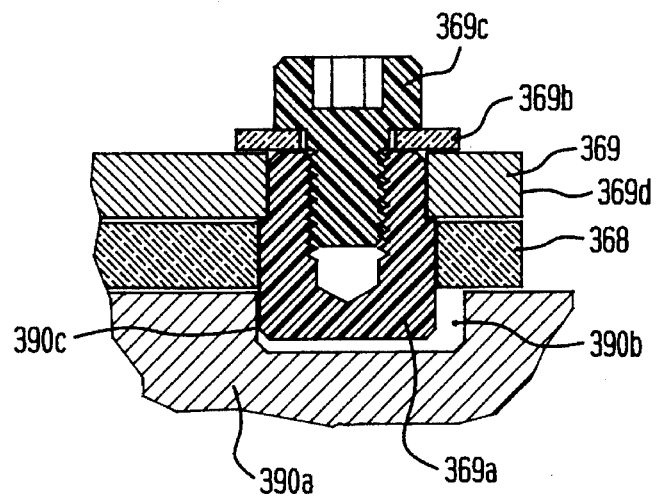
FIG. 16(b) is a detailed view of the swage stop mechanism for swage assembly 390.

FIG. 15(f) shows the completed swage stroke. The swage die 369 has been driven to a fixed stop by the swage cylinder, which exerted sufficient force to deform the suture receiving end 7 of needle 9. As deformation takes place, suture alignment die 368 further displaces funnel die 362, causing additional compression of spring 361c. In the preferred embodiment, the moveable swage die 369 comes to an automatic stop by a swage stop mechanism herein described. As shown in FIG. 16(b), movable swage die 369 and suture alignment die 368 are mechanically held coincident to each other by shouldered post 369a, the smaller diameter of which is a light press fit into the mating hold in die 369. Cap screw 369c, with washer 369b retain the post in die 369. The larger diameter of post 369a, below die 369, extends through a light press fit hole in funnel die 368, so that the right hand swage and funnel dies are linked to move together laterally during the swaging cycle. The lower portion of shouldered post 369a extends through funnel die 368, into groove 390b, which is cross milled into swage assembly frame 390a. When the swage stroke is performed, the swage cylinder drives this die assembly to the left until it is positively stopped by the lower portion of post 369a striking wall 390c of groove 390b. This stalls air cylinder 365, so that the stroke of the moveable right hand die assembly shown is always the same for repeating cycles of the machine.

Figure 3E:
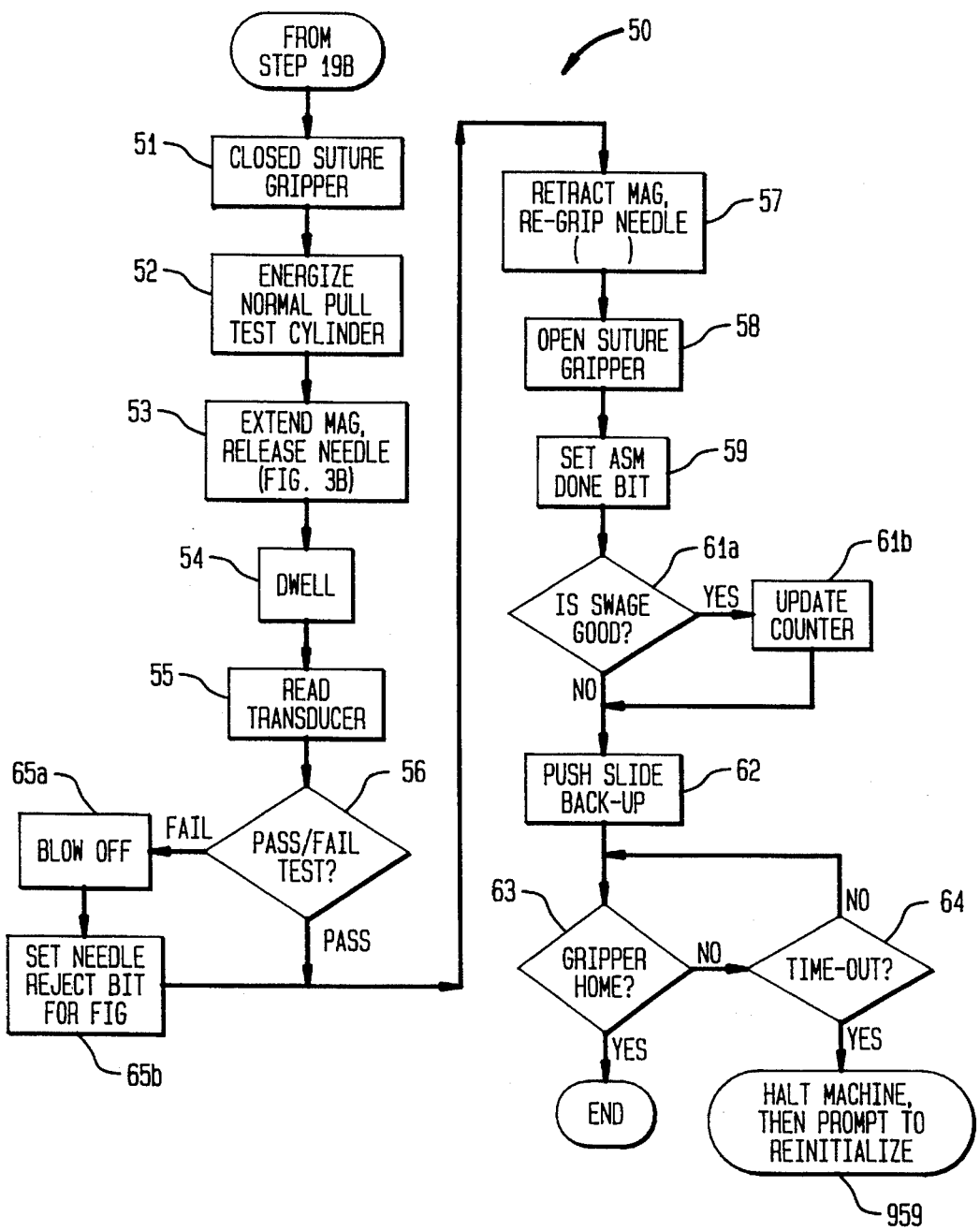
Figure 3F:
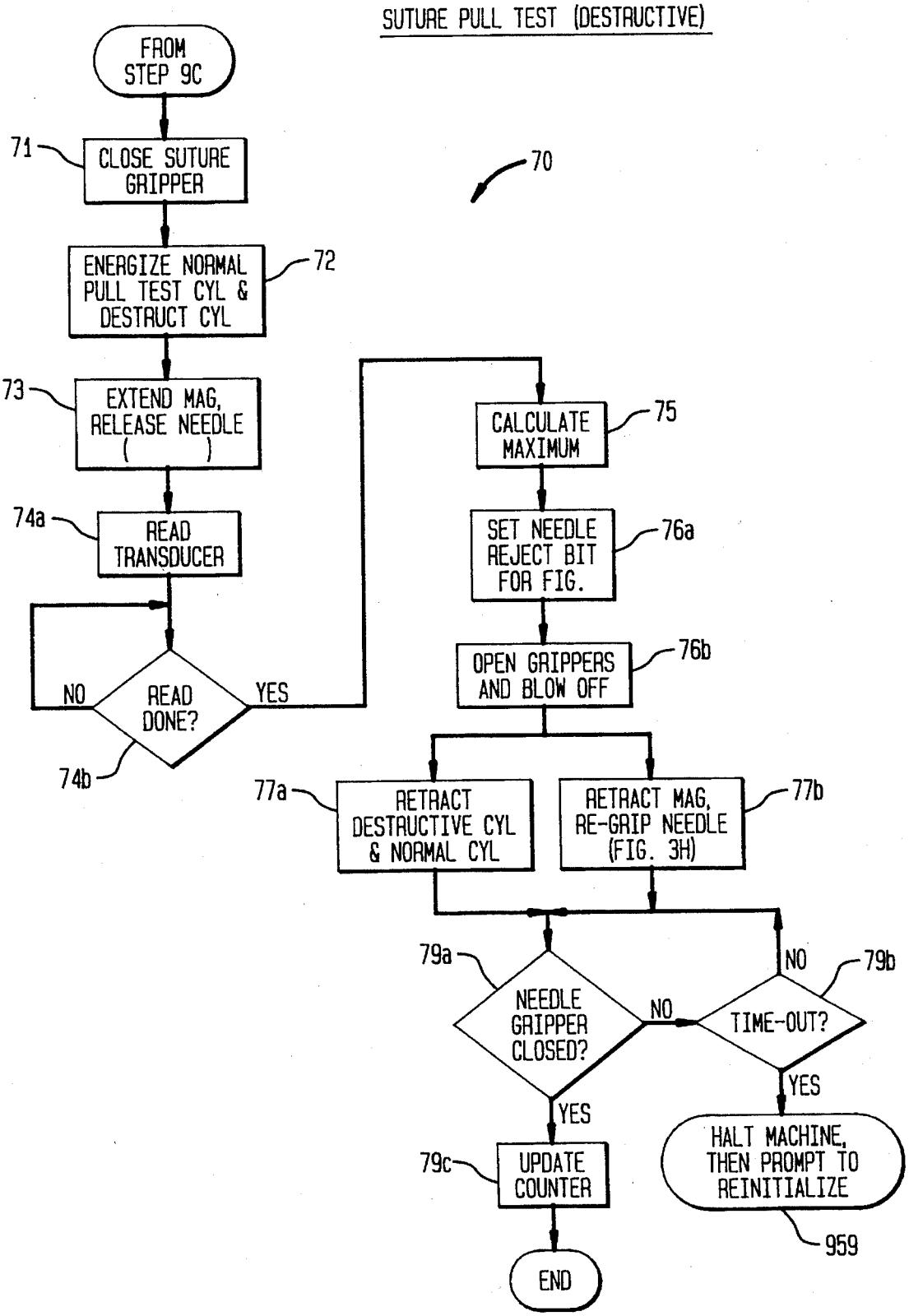
Figure 3G:
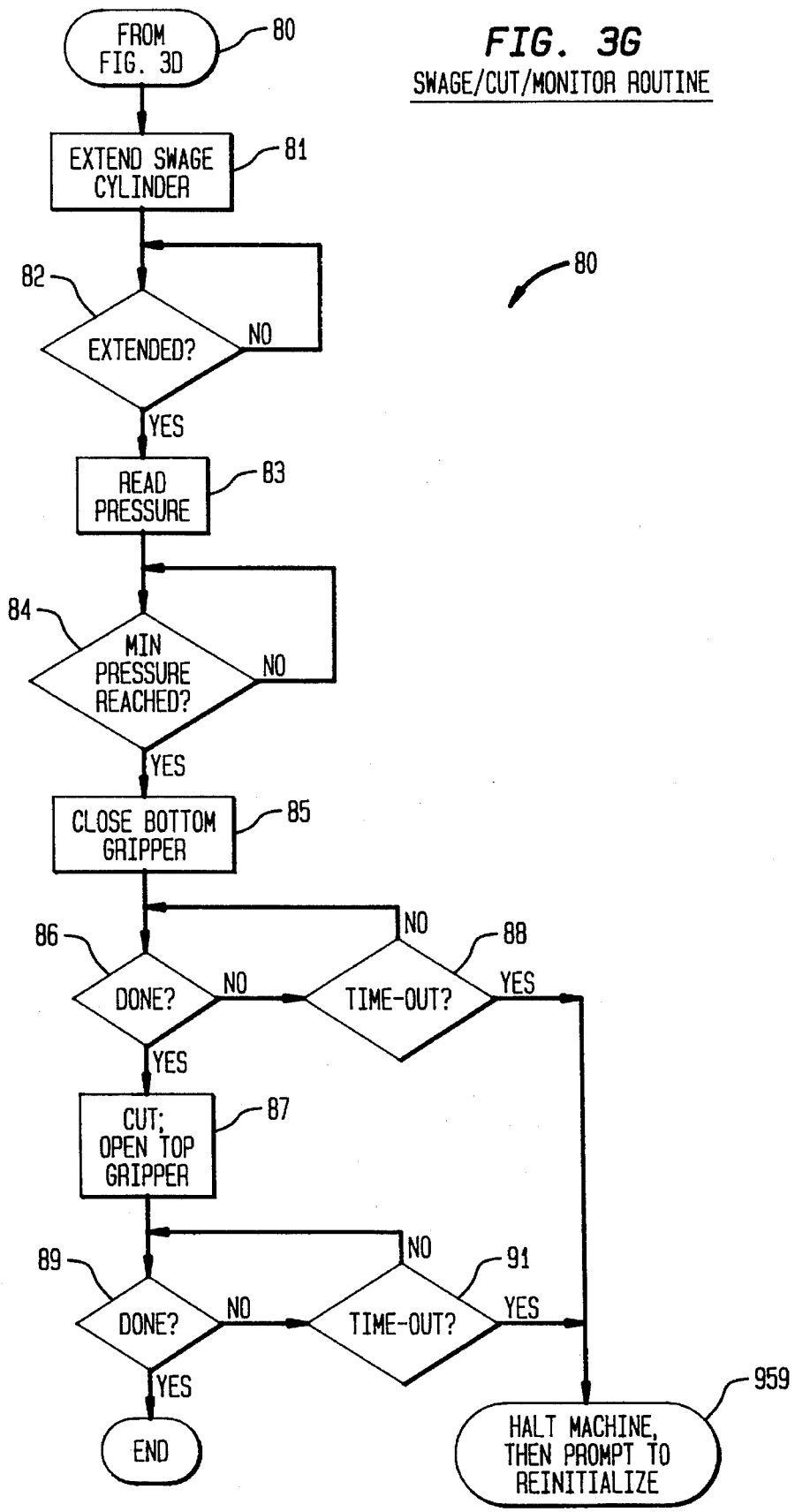

At step 82 of FIG. 3(g), a check is made to determine if the swage cylinder had been fully extended to its predetermined position as commanded by the control system 99. This is accomplished by a proximity sensors located at the swage assembly (not shown). If the swage cylinder is not fully extended, the cylinder continues to extend until it reaches its predetermined position. If the swage cylinder has been fully extended, the swaging pressure used to accomplish the swaging is measured at step 83 in FIG. 3(g) by appropriate pressure transducers located in the air pressure lines (not shown).

The swaging pressure applied to the moveable swage die 369 can be adjusted by the control system 99. Thus, if a minimum swaging pressure has not been achieved, the air pressure supplied to the swaging cylinders will be stepped up until the minimum predetermined pressure is supplied as shown as step 84 in FIG. 3(g).

The degree of swage compression imparted on the needle, and resulting strength of grip by the needle on the suture, is adjusted by precise positioning of the fixed die 361. As shown in FIG. 16(a), servomotor 345 drives pulley 344 via timing belt 461, which rotates the swage adjust screw 347. The pitch of the swage adjust screw 347 is selected to move sliding wedge 348 a small distance as sensed by proximity sensor 389 interfaced with control system 99. The swage die 361 has a follower 343 at the opposite end which bears on the wedge 348 to retract or advance the position of the swage die 361 a precise distance proportional to the movement of the sliding wedge. Thus, the rotation of the swage adjust screw 347 and motion of the sliding wedge 348, results in transverse movement of the swage die 361 to thereby finely adjust its fixed position. For example, when a larger suture is to be swaged to a needle, the position of the fixed die 361 may be moved further away from the suture drawing axis so as to provide the desired amount of deformation when the swaging pressure is applied to the needle by the movable swage die 369. In the preferred embodiment shown in FIG. 16(a), the control system 99 will send the appropriate signals to automatically direct the servomotor 345 to adjust the position of the swage adjust screw 347, and hence, the position of the fixed die 361, in accordance with the pull-out test values of the needle-suture bond as measured by automatic pull-test system as explained in further detail below. Specifically, appropriate signals may be sent to automatically direct the servomotor 345 to adjust the rotational position of the swage adjust screw 347 in accordance with stored statistical results of the pull-testing occurring at the pull-test station. Automatic pull-testing of the armed needle is desirable to ensure that the upstream swaging dies are optimally positioned to avoid over-swaging the needle-suture bond and hence, preventing the likelihood of clip-off, and, to avoid under-swaging the needle-suture bond to prevent the chance of suture pull-out.

As indicated at step 85 in FIG. 3(*g*), immediately after swaging of the suture to the needle, the left or bottom gripper 230 engages the suture strand at the home position. A continuous monitoring is provided as indicated at step 86 in FIG. 3(*g*) to determine whether the bottom gripper has engaged the suture strand. While the left gripper engages the suture strand at the home position, the system performs a check at step 88 to determine whether a time-out flag has been generated by the control system indicating a time-out error. If the time-out flag is detected, the process will be terminated and prompted for reinitialization at step 89. If a time-out flag has not been generated, then the left (or bottom) gripper 230 has engaged the suture strand at the home position and two simultaneous operations are then performed as indicated at step 87 in FIG. 3(*g*). One operation is to cut the suture strand at a position just above the location where the bottom gripper is gripping the indefinite length suture strand. The other operation is to open the top gripper to release its grip of the swaged definite length suture strand.

Figure 14:
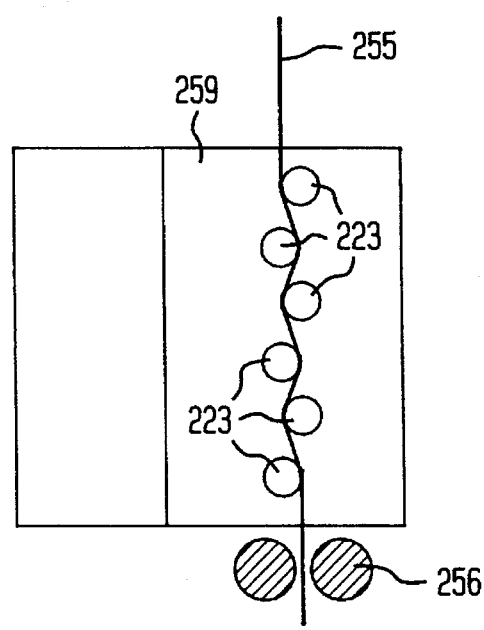
FIG. 14 is a detailed view of the optional suture tensioning (dancer) assembly.

Cutting of the indefinite length suture strand is accomplished by the retractable cutter assembly 280, shown in FIG. 14 as suitably mounted on tip and cut carrier 100 and positioned slightly above the left or alternate gripper 230 so that the indefinite length suture strand 255 will be gripped when the swaged strand is cut.

Cutter Assembly

Figure 18:
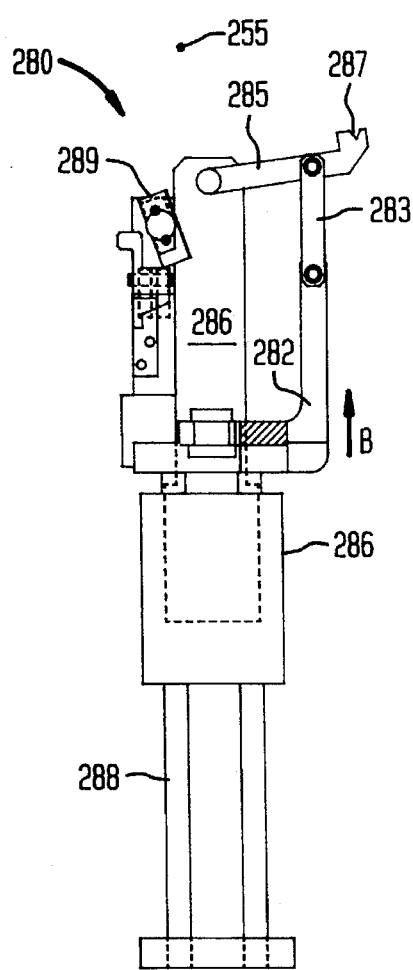
FIG. 18 is a detailed top view of the cutter assembly 280 shown in a fully retracted position.
Figure 19:
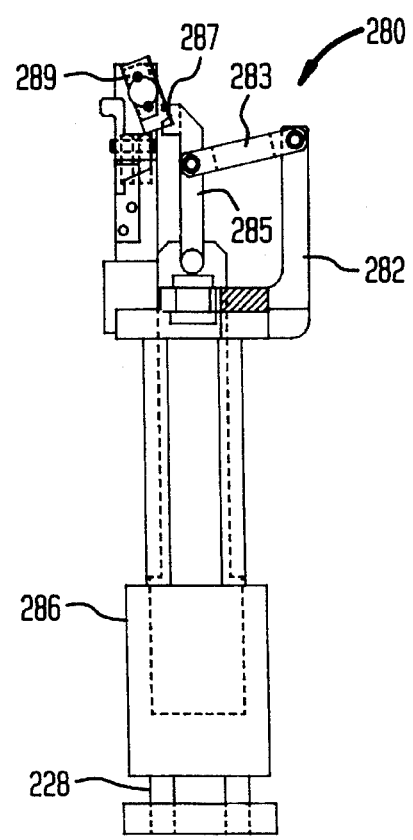
FIG. 19 is a detailed top view of the cutter assembly 280 shown in a fully extended (cutting) position.
Figure 17:
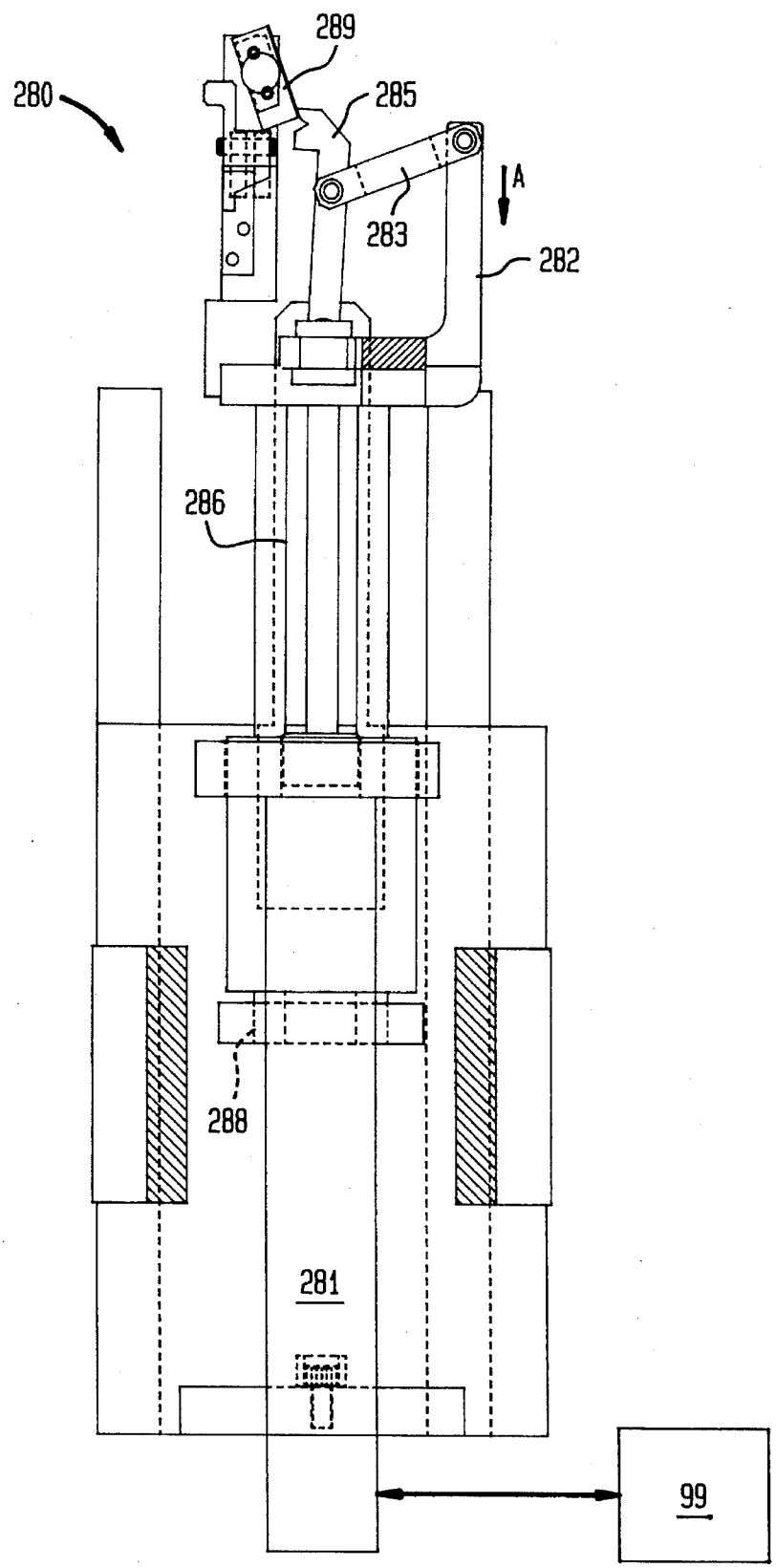
FIG. 17 is a detailed top view of the cutter assembly 280.

FIGS. 17–19 illustrate in detail the cutter assembly 280. As shown in FIG. 17, the cutter assembly comprises overcenter linkage 282 having a link arm 283 pivotally connected at one end thereof. A pivotal locator arm 285 is fixedly connected to link arm 283 at a second end thereof and is illustrated in FIG. 18 as substantially transverse thereto. The other end of locator arm 285 is pivotally connected to a stationary guide mechanism 286. Note, that all pivotal linkages described herein are simple pin linkages, the actuation of which creates the dwell moment for cutting the suture strand and obviates the need for complicated cam, slots, and sliding mechanisms.

As shown in FIG. 18, the stationary guide 286 is located in a plane perpendicular to the drawing axis of the suspended strand of material 255, and is located a distance from the strand approximately equivalent to the length of locator arm 285. In addition, overcenter linkage 282, locator arm 285, and cutting blade 289 all lie in planes perpendicular to the drawing axis of the strand of material 255.

A retractable ball slide 288 is mounted on the stationary guide 286 and coupled to overcenter linkage 282 for moving the overcenter linkage and blade 289 along the stationary guide 286 in the direction indicated by arrow "A" in FIG. 17 from a cutting position to a retracted position shown in FIG. 18. As the ball slide 288 moves overcenter linkage 282 to a retracted position, the locator arm 285 is pivoted away from the strand 255 and the blade 289 is retracted. Thus, when the cutter assembly 280 is in the retracted position prior to cutting of the strand and immediately thereafter, the blade 289 and locator arm 285 do not interfere with the reciprocating motion of the grippers 232,230 along the drawing tower 220, nor do they come in contact with the suspended strand 255. In the preferred embodiment, pneumatic air cylinder 281 enables reciprocating movement of the ball slide 288 along stationary guide 286 as shown in FIG. 17.

As shown in the pneumatic schematic diagrams of FIGS. 50(*c*) and 50(*d*), supply line 701*a* supplies the pressurized to air cylinder 281 for enabling pneumatic reciprocating movement of the ball slide 288, and hence, the cutter assembly. The operation of the ball slide 288 is controlled by control lines 704*c,d* which operate the switch 707*x* under the timing and control of the control system 99.

When cutting the strand of material 255, the retractable ball slide 288 reciprocates in the direction toward the strand 255 indicated by arrow "B" in FIG. 18 to bring the overcenter linkage 282, cutting blade 289 and locator arm 285 to the cutting position shown in FIG. 19. As the overcenter linkage 282 moves to the cutting position, the link arm 283 translates the movement of the ball slide 288 into pivotal movement of the locator arm 285. Locator arm 285 is provided with a V-shaped support notch 287 which functions to engage and position the strand of material 255 to be cut as the arm is pivoted into the cutting position. The V-shaped notch also functions to support the strand on two sides of the strand 55 while it is being horizontally cut on a third side. This enables clean, broom-free cuts especially of multi-filament suture material, which has a tendency to form a broom end when the strand is under tension and is cut by scissors, or, when the multi-filament strand is sliced and otherwise, not properly supported.

The cutting blade 289 of cutter assembly 280 is fixedly mounted to reciprocating ball slide 288 at a slight angle relative thereto and in a plane parallel with that of the locator arm 285. In the preferred embodiment, a single action by the pneumatic air cylinder 281 will enable movement of the reciprocating ball slide 288 along stationary guide 286. This consequently enables pivoting of locator arm 285 from its retracted position (FIG. 18), so that V-shaped notch 287 supports the strand 255 at two sides thereof while a third side of the strand bears upon the cutting edge of blade 289 as the blade moves towards the supported strand 255 traversing the drawing axis thereof. Thus, the strand 255 is cut in a dwell moment of the locator arm after the locator arm 285 has pivoted in the direction toward the blade 289 to the cutting position shown in FIG. 19. The blade 289 slices the strand of material while it is held stationary by locator arm 285 by virtue of the angled orientation of the blade with respect to the axis of reciprocation illustrated in FIGS. 18 and 19. In the preferred embodiment, the slice ratio is 1:1, with the blade 289 angled at approximately 45 degrees relative to the axis of reciprocation, so that the strand 255 is cut as the blade 289 traverses the drawing axis.

After the strand of suture material is cut, the right or lead gripper 232 is then actuated to release its grip on the definite length suture strand 255 as indicated above at step 87 in FIG. 3(*g*). A continuous check is made, as indicated at step 89 to determine whether the indefinite length suture strand has been cut and whether the right or lead gripper 232 has released its grip of the cut suture strand. Until the indefinite length suture strand is cut and the right or lead gripper releases its grip of the definite length suture strand, the system will perform a check at step 91 to determine whether a time-out flag has been generated by the control system indicating a time-out error. If a time-out flag has not been generated, the monitoring check continues (step 89). If the time-out flag is detected, the process will be terminated and prompted for reinitialization at step 959.

Automatic Pull-test Station

A test of the strength of the swaging bond of the armed needle indexed at the automatic pull-test station 300 may be performed as described in detail below and in further detail in copending patent application Ser. No. 08/181,601 (attorney docket No. 8923) assigned to the same assignee of the present invention and incorporated by reference herein. Automatic pull-testing of the armed needle is desirable to ensure that pull-test requirements are met. Specifically, as described in detail below, either a minimum pull-test, indicated as step 19b in FIG. 3(a), or, a destructive pull-test, indicated as step 19c in FIG. 3(a) is being performed at the pull-test station 300. A bit status check is always made at step 19a to determine if a destructive pull-test is to be performed in the current machine cycle.

Figure 20:
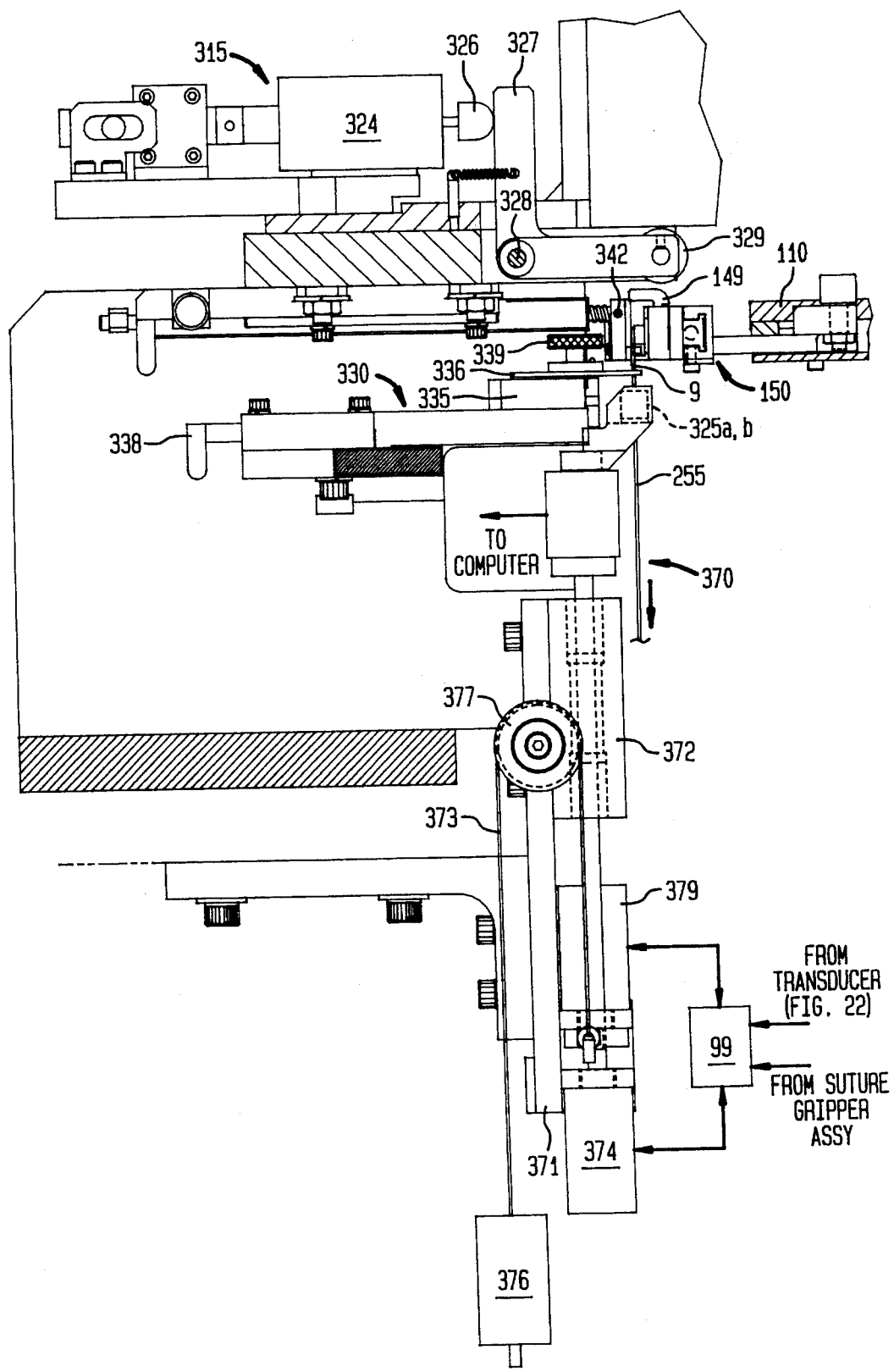
FIG. 20 is an assembly drawing of the automatic pull-test station 300 of the instant invention.
Figure 21A:
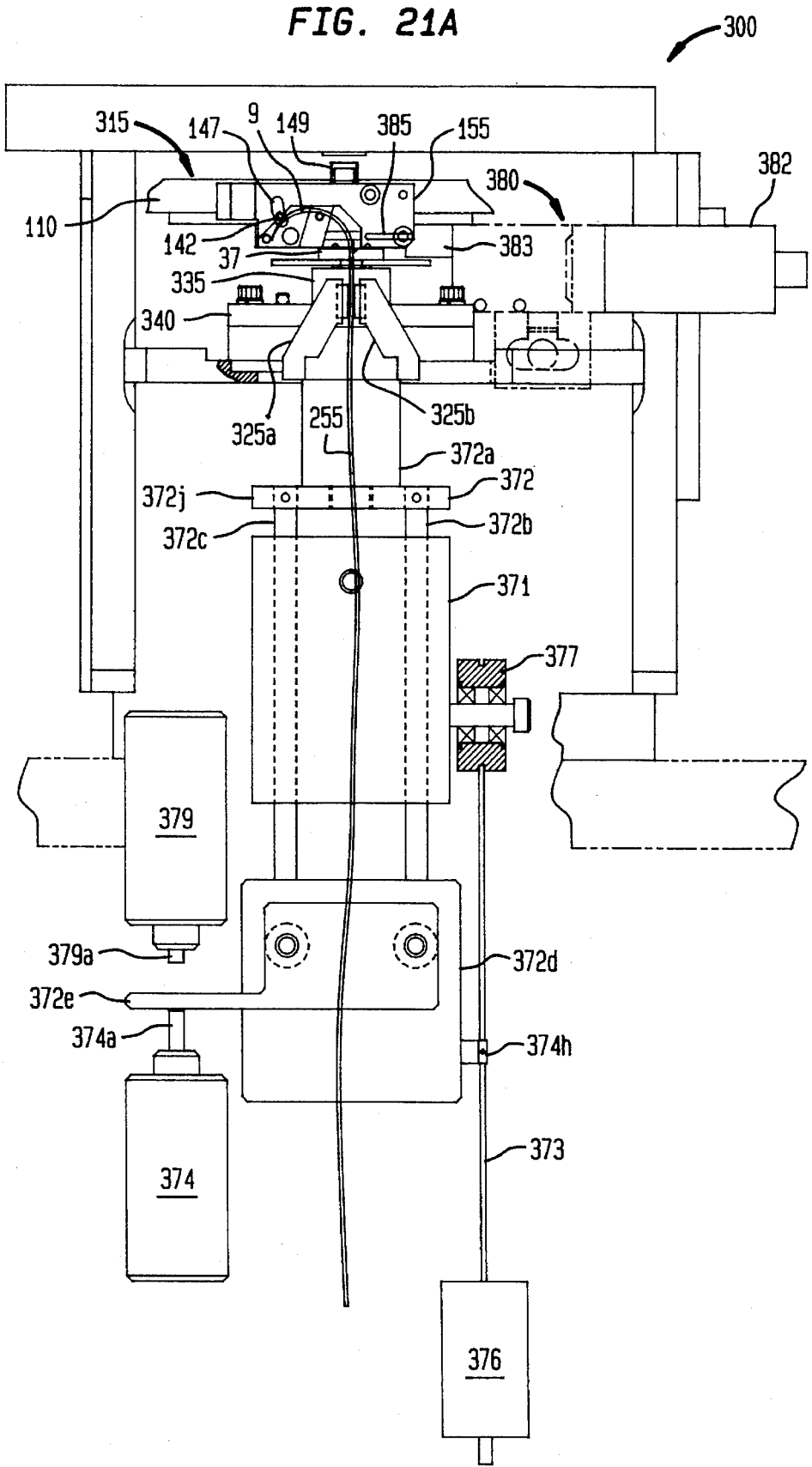
FIG. 21(a) is a front view of the automatic pull-test station 300 of the instant invention with the needle fence assembly 340 partially removed.

The automatic pull-test assembly 300 for accomplishing automatic pull-testing of an armed surgical needle generally comprises a load cell mounting assembly 330 for mounting a load cell 335 which functions to receive the armed needle 9 from the multi-axis gripper 155 which is indexed thereto as shown in FIGS. 20 and 21(a). A needle release assembly 315 is provided for relaxing the armed needle from the grip of the multi-axis gripper 155. Pull-test fence assembly 340 is provided to prevent the armed needle 9 from tipping over or becoming misaligned when the armed needle is relaxed. Suture gripping assembly 370 containing retractable gripper arms 325a,b for gripping the suture 255 during the pull-tests, and which are connected to the weighted slide block assembly 372 for performing the pull-test is provided as shown in FIG. 20.

As shown in FIGS. 20 and 21(a), an armed surgical needle 39 is retained by a multi-axis gripper 155 and, in the manner described above, is indexed to the automatic pull test station 300 by the rotary swage dial 150 partially illustrated in the FIG. 20. To position the armed needle 9 in the load cell 335, the multi-axis gripper is extended from the swage dial 150 so that the end portion of needle 39 is positioned above a corresponding receiving blade 336 of the load cell 335 as shown in FIG. 21(a).

Figure 22:
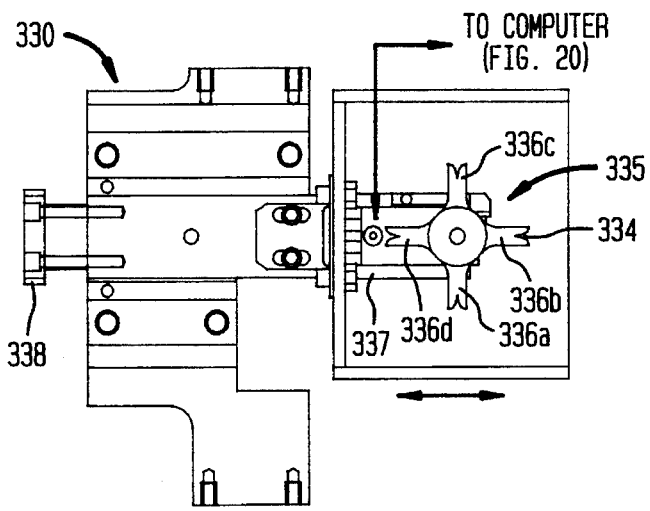
FIG. 22 is a top view of the load cell assembly 330 of the automatic pull-test assembly.
Figure 23:
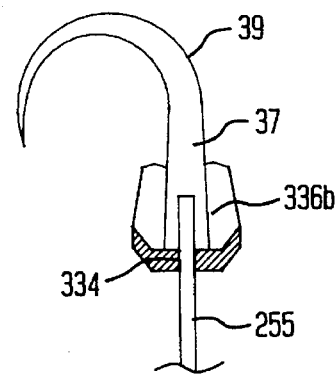
FIG. 23 is an enlarged view of an armed needle 9 supported by the suture receiving blade 336b of the load cell 335 with the suture threaded between the suture receiving opening 334.

FIG. 22 illustrates a top view of the load cell mounting assembly 330 with load cell 335 mounted thereon. In the preferred embodiment, load cell 335 has mounted thereon four (4) thin needle supporting blades 336a,b,c,d for supporting the suture receiving end portion 37 of various size surgical needles with the suture material 255 depending therefrom. For instance, load cell needle supporting blade 336a labelled "1/0" accommodates a larger sutures having a diameter of approximately 0.017+/−0.001 inches; load cell needle supporting blade 336b labelled "2/0" accommodates sutures having a diameter of approximately 0.014+/−0.001 inches; load cell needle supporting blade 336c labelled "3/0" accommodates sutures having a diameter of approximately 0,011+/−0.001 inches; and load cell needle supporting blade 336d labelled "4/0" accommodates a smaller suture with a diameter of approximately 0.009+/−0.001 inches in the preferred embodiment. Depending upon the batch of surgical needles currently being pull tested, the appropriate needle supporting blade 336a,b,c,d will be positioned to receive the needle from the multi-axis gripper. Knob 339 located centrally on top of the load cell 335 may be manually operated to rotate the load cell and position the correct sized suture receiving blade prior to carrying out automatic pull-testing. Additionally, the load cell 335 may be laterally positioned by moving slide handle 338 and consequently load cell platter 337 towards or away from the suture needle indicated by the arrow in FIG. 22.

The multi-axis gripper 155 is initially positioned so that the end portion of armed needle 9 is supported by the appropriate needle supporting blade 336 (e.g. blade 336b). FIG. 33 is a front cross sectional view illustrating the suture receiving end portion 7 of needle 9 resting upon the needle supporting blade 336b with the suture strand 255 threaded between the suture receiving guide 334.

The control process 50 for performing non-destructive suture pull testing of the armed surgical needle 9 is described in detail with reference to FIGS. 3(e), 21(a), and 21(b).

After positioning the multi-axis gripper as heretofore described, gripper arms 325a,b of suture gripping assembly 370 are extended from a retracted position to grip the suture strand 255 slightly below the needle supporting blade 336 of load cell 335 as shown in FIG. 21(a) and as indicated as step 51 in FIG. 3(e). A gripper actuator 372a is provided for opening and closing gripper arms 325a,b, as shown in FIG. 20, and is controlled by control system computer 99.

Figure 50B:
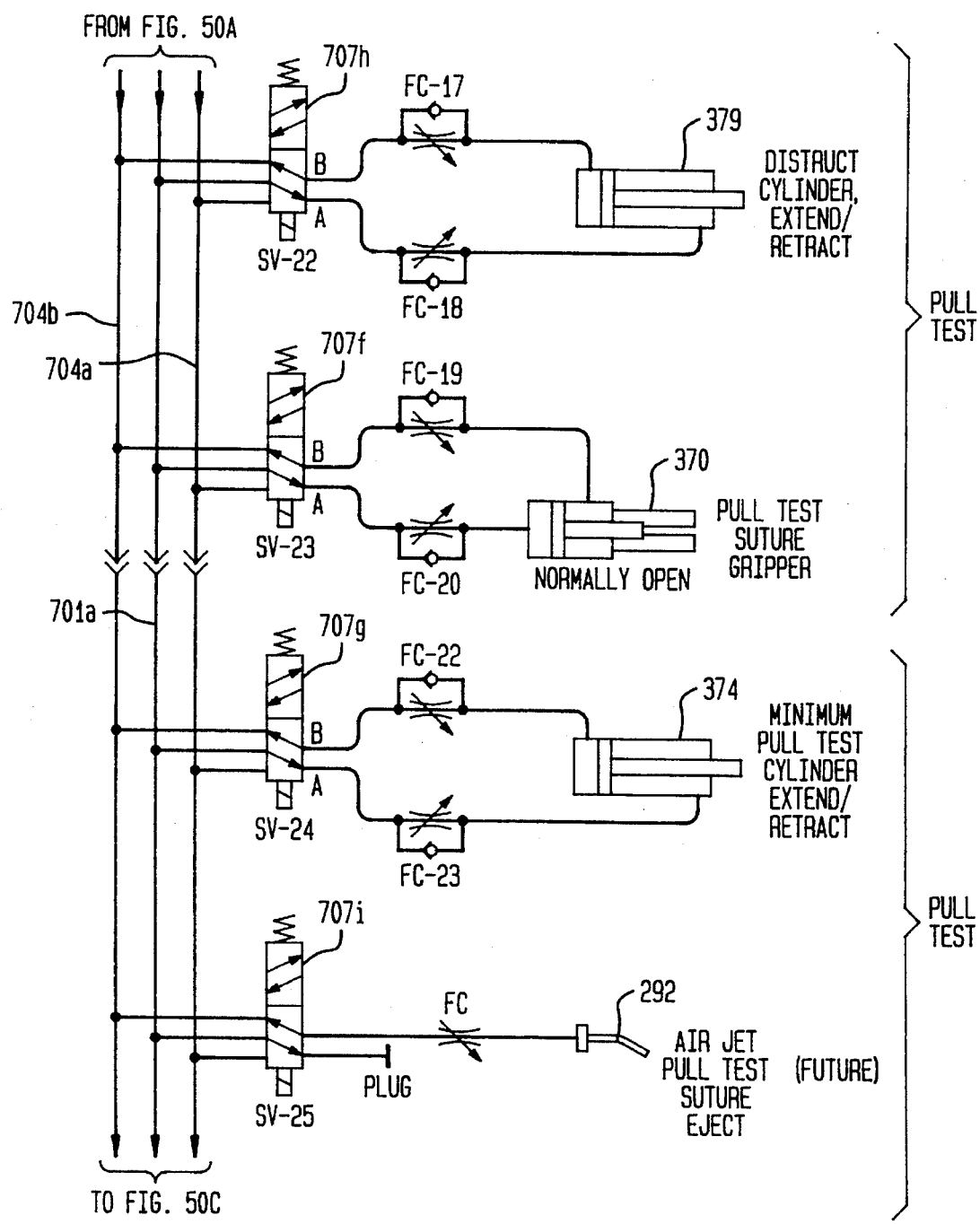

As shown in the pneumatic schematic diagram of FIG. 50(b), supply line 701a supplies pressurized air that has been filtered and monitored by filter 702 and monitoring device 703a, respectively, and, through switching device 707f to provide the pressurized air for opening and retracting the gripper arms 325a,b of suture gripping assembly 370. Control signal lines 704a,b of control system 99 control the timing and positioning of switching device 707f as well as the opening and closing of the gripper arms 325a,b of retractable suture gripper actuator 372a that control gripper arms 325a,b.

FIGS. 20 and 21(a) illustrate the slide block assembly 372 that is composed of slide rods 372b,c that are connected to a lower slide block 372d. Slide block 372d includes a slide finger 372e upon which air cylinder piston rods 374a and 379a, of respective air cylinders 374,379, apply respective upward and downward forces depending upon the type of pull-test that is to be performed. As shown in FIG. 21(a), piston rod 374a is shown in an extended position providing an upward force that supports slide finger 372e and consequently maintains slide block 372d of slide assembly 372 at a fixed vertical position.

Slide block 372d is counterweighted to a net downward weight of 2 to 5 ounces by appropriately sized counterweight 376 that acts through cable 373, around pulley 377, and through attachment point 372h. This counterweight 376 acts to pull upward on slide block 372d at the attachment point 372h.

Figure 21B:
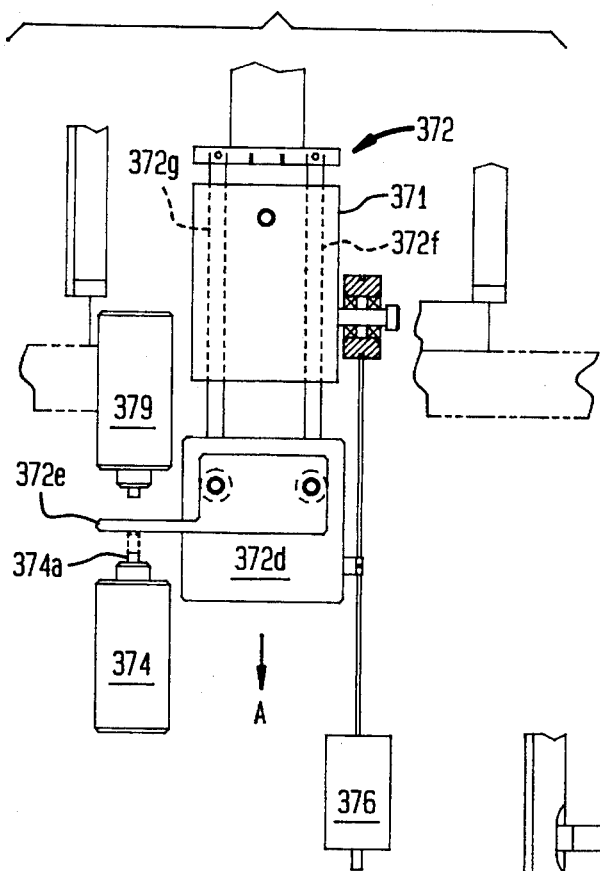
FIG. 21(b) is a detailed front view of the slide assembly means while performing a minimum pull-test.

To accomplish the non-destructive pull test, piston rod 374a of air cylinder 374, mounted on the mechanism frame 371 and controlled by system computer 99, is retracted from its extended position (FIG. 21(a)) supporting the slide finger 372e as shown in dashed line in FIG. 21(b), by reversing its air supply (not shown), to the position shown in the figure. This is indicated as step 52 in FIG. 3(e) and occurs immediately after the gripper arms 325a,b grip the suture. The piston rod 374a is thus retracted to remove the upward force on slide finger 372e, as shown in the FIG. 21(b), to thereby impose the counterbalanced net weight of 2 to 5 ounces of slide block 372d on the swage attachment means of suture 255 in needle 9, in the direction of arrow "A". Accuracy of this system is enhanced because slide block 372d, suspended on slide rods 372b,c, are mounted in low friction ball bushings, 372f and 372g, that are pressed into slide mount 371, thereby imposing minimal mechanical drag on the system.

As shown in the pneumatic schematic of FIGS. 50(a) and 50(b), supply line 701a supplies filtered and regulated air under pressure to switching device 707f for controlling the air cylinder 374 that provides the force for maintaining the position of slide block assembly 372 on slide block 371, and releasing the slide block therefrom. The operation of the air cylinder 374 is controlled by control lines 704a,b which operate the switch 707f under the timing and control of the control system 99.

Simultaneous with or momentarily before the slide assembly 372 is released, the needle release assembly 315 is actuated to enable multi-axis gripper 155 to disengage its grip on the armed needle 9. Releasing the armed needle from the grip of the gripper 155 is necessary to ensure that it is firmly positioned on the load cell needle supporting blade 336. Moreover, to provide an accurate pull-test, the needle must be released so that there is no existing upward force that would cause false results. The releasing of the armed needle for testing is indicated at step 53 in FIG. 3(e) and described above with respect to FIG. 3(b). The dwell time for minimum pull-testing is short, preferably ranging in milliseconds, as indicated as step 54 in FIG. 3(e).

As shown in FIG. 20, needle release assembly 315 comprises needle release solenoid 324 that is actuated to extend pusher 326 into pivotal lever arm 327. Pivotal lever arm 327 pivots about pin 328 to depress plunger 149 of the multi-axis gripper 155 at one end 329 thereof.

To prevent the armed needle 9 from becoming misaligned or from tipping over after the multi-axis gripper 155 releases its grip on the needle, a needle fence assembly 340 is provided. As shown in FIG. 20, the needle fence assembly 340 includes vertical fence plate 342 which can be adjusted to lie flush against the gripper 155 to retain the armed needle in an upright position. Adjusting the lateral positioning of the vertical fence plate 342 is accomplished by moving slide handle 343 for an appropriate distance as shown in FIG. 20. In the preferred embodiment, the configuration of the face of the vertical needle fence plate 342 (not shown) may be changed to accommodate the configurations of different size needles.

In the preferred embodiment of the minimum and destructive pull-test systems shown in FIGS. 20–23, the load cell 335 and the needle support blades 336a,b,c,d thereof comprise a piezoelectric transducer that measures the force applied by the suture gripping assembly to the needle-suture assembly 9. The transducer load cell 335 may be interfaced with the control system computer 90 by conventional means as shown in FIGS. 20 and 22, and, in the preferred embodiment, is a 1000 gram transducer manufactured by Techniques Co. (Model No. GS-1K). The determination of whether the minimum-pull test has passed or failed is made at step 56 shown in FIG. 3(e).

If the test is successful, i.e., the suture meets the minimum pull-test requirements, the needle is re-gripped by the multi-axis gripper 155 as indicated at step 57 in FIG. 3(e). This is accomplished by deactuating the needle release solenoid 324 (FIG. 20). which releases the force on plunger 149. Next, as indicated at step 58 in FIG. 3(e), the suture grippers 325a,b are retracted to their open position to release their grip on the suture 255. At step 59, a flag indicating that the minimum pull-test was successful and that the armed needle may be conveyed downstream for packaging thereof, is set for later use by the control system. Furthermore, if the suture pull-test was successful indicating that the upstream swage was good as shown as step 61a in FIG. 3(e), then a counter is incremented to reflect this at step 61b. A current count is kept of all the needles that are pull-tested so that for every $n^{th}$ needle, 50 in the preferred embodiment, a destructive pull-test may be performed.

It should be understood that only the destruct forces applied to the suture 9 and measured by the load cell transducer 335 during the destructive pull-testing are stored for statistical purposes or for real-time monitoring during a swage die setup routine that may take place when a new batch of surgical needles are to be swaged. For instance, if the destructive pull-tests fail and the forces measured by the transducer are determined to be at the low end of a predetermined range, then the control system computer 99 will acknowledge this and prompt the operator to perform a die setup routine to re-adjust the location of the fixed die of the upstream swaging assembly 390 to increase the force provided by the swage stroke. Alternatively, the control system computer 99 may send the appropriate signals to the upstream swaging assembly 390 (FIG. 16(a)) during run-time causing a fixed swaging die to be advanced an incremental amount toward the moveable swage die, resulting in subsequent swages being stronger. If the destructive pull-test passes, i.e., the forces measured by the transducer are determined to be above the minimum and below an upper limit, then no upstream swage die adjustment need be made.

To prepare for the next armed needle to be pull-tested, the slide assembly 372 and retracted gripper arms 325a,b are pushed back up the slide mount 371 to their unloaded position by an appropriate upward force supplied by the air cylinder 374 and piston rod 374a as controlled by the control system computer 99 and as indicated as step 62 in FIG. 3(e). At this time, another flag may be sent for storage to the control system computer that indicates that the pull-test performed on the particular needle 9 was successful and that the armed needle may be conveyed downstream for packaging thereof. A continuous check is made, as indicated at step 63 in FIG. 3(e), to determine if the grippers 325a,b have reached their home position. Until the gripper 325a,b and slide block 372 are pushed back to their home position, the system will perform a check at step 64 to determine whether a time-out flag has been generated by the control system indicating a time-out error. If a time-out flag has not been generated, the monitoring check continues (step 63). If the time-out flag is detected, the process will be terminated and prompted for reinitialization at step 959. If the suture fails the minimum pull-test, i.e., if the suture 255 is dislodged from the surgical needle 9 as a result of the controlled release, a NEEDLE REJECT bit is set in the control system computer 99 as indicated at step 65b in FIG. 3(e) so that the disarmed needle 9 will be ejected at the pull-test station. As indicated at step 37 in FIG. 3(a), the dislodged suture strand 255 will subsequently be sucked into a vacuum assembly and the needle 9 will be ejected by a needle stripper blade 385 of the needle assembly 380 shown located next to the needle 9 in FIG. 21(a). Alternatively, the suture strand may be ejected by a suitable blast of air provided by an air jet 292. As shown in the pneumatic schematic of FIGS. 50(a) and 50(b), supply line 701a supplies filtered and monitored air under pressure to the switching device 707i for controlling the air jet 292 that provides the blast of air for ejecting the suture strand that has become dislodged from the needle after failing a minimum pull-test.

Figure 24:
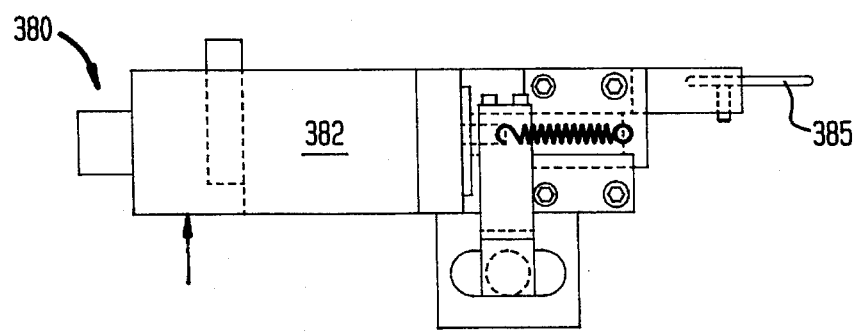
FIG. 24 is a detailed view of the needle stripper assembly 380 for removing the needle 9 after a destructive pull-test or after minimum pull-test failure.

As shown in FIG. 24, needle stripper solenoid 382 will be actuated by a control signal output from the control system computer 99 to extend needle stripper blade 385 mounted on a slide block 383. Thus, when the needle is in its relaxed state on the multi-axis gripper 155 and the minimum pull-test fails, the needle stripper blade 385 is extended to remove the needle from the gripper as indicated at step 65a in FIG. 3(e). The needle will fall and be collected by appropriate collection means (not shown) located at the pull-test station.

As previously mentioned, the automatic pull-test assembly 300 is used to perform a minimum pull-test upon every armed surgical needle indexed thereto prior to automatic packaging thereof. A destructive pull-testing of the armed surgical needle is performed at every nth needle indexed thereto. The purpose of performing a destructive pull-test is to set the swage dies located at the upstream swaging station for correct maximum swage pull-out value. This is by necessity a destructive test, and the test frequency, which is programmable, is set high enough to maintain control of the operation, but low enough to avoid excessive product waste. In the preferred embodiment, this frequency is set at every 50th needle, but can be modified to be every 75th or 100th needle.

Another purpose of the destructive pull test is to aid in installing a new swage die set during a changeover procedure, which is a procedure that is used to prepare the needle sorting and swaging apparatuses (swage dies) for processing a new batch of needles when they are of a different size from a previously processed batch. Contrary to the non-destructive pull-test described above, the pull-test apparatus is programmed for 100% destructive test of a swaged needle, while the swaging assembly is operating and feeding the armed needles to the pull-test station. The die adjustment system at the upstream swaging assembly will receive a signal from the transducer load cell 335, at each machine cycle, and immediately perform a correct adjustment of the swage dies.

Destructive test pull-out values are recorded in the system computer 99 and are used to compute statistical process control information which is fed back to the machine operator through display screens.

Destructive pull testing of the armed surgical needle 9 is accomplished similarly as described herein above with respect to the minimum pull test. However, the fundamental difference is that a fixed mechanical stroke that is great enough to pull the suture out of the needle replaces the minimum 2 to 5 ounce force of the minimum pull test. It should be noted that if the knot detector 256 at the swaging station 200 determines that the length of suture strand is defective, the control system 99 informs the pull-test station to automatically perform a destructive pull-test (step 19c) on the suture having the bad strand. Thus, the needle 9 and the defective suture strand may be rejected in the manner described below however, however the measured force values will not be used for statistical control purposes and an updatable counter (step 79c) will not be incremented as it is for the other pull-tests.

Figure 21C:
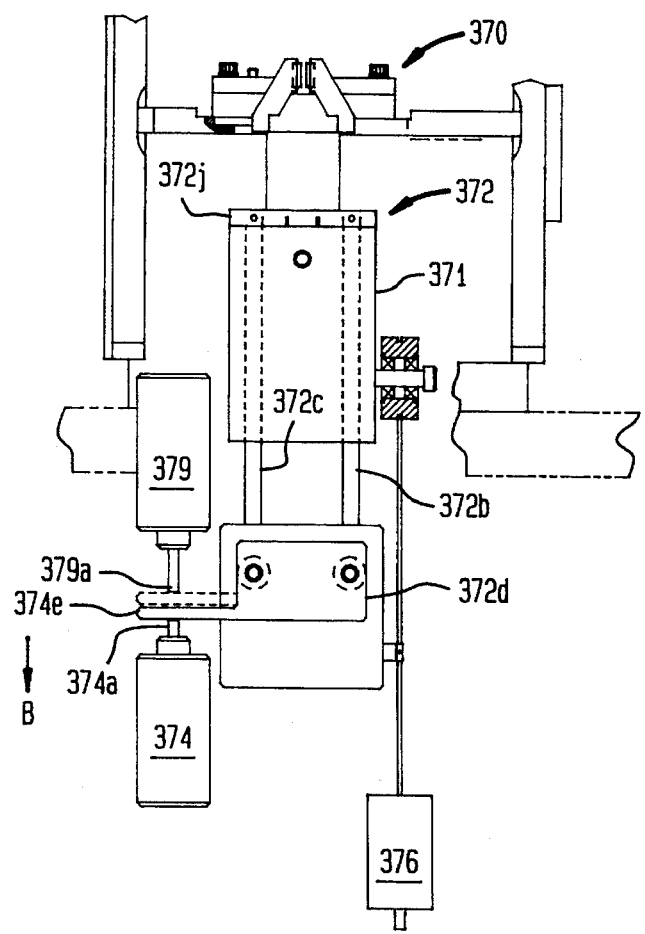
FIG. 21(c) is a detailed front view of the slide assembly means while performing a destructive pull-test.

The control process 70 for performing destructive pull-testing of the armed surgical needle 9 is described in detail with reference to FIG. 3(f). First, gripper arms 325a,b of suture gripping assembly 370 are extended from their retracted position to grip the suture strand 255 slightly below the needle supporting blades 336 as described above and indicated as step 71 in FIG. 3(f). Piston rod 379a of second air cylinder 379 located opposite air cylinder 374, is programmed to provide a fixed stroke against slide finger 372e from a non-actuating position shown in FIG. 21(a) to the position shown in FIG. 21(c). This results in the vertical displacement of slide finger 372e from a position shown by the dashed line to a position shown by the solid line. This further results in a downward force upon slide block 372d, which, through slide rods 372b and c, moves slide assembly 372, including grippers 325a,b and suture 255, in the direction of the arrow "B" as shown in FIG. 21(c) as indicated as step 72 in FIG. 3(f).

AS shown in the pneumatic schematic of FIGS. 50(a) and 50(b), supply line 701a supplies pressurized air that has been filtered and monitored to the switching device 707h to provide the pressurized air for controlling the air cylinder 379 that provides the destruct force against slide finger 372e for pulling the slide block assembly 372 an amount necessary to dislodge the suture from the needle. Air pressure to cylinder 379 is set high enough to always pull suture 255 out of needle 9. This stroke is limited by the top portion 372j of slide assembly 372 striking the top of stationary block 371. The operation of the destruct air cylinder 379 is controlled by control lines 704a,b which operate the switch 707h under the timing and control of the control system 99.

Again, to provide an accurate destructive pull-test, the needle 9 must be released from the grip of the multi-axis gripper 155 so that there is no existing upward force that would cause false results. Thus, the armed needle is released for testing as indicated at step 73 in FIG. 3(f).

The force necessary to accomplish the destructive pull-test is measured by the piezoelectric load cell transducer 335 as discussed above. This measurement is continuously made, i.e., anywhere upwards of 100 pressure readings may be taken, as indicated at step 74a in FIG. 3(f). When the measurement is finished, as indicated at step 74b in FIG. 3(f), the maximum value of the destructive force is calculated from the approximately 100 readings, and finally stored in the computer 99 for statistical process control at step 75. Since the suture pull-test was destructive, a NEEDLE REJECT bit is set in the control system computer 99 as indicated at step 76a in FIG. 3(f) so that the disarmed needle 9 will be ejected at the pull-test station.

If it is determined by the process control algorithm (not shown) that the destructive pull-test forces as measured by the transducer load cell are lower than a predetermined range of pull-test values, the control system computer 90 will send out appropriate control signals to increase the swaging die stroke applied when swaging the suture to the needle at the upstream swaging station 200. If it is determined that the destructive pull-test forces as measured by the transducer load cell are higher than the predetermined range, the control system computer 99 will send out appropriate control signals to the upstream swaging assembly to move a fixed swage die a small incremental distance away from the suture, thereby decreasing the swaging pressures applied when swaging the suture to the needle.

Since the destructive pull-test necessarily results in the suture strand being dislodged from the needle 9, the needle is removed from the grip of the multi-axis gripper 155 by the needle stripper blade 385 as indicated at step 76b in FIG. 3(f), and as described above with respect to step 65a in FIG. 3(e). Additionally, the gripper arms 325a,b are retracted to their open positions. As indicated at step 77a in FIG. 3(f), air cylinder piston rod 379a is retracted and air cylinder 374 provides the upward force to restore the gripping assembly 370 and slide block assembly 372 back to their normal position in preparation for the next pull-test.

Simultaneously therewith, the multi-axis gripper is then reverted back to its needle gripping position at step 77b, as will be described in detail below. While multi-axis gripper is enabled to its gripping state, a continuous check is performed at step 79a to verify when the needle gripper has closed. Simultaneously therewith, the system will perform a check at step 79b to determine whether a time-out flag has been generated by the control system indicating a time-out error. If a time-out flag had not been generated, then the needle gripper has closed. If the time-out flag is generated by the control system as a time-out error, the process will be terminated and prompted for reinitialization at step 959. Since a current count is kept of all the needles that are pull-tested, the counter is incremented at step 79c.

Swage Die Setup Procedure

The die setup procedure utilizes the swage bond values obtained from a sample of needle suture assemblies pull-tested at pull-test station 300, to adjust the positioning upstream swage dies. As mentioned above, this procedure is usually run off-line at the beginning of a batch run or needle changeover procedure, or, it can be run as part of a reinitialization or error correction routine.

Essentially, during the die setup procedure, the swage assembly produces a sample of 25–30 and preferably 28 needle-suture assemblies for conveyance to the upstream pull-test station. In the manner explained above, all of the sample needle-suture assemblies are destructively pull-tested and the needle-suture destruct values, as measured by the transducer, are stored, analyzed, and compared to a predetermined value that corresponds to either a minimum pull-test force, to an acceptable predetermined maximum destruct value, or to combinations thereof as implemented by the process control algorithm (not shown). After each successive pull-test, the position of the fixed swage die of the upstream swaging station will vary in accordance with the destruct values obtained and the control algorithm that is implemented to perform the comparisons. It is understood that minimum and maximum pull-test values will vary in accordance with the type of surgical needle and the attached suture being processed.

After either of the pull-test routines of FIGS. 3(e) and 3(f) are performed at the pull-test station 300, and the swage/cut/monitor process of FIG. 3(g) is performed at the swaging station 200, and after the next needle is handed off to the multi-axis gripper at station 100 or after the needle is handed off to the suture wind and packaging dial at station 600, the control system 99 enables each multi-axis gripper to revert to its respective needle or needle-suture assembly engaging state. Thus, as indicated in the RETRACT MAG (Grip needle) steps 31a,b,c,d in FIG. 3(a), the process of biasing pin 142 from its non-engaging position back into its needle engaging position as shown in FIG. 11(b) is initiated.

Figure 3H:
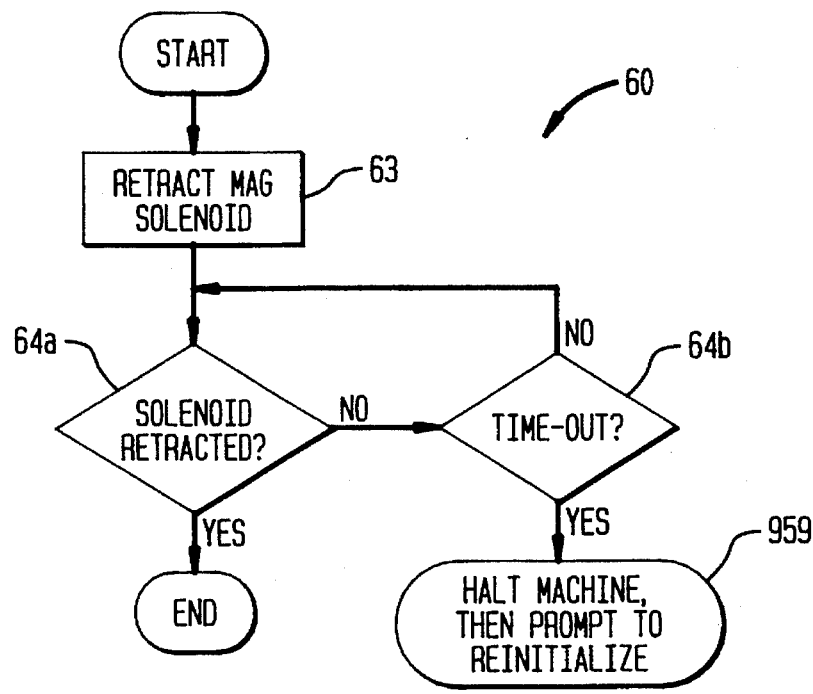

The control process 60 for enabling each multi-axis gripper 155 to re-grip each needle after processing at each respective station is illustrated in FIG. 3(h). First, at step 63, the control system 99 enables the cam solenoid 143 to retract from the plunger 149 as shown in FIG. 11(b), so that pin 142 of each multi-axis gripper is biased back into its needle engaging position. While the cam is being retracted, a continuous check is performed at step 64a to verify when the motor operating the cam solenoid has stopped running. If the cam has not been retracted, the system will perform a check at step 64b to determine whether a time-out flag has been generated by the control system indicating a time-out error. If a time-out flag has not been generated, then the cam solenoid has been fully retracted (step 64a). If the time-out flag is generated by the control system as a time-out error, the process will be terminated and prompted for reinitialization at step 959.

After each multi-axis gripper regrips a respective needle or needle-suture assembly (steps 31a,b,c,d) while extended at a respective station, the multi-axis gripper 155 is retracted back from its extended position to its initial position on the rotary swage dial 150, as indicated at step 20 in FIG. 3(a). To retract each multi-axis gripper from its extended position, the cam dial plate 125 is rotated in the counterclockwise direction for approximately 45°–55° degrees with respect to the swage plate 110, forcing cam follower 165a in its respective cam track 160a to move to its retracted position (FIG. 8(a)). When cam dial plate 125 rotates counterclockwise with respect to swage dial 110, each multi-axis gripper 155 is retracted within its respective cam track. Thus, the system is designed so that after needle hand-off at station 100, and needle-suture assembly insertion at station 600, and after respective processing at stations 200 and 300, each multi-axis gripper may then be retracted as indicated at step 20 in FIG. 3(a), prior to being indexed to the next successive processing station.

After a needle is engaged by the multi-axis gripper 155 at each respective workstation and retracted after hand-off or processing as described above, the rotary swage dial assembly and cam dial assembly 125 are both rotated counterclockwise to index the needle to the next successive workstation as indicated at step 39 in FIG. 3(a). Specifically, to index the needle to another station, both swage dial plate 110 and cam dial plate 125 are rotated together for approximately 90° degrees to position each multi-axis gripper at the next successive station. For example, when the cam dial plate 125 and the swage dial plate 110 are simultaneously rotated 90 degrees counterclockwise in FIG. 10, the gripper 155 that had received the needle at station 100 is now indexed to a position at station 200 for swaging a suture thereto. Similarly, the needle having the suture attached thereto at station 200 is indexed to the position at station 300 for pull-testing thereof. Additionally, after pull-testing, the armed needle engaged by a multi-axis gripper at pull-test station 300 will be indexed to the needle/suture load to package station 600 for discharge thereof. After rotating the rotary swage dial 150 to index each multi-axis gripper to its successive workstation at step 39, the control system performs a check at step 39a to determine whether the motor controlling the rotation of the rotary swage dial 150 for the indexing function (step 39) has finished. A continuous check is made at step 39b to determine whether a time-out flag has been generated by the control system 99 indicating that the motor indexing has not occurred within a predetermined time. If a time-out flag has not been generated, the motor has stopped driving the swage dial 150 in the allotted time. If the motor does not perform the indexing of the dial within the allotted time, a time-out flag is generated by the control system indicating an error, and the process will be terminated and prompted for reinitialization at step 959, to be described in detail below.

After the right or lead gripper 232 has released its grip of the cut suture strand, the control system 99 enables swage cylinders 361,369 to be positioned apart while enabling pin 142 of the multi-axis gripper 155 to engage the armed needle as described above with respect to step 31b in FIG. 3(a). Simultaneously therewith, as indicated at step 27 in FIG. 3(a), the control system 99 commands the left and right servomotors 236,238 to reciprocate the respective left and right grippers with the right or lead gripper reciprocating to the home position in a non-engaging position along the right guide rod, and the left or bottom gripper reciprocating to the suture insertion position along the left guide rod while drawing the indefinite length of suture material 255 for the long stroke as described above with respect to step 16. The process of advancing suture material 255 by alternating left and right grippers at each cycle eliminates the recycle or return time for retaining the gripper to the original position. This makes faster machine speeds and hence, higher production rates possible.

Immediately after the lead gripper advances the long stroke distance and the alternate gripper reciprocates to its home position and comes to a halt, a portion of the suture material 255 may be heated (tipped) as indicated as step 35a in FIG. 3(a). Heating of the suture under tension and the subsequent cooling thereof will stiffen the suture material for cutting and aid in the subsequent insertion of the tip of the material within the suture receiving end 7 of the surgical needle. In the preferred embodiment, the control system computer 99 controls the duration and temperature of a heat pulse that is applied to the suture material so that it is adequately heated and will have sufficient time to cool before the cutting operation. The operation of the tipping assembly 290 mounted on tip and cut carrier 180 is explained in greater detail in copending patent application Ser. No. 08/181,595 (attorney docket No. 8924) assigned to the same assignee of the present invention. As described therein, the tipping assembly 290 is located at a position that is located slightly below the alternate gripper, for e.g., left gripper 230, so that when the suture material 255 is advanced the short stroke distance for insertion within the needle 9, the tipped portion of material 255 that had been subject to the heated air advances to a position just above the home position of the left gripper 230 and adjacent the cutter assembly 280. Then, the left gripper 230 (lower gripper) is actuated to grip the material 255 at or below the tipped portion, i.e., the portion of the suture material heated by tipping assembly 290 as shown in FIG. 13, and the cutter assembly 280 is actuated to cut the tipped portion of the suture material 255 so that the left gripper 230 is now gripping an indefinite length suture strand 255 having a tipped end 258 for the next suture draw/insert cycle.

After accomplishing the optional step of heat tipping a portion of the suture material (step 35a), a cool air jet 291 appropriately positioned at the drawing tower 220 may be provided to apply a blast of cool air to the tipped portion of the suture material as shown at step 35b in FIG. 3(a). As shown in the pneumatic schematic of FIG. 50(a), supply line 701a supplies pressurized air through suitable filter 702, pressure monitoring device 703a and through switching device 707e to provide an air jet pulse for cooling the heated (tipped) portion of the suture strand. The operation of the air jet is controlled by control lines 704a,b which operate the switch 707e under the timing and control of the control system 99.

Automated Packaging Machine

During the process of arming surgical needles at the needle threading and swaging dial 150, as described above, a simultaneous packaging process occurs at the suture wind and packaging machine 500. In essence, the rotary packaging turret 500 comprises rotary dial member 514, is indexed forwardly in the direction of arrow "B" in FIG. 1 such that each tool nest located on dial 500 is adapted to be advanced in succession to a number of workstations located about the periphery of the rotary turret 500.

Figure 4C:
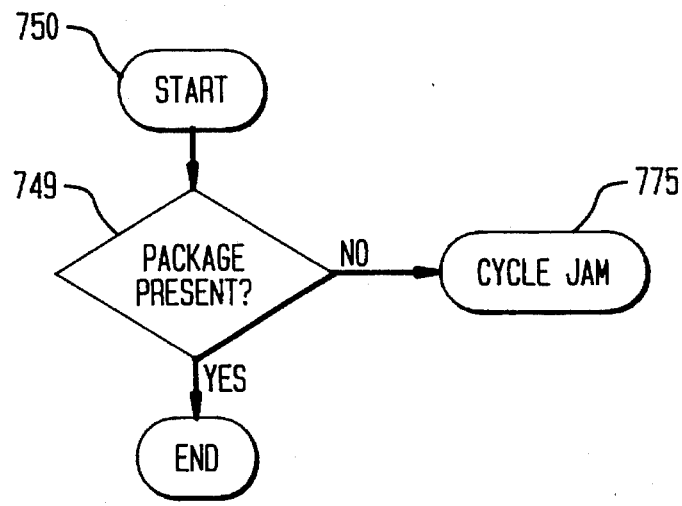
FIGS. 4(a)–4(n) are flow diagrams illustrating the sequential processes taking place at the suture winding and packaging dial and operable under the control system of the instant invention.
Figure 4A:
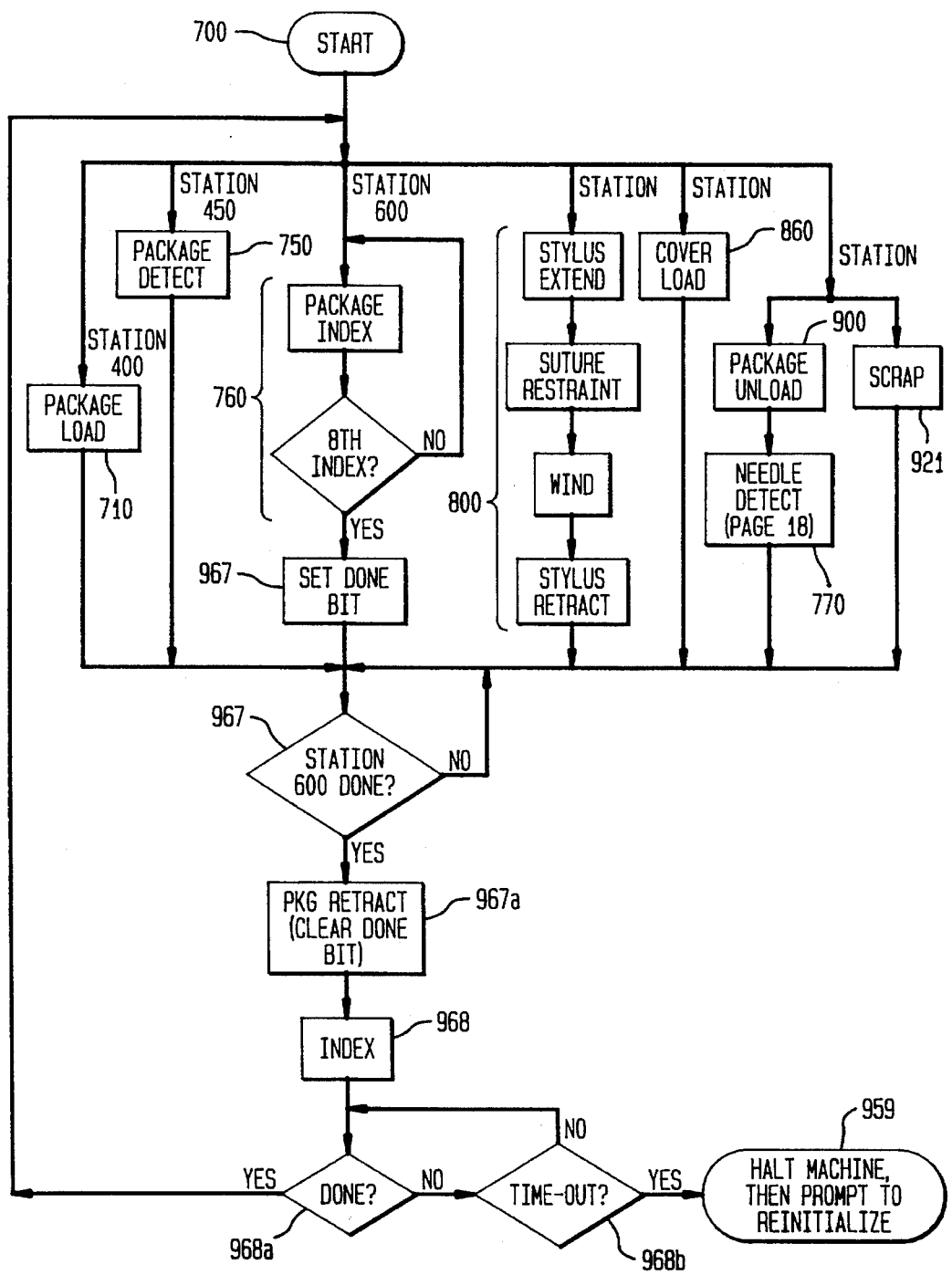

FIG. 4(a) is a general flow chart illustrating the automatic needle-suture packaging processes 700 operable under the control of the control system 99 of the instant invention. To the extent possible, each process performed at each workstation as illustrated in FIG. 4(a) will be described in the sequential manner as illustrated in the figure.

The foregoing indexing motions of the rotary turret 500 are implemented in order to produce a completed suture package and are correlated with each other through the program-controlled operation of the machine such that the dwelling-time periods at each of the respective workstations is computed to allow sufficient time for the preceding step to be completed at the preceding workstation or workstations. This enables a smooth and continuous flow of product from the automated packaging machine and provide for high-speed and efficient manufacturing cycles.

Suture Wind And Package Dial

Figure 25:
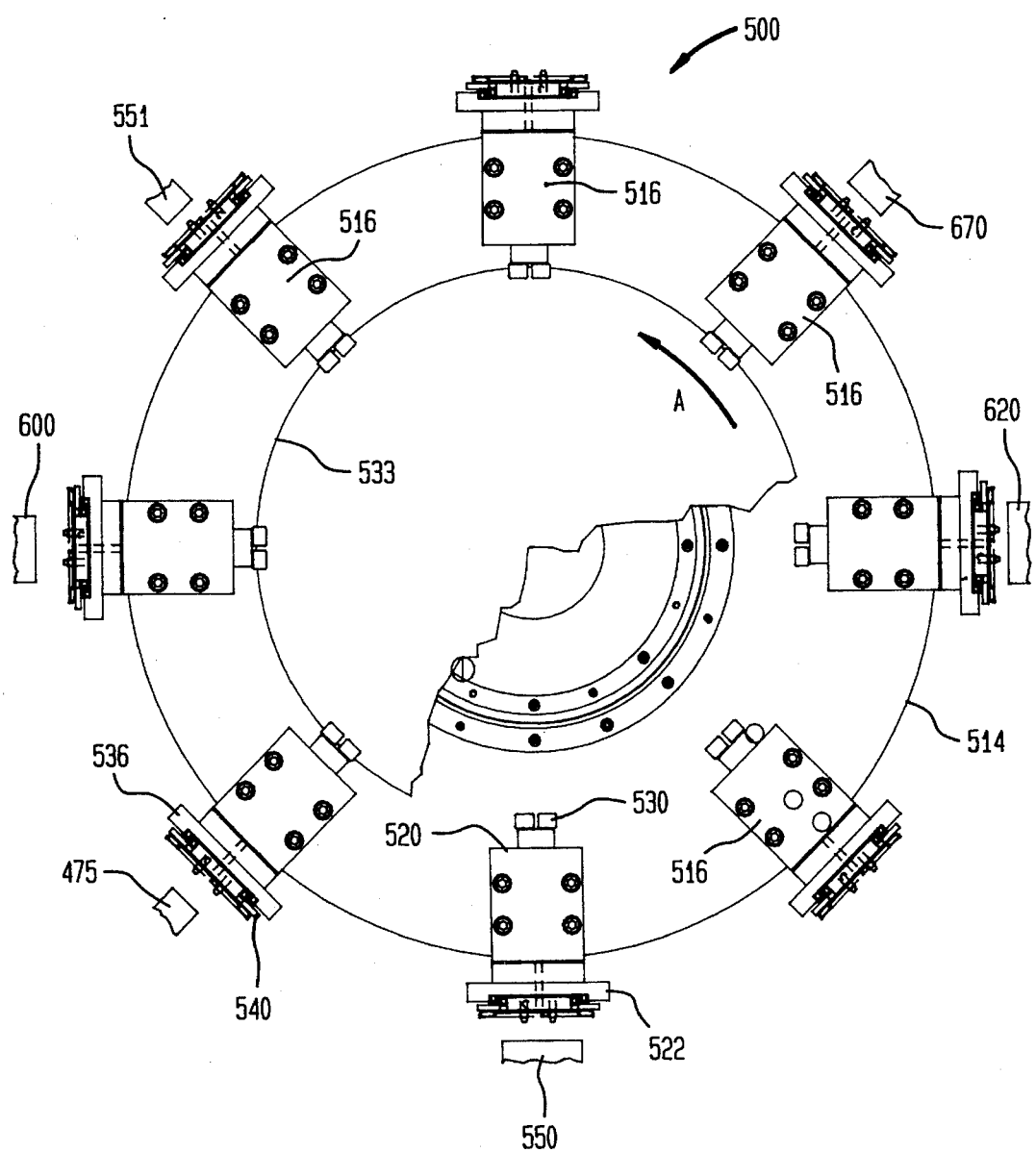
FIG. 25 illustrates a top plan view of the suture wind and packaging turret of the automatic packaging machine for needle-suture assemblies.
Figure 26:
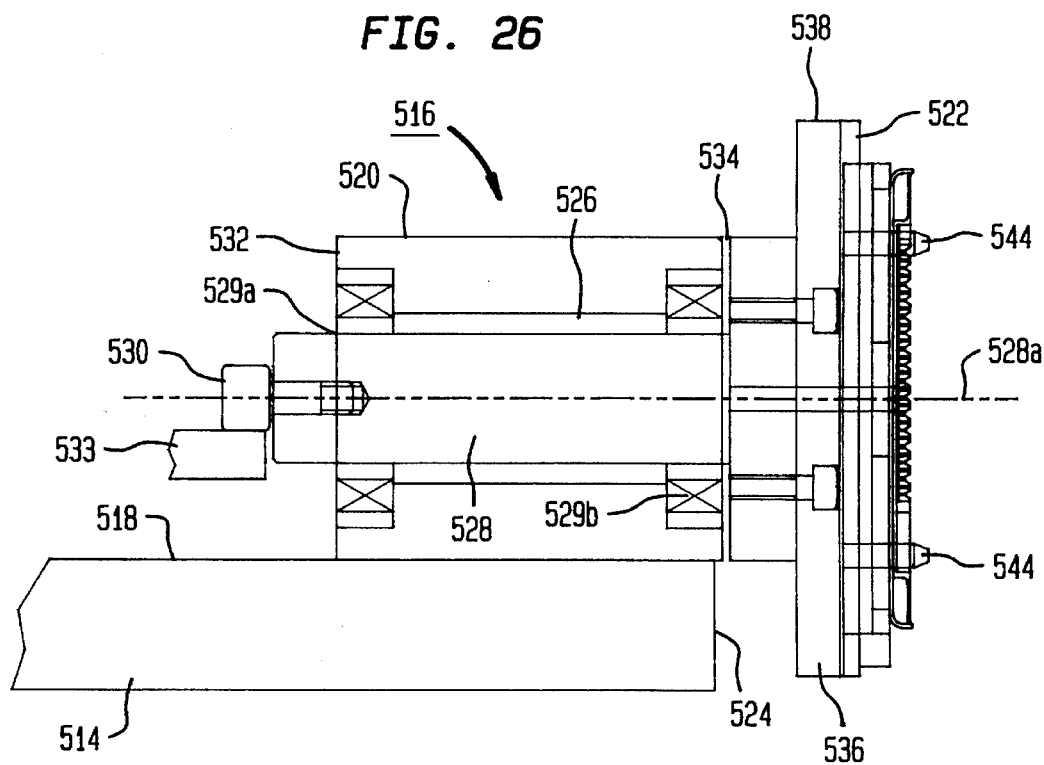
FIG. 26 illustrates, on an enlarged scale, a detailed side view of the rotary disk showing one of the tool nests for mounting a needle and suture-receiving tray.

As shown in FIGS. 25 and 26 the rotary suture wind and package turret 500 is essentially constituted of a circular disc-shaped dial 514 having a plurality of tool nests 516 located thereon in uniformly spaced circumferential array on the upper surface 518 of the rotary package turret 500, and with each tool nest extending radially outwardly of the periphery thereof.

Figure 28A:
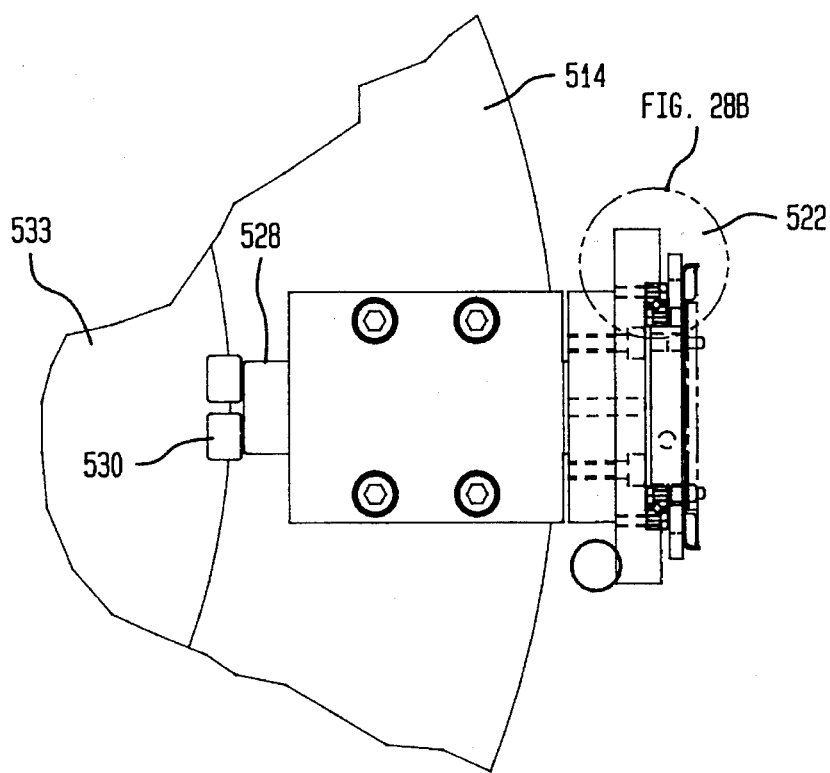
FIG. 28(a) illustrates a fragmentary top view of the rotary turret, showing an enlarged portion thereof incorporating one of the tray-mounting tool nests.
Figure 28B:
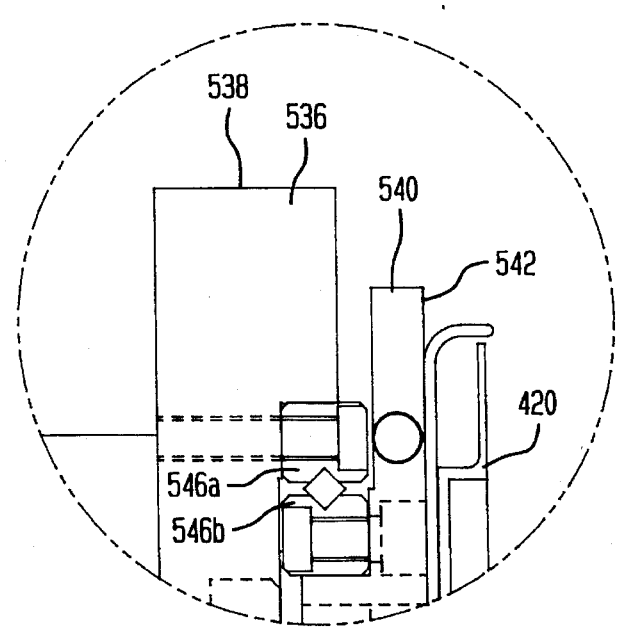
FIG. 28(b) illustrates an enlarged fragmentary detail of the encircled portion in FIG. 28(a)
Figure 27:
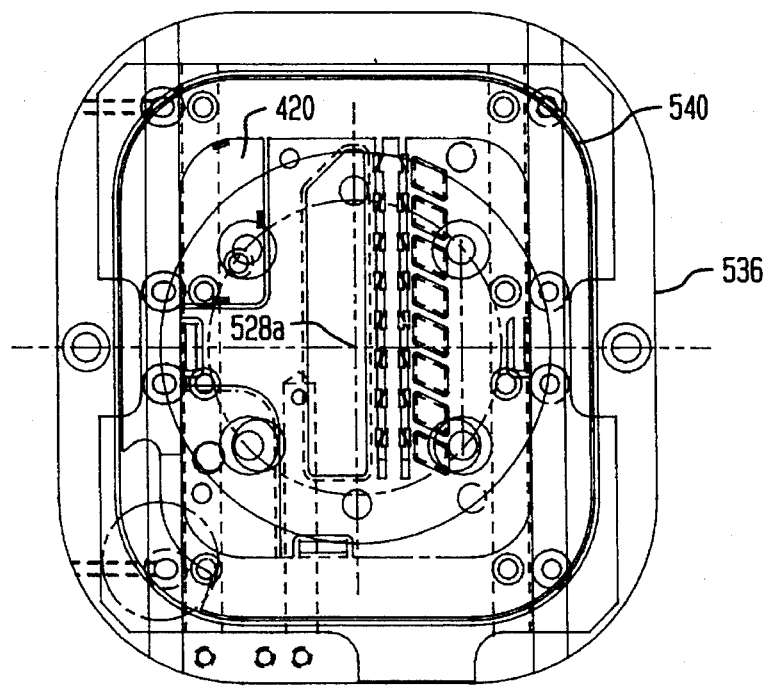
FIG. 27 illustrates a front view of the tool nest of FIG. 26.

Generally, as shown in FIG. 25, there are provided eight tool nests 516 arranged at 45° angular spacings from each other about the circumference of the dial 514. As shown in detail in FIGS. 26 through 28 of the drawings, each tool nest 516 consists of a housing 520 which is fixedly mounted on the upper surface 518 of the disc-shaped dial 514 of rotary dial 500, and includes a portion 522 radially outwardly projecting from the circumferential edge 524 of the disc member 514 which is operative to receive and support flat-bottomed injection-molded plastic trays utilized in the forming of suture packages containing surgical needles and attached sutures, as described hereinbelow.

Figure 46:
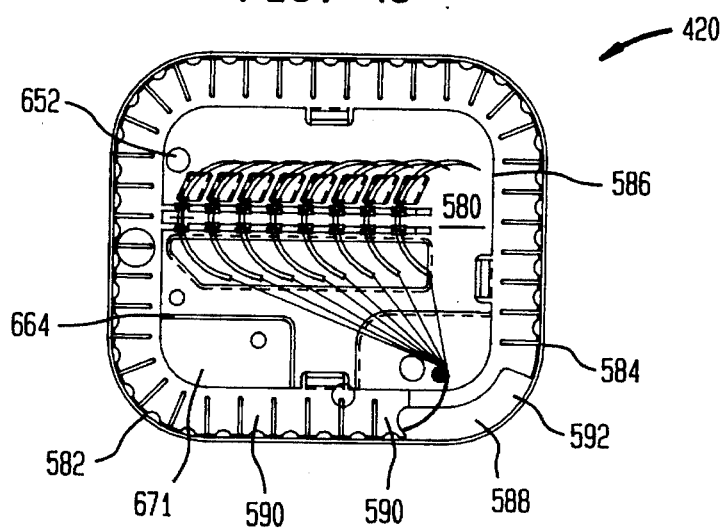
FIG. 46 illustrates a front view of a tray having needles and sutures arranged therein.
Figure 47:
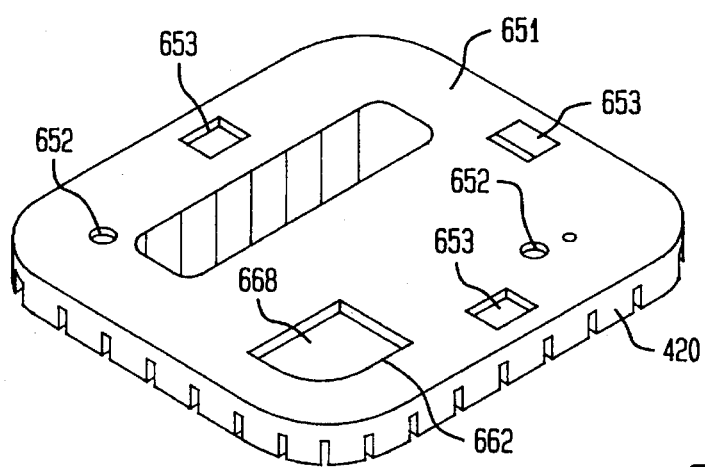
FIG. 47 illustrates a perspective view of a completed suture package.

As illustrated in FIGS. 26 through 28(a), each of the tool nests 516 comprises a housing or block 520 fixedly mounted through suitable fasteners to the upper turret surface 518 proximate the peripheral outer rim or edge 524 of the dial 514 of turret 500. Each housing 520 includes a horizontal radially extending central bore 526 having a shaft 528 supported on bearings 529a and 529b rotatably journaled therein, with the shaft being connected to a suitable drive source (as subsequently described). Cam rollers 530 mounted at the radially inner end 532 of the housing 520 are adapted to contact a cam plate dial 533 extending over the dial surface 518 during the rotation of the turret 500 for purposes as described in more specific detail hereinbelow. At the radially outer end 534 of the housing 520, there is provided structure for supporting the components for forming a suture package, the latter initially comprising a generally flat injection-molded tray 420 for receiving and retaining therein a plurality of surgical needles and attached sutures; for example, as illustrated in FIG. 46 of the drawings, and with an applied tray 420 cover as shown in FIG. 47, as disclosed in U.S. Pat. No. 5,230,424 entitled "Multi-Strand Suture Package and Cover-Latching", the disclosure of which is incorporated herein by reference.

The radially outer structure of the housing 520 for initially mounting the plastic suture tray 420 includes a generally rectangular, round-cornered and vertically extending plate member 536 of which the outer peripheral surface 538 forms a cam surface, employed for a suture-winding purpose as described hereinbelow, and with the plate member 536 being secured to the radially outer end of the shaft 528 for rotation therewith. Mounted on the front surface of cam plate member 536 is a plate 540 having a radially outwardly facing, vertically-oriented support surface or platform 542 possessing projecting guide pins 544 for the positioning and mounting thereon of an injection-molded plastic tray 420 adapted to be supplied with surgical needles and attached sutures. The cam plate member 536 and the plate 540 for supporting the suture tray 420 are connected with each other so as to be secured against relative rotation, both being jointly rotatable about the longitudinal horizontal axis 528a of the shaft 528 extending through the block or housing 520. However, the plate 540 for mounting the tray 420 is linearly displaceable relative to the cam plate member 536 through the provision of cooperating slide guides 546 located between these elements. These slide guides 546 are disclosed in more extensive detail in the enlarged fragmentary illustration of FIG. 28(b), where they are illustrated as mating guide rails 546a and 546b, and are provided to facilitate the successive insertion of an array of surgical needles into the tray 420 which is mounted on the guide pins 544 extending from the support surface 542 of the plate 540 of the tool nest 516.

The external configuration of both the cam plate member 536, i.e. its camming surface 538, and the support plate 540 is substantially in conformance with the outer shape of the suture tray, although larger in external dimensions than the latter.

Further details of the automatic packaging system can be found in copending patent application Ser. No. 08/181,626 (attorney docket No. 8925) assigned to the same assignee of the present invention and incorporated by reference herein.

The automated process 700 of packaging needle-suture assemblies as controlled by the control system 99 of the invention, are generally illustrated in FIG. 4(a). As shown therein, each process performed at each station occurs approximately simultaneously to ensure efficient operation as the packaging dial 500 rotates.

(1) The first of the successive workstations located about the rotary suture wind and package dial 500, is the package load station 400 shown in FIG. 4(a) as step 710. At the package load station 400, empty suture trays 420 are positioned on the radially outwardly facing platform or support surface 542 of the plate 540 on tool nest 516, and retained thereon by means of the guide pins 544 extending through positioning apertures in the tray 420 so as to be in a generally vertical orientation relative to the horizontal plane of rotation of the rotary disc member 510. Suitable grippers of a tray 420 feeding apparatus or mechanism (not shown), may be provided to supply empty tray 420 to successive plates 540 and position the tray 420 thereon. The grippers may obtain individual tray 420 from a suitable supply source, such as a stack of trays 420, and position the tray 420 one each on successive forwardly indexed platforms 540 of the tool nests 516. Alternatively, in the absence of gripper mechanisms the tray 420 may optionally be manually positioned on the guide pins 544 of platform 540 such that the rear surface of each tray 420 contacts the support surface or platform in a flat, surface-contacting relationship so as to be firmly mounted thereon.

The control process 710 for package loading at station 400 is illustrated in FIG. 4(b). The first step indicated as step 713 in FIG. 4(b), is to turn on the air and vacuum supply for the commercially available vacuum gripper, indicated as element 759 in FIG. 50(c), that grips each empty package tray 420 from the stack and loads it onto the plate 540, is operational. Additionally, the air and vacuum supply is supplied to a manipulating gripper arm, indicated as element 758 in FIG. 50(c), for extending the vacuum gripper 759 to grasp an empty package tray 420 prior to placing an empty package tray 420 onto the plate 540.

Figure 50C:
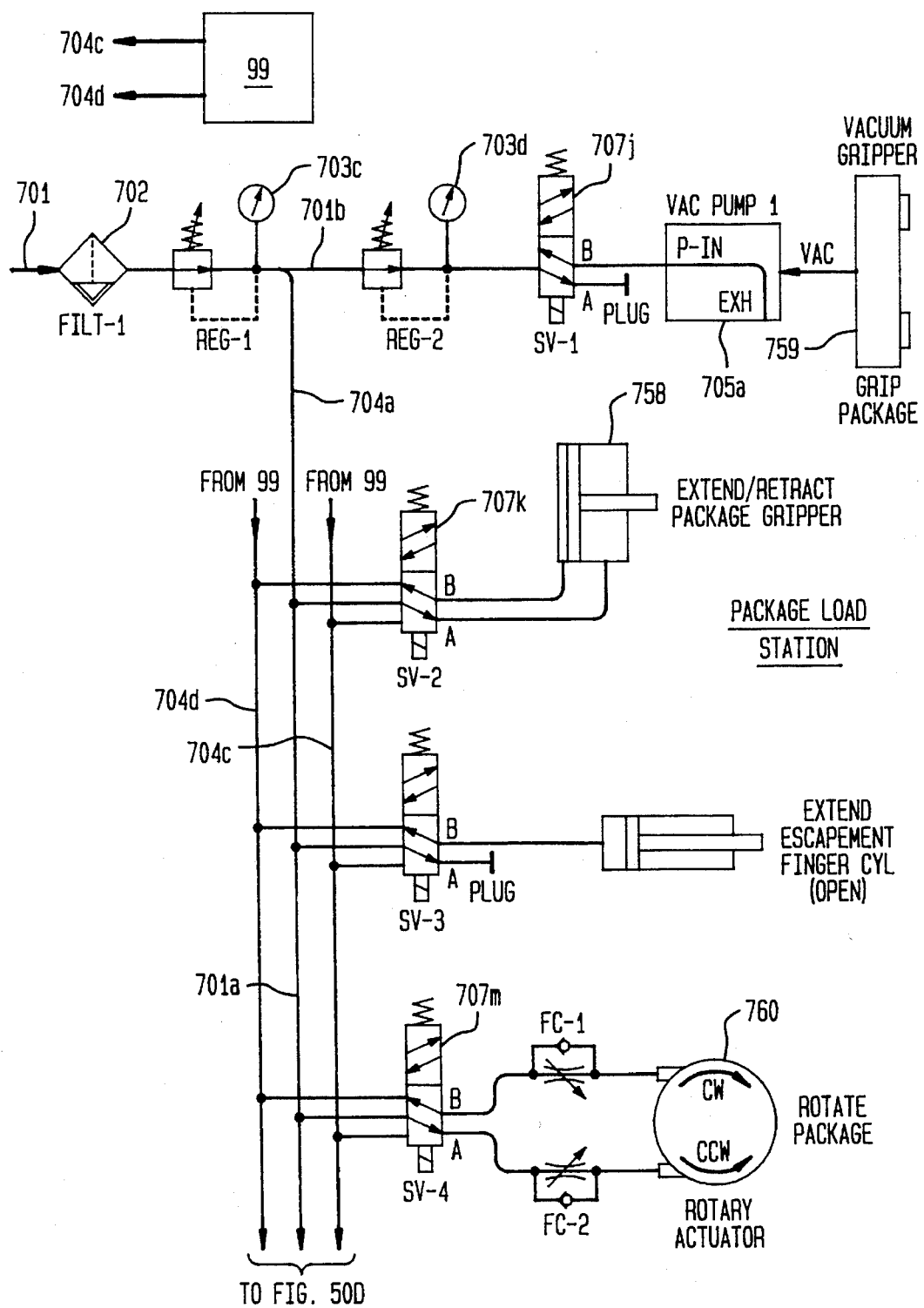

As shown in the pneumatic schematic diagram of FIG. 50(c), supply line 701 supplies air through suitable filter 702, and through pressure regulator 703c before being split into supply lines 701a and 701b. Air supply line 701b supplies the pressurized air through another pressure monitoring device 703d to a vacuum pump 705a which provides the vacuum for the vacuum gripper 759 to grasp each empty package tray 420 by vacuum suction. The operation of the vacuum gripper 759 is controlled by switch 707j under the timing and control of the control system 99. A verification is made at step 714a of FIG. 4(b) to determine if the vacuum has been turned on. The system will perform a check at step 714b to determine whether a time-out flag has been generated by the control system indicating a time-out error. If a time-out flag has not been generated, then the vacuum is on (step 714a). If the time-out flag is generated by the control system as a time-out error, then the cycle jam procedure will be implemented at step 775 shown in FIG. 4(b).

Additionally, air supply line 701a provides the air supply for the gripper arm 758 utilized to manipulate, i.e., extend and retract, the vacuum gripper 759. The operation of the package load gripper arm 758 is controlled by control lines 704c,d which operate the switch 707k under the timing and control of the control system 99. If it is determined that the air supply is off or not at the correct operational level as monitored by monitoring device 703c, then the cycle jam procedure will be implemented at step 775 shown in FIG. 4(b) and explained in further detail below.

At step 715 in FIG. 4(b), the control system 99 performs a check on the stack of empty package trays (not shown) to ensure that the stack level is not too low. If it is determined that the stack of package trays 420 is too low, then the control system will check if the package tray counter (not shown) is equal to zero (0) at step 717 in FIG. 4(b). If the counter for the stack of trays 420 is not equal to zero (0) the counter is decremented at step 719 and the extend stack release signal is given at step 721 to enable a release lever to extend and enable the package gripper arm to access and vacuum grip the next empty package tray 420 from the stack as shown at step 723.

While the stack release lever is being extended, the system will perform a check at step 722 to determine whether a time-out flag has been generated by the control system indicating a time-out error. If a time-out flag has not been generated, then the release lever has not fully extended (step 723). If the time-out flag is generated by the control system as a time-out error, then the cycle jam procedure will be implemented at step 775 shown in FIG. 4(b).

As shown in FIG. 4(b) once the package load gripper arm 758 has reached its extended position and has grasped an empty package tray 420 (step 723), the control system initiates a retract stack release signal at step 724 so that the next accessible empty package tray is retained in the stack by the stack release lever as the gripper is retracted and rotated to a horizontal position for package loading.

While the stack release lever is retracting (step 725), the system will perform a check at step 726 to determine whether a time-out flag has been generated by the control system indicating a time-out error. If a time-out flag has not been generated at step 726, then the release lever has fully retracted (step 725). If the time-out flag is generated by the control system as a time-out error, then the cycle jam procedure will be implemented at step 775 shown in FIG. 4(*b*).

As indicated at step 727 in FIG. 4(*b*), the extended pneumatic package load gripper arm 758 and vacuum gripper 759, that is now carrying an empty package tray 420, is caused to retract to a position to facilitate its rotation to a horizontal position (step 729). While the pneumatic package load gripper arm 758 is retracting, the system will perform a check at step 727*b* to determine whether a time-out flag has been generated by the control system indicating a time-out error. If a time-out flag has not been generated, then the package load gripper arm has reached its fully retracted position (step 727*a*) while grasping an empty package tray 420. If the time-out flag is generated by the control system as a time-out error, then the cycle jam procedure will be implemented at step 775 shown in FIG. 4(*b*).

After the pneumatic package load gripper arm 758 carrying an empty package tray 420 has retracted while retaining an empty package tray, it must be rotated to an oriented position to enable placement of the package tray on the guide pins 544 extending from the support surface 542 of the plate 540 of the tool nest 516. As shown at step 728 in FIG. 4(*b*), the vacuum gripper 759 gripping empty package tray 420 is rotated to a horizontally oriented position to aid in the positioning of the empty package tray 420 onto the nest plate 540. While the rotary actuator enables pneumatic package load gripper arm to rotate the empty package tray 420 to a fully horizontal position, the 5 system will perform a check at step 728*a* to determine whether a time-out flag has been generated by the control system indicating a time-out error. If a time-out flag has not been generated, then the package load arm has fully rotated (step 728*a*). If the time-out flag is generated by the control system as a time-out error, then the cycle jam procedure will be implemented at step 775 shown in FIG. 4(*b*).

As shown in the pneumatic schematic diagram of FIG. 50(*c*), supply line 701*a* supplies filtered, monitored, and pressurized air to the rotary actuator 760 which rotates the package tray 420. The clockwise and counterclockwise operation of the rotary actuator 760, is controlled by control lines 704*c,d* which operate the switch 707*m* under the timing and control of the control system 99.

The next step of the package load process 710, is to transfer the empty package tray 420 from the vacuum gripper 759 onto the guide pins 544 of plate 540 of package tool nest 516. To accomplish this, the package load gripper arm 758 is again extended and the vacuum mode is switched, i.e., turned off, at step 730 to accomplish the transfer. While the pneumatic package load gripper arm 758 is extending and the vacuum mode is switched off to enable the transfer of the empty package, the system will perform a check at step 732 to determine whether a time-out flag has been generated by the control system indicating a time-out error. If a time-out flag has not been generated, then the vacuum mode has been switched (step 731). If the time-out flag is generated by the control system as a time-out error, then the cycle jam procedure will be implemented at step 775 shown in FIG. 4(*b*).

After the transfer of the empty package onto the package tray 420 has been completed, the package load gripper arm 758 is retracted from its extended position at the tool nest 516 as shown at step 733 in FIG. 4(*b*). While the pneumatic package load gripper arm 758 is retracting from its position at the tool nest after transferring an empty tray 420, the system will perform a check at step 735 to determine whether a time-out flag has been generated by the control system indicating a time-out error. If a time-out flag has not been generated, a check is made again to determine if the arm has been fully retracted (step 734). If the time-out flag is generated by the control system as a time-out error, then the cycle jam procedure will be implemented at step 775 shown in FIG. 4(*b*).

The last step of the package load process 710, is to rotate the package load gripper arm 758 back to its initial vertical position for enabling the vacuum gripper 759 to pick up the next empty tray 420 from the stack of empty packages. To accomplish this vertical rotation, the rotary actuator 760 is enabled to rotate as indicated at step 736 in FIG. 4(*b*). While the rotary actuator enables pneumatic package load gripper arm 758 to rotate to its initial vertical position, the system will perform a check at step 738 to determine whether a time-out flag has been generated by the control system indicating a time-out error. If a time-out flag has not been generated, a check is made again to determine if the package load arm has fully rotated (step 739). If the time-out flag is generated by the control system as a time-out error, then the cycle jam procedure will be implemented at step 775 shown in FIG. 4(*b*).

The final step of the package load process 710 is to update the counter that keeps track of the number of empty packages in the package supply stack. This is indicated as step 740 in FIG. 4(*b*).

Figure 29:
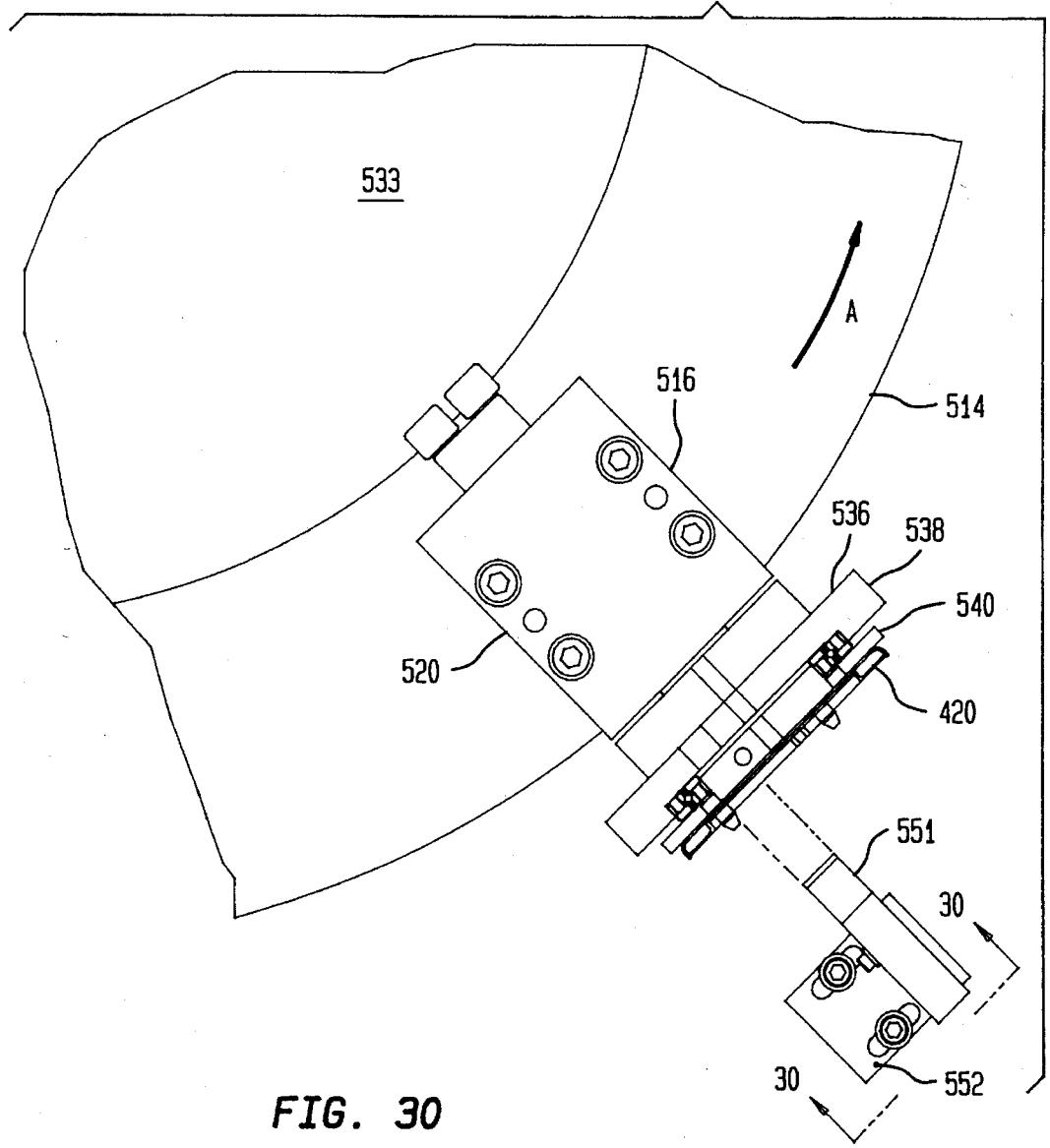
FIG. 29 illustrates, generally diagrammatically a package detector assembly operatively utilized in conjunction with the rotary disk as shown in FIG. 25.
Figure 30:
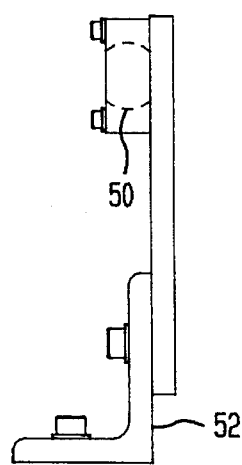
FIG. 30 illustrates an elevational view of the detector assembly as viewed in the direction of line 30—30 in FIG. 29.

(2) The second of the successive workstations located about the rotary suture wind and package dial 500, is the package detection station 450 shown in FIG. 4(*a*) as step 750. The package or tray 420 detecting workstation 450, as shown in FIGS. 29 and 30, which may be optional on the machine, includes a suitable sensor 551 which is mounted on the arm of a stationary bracket arrangement 552 to provide assurance that a tray 420 has actually been physically positioned on the support surface or platform 542, and retained thereon by means of the guide pins 544 projecting radially outwardly through the apertures in the tray 420. Specifically, sensor 551 is interfaced with and adapted to provide this information to the control system 99 for the packaging machine as to the required presence of a tray 420 in order to enable subsequent packaging steps to be implemented by the packaging machine responsive thereto.

The control process 750 for package tray 420 detection at station 450 is illustrated in FIG. 4(*c*). The only step indicated as step 749 in FIG. 4(*c*), is to verify by the sensor 550 that the package tray 420 is present. If it is not present, then the cycle jam procedure will be implemented at step 775 shown in FIG. 4(*c*).

Needle-Suture Load to Package Station (3) The third workstation indexed in the direction of arrow "A" shown in FIG. 25 involves the multi-axis gripper 155 of the rotary swage dial 150 for inserting a specified number of surgical needles and attached sutures into the suture tray 420 indexed by the packaging dial 500 in a confrontingly opposed relation to the multi-axis gripper. The needles are fed by the multi-axis gripper 155 so as to be positioned on a suitable clamping structure formed integrally with the central surface portion of the suture tray 420, as shown in FIG. 46 of the drawings and explained in detail in copending patent application Ser. No. 08/181,626 (attorney docket No. 8925) assigned to the same assignee of the present invention and incorporated by reference herein.

Figure 31:
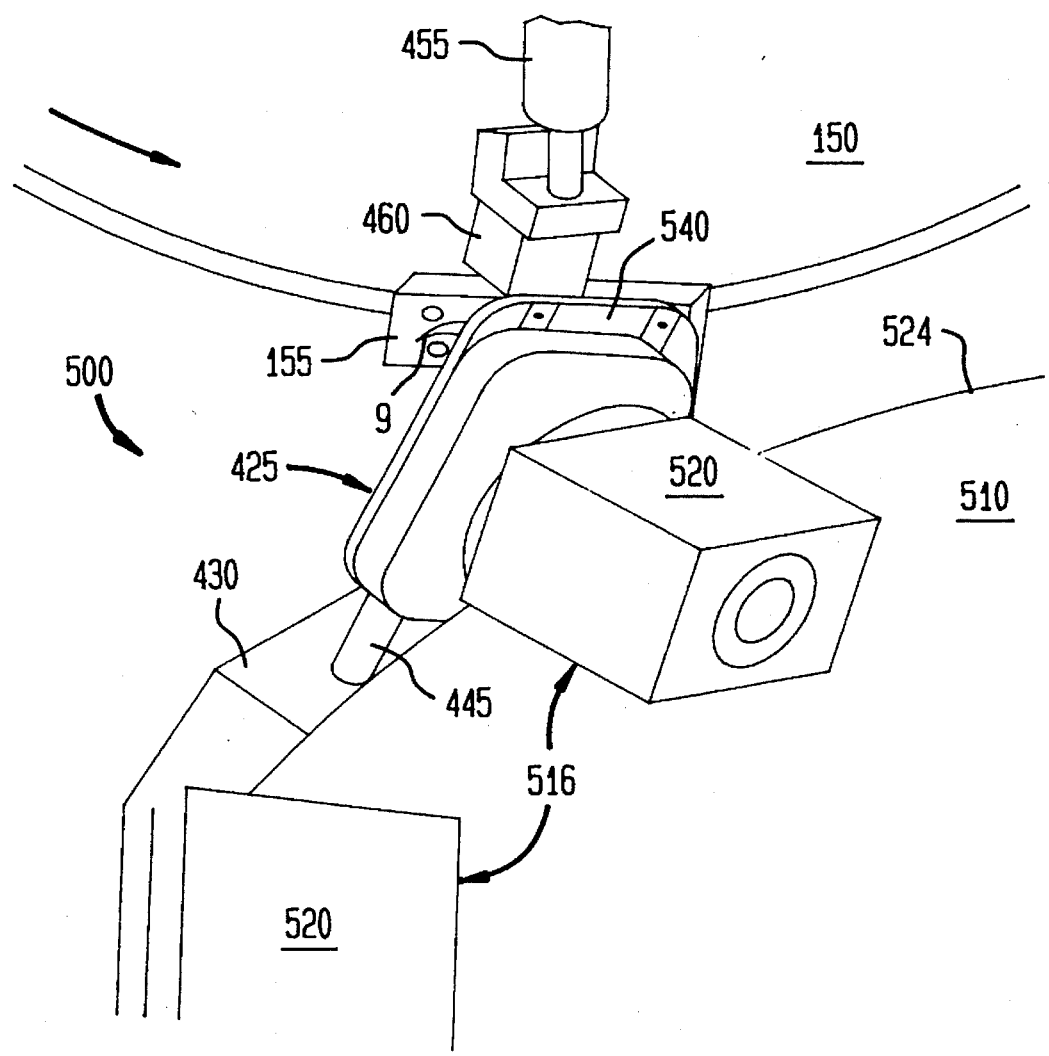
FIG. 31 is a perspective view of the discharge station 600 where rotary suture winding and packaging turret 514 indexes empty package 420 for receiving an armed needle from the multi-axis gripper 155.

Generally, to load the first armed needle into the empty package 420, the tool nest 516 is brought to station 600 in its home position as shown in FIG. 31. Simultaneous therewith, the multi-axis gripper 155 is indexed from the pull-test station 300 to station 600 where it is then extended toward the empty package 420, as described above with respect to step 14 of FIG. 3(a), to deposit the needle 9 within a pair 418 of needle receiving notches or clamping grooves 416 formed between integrally molded protruding fences 419 in the face 426 of the tray 420. Specifically, after the multi-axis gripper 155 has been extended toward the tray in the manner described above, the control system 99 actuates solenoid 455 to enable push rod 460 to depress the plunger 149 on the multi-axis gripper so that it may release its grip of the armed needle 9 and park the needle onto the package. This constitutes needle handoff as indicated at step 25 in FIG. 3(a). After depositing each needle, the pins of the multi-axis gripper are returned to their gripping (but empty) position as indicated at step 31(c) in FIG. 3(a) for subsequent indexing to the next workstation, where a new needle will be picked up for swaging.

Figure 32A:
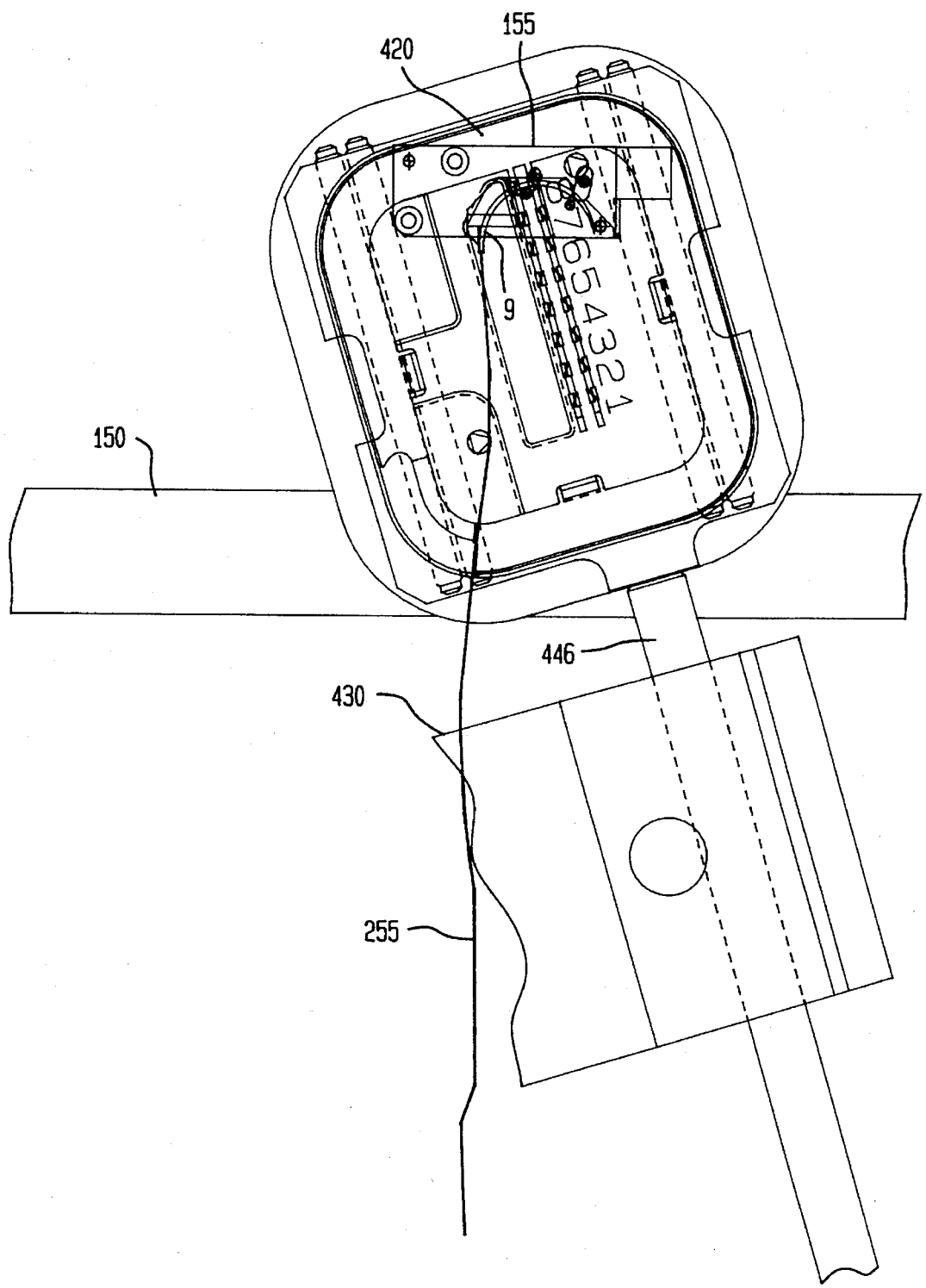
FIG. 32(a) illustrates, on an enlarged scale, the suture tray of FIG. 46 with the device for elevating the tray to enable a plurality of needles to be parked therein.
Figure 32B:
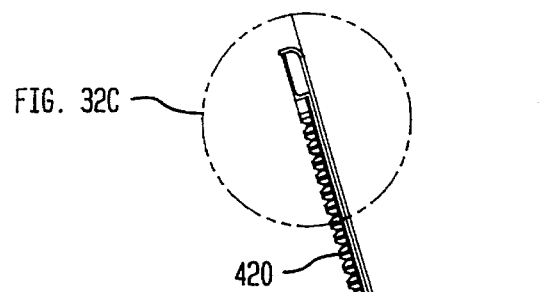
FIG. 32(b) illustrates a side view of the suture tray.
Figure 32C:
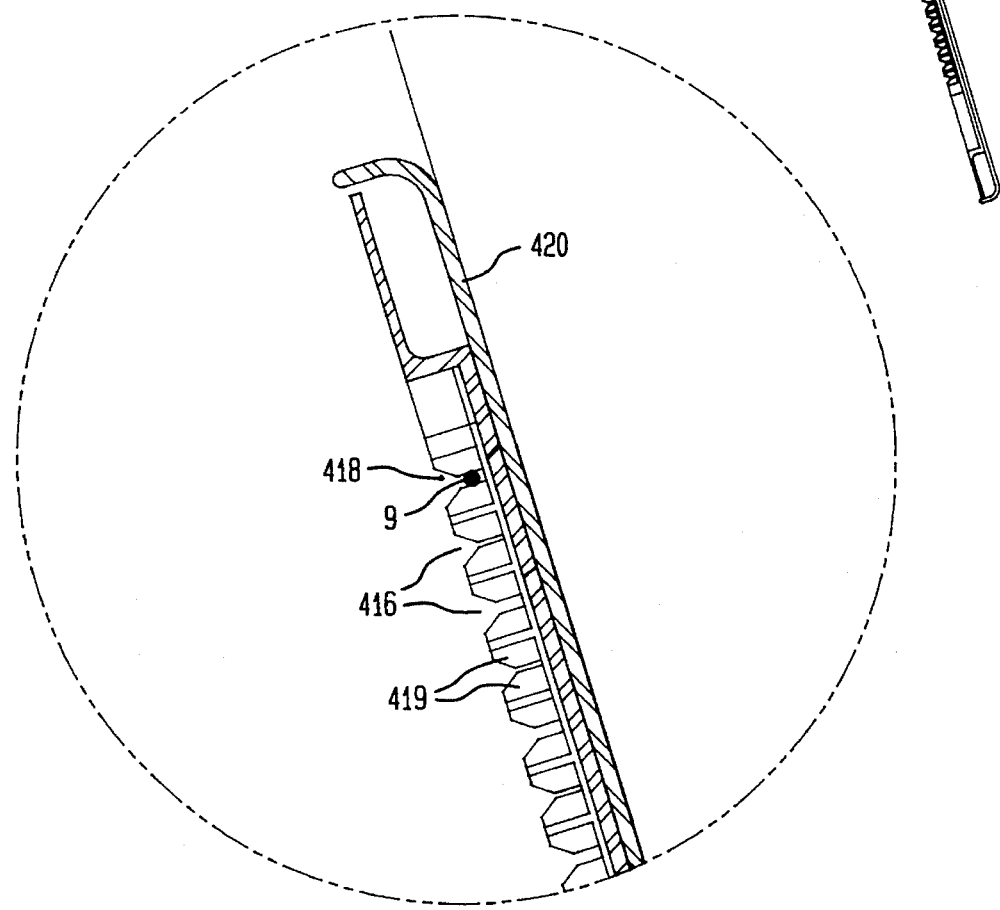
FIG. 32(c) illustrates an enlarged fragmentary view of the encircled portion of FIG. 32b.

As shown in FIG. 32(a), each paired set of notches 418 are consecutively numbered and lie approximately 0.25 inches apart. The first needle is preferably loaded at the eighth or "home" position as shown in FIG. 32(a), but it can be just as easily loaded in the first position labelled "1". As illustrated in FIGS. 31 and 32(a) through 32(c), the tool nest 516 assembly and, consequently, the empty tray 420 is slightly tilted from the vertical with respect to the orientation of the multi-axis gripper 155 so that the curved needle will be accurately deposited within the paired notches formed in the package. This tilt, which may be about 10°–20° from the vertical, and about 16° from the vertical, may be effected due to the contact between the cam rollers 530 and an angled or sloped camming surface on cam dial plate 533 at workstation (3), as shown in FIG. 26. As a result of this tilting offset, the needles are slightly shifted relative to each other, and the sutures depending downwardly therefrom will not tend to tangle with each other.

As shown in FIGS. 31, 32(a) through 32(c), and 33(a) and 33(b), there is located at the workstation 600 a package elevator assembly 430 that registers the empty tray 420 to receive eight individual armed needles, one at a time.

As illustrated in drawings, the tool nest 516 includes the fixed body structure 520 containing the rotatable shaft 528 at which there is mounted the package tray holding platform or support surface 542 and the previously-described structure. Most of the turret stations, which as shown in FIG. 25 of the drawings are in this case eight (8) in number, require that the tool nest 516 is precisely maintained in a non-rotated vertical position, as illustrated specifically in FIGS. 26 and 28(a). This particular vertical orientation is maintained in that the circular stationary cam dial plate 533 extending between the collective workstations is contacted by the two cam followers 530, which are in the form of cam rollers 530a and 530b mounted on shaft 528 so as to straddle the longitudinal centerline of the latter, for each of the tool nests mounted on dial 514.

Figure 33A:
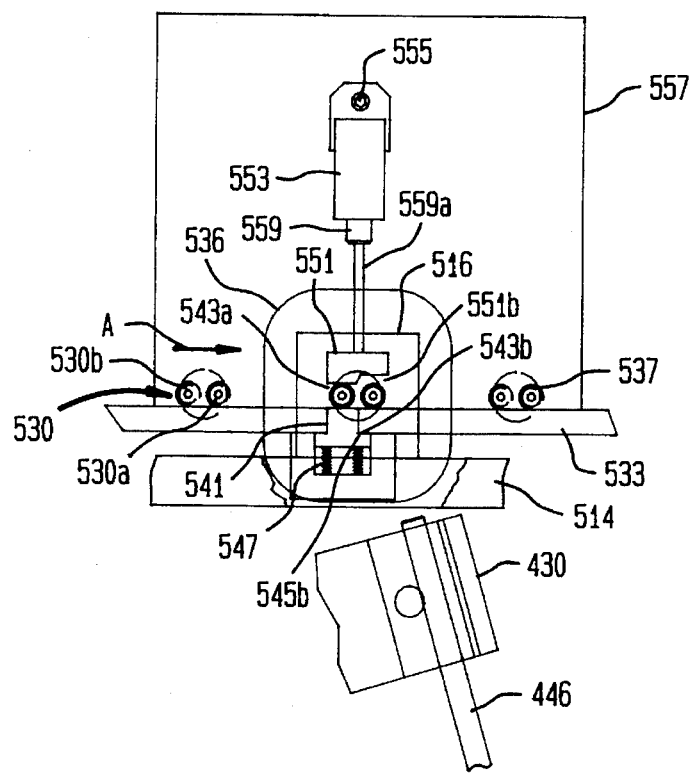
FIGS. 33(a) through 33(c) illustrate tilting mechanisms which are operatively associated with the tray elevating device of FIG. 32.

Prior to needle insertion at the needle inserting workstation, the tray 420 is adapted to be rotated into a tilted orientation through preferably an angle of 16° counterclockwise so that needles are to be positioned in a correct array and orientation in the needle park structure of the tray. This is attained by a tool nest rotating structure, as illustrated in drawing FIGS. 33(a) and 33(b), operating in functional sequence essentially as follows:

FIG. 33(a) is an elevational view of the needle-suture load to package station 600 showing the indexing turret 514 upon which the tool nest 516 has been mounted, consisting of the tray holding plate 540, including the tray supporting surface or platform 542. The shaft 528 is mounted in suitable bearings, (i.e. 529a and 529b) so as to be freely rotatable within the housing 520 of the tool nest 516, if required to do so.

As a specific tool nest 516 which has the tray mounted thereon at the first workstation, and which is adapted to be supplied with the needles, enters the needle and suture load to package workstation, in the direction of arrow A, the tool nest 516 enters the tilt mechanism 535. The two cam followers 530, hereinafter designated as cam rollers 530a and 530b, roll along the upper surface of the stationary cam dial plate 533, as illustrated by phantom lines at the left-hand side, and then pass into the index mechanism 535 stopping in the position shown in solid lines in FIG. 33(b).

A track section 541 which consists of an insert having upper surface 543 normally in coplanar relationship with the upper surface of the cam dial plate 533, and which extends through a cutout 545 formed in the cam dial plate 533, has its uppermost position determined by shoulders 543a and 543b bearingly contacting against mating lower surfaces 545a and 545b on the lower side of the stationary cam dial plate 533. Normally, the track section 541 is biased upwardly into the cutout 545 under the urging of compression springs 547 which are supported against a suitable spring support member 549. At this position, the upper surface 543 of the insert 541 is in the same plane as the upper surface of the cam dial plate 533.

A displacement cam element 551 is in a normally raised position above the cam rollers 530a, 530b to enable the latter to roll into the index mechanism 535 workstation and enabling the tilting mechanism to operate without any interference of components in the rest or dwelling position, as illustrated.

In order to rotate or tilt the tool nest 516 for appropriate needle insertion, an air cylinder 553 of the mechanism 551, which is attached by means of suitable screws 555 to a plate structure 557 mounted above the camming dial plate 533; through a cylinder rod 559a of a piston device 559 causes the downward displacement of the cam element 551. This downward motion is guided by a suitable sliding device (not shown). The lower cam surface 551a of the displacement cam element 551 exerts a downward force against cam roller 530b which, in turn, forces the insert 541 to move downwardly within the cutout 545 provided in the cam dial plate 533, compressing the springs 547, and thereby rotating the shaft 528 in the housing 520 of the tool nest 516 counterclockwise about axis 528a. The downward movement continues until the upper surface portion 551b of the displacement cam element 551 contacts the other cam roller 530a which has been displaced upwardly an amount equal to the downward displacement of cam roller 530b, and the system reaches the end of travel, causing the air cylinder to maintain the position, as shown in FIG. 33(a). The foregoing results in a rotational movement of shaft 528 to which the cam rollers 530a and 530b are fastened, and resultingly of the support surface 542 and tray mounted at the opposite other end of the shaft 528 in a counterclockwise direction, preferably to a tilting angle of 16°.

Figure 33B:
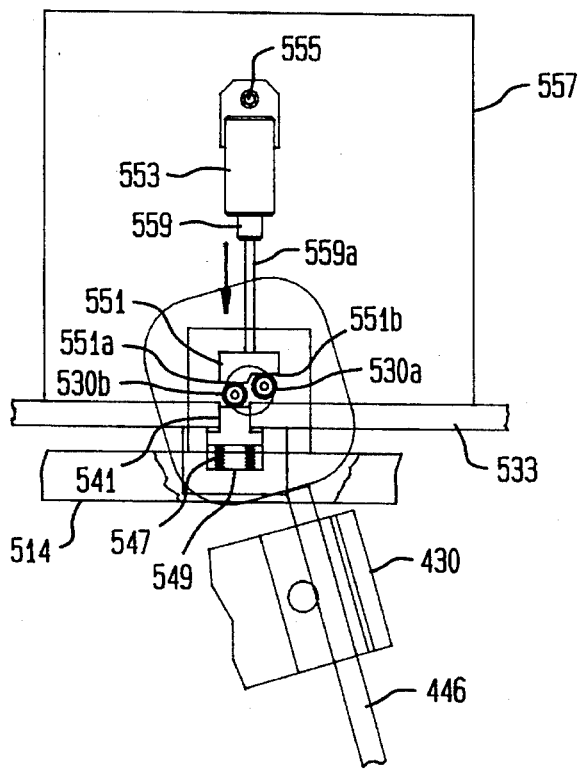

After completion of the needle insertion operation, this sequence is reversed in that the air cylinder receives compressed air so as to raise the displacement cam element 551. As a consequence, the springs 547 cause the insert 541 to be biased upwardly, causing the upper surface 543 thereof to press against the cam roller 530b and causing shaft 528 to rotate clockwise. This continues until the shoulders 543a, 543b contact the stationary surfaces 545a, 545b at the lower side of the cam dial plate 533, thereby stopping this rotational motion. This clockwise rotation of the shaft 528 causes the cam roller 530a to move a lower position until it contacts the upper surface 543 of the insert 541 which is now located in the same plane as the upper surface of the stationary cam dial plate 533. A suitable switch, for example, a proximity switch (not shown) now indicates that all of the mechanical components of this arrangement have been returned to the original position of FIG. 33(a), and the dial 514 indexes the tool nest forward for the next operating cycle. FIG. 33(b) shows a dashed line representation of the cam rollers 530a and 530b rolling on the surface of the tool cam dial plate 533 towards the right, and the shaft 528 being displaced from this workstation.

This aspect provides a structure of providing a rotary tilted positioning of a product on an indexing turret, in this application rotation of the shaft 528 and tilting the package or tray mounted thereon by means of the support plate 536 and platform 542, such as through an angle within the range of 10° to 30°, and preferably about 16°, due to the parallel offset distance between the camming surfaces 551a, 551b on the displacement cam element 551 which contact the cam rollers 530a and 530b.

Figure 33C:
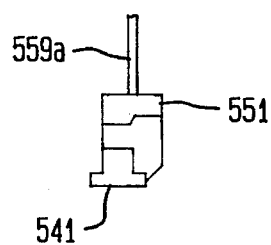

In FIG. 33(c) there is disclosed schematically an alternative design, similar to the foregoing, however, in which the individual structural components of the tilting arrangement are combined into an integral modular unit.

A shaft 446 of elevator assembly 430, as shown in FIG. 32(a), raises the plate 540 essentially vertically but slightly skewed (at about 16°) in 0.25 inch increments to sequentially receive eight needles from the multi-axis gripper 155 as described above. In this embodiment, the rotation of the swage dial 150 supplying armed needles from the pull-test station 300 at a rate of approximately 60/min. is synchronized with the vertical incrementing of the plate 540 mounting the tray 420 to maximize production rates. For example, after inserting the first armed needle 9 into the empty tray 420 into the paired notches numbered "8" as described above, the elevator shaft 446 raises the plate 540 vertically for 0.25 inches so that the next armed needle 9 may be deposited in the pair of notches 418 numbered "7." Simultaneous with the registering of the tool nest plate 540, the rotary swage dial 150 indexes the next multi-axis gripper 155 carrying the second armed needle, so that it may insert the next needle in the second position (notch "7") of the tray 420. This process takes place eight (8) times to fill a reduced size organizer package containing eight (8) armed surgical needles. After the eighth needle has been inserted in the package, the elevator assembly 430 retracts the elevator shaft 446 by conventional means such as a pneumatic air cylinder (not shown). Thus, the tray 420 which is now equipped with eight armed needles is in its initial position on the tool nest 516 and the tray is ready for further treatment at successive workstations.

In the preferred embodiment, the rotation of the swage dial 150 supplying armed needles from the pull-test station at a rate of approximately 60/min. is synchronized with the vertical incrementing of the package nest carriage to maximize production rates. As shown in FIG. 4(a) the process 760 of indexing the empty package tray 420 to receive an armed needle takes place eight (8) times until the package tray 420 has been fully loaded.

Figure 4D:
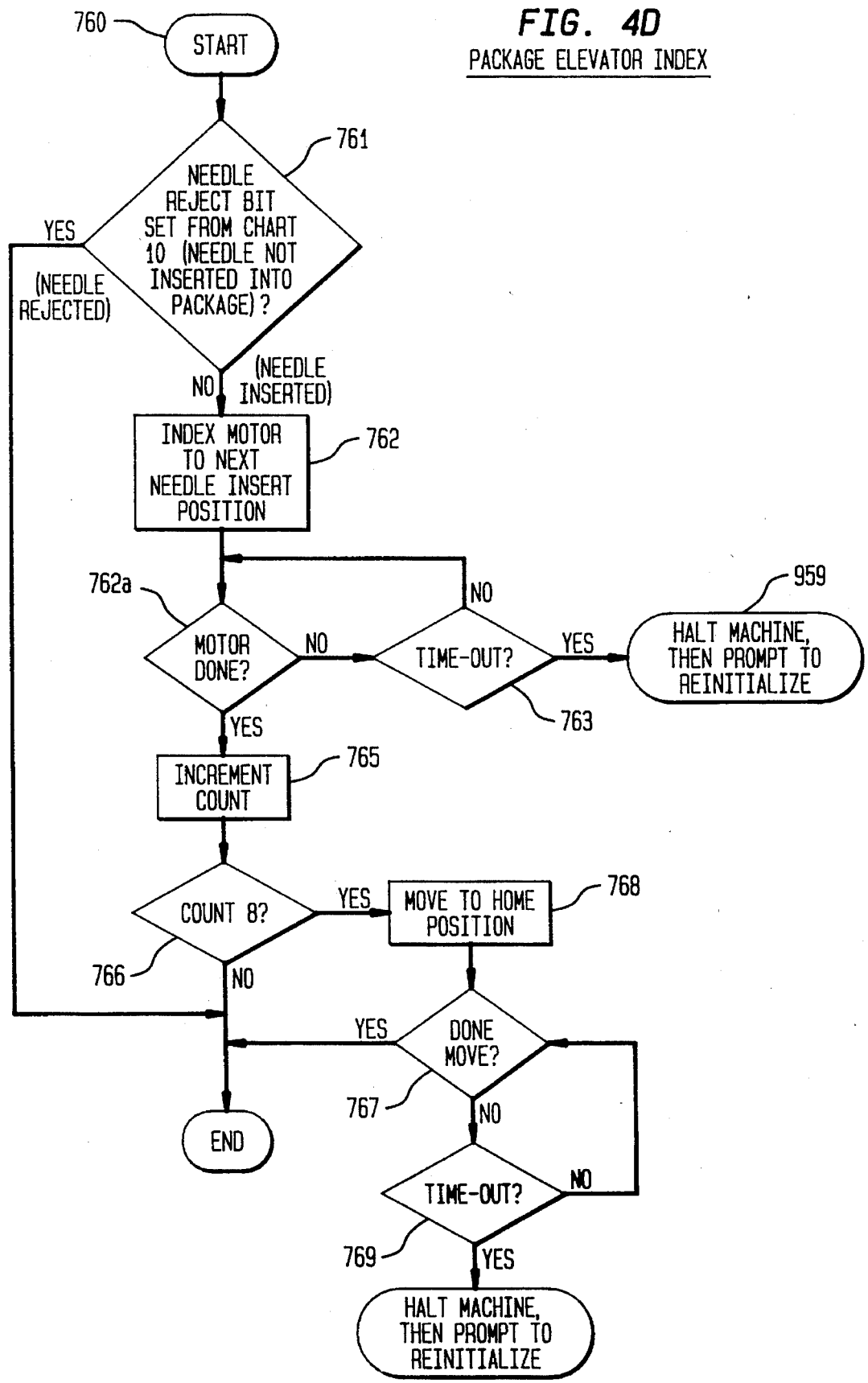

As illustrated in FIG. 4(d) the process 760 of loading armed needles to the empty package tray 420 begins with the step 761 of determining whether the NEEDLE REJECT bit had been set as a result of the needle-suture assembly failing the minimum pull-test at steps 65b (FIG. 3(e)) or 76a (FIG. 3(f)) described above. If the needle was rejected by failure of the pull-test, the process 760 ends. Otherwise, the needle-suture will be inserted into the package.

At step 762, the motor that controls the elevator assembly 430 that raises elevator shaft 445 is indexed to the next needle insert position if it is not the first needle being indexed. The status of the suture wind and package dial drive motor (not shown) is continuously monitored, as indicated at step 762a in FIG. 4(d), to ensure that the package tray 420 is properly indexed at the needle-suture load to package station 600. Until the motor is done, the system will perform a check at step 763 to determine whether a time-out flag has been generated by the control system indicating a time-out error. If a time-out flag has not been generated, the monitoring continues (step 762a). If the time-out flag is generated by the control system as a time-out error, the process will be terminated and prompted for reinitialization at step 959. Once the motor has properly indexed the empty package tray 420 with the multi-axis gripper, a counter (not shown) is incremented at step 765 to keep track of the amount of needles loaded into the respective package tray 420. For example, after inserting the first armed needle into the first set of paired notches 416 numbered "8," the plate 540 is raised vertically by elevator shaft 445 of elevator assembly 430 so that the next armed needle 9 may be deposited in the pair of notches 416 numbered "7". Simultaneous with the registering of the plate 540, the rotary swage dial 150 rotates to index the next multi-axis gripper 155 carrying the second armed needle, so that it may be inserted in the second position (notch "7") of the package 420. Each time this process takes place as indicated at step 765 the counter is incremented until the eighth count is reached. Then, when the eighth count is reached, a signal is generated by the control system 99 to enable the plate 540 and platform 542 to return to its home position on the suture wind and package dial 500 as indicated at step 768 of FIG. 4(d). A continuous check is made at step 767 in FIG. 4(d) to determine whether the package tray 420 has been returned to the home position. Until the package tray 420 has been indexed back to its home position, the system will perform a check at step 769 to determine whether a time-out flag has been generated by the control system indicating a time-out error. If a time-out flag has not been generated, the monitoring continues (step 767). If the time-out flag is generated by the control system as a time-out error, the process will be terminated and prompted for reinitialization at step 959. When the package tray 420 carrying the eight armed needles is in its home position, it is ready for further packaging at the subsequent stations along the suture winding and packaging dial 500. As indicated at step 967 in FIG. 4(a), a set DONE bit is generated for use by the control system computer 99.

In an alternative embodiment, the needle-suture assemblies may first be parked in the package tray notch labelled "1" with the elevator assembly 430 in its most raised position. Contrary to the operation described above, the elevator assembly may be subsequently decremented in equal steps with the needles successively inserted in locations "2"–"8" i.e., with the last (eighth) needle-suture assembly being parked in the eighth position in the tray 420 and the package tray and tool nest in its home position.

A suture check may also be performed at the needle-suture load to package station 600. One way of implementing this suture check would be to situate a suitable LED and phototransistor (or photodiode) combination in the travel path of the needle-suture assembly. If a suture portion of the needle-suture assembly is present, then the suture will break the light beam of the LED combination which would indicate that a suture is present. If the light beam of the LED combination is not broken in the machine cycle, this would indicate that a suture is not attached to the needle, and the package will be flagged as being defective. Note that this suture check may be performed at the swaging station after a needle is swaged or even after minimum pull-testing.

Figure 34:
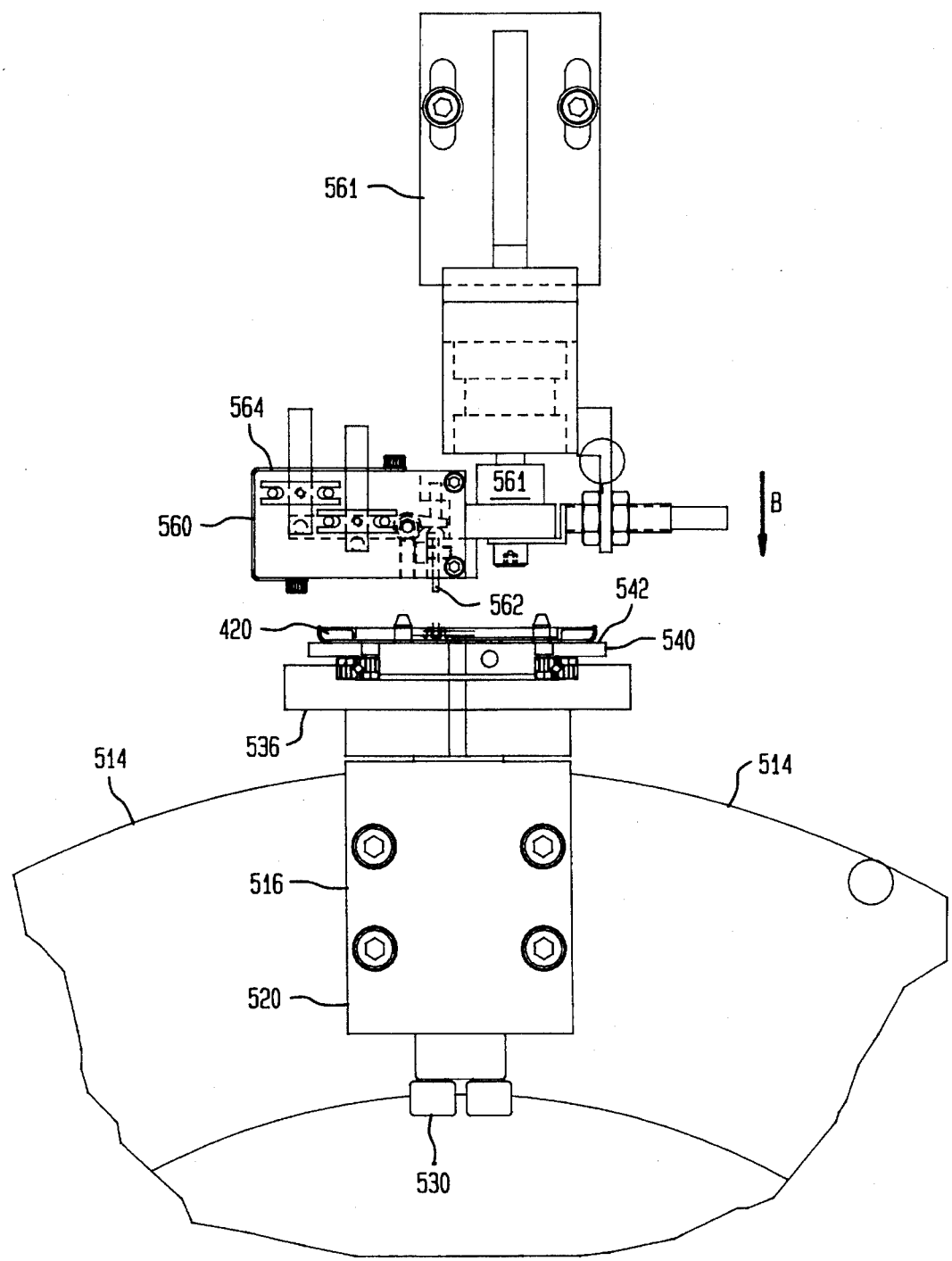
FIG. 34 illustrates a side view of the needle detector arrangement.

(4) Although not indicated in FIG. 4(a) an optional needle detector workstation 475 may be provided for verification of the presence and proper positioning of the needles and sutures having been introduced into the tray 420 by the multi-axis gripper 155, as illustrated in FIG. 1. As shown in FIG. 34, needle detector unit 560 consisting of a stationary bracket unit is adapted to be positioned opposite the platform 542 indexed in front thereof and mounting the needle-filled tray 420, and then advanced axially towards the latter to enable a plurality of sensors 562 mounted on a housing 564 movable thereon and interfaced with control system 99 to ascertain that the appropriate number of surgical needles have been properly introduced into and parked in proper array in the tray 420 by the multi-axis gripper 155 at the preceding workstation 600. Upon the needle sensors 562 verifying to the control system 99 the presence of the required quantity and parking of the surgical needles in the tray 420, the sensors 562 and housing 564 are retracted away from the tray 420 on platform 542 to enable the suture wind and packaging dial 500 to index the tool nest 516 forwardly to a further workstation.

Figure 4E:
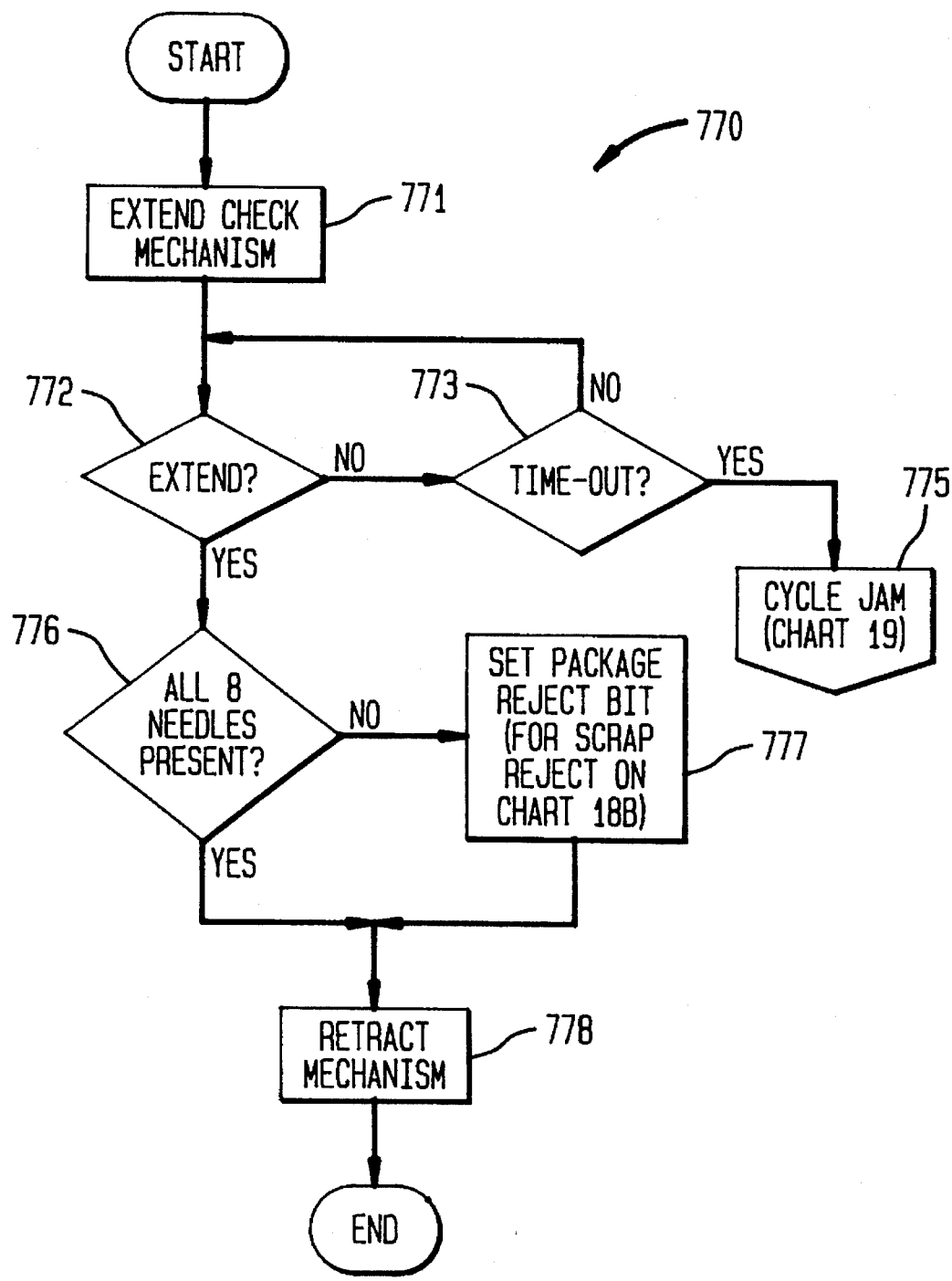

The control process 770 for needle detection at station 475 is illustrated in FIG. 4(e). The first step indicated as step 771 in FIG. 4(e), is to extend the needle detector unit 560. A continuous check is made at step 772 in FIG. 4(e) to determine whether the needle detector unit 560 has been extended. Until the needle detector unit has been fully extended, the system will perform a check at step 773 to determine whether a time-out flag has been generated by the control system indicating a time-out error. If a time-out flag has not been generated, the check is made again to determine if the needle detector unit has been fully extended (step 772). If the time-out flag is generated by the control system as a time-out error, then the cycle jam procedure will be implemented at step 775 shown in FIG. 4(e).

Prior to step 771, an optional step 771a may include extending a cylinder or suitable steadying device (not shown) to aid in holding the package steady as the needle detect mechanism checks the presence of needles in the package tray.

Next, at step 776 a determination is made whether all eight (8) needles are present within the package tray 420. If not, a set PACKAGE REJECT bit is generated at step 777 for subsequent use by the control system 99 to initiate a rejection of the completed package at the cover load station 650. If, all eight (8) needles are present, then the control system initiates the retraction of the needle detector unit 560 at step 778. It should be understood that this station is optional and could very well be placed downstream of the suture winding station 550 for needle detection after the sutures have been wound around the tray.

(5) A suture winding workstation 550, to which the tray 420 is adapted be indexed, comprises a suture winding apparatus 570, by means of which sutures depending from the needles outwardly of and hanging downwardly from the tray 420 are wound into the confines of the tray 420, and particularly the peripheral channel as illustrated in FIG. 46, and as shown in FIGS. 35(a), 35(b), 35(c) and 36 of the drawings. The downwardly loosely hanging sutures extending from each of the needles, as described hereinbelow, are positionable so as to be tensioned in a stationary vacuum device or unit 572 located below the tool nest 516 supporting the suture tray 420 at this workstation, and to thereby cause the sutures to be tensioned and bundled into a compact strand, the operational sequence of which is illustrated in and described in more extensive detail hereinbelow with regard to FIGS. 35(a) through 35(c) of the drawings directed to the operational aspects of winding apparatus 570.

The cam plate member 536 of the tool nest mounting the needle and suture-filled tray 420 on platform 542 at this workstation is adapted to be contacted along the cam surface 538 thereof by cam follower components 574 located on a stylus arrangement 576 of apparatus 570, which is employed for guiding and winding the sutures into the peripheral channel of the tray 420. The stylus arrangement 576 includes a stationary cylinder 578 having a pneumatically-actuatable central piston 580 longitudinally reciprocable therein for movement towards and away from the tray 420. The cam follower components 574 comprise articulatingly connected rollers 574a and 574b contacting the peripheral cam surface 538 of the cam plate member 536, the latter of which, in conjunction with the support plate 540 mounting the tray 420, is rotated by the computer-controlled rotation of shaft 528 about a horizontal central axis 528a extending normal to the plane of the plates 536, 540 and the tray 420 so as to facilitate winding of the sutures into the peripheral channel of the tray 420, as shown and elucidated with regard to the description of operation of FIGS. 35(a) through 35(c) and 36.

Referring more specifically to the construction of the tray 420 shown in FIG. 46 of the drawings, which as indicated hereinabove is essentially the needle and suture-containing tray 420 constituting, in combination with an attached cover, the components of the multi-strand suture package of the above-mentioned U.S. Pat. No. 5,230,424. Referring to the basic constructional features thereof, the tray 420 has a planar base 580 of generally rectangular configuration extending into rounded corners 582. Extending about the periphery of the base 580 is an upstanding wall 584, and spaced inwardly thereof in parallel relationship is a further upstanding wall 586 so as to form a peripheral channel structure 588 therebetween. Extending over the channel 588 outwardly from the inner wall 586 are a plurality of contiguously arranged essentially resilient retaining fingers 590, which are cantilevered so as to extend most of the way over the channel 588 from the upper edge of the inner wall thereof for preventing sutures from lifting up out of the channel. A gap 592 formed in the array of the retaining fingers 590 along the length of the channel, preferably proximate the juncture or corner between two of the rectangular sides of the tray 420 permits the end of each of the sutures to emerge from the channel 588, as shown in FIG. 46 of the drawings.

The central region of the base 580 of the tray 420 within the inner wall 586 includes integral structure which provides a plurality of spaced-apart gaps enabling the clamping therein of the suture needles so as to "park" the latter in the tray 420, as is clearly shown in the drawing and described in detail above, and with each of the needles having one end of a respectively associated suture attached or swaged thereto.

The functioning of the components of the stylus arrangement 576 for winding the suture into the tray 420 is described in more extensive detail in connection with FIGS.

35(a) through 35(c) of the drawings, illustrating more specifically the vacuum unit 572, a pivotable lever which is operable in conjunction therewith for tightening and tensioning the suture bundle, and the stylus arrangement 576 cooperating with the resilient fingers 590 of the tray 420 in order to feed the sutures into the channel in a winding motion as the tray 420 is being rotated by its supporting platform 542 due to rotation of shaft 528 about axis 528a.

Figure 37:
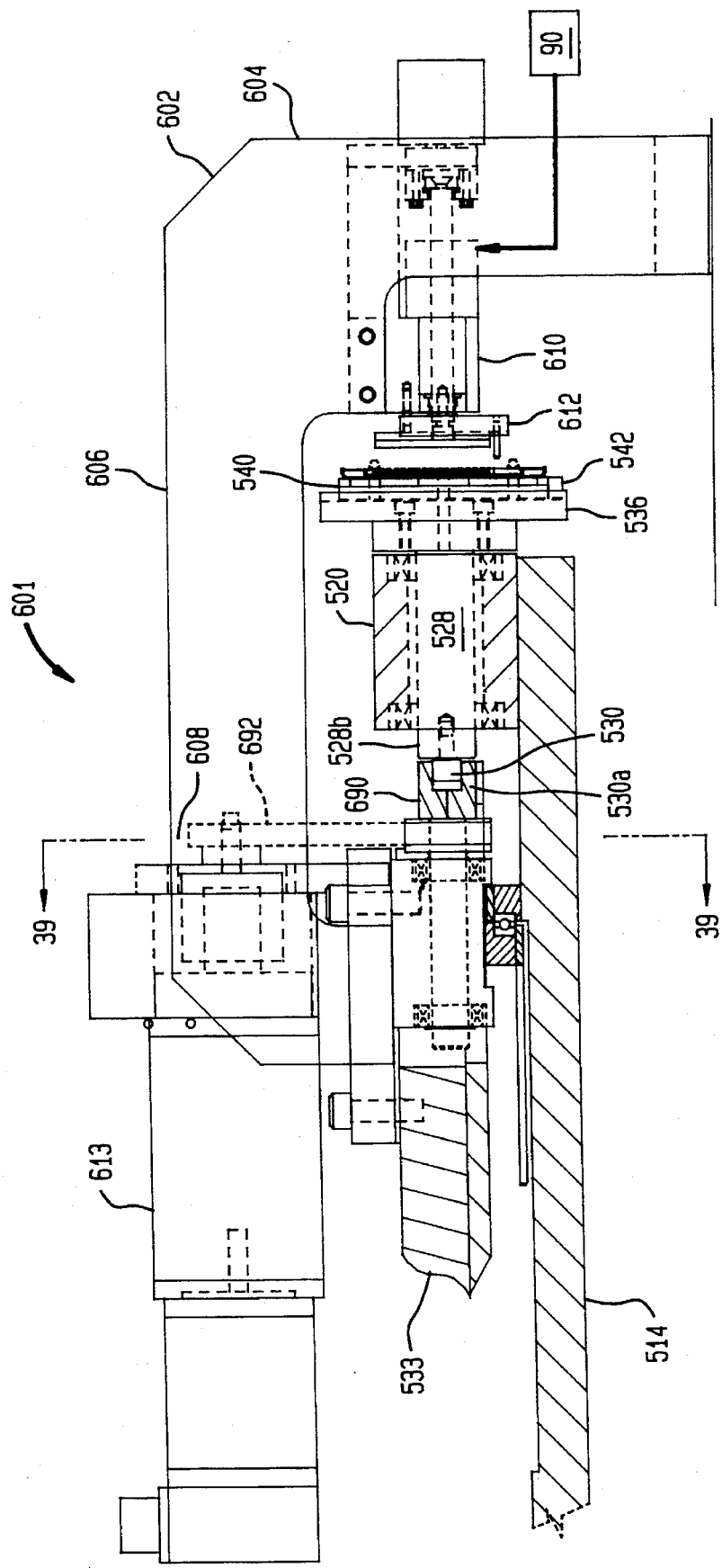
FIG. 37 illustrates a side view of a suture retaining unit in operative cooperation with the winding arrangement of FIGS. 35(a) through 35(c)
Figure 38:
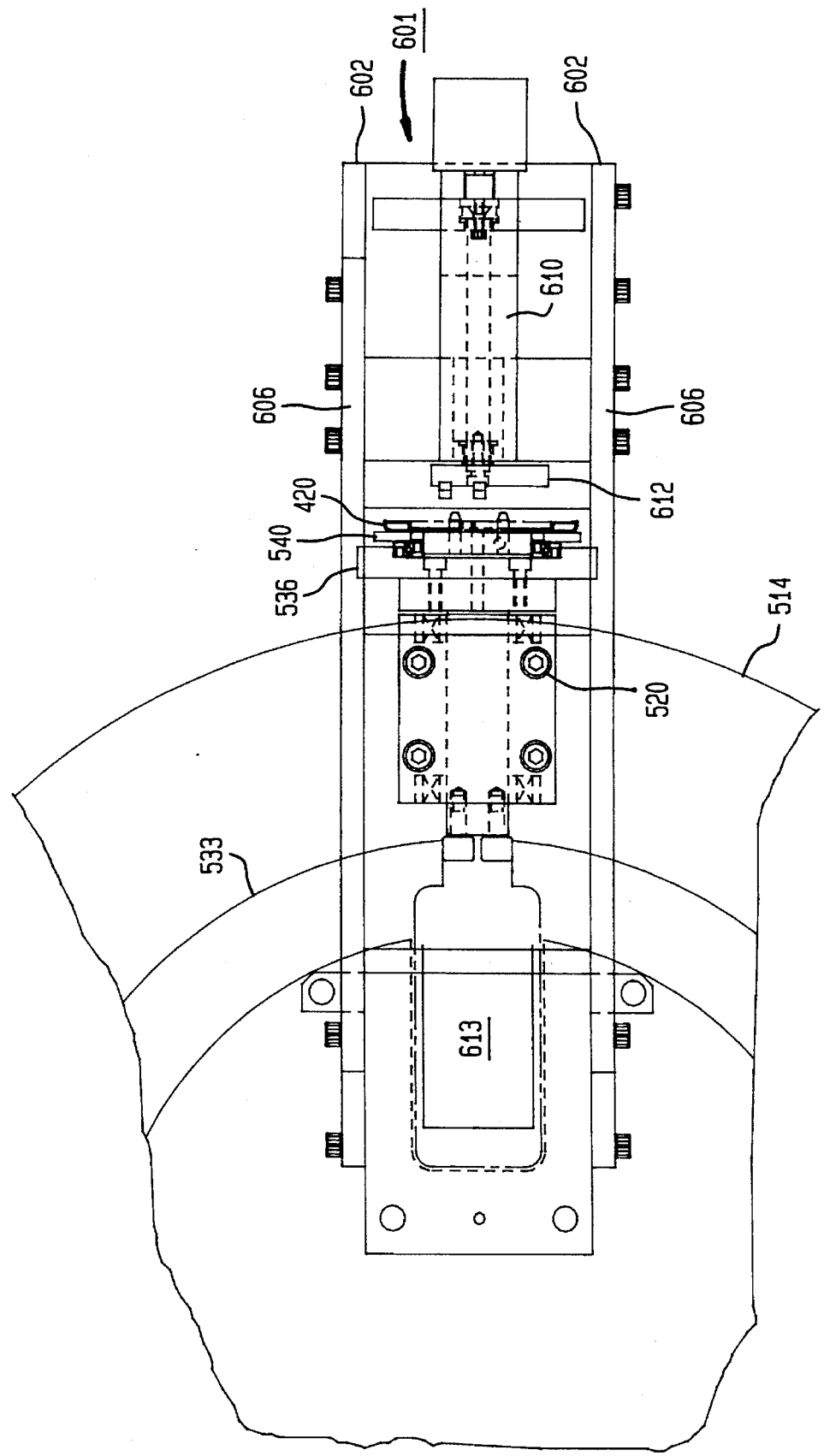
FIG. 38 illustrates a top view of the suture retaining unit of FIG. 37.

Adjacent the winding station and extending over the stylus arrangement 576 as shown in FIGS. 37 and 38 of the drawings, there is arranged a tray restraint device 601 which comprises L-shaped brackets 602 having upright legs 604 thereof fastened to a stationary surface, and top portions 606 extending horizontally over the rotary dial 514 and the dial cam plate 533 thereon, and being operatively connected through a suitable drive arrangement 608 with an inner end of the shaft 528 extending through the housing 520 and which is connected with the cam plate 536 and plate 540 mounting the suture tray. A shaft 610 extends through legs 604 of the stationary bracket 602 and upon initiation of the suture winding operation, is displaced axially towards the tray 420, either pneumatically or electrically by control means 99 such that a restraint plate 612 contacting the outwardly facing tray 420 surface comes into operative engagement with at least a center portion thereof so as to inhibit the tray 420 from being expelled outwardly from its mounted position on the platform 542 during the suture winding sequence, and, to prevent the sutures from being pulled out from their associated needles by the tension imparted to the bundled suture strands. The interengagement of the restraint plate 612 and the tray 420, and the rotation imparted to the shaft 528, will cause the shaft 610 in the leg member 604 of the bracket 602 of the restraint arrangement to rotate in conjunction with the rotation of shaft 528. Upon completion of the winding procedures, the control system 99 will cause the restraint plate 612 to be shifted away from the tray 420 into an inoperative position, so as to enable the tray 420 on its tool nest 516 to be indexed to a further workstation by the advance of the rotary dial 514 in the direction of arrow A of FIG. 38.

Figure 35C:
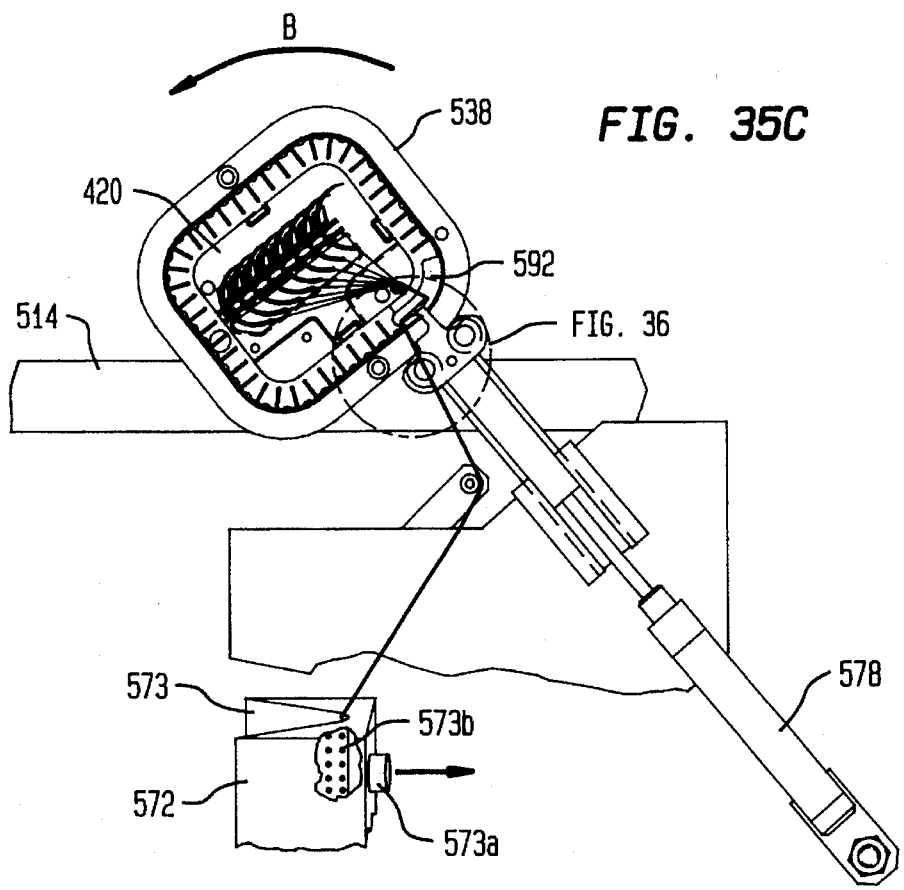
Figure 36:
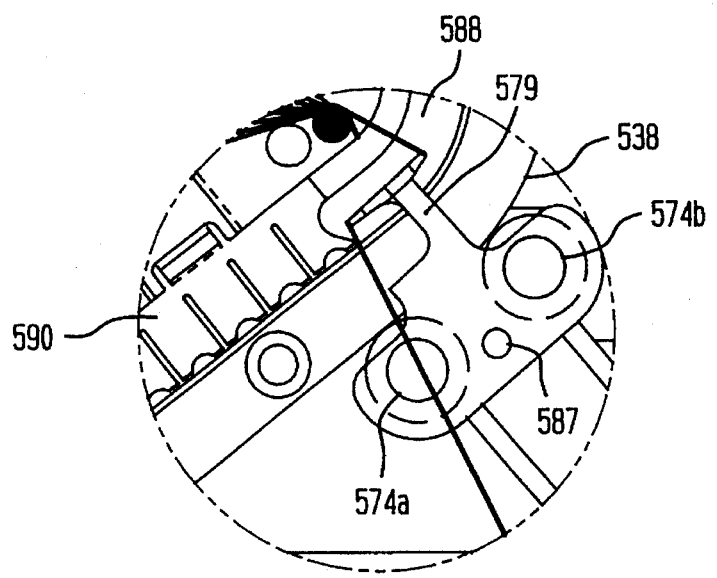
FIG. 36 is an enlarged fragmentary view of the encircled portion of FIG. 35(c)

As shown in FIG. 35(a), the rotary dial 514 has just indexed to the suture winding workstation with a tray 420 attached to its platform 542. In this position, the bundle of sutures, in this instance, eight sutures each respectively attached to one of the surgical needles parked in the tray, hang downwardly from the tray and enter the vacuum gathering device 572 which has an internal V-section 573 wherein a generated vacuum applies tension to the sutures and collects and stretches them into a bundled strand. The vacuum is created by a vacuum being pulled from an exhaust port 573a which creates an airflow into the "V" shape through suitable vent holes 573b. Concurrently, as shown in FIGS. 35(a) through 35(c), the entire tray supporting platform 542 and cam plate member 536 are subjected to rotation about axis 528a in the direction of arrow B responsive to the operation of shaft 528 by means of a programmable servomotor 613, as illustrated schematically in FIGS. 37 and 38.

As shown in FIG. 35(a), the turret index which has moved the tray to the suture winding station is complete, and this motion has dwelled in preparation for the winding function for the sutures.

The suture winding workstation as illustrated in FIG. 25 of the turret 500 includes structure for rotating the package and to accomplish the suture winding operation. This is accomplished by a motorized driving mechanism as shown in FIGS. 39(a) through 39(c) and 37. The primary rotary dial 514 as shown in FIG. 37 which has the tool nest 516 thereon containing shaft 528 mounted in suitable bearings 529a, 529b in housing 520.

Figure 39A:
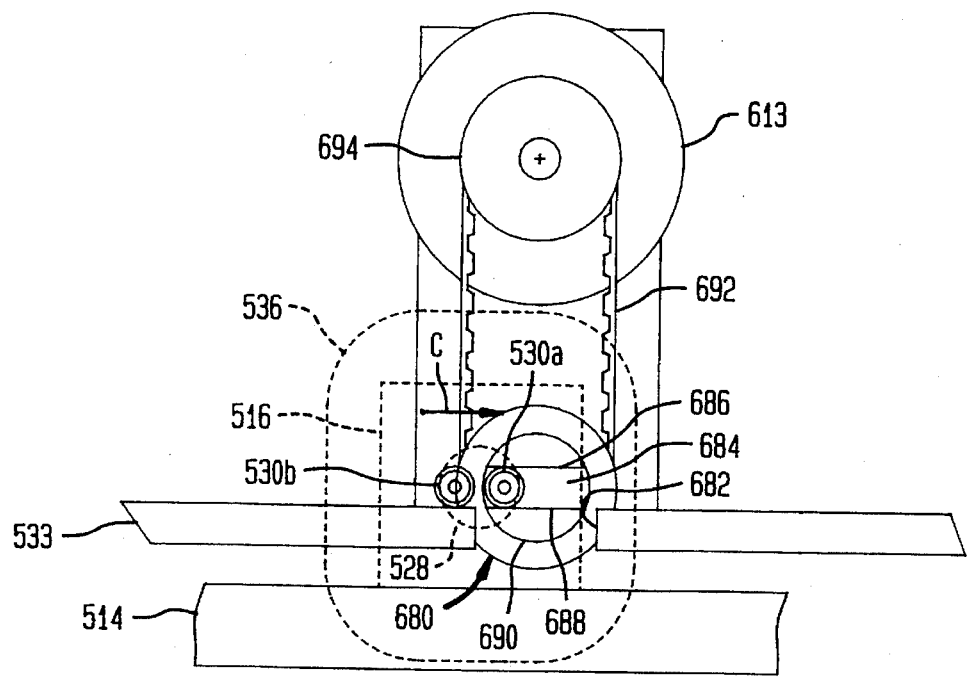
FIGS. 39(a) through 39(c) illustrate, respectively, operative drive structure for the suture winding arrangement, shown on an enlarged scale, taken along line 39—39 in FIG. 37.
Figure 39B:
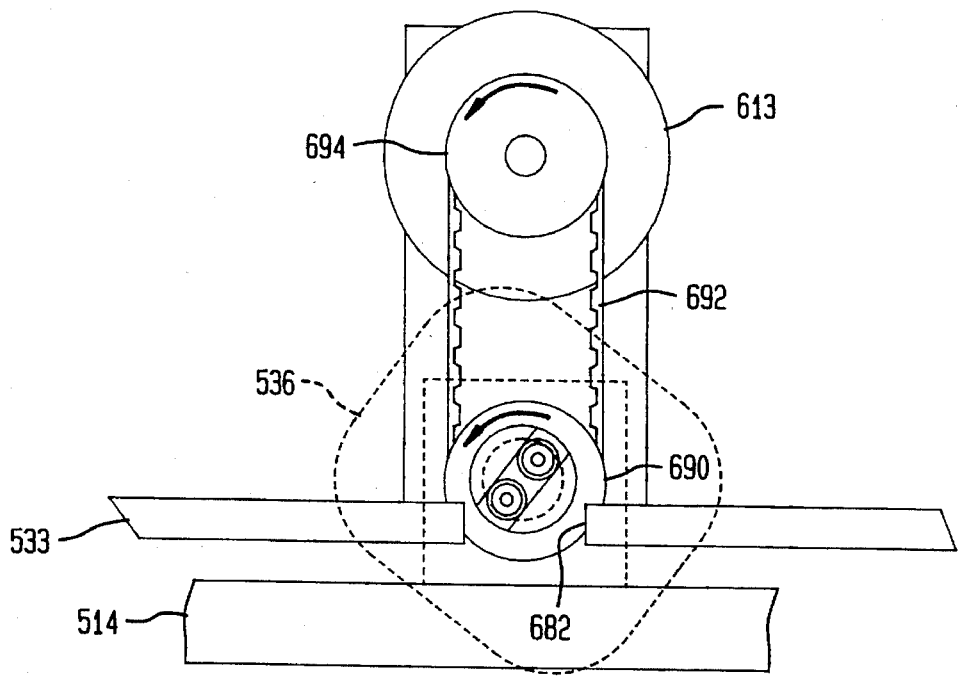
Figure 39C:
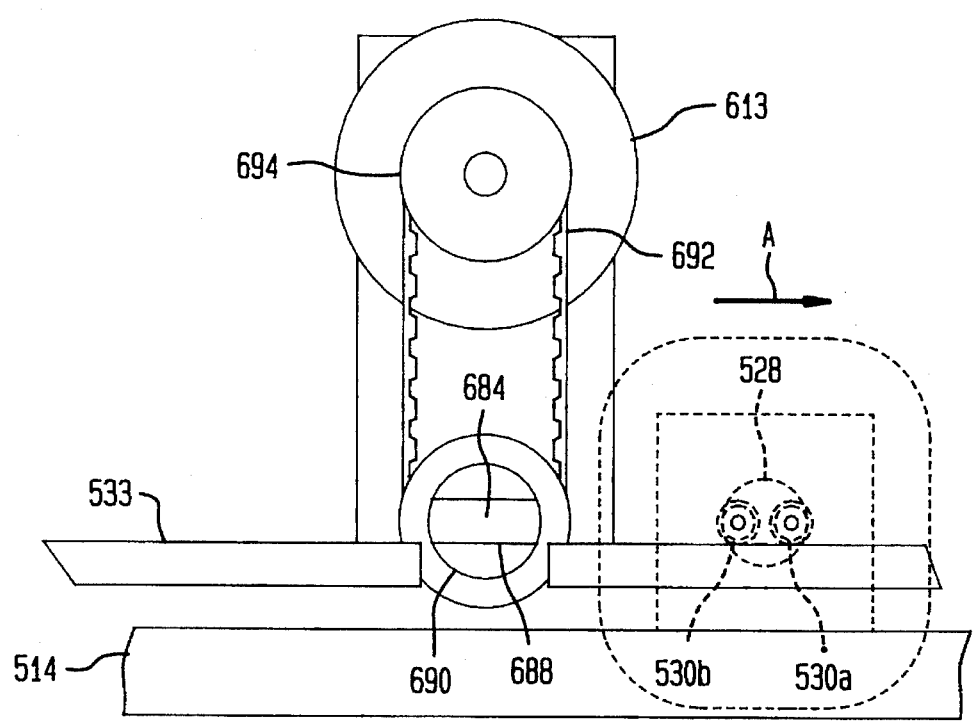

As the winding machine is indexed for a next suture winding cycle, the tool nest 516 is moved into the rotational station 680 as shown in FIG. 39(a), indicated by arrow C. The cam rollers 530a and 530b cross a gap 682 provided in the stationary cam dial plate 533 and enter a slot 684 formed by opposite parallel surfaces 686, 688 formed in a driven roller 690, the latter of which extends partly into the gap 682 produced by a cutout provided in the cam dial plate 533. The lower surface 688 of slot 684 is normally substantially in coplanar and axial alignment with the upper surface of the cam dial plate 533 enabling the rollers 530a and 530b to be centered therein. This centering action takes place in a dwell position of the dial 514 in the suture winding workstation, whereby the longitudinal centerline 528a of shaft 528 is coincident with the centerline of the driven roller 690. The drive roller 690 is mounted in suitable bearings such as to be able to be rotated by the servomotor 613 driving a timing belt 692 extending from a driving roller 694 to the driven roller 690 so as to operatively interconnect the rollers 690, 694.

When the winding cycle is started at the suture winding station, as shown in FIG. 35(a), the servomotor 613 drives the driving roller 694 which, in turn, drives the driven roller 690 through the timing belt 692. At the end of the winding operation, the driven roller 690 is stopped to cause a horizontal orientation to be assumed by the slot 684 and the opposite surfaces of the slot are coplanar or coextensive with the upper surface of the cam dial plate 533. The dial 514 then indexes in the direction of arrow D, advancing the cam rollers 530a and 530b out of the slot 684 of the driven roller 690 and onto the upper surface of the tool camming plate 533, thereby locking the support plate and tray into a vertical tray orientation which is secured against rotation. A suitable switch, such as a proximity switch (not shown) assures that the driven roller 690 is in the horizontal slot orientation before indexing the dial 514 forwardly, thereby preventing any mechanical interference between components which could damage the latter. The rollers 690 and 694 may be suitable sprocket wheels, and the timing belt 692 a sprocket belt or chain.

The programmable servomotor 613 which rotates shaft 528 having the tool nest 516 fastened thereto and, effectively, the support platform 542 and cam plate 536 for the tray 420 about its center rotational axis 528a has completed an initial counter-clockwise rotation in the direction of arrow B, causing the suture bundle to wrap around a pin 575 which protrudes from the suture tray towards the viewer, when looking into the plane of the drawing. This rotation pulls the suture bundle partially out of the vacuum gathering device 572, which imparts a predetermined tension to the suture bundle causing it to become straight and the individual strands or sutures to be collected into a parallel and tightly confined group. The winding stylus assembly 576 which is mounted on a stationary plate is shown in its retracted position in cylinder 578, as it is during turret index.

In FIG. 35(b), the subsequent phase of the winding operation is illustrated wherein a suture positioning arm 577 has been actuated to rotate clockwise, bringing a roller 577a to bear against the suture bundle, thereby implementing two functions:

(a) The suture bundle length is increased between the pin 575 and the vacuum device 572 causing additional suture length to be drawn out of the vacuum device and resulting in a tighter more confined suture bundle.

(b) Moreover, the foregoing displaces the suture bundle towards the right, so that a winding stylus 579 having fingers or legs 579a and 579b can straddle the bundle in the now extended position of the stylus arrangement, and be dropped on the floor of the tray channel 588 (in a motion perpendicular to the plane of view into the drawing) with a reasonable assurance that the bundle strands will not become pinched or fall outside of the stylus legs 579a, 579b.

FIG. 35(b) also illustrates the winding stylus assembly 576 extended towards the tray 420 by the extension of the air cylinder 581 until the stylus guide rollers 574a, 574b contact the peripheral cam surface 538 of the tool nest. The air cylinder 581 maintains a force against the rollers 574a, 574b during rotation of the tray 420 for winding, acting in a manner of a spring as the rollers force the stylus head 579 and the slide 583 to oscillate. The slide oscillates within the stationary slide holder 585.

FIG. 35(c) illustrates the commencement of the tray rotation on the support surface 542 for effectuating winding of the sutures. The air cylinder exerts a constant force on the slide 583, and through a pivot pin 587 to the roller assembly 574a, 574b. The stylus 579, which is mounted in the roller assembly is maintained at 90° relative to the suture track by this action. The enlarged encircled detail view of FIG. 36 discloses the suture bundle after it is positioned below the resilient suture-retaining tray fingers 590. This also illustrates the manner in which the stylus 579 plows under the tray fingers, raising and lowering them progressively as it leads the suture bundle therebeneath and guides the bundle into the peripheral channel 588 of the tray 420. As this winding takes place, the vacuum device 572 maintains a constant essentially gentle tension on the suture bundle as it is withdrawn therefrom, and this action continues until the suture bundle ends withdrawn from the vacuum device are fully inserted by the stylus 579 under the resilient tray fingers 590 into the peripheral suture tray channel 588. At this final point of the winding cycle, the tool nest 516 mounting the tray is rotated to position the stylus in the suture channel window or gap 592, as shown in FIG. 46, whereupon the stylus 579 is raised upwardly out of the tray and the air cylinder retracts the stylus assembly, i.e. the piston rod mounting the latter, to the position shown in FIG. 35(a). Rotation of the tool nest mounting the tray with the needles parked therein and the sutures wound into the channel 588 continues in a counter-clockwise direction until the needle park is vertical with the needle points extending downwardly. The rotary disc 514 is then indexed for the next cycle, in effect, for receiving and winding a subsequent tray.

During the foregoing suture winding sequence of operation, as previously mentioned, the restraint device 601 continually maintains its contact with the tray so as to prevent the tray and the contents therein from being expelled from the support platform 542 on which the tray 420 is mounted, and also to prevent the sutures from being pulled out from the needles. The restraint device 601 is withdrawn from the tray 420 upon completion of the suture-winding procedure to enable the continued forward indexing rotation of rotary turret 510. Additionally, drive member 530a and cam followers 530 located therein are returned to a horizontal position so the cam followers can leave the slot 684 and re-enter on top of cam plate 533 without mechanical interference as dial 510 indexes for the next cycle.

The control process 800 for the package wind station 550 is illustrated in FIG. 4(f). The first step, indicated as step 801 in FIG. 4(f), is the command to rotate the positioning arm (cylinder 578) of the winding apparatus 570 to position the stylus arrangement 576 proximate the tool nest and the dwelled suture package carrying the needle suture assemblies. A continuous check is made at step 801a in FIG. 4(f) to determine whether the stylus arm has rotated to the suture winding position. Until the positioning arm has fully rotated, the system will perform a check at step 801b to determine whether a time-out flag has been generated by the control system 99 indicating a time-out error. If the time-out flag is generated by the control system as a time-out error, the process will be terminated and prompted for reinitialization at step 959 in FIG. 4(f).

The next step, indicated as step 803, is to extend the suture restraint device 601 and supply the vacuum to the vacuum unit 572 for gathering and tensioning the suture bundle. A continuous check is made at step 802a in FIG. 4(f) to determine whether the suture restraint device 601 has been extended. Until the restraint device has been fully extended, the system will perform a check at step 803 to determine whether a time-out flag has been generated by the control system 99 indicating a time-out error. If a time-out flag has not been generated, the check is made again to determine if the suture restraint device has been fully extended (step 802a). If the time-out flag is generated by the control system as a time-out error, the process will be terminated and prompted for reinitialization at step 959 in FIG. 4(f).

As shown in the pneumatic schematic diagram of FIG. 50(c), supply line 701a supplies filtered, monitored, and pressurized air to the suture restraint plate 612 which engage the rotating tray 420 and prevents it from being expelled while in suture winding rotation. The retractable operation of the suture restraint plate 612, is controlled by control lines 704c,d which operate the switch 707n under the timing and control of the control system 99.

The next step of the suture wind process is to extend the stylus arrangement 576 from its retracted position within cylinder 578 of suture winding apparatus 570, prior to winding the bundled sutures in the suture receiving channel of the tray 420, as indicated at step 805 in FIG. 4(f). A continuous check is made at step 806 in FIG. 4(f) to determine whether the stylus has been extended. Until the winding stylus 576 has been fully extended, the system will perform a check at step 807 to determine whether a time-out flag has been generated by the control system 99 indicating a time-out error. If a time-out flag has not been generated, the check is made again to determine if the stylus unit has been fully lifted (step 806). If the time-out flag is generated by the control system as a time-out error, the process will be terminated and prompted for reinitialization at step 959 in FIG. 4(f).

As shown in the pneumatic schematic diagram of FIG. 50(c), supply line 701a supplies pressurized air 5 through suitable filter 702 and pressure monitoring device 703c to the stylus slide arrangement 576 that manipulates the resilient fingers 590 as the tray 420 rotates to enable the suture bundle to wrap around the channel. The retractable operation of the stylus arrangement 576, is controlled by control lines 704c,d which operate the switch 707p under the timing and control of the control system 99.

The next step of the suture wind process is to extend the pivotable lever 577 for tightening and tensioning the suture bundle prior to winding thereof as indicated at step 811 in FIG. 4(f). A continuous check is made at step 812 in FIG. 4(f) to determine whether the lever has been extended. Until the pivotable lever has been fully extended, the system will perform a check at step 813 to determine whether a time-out flag has been generated by the control system 99 indicating a time-out error. If a time-out flag has not been generated, the check is made again to determine if the lever has been fully extended (step 812). If the time-out flag is generated by the control system as a time-out error, the process will be terminated and prompted for reinitialization at step 959 in FIG. 4(f).

After the suture bundle has been gathered and tensioned by cooperation of the pivotable lever 577 and vacuum unit 572, the motor 614 that drives the platform 540 rotates the package tray 420 from its vertical position for approximately 114° degrees to further tension the suture bundle and to position the bundled sutures within the gap 592 of the package tray to facilitate winding as indicated at step 815 in FIG. 4(f). In the preferred embodiment, the motor 614 will rotate the package tray 420 anywhere from 90° degrees to 114° as programmed in the control system. A continuous check is made at step 816 in FIG. 4(f) to determine whether the motor has rotated the package tray 420 for the appropriate angle necessary to further tension the suture strand bundle. Until the motor has been rotated, the system will perform a check at step 817 to determine whether a time-out flag has been generated by the control system 99 indicating a time-out error. If a time-out flag has not been generated, the check is made again to determine if the motor has finished rotating the platform (step 816) for 114° degrees. If the timeout flag is generated by the control system as a timeout error, the process will be terminated and prompted for reinitialization at step 959 in FIG. 4(f).

Figure 4G:
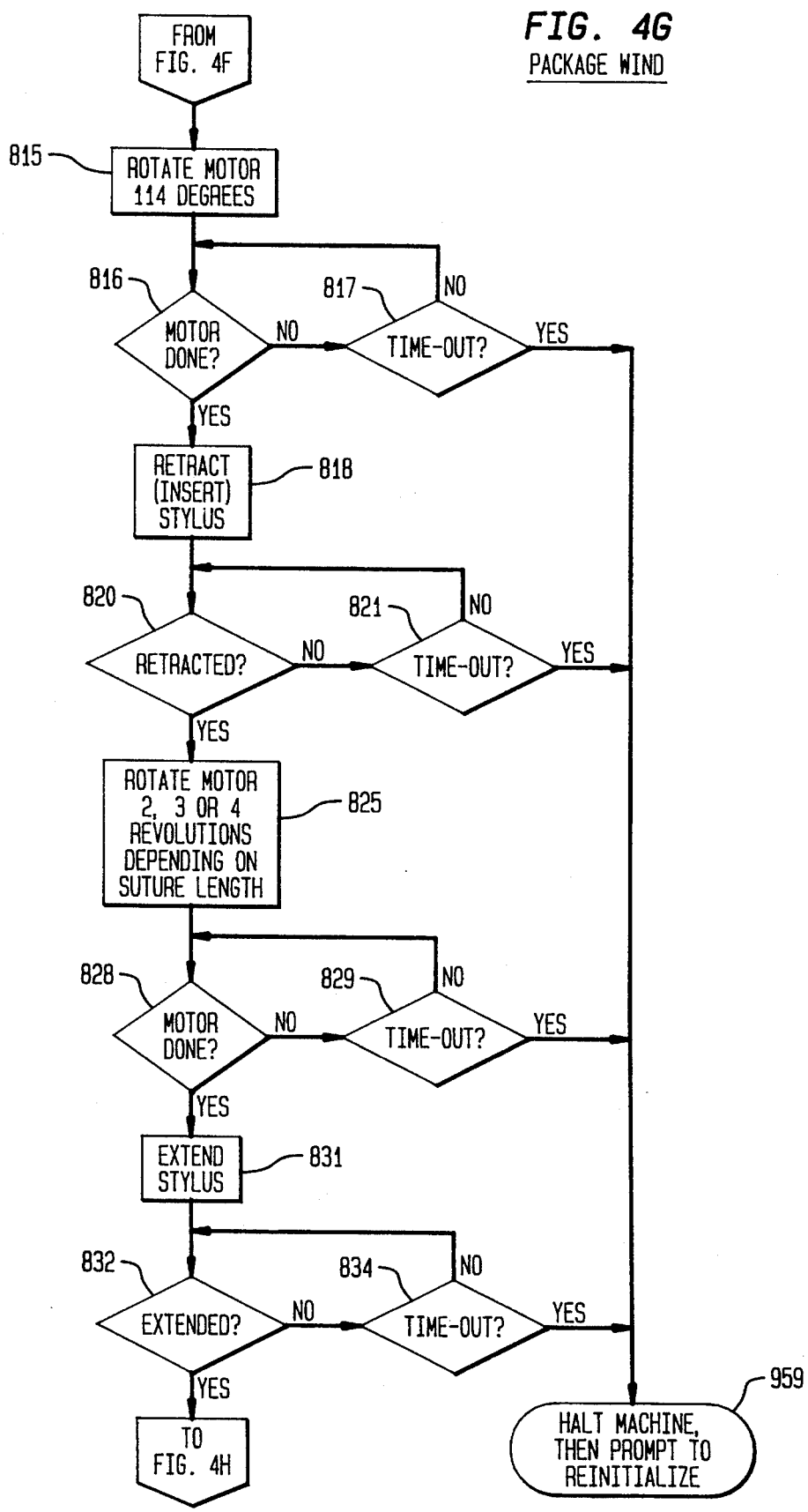

The next step of the suture wind process is to position the winding stylus 579 having legs 579a,b to straddle the suture bundle under the first resilient finger and within the suture receiving channel of the package tray 420 prior to winding thereof, and, to cause the stylus guide rollers 574a,b to contact the peripheral cam surface 538 of the tool nest in preparation for winding, as indicated at step 818 in FIG. 4(g). A continuous check is made at step 820 in FIG. 4(g) to determine whether the winding stylus has been so positioned as shown in FIG. 35(b). Until the stylus 579 is brought to its straddling positioned, the system will perform a check at step 821 to determine whether a time-out flag has been generated by the control system 99 indicating a time-out error. If a time-out flag has not been generated, the check is made again to determine if the winding stylus has been positioned (step 820). If the time-out flag is generated by the control system as a time-out error, the process will be terminated and prompted for reinitialization at step 959 in FIG. 4(g).

As shown in the pneumatic schematic diagram of FIG. 50(c), supply line 701a supplies pressurized air through suitable filter 702 and pressure monitoring device 703c, to the stylus arm cylinder 580 that positions the suture bundle within the suture receiving channel. The retractable operation of the stylus arm 581 822 is controlled by control lines 704c,d which operate the switch 707q under the timing and control of the control system 99.

After the winding stylus has been positioned to place the tensioned suture bundle under one of the resilient fingers of the channel, the motor 613 for driving the platform 540 to rotate the package tray 420 about its center rotational axis 528a, is enabled to wind the full length of the bundled sutures within the suture receiving channel of the package tray 420 as indicated at step 825 in FIG. 4(g). In the preferred embodiment, the motor will rotate the package tray 420 for three revolutions (corresponding to a suture length of approximately 18 inches), but, may be rotated for either two or four revolutions commensurate with the length of the suture to be wound. A continuous check is made at step 828 in FIG. 4(g) to determine whether the motor has rotated the package tray 420 for the appropriate amount of revolutions sufficient to secure the suture bundle within the channel of the package tray 420. Until the motor has been rotated, the system will perform a check at step 829 to determine whether a time-out flag has been generated by the control system 99 indicating a time-out error. If a time-out flag has not been generated, the check is made again to determine if the motor has finished rotating the platform (step 828). If the time-out flag is generated by the control system as a time-out error, the process will be terminated and prompted for reinitialization at step 959 in FIG. 4(g).

In the exact reverse to the procedure of positioning the stylus arm of step 818, the stylus arm is extended above the resilient fingers as indicated at step 831 in FIG. 4(g). A continuous check is made at step 832 in FIG. 4(g) to determine whether the stylus 579 has been extended. Until the stylus has been fully extended, the system will perform a check at step 834 to determine whether a time-out flag has been generated by the control system 99 indicating a time-out error. If a time-out flag has not been generated, the check is made again to determine if the stylus unit has been fully extended (step 831). If the time-out flag is generated by the control system as a time-out error, the process will be terminated and prompted for reinitialization at step 959 in FIG. 4(g).

The next step of the suture wind process is to retract the pivotable lever 577 that had performed the suture tensioning function during winding operation as indicated at step 835 in FIG. 4(f). A continuous check is made at step 836 in FIG. 4(f) to determine whether the lever has been retracted. Until the pivotable lever has been fully retracted, the system will perform a check at step 837 to determine whether a time-out flag has been generated by the control system 99 indicating a time-out error. If a time-out flag has not been generated, the check is made again to determine if the lever has been fully retracted (step 836). If the time-out flag is generated by the control system as a time-out error, the process will be terminated and prompted for reinitialization at step 959 in FIG. 4(f).

The next step is to fully retract the stylus slide back to its initial position within the stylus cylinder 581 as indicated at step 841 in FIG. 4(g). A continuous check is made at step 843 in FIG. 4(g) to determine whether the stylus slide 578 has been retracted. Until the stylus slide unit has been retracted, the system will perform a check at step 844 to determine whether a time-out flag has been generated by the control system 99 indicating a time-out error. If a time-out flag has not been generated, the check is made again to determine if the stylus slide unit has been fully retracted (step 843). If the time-out flag is generated by the control system as a time-out error, the process will be terminated and prompted for reinitialization at step 959 in FIG. 4(g).

Figure 4H:
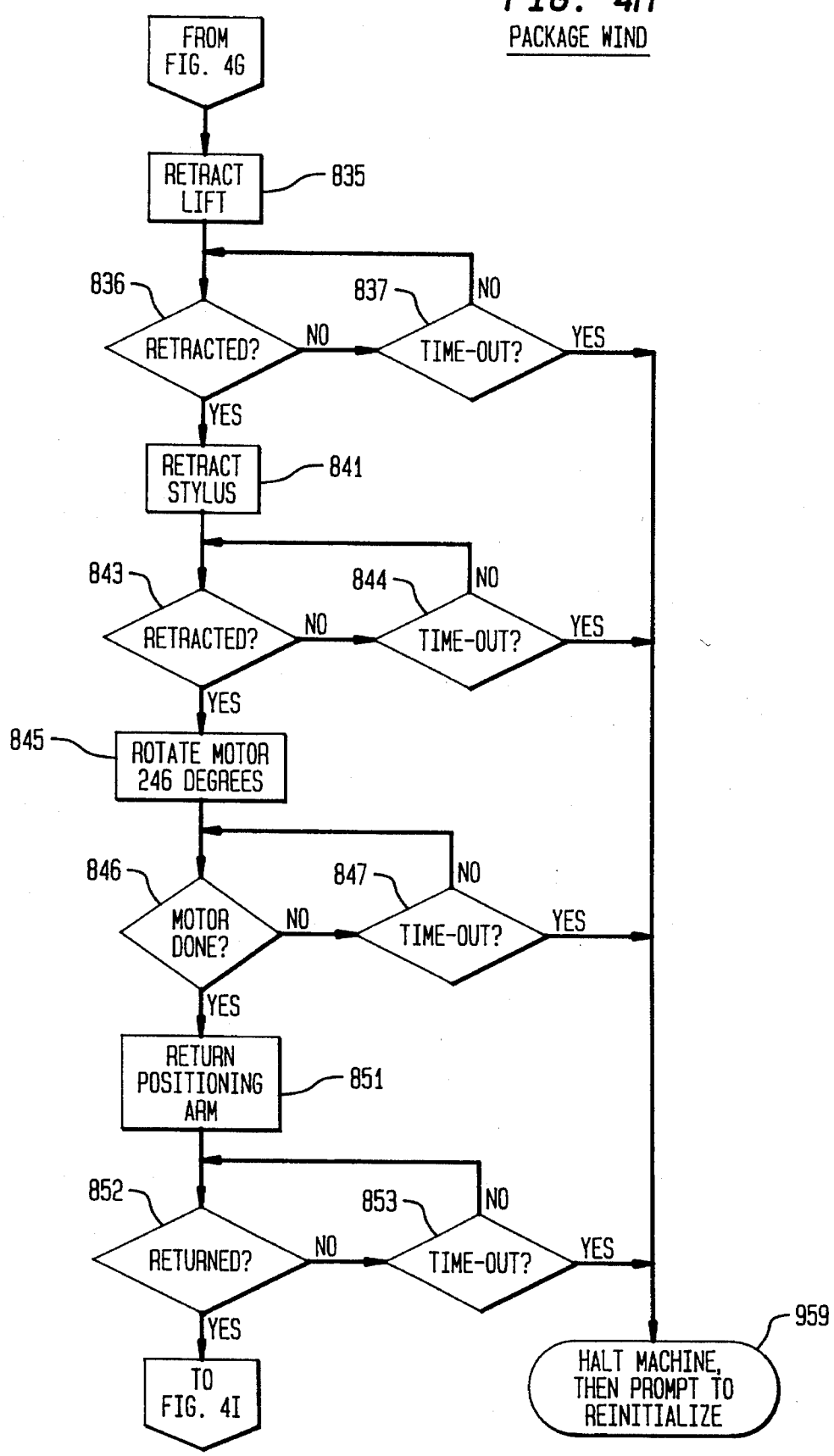
Figure 4I:
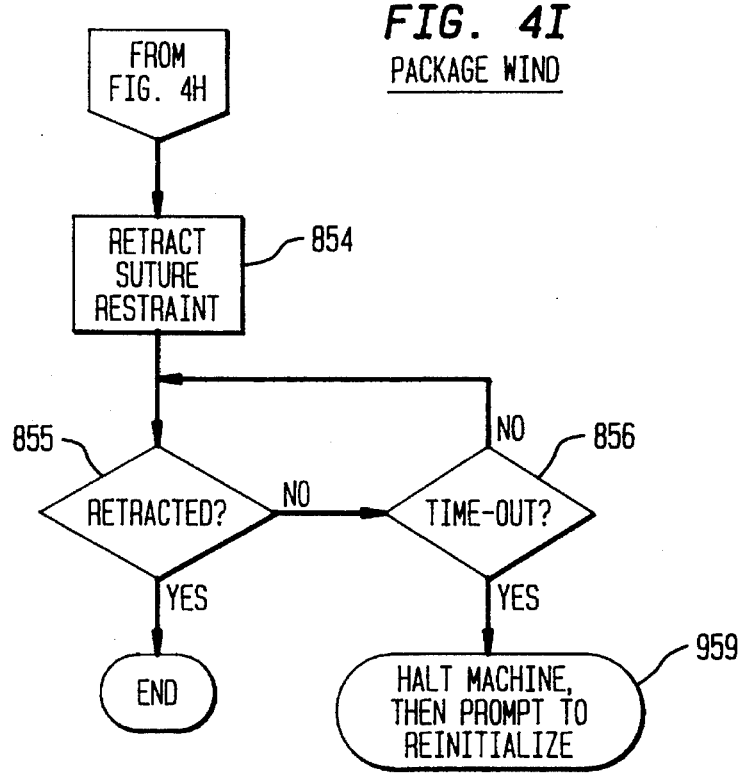

After the stylus has been retracted to its initial position, the motor 613 that drives the platform 542 to rotate the package tray 420, is enable to rotate the package tray 420 an additional 246° degrees to orient the package tray 420 back to its initial vertical positioning with the surgical needle points extending downwardly as indicated at step 845 in FIG. 4(h). In the preferred embodiment, the motor will rotate the package tray 420 for 246° degrees, or, for an angle up to 270° as programmed in the control system. A continuous check is made at step 846 in FIG. 4(h) to determine whether the motor has rotated the package tray 420 for the appropriate angle necessary to correctly orient the package tray 420. Until the motor has been rotated, the system will perform a check at step 847 to determine whether a time-out flag has been generated by the control system 99 indicating a time-out error. If a time-out flag has not been generated, the check is made again to determine if the motor has finished rotating the platform (step 846) for 90 degrees. If the time-out flag is generated by the control system as a time-out error, the process will be terminated and prompted for reinitialization at step 959 in FIG. 4(*h*).

The next to last step, indicated as step 851 in FIG. 4(*h*), is the command to return the positioning arm 578 to its retracted position away from the package and tool nest. A continuous check is made at step 852 in FIG. 4(*h*) to determine whether the positioning arm has been rotated. Until the stylus arm 578 has been fully rotated, the system will perform a check at step 853 to determine whether a time-out flag has been generated by the control system 99 indicating a time-out error. If a time-out flag has not been generated, the check is made again to determine if the suture restraint device has been fully extended (step 852). If the time-out flag is generated by the control system as a time-out error, the process will be terminated and prompted for reinitialization at step 759 in FIG. 4(*h*).

The last step of suture winding process 800, indicated as step 854 in FIG. 4(*i*), is the command to retract the suture restraint device. A continuous check is made at step 855 in FIG. 4(*i*) to determine whether the suture restraint device 601 has been retracted. Until the restraint device has been fully retracted, the system will perform a check at step 856 to determine whether a time-out flag has been generated by the control system 99 indicating a time-out error. If a time-out flag has not been generated, the check is made again to determine if the suture restraint device has been fully extended (step 855). If the time-out flag is generated by the control system as a time-out error, the process will be terminated and prompted for reinitialization at step 959 in FIG. 4(*i*).

(6) At the above-mentioned optional workstation 625 of FIG. 1, the package tray 420 and its contents are exposed to external visual inspection to facilitate a viewer or video camera to ascertain whether any of the sutures are missing, as a result of the suture winding process, or, whether any sutures extend outwardly of the channel or tray, and whether the needles are properly parked in the tray and attached to their associated sutures.

(7) At a cover-applying and attaching workstation 650, as shown in FIG. 1, to which the tray 420 is to be indexed from the preceding workstation, there is located a cover-applying apparatus 620 incorporating a pressing die structure 622 for attaching a cover to the tray 420, as illustrated in FIGS. 40 through 44 of the drawings, and for producing the suture FIG. 50(*c*), supply line 701*a* supplies pressurized air package as shown in FIG. 47.

The apparatus 620 which is essentially mounted on a suitable fixed support proximate the perimeter of the rotary turret, includes an upstanding framework 624 which includes a pivot arm structure 626 hingedly mounted therein and being articulatable about a horizontal pivot axis 628 for movement between a vertical position facing the bottom end 630 of a cover supply hopper or chute 632 and a horizontal position facing a tray mounted on platform 542 which has been indexed to this workstation. A cover pressing die 622 is mounted at the outer or free end of the pivot arm structure 626, with a plurality of resistant vacuum cups for engaging and holding the cover as it is withdrawn from hopper 632.

The pivot arm structure 626 with a pressing die 622 thereon, when upright, is adapted to engage and withdraw a tray cover which is dimensioned in conformance with the configuration of the tray. The pivot arm 626 with the pressing die 622 at its outer free end and the cover positioned thereon is swung into horizontal axial alignment with the tray on the support platform 542, as shown in FIG. 40, and through suitable actuating means, such as by means of a pneumatic cylinder, the pressing die 622 is extended towards and into contact with the tray on platform 542 so as to position the cover on the tray. The pressing die 622 contains suitable surface structure, as shown in FIG. 39, for fastening the cover to the tray, as set forth hereinbelow.

The tray cover 651 is basically a flat cover which may be of a suitably imprinted paperboard or the like material, and is applied to be fastened to the tray 420 by means of pressure die 622, as shown in FIG. 45, with the outer dimensions of the cover as previously mentioned being substantially coextensive with the peripheral dimensions of the tray, and with the cover also having apertures 652 in registration with the upstanding guide pins 544 on the platform 542.

Hereby, the surface of the pressure die 622 facing the cover includes a first surface portion 638 substantially in conformance with the flat surface of the cover 651 which has been superimposed on the tray 420, and includes three projecting posts 634, preferably at three sides about the surface 638, and as shown in enlarged scale in FIG. 46 of the drawings, which will engage tabs 656 which overlie recessed portions 654 of the tray, and cause the pre-cut tabs 656 to be separated along three edges thereof, and thereby forming latching tabs 656 which are pressed in V-shapes downwardly into the respective recesses 654 so as to have the separated edge of the folded tab 656 at that particular location engage beneath a horizontal wall structure 658 of the tray 420 extending partially over the recess 654, thereby latching the cover 651 into cooperative engagement with the upper surface of the tray at three locations.

The control process 860 for the cover load station 650 is illustrated in FIG. 4(*j*). The first step indicated as step 861 in FIG. 4(*j*), is to verify the status of the PACKAGE REJECT bit. This bit may or may not have been set at step 777 of the prior needle detect process 770 (FIG. 4(*e*)) at the needle detect station. If the bit was set, the cover will not be applied to the needle-suture package and the process will end. If all needles were detected, then the PACKAGE REJECT bit was not set, and the package cover 651 will be applied.

At step 862 in FIG. 4(*j*), the air and vacuum supply for the commercially available vacuum gripper that grips each package cover 651 from the cover stack and loads it onto the plate 540, is turned on. Additionally, a check is made to determine that the pressing die 622 structure of pivot arm 626 is operational and extended toward the stack of covers. The air and vacuum supply is supplied to the pressing die 622 having vacuum cups for retrieving a package tray from the stack, and placing a package tray cover 651 onto the package tray 420. As shown in the pneumatic schematic diagram of FIGS. 50(*c*) and 50(*d*), supply line 701*a* supplies filtered air to vacuum pump 705*b* which provides the vacuum for the vacuum gripper 821 to grasp each package cover 651 by vacuum suction. The operation of the vacuum gripper 821 is controlled by switch 707*r* under the timing and control of the control system 99.

Additionally, air supply line 701*a* provides the air supply for the gripper arm 626 utilized to manipulate, i.e., extend and retract, the vacuum gripper 821. The operation of the pivot arm 626 is controlled by control lines 704*c,d* which operate the switch 707*s* under the timing and control of the control system 99. If it is determined that the air supply is off or not at the correct operational level as monitored by monitoring device 703*e*, then the cycle jam procedure will be implemented at step 775 shown in FIG. 4(*j*) and explained in further detail below. A verification is made at step 863 of FIG. 4(j) to determine if the vacuum has been turned on. The system will perform a check at step 864 to determine whether a time-out flag has been generated by the control system indicating a time-out error. If a time-out flag has not been generated, then the vacuum is on (step 862). If the time-out flag is generated by the control system as a time-out error, then the cycle jam procedure will be implemented at step 775 shown in FIG. 4(j).

At step 865 in FIG. 4(j), the control system 99 performs a check on the stack of empty package covers (not shown) to ensure that the stack level is not too low. If it is determined that the stack of package covers is too low, then the control system will check if the package cover counter is equal to zero (0) at step 866 in FIG. 4(j). If the counter for the stack of covers is not equal to zero (0) the counter is decremented at step 867 and the extend stack release signal is given at step 868 to enable a release lever of cover supply chute 632 to extend which enables the pressing die 622 to access and vacuum grip the next package tray cover 651 from the stack as shown at step 869.

While the stack release lever is being extended, the system will perform a check at step 870 to determine whether a time-out flag has been generated by the control system indicating a time-out error. If a time-out flag has not been generated, then the release lever has not fully extended (step 869). If the time-out flag is generated by the control system as a time-out error, then the cycle jam procedure will be implemented at step 775 shown in FIG. 4(j).

As shown in FIG. 4(j) once the cover load gripper (pressing die) 622 has reached its extended position and has grasped a package tray cover 651, (step 868), the control system initiates a retract stack release signal at step 871 so that the next accessible package tray cover is retained in the cover supply chute 632 by the stack release lever as the gripper is retracted and rotated to a horizontal position for cover application.

While the stack release lever is retracting (step 871), the system will perform a check at step 872 to determine whether a time-out flag has been generated by the control system indicating a time-out error. If a time-out flag has not been generated at step 872, then the release lever has fully retracted (step 873). If the time-out flag is generated by the control system as a time-out error, then the cycle jam procedure will be implemented at step 775 shown in FIG. 4(j).

Figure 50D:
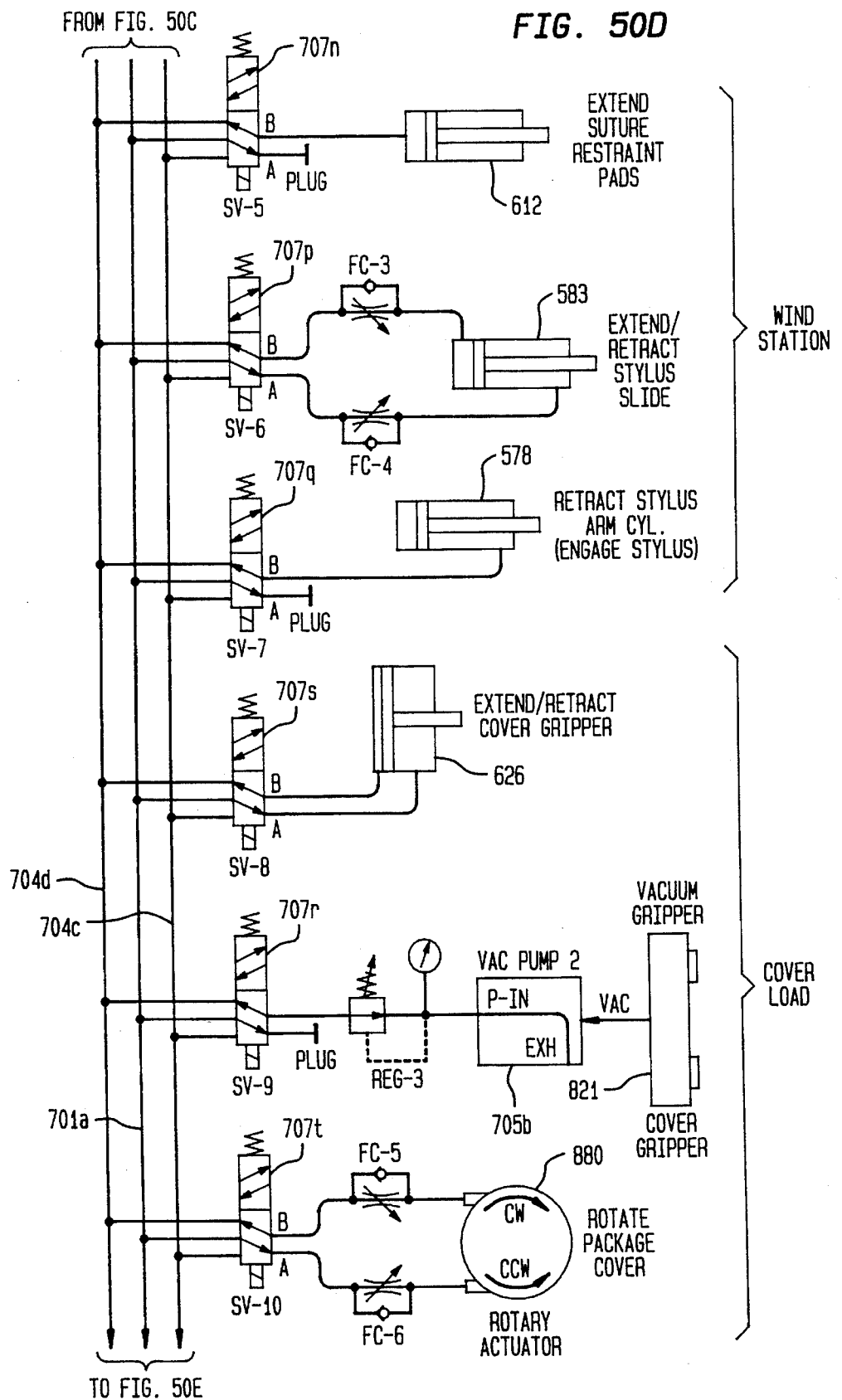
Figure 50E:
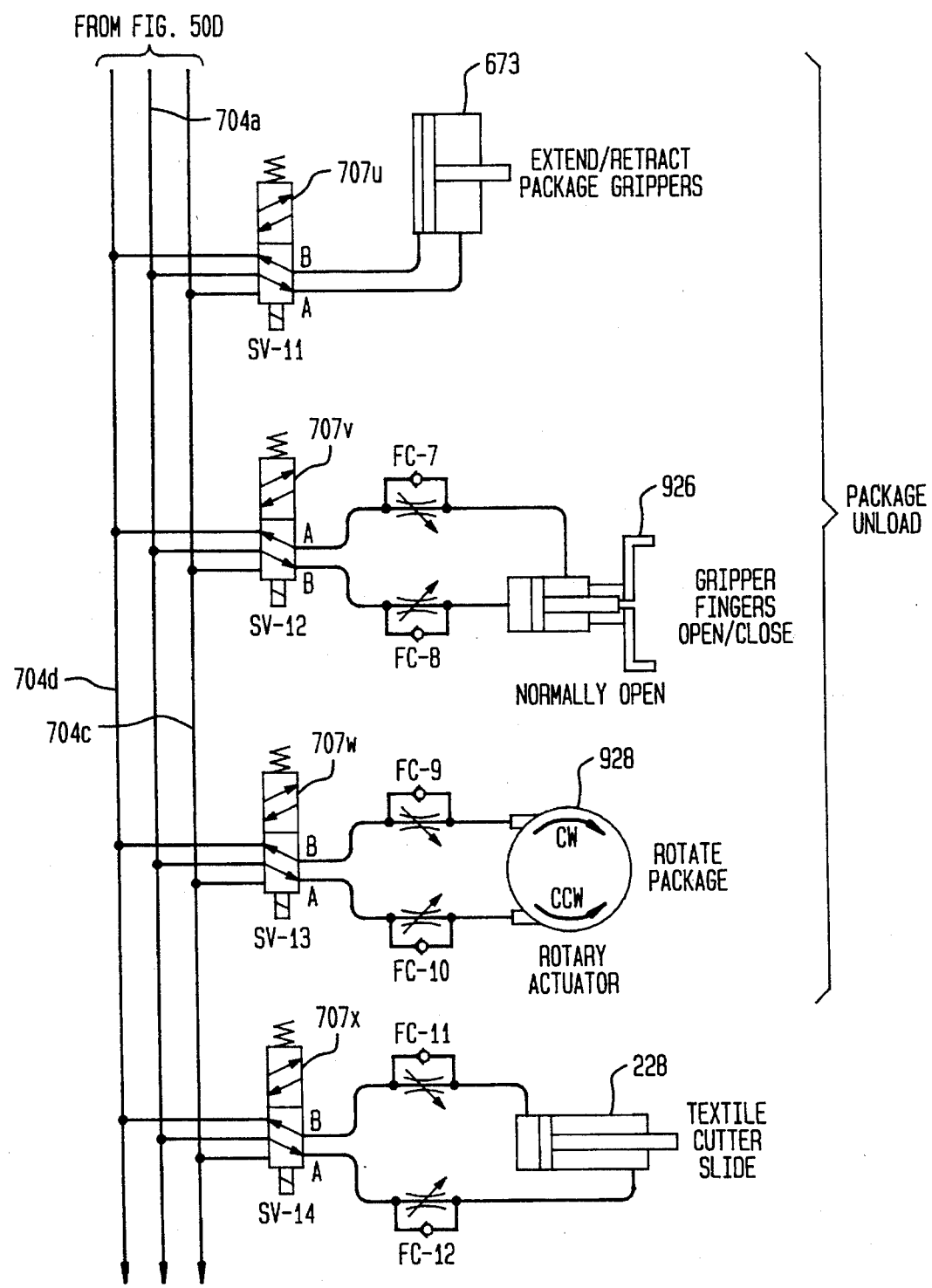

After the pivot arm 626 carrying a package cover is retracted, it must be rotated to an oriented position before being placed upon the package tray 420. As shown at step 878 in FIG. 4(j), the pivot arm structure having pressing die 621 gripping package cover 651 is rotated to a horizontally oriented position to aid in the positioning of the package cover onto the package. As shown in FIG. 50(d), pneumatically operated rotary actuator 880 rotates actuator 880 enables pivot arm 626 to rotate the package cover to a fully horizontal position. While the rotary actuator enables pivot arm to rotate the package tray cover 651, to a fully horizontal position, the system will perform a check at step 878b to determine whether a time-out flag has been generated by the control system indicating a time-out error. If a time-out flag has not been generated, then the cover applying pivot arm has fully rotated (step 878a). If the time-out flag is generated by the control system as a time-out error, then the cycle jam procedure will be implemented at step 775 shown in FIG. 4(j).

As shown in the pneumatic schematic diagram of FIGS. 50(c) and 50(d), supply line 701a supplies filtered, monitored, and pressurized air to the rotary actuator 880 which rotates the package cover 651. The clockwise and counterclockwise operation of the rotary actuator 880, is controlled by control lines 704c,d which operate the switch 707t under the timing and control of the control system 99.

Figure 48:
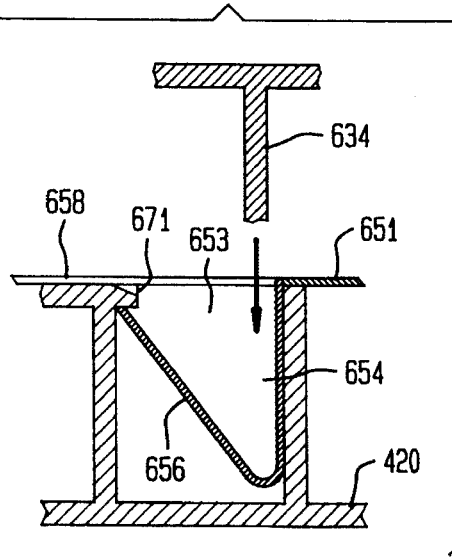
FIG. 48 illustrates, on an enlarged scale, a sectional view of one of the latching elements between the tray and an associated tray cover.

The next step of the cover applying process 860, is to transfer the package cover 651 from the vacuum gripper 821 onto the guide pins 544 of the package tray 420. To accomplish this, the pressing die 622 of pivot arm 626 is slightly extended and the vacuum mode is off switched at step 882 to accomplish the transfer. While the pivot arm is extending the system will perform a check at step 884 to determine whether a time-out flag has been generated by the control system indicating a time-out error. If a time-out flag has not been generated, a check is made again to determine if the vacuum mode has been switched (step 883). If the time-out flag is generated by the control system as a time-out error, then the cycle jam procedure will be implemented at step 775 shown in FIG. 4(j). The extension of the pneumatic cover gripper arm will drive dies 634 through tab opening 653 to position the tabs 656 into the tray recesses 654 as illustrated in FIG. 48.

After the transfer of the package cover 651 onto the package tray 420 has been completed, the cover pressing die 622 of pivot arm structure 626 is retracted from its position at the package dial 500 as shown at step 885 in FIG. 4(j). While the cover pivot arm 626 is retracting from its position at the tool nest 516 after transferring a cover, the system performs a check at step 887 to determine whether a time-out flag has been generated by the control system indicating a time-out error. If a time-out flag has not been generated, a check is made again to determine if the arm has been fully retracted (step 886). If the time-out flag is generated by the control system as a time-out error, then the cycle jam procedure will be implemented at step 775 shown in FIG. 4(j).

The next to last step of the cover applying process 860, is to rotate the pivot arm 626 to its initial vertical positioning for enabling the vacuum gripper 821 to pick up another package cover from the stack of package covers. To accomplish this vertical rotation, the rotary actuator 880 is enabled to rotate as indicated at step 889 in FIG. 4(j). While the rotary actuator enables pivot arm 626 to rotate to its initial vertical position, the system will perform a check at step 891 to determine whether a time-out flag has been generated by the control system indicating a time-out error. If a time-out flag has not been generated, a check is made again to determine if the cover pivot arm 626 has fully rotated (step 890). If the time-out flag is generated by the control system as a time-out error, then the cycle jam procedure will be implemented at step 775 shown in FIG. 4(j).

The final step of the cover load process 860 is to update the counter that keeps track of the number of package tray covers in the cover supply chute 632 for later comparison (step 865). This is indicated as step 892 in FIG. 4(j).

Figure 41:
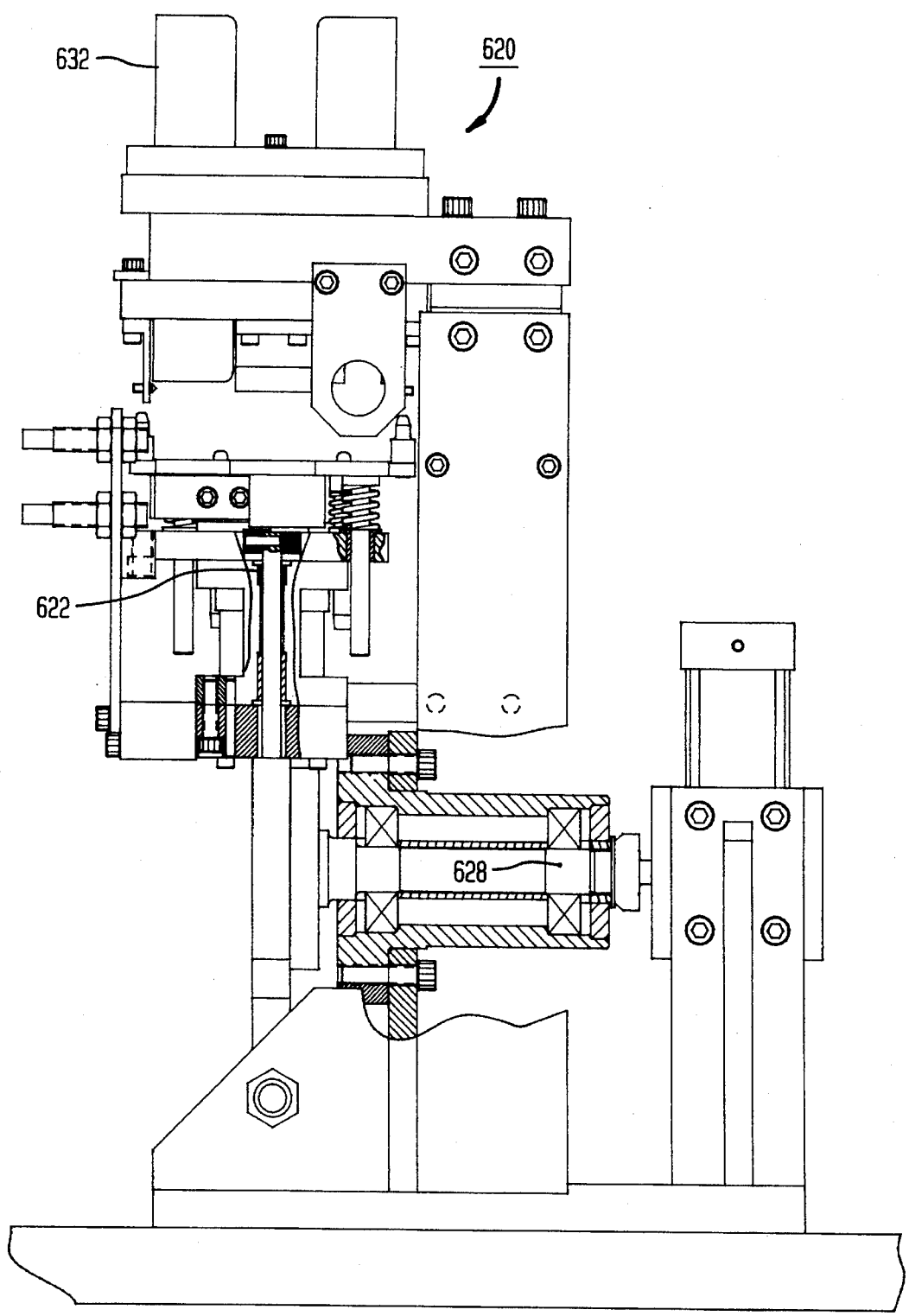
FIG. 41 illustrates a side elevational view of the cover-applying device of FIG. 40.
Figure 42:
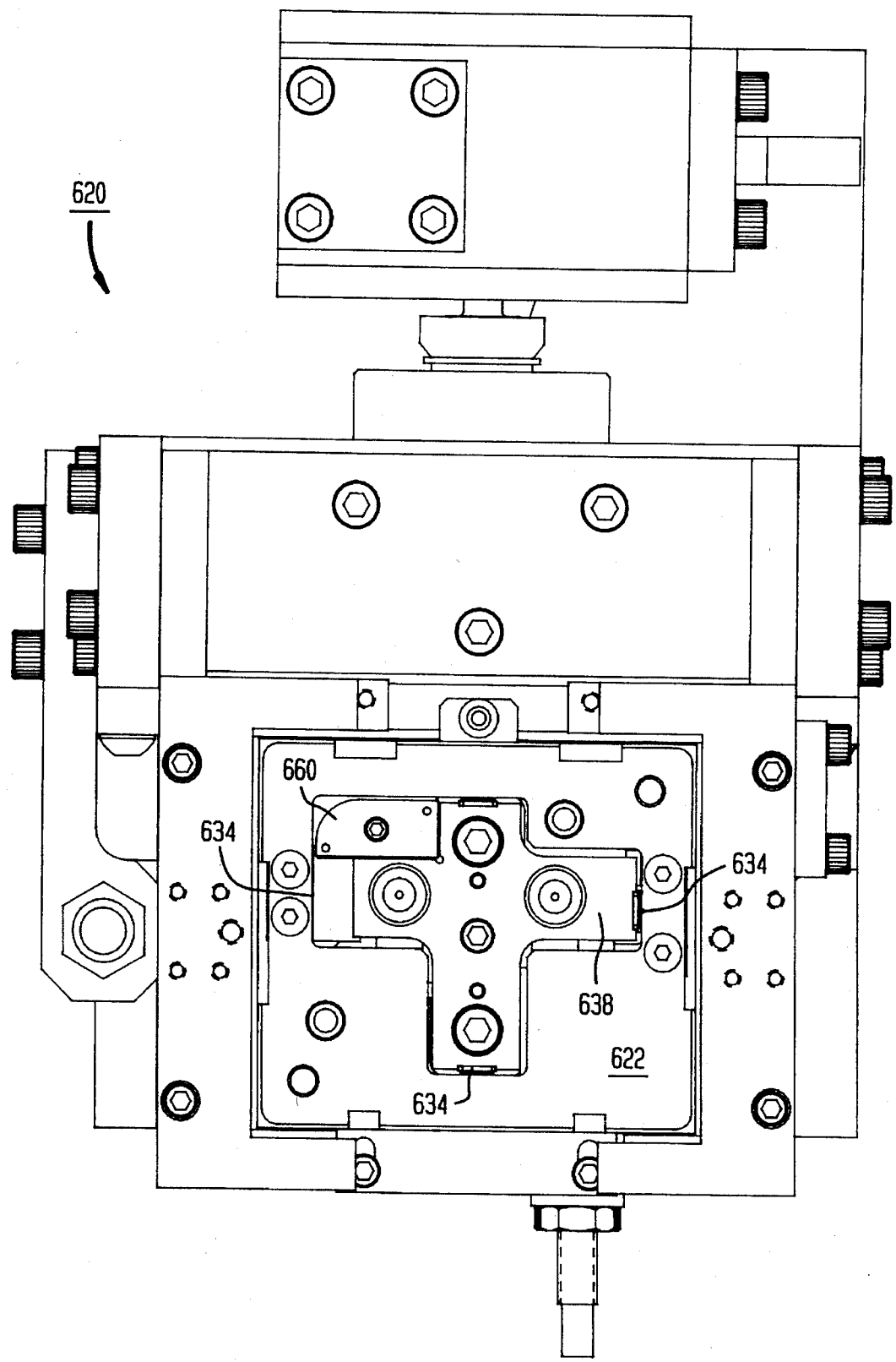
FIG. 42 illustrates a top plan view showing the cover-applying device and the cover-pressing die of FIG. 40.
Figure 43:
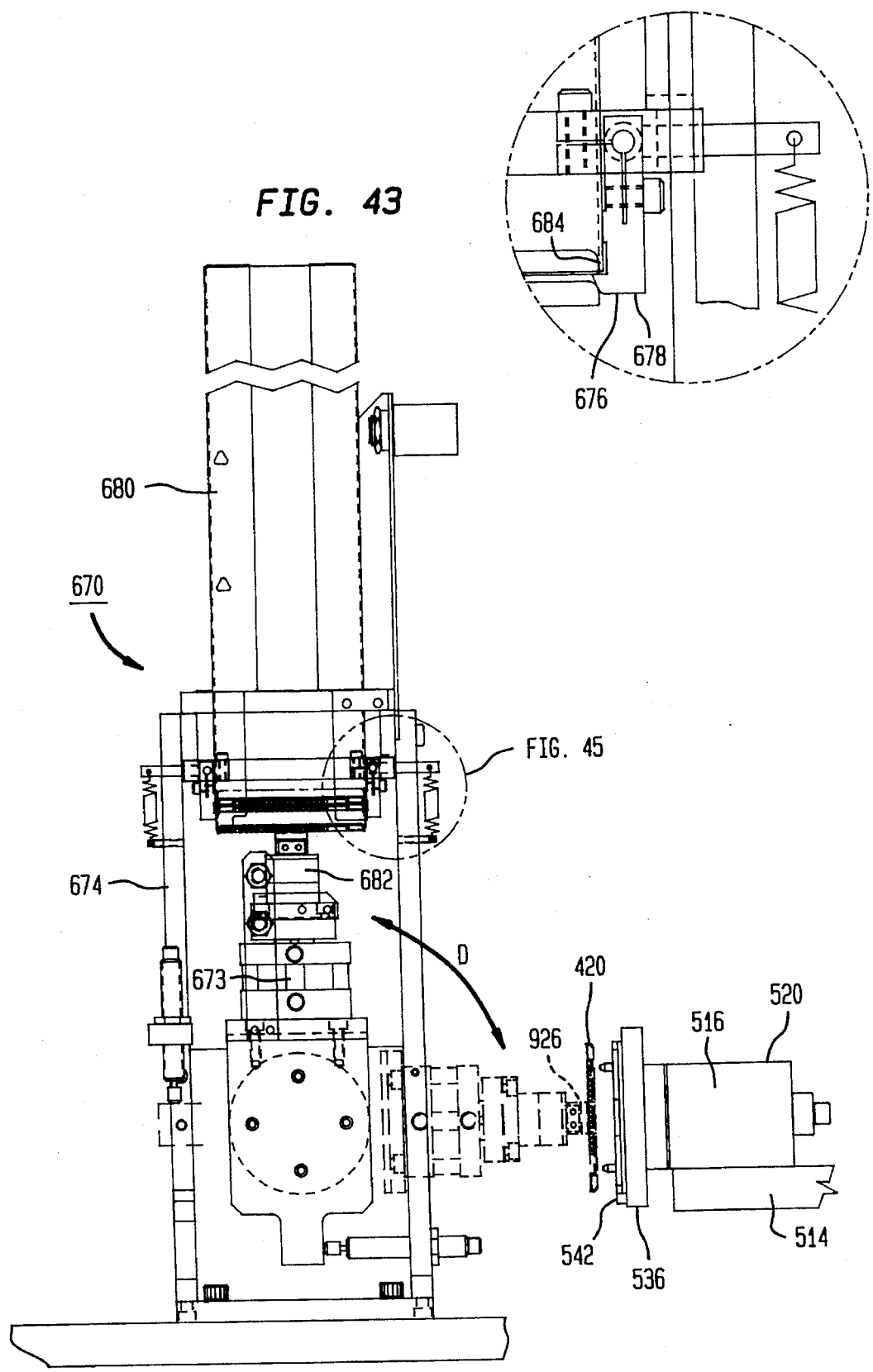
FIG. 43 illustrates an elevational side view of a suture package unloading arrangement in two operative conditions thereof.
Figure 44:
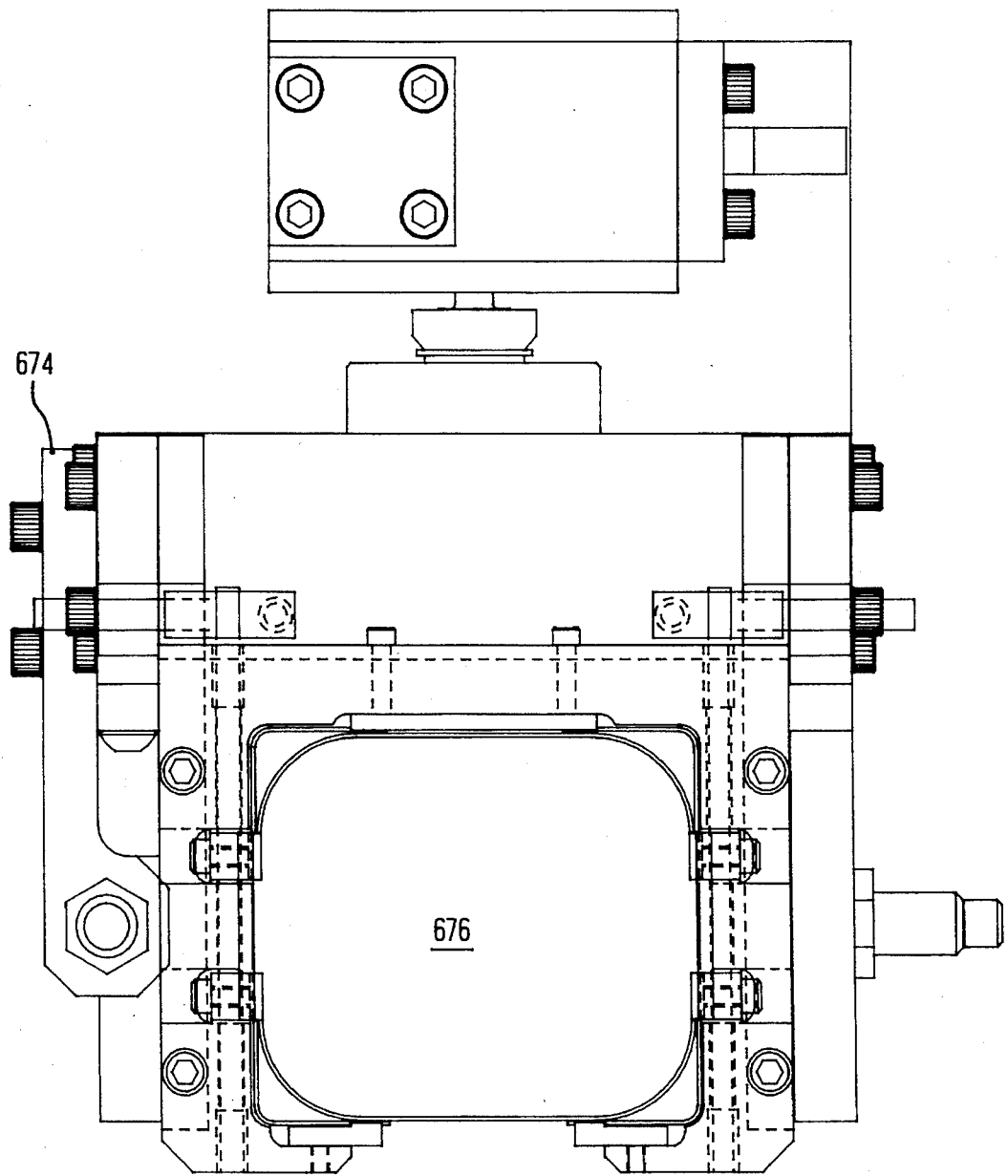
FIG. 44 illustrates a view in the direction of the arrow 44—44 in FIG. 43.

(8) Responsive to indexed forward rotation of the package dial 500 to a successive workstation, the suture package consisting of the needle and suture-containing tray 420 and attached cover 651, as shown in FIG. 47, is positioned in alignment on the platform 542 with a package removal unit 670, as illustrated in FIGS. 43 to 45. In FIG. 43 of the drawings, a pivoting arm structure 673 is illustrated in both its horizontal and vertical operative positions, being pivotable along the direction of double-headed arrow D. Suitable grippers 926 are mounted on the pivoting arm structure 673 which is journaled on a stationary frame 674 the latter of which is somewhat similar in structure to the framework 624 of the cover-applying apparatus 620. These grippers 926 are pivotable into a horizontal orientation and extend outward from arm 673 as a result of pneumatically operated ram 682, as shown in FIG. 41, for gripping engagement with the suture package. The ram 682 and grippers 926 are then operated to retract and withdraw the suture package from its support surface or platform 542 and the pins mounted thereon. The grippers 926 with the therewith clamped suture package is then adapted to be pivoted upward into a vertical orientation in alignment with the opening 676 in the bottom 678 of a hopper or chute 680 for receiving a stack of completed suture packages through the upward pushing action of a pneumatic cylinder 682 biasing the suture packages into the chute 680, as shown in FIGS. 43 and 45. The bottom 678 of the chute includes a retaining lip 684 to prevent the suture packages from falling downwardly out of the chute. Subsequently, the grippers 926 are pneumatically retracted within the arm structure 673 which is pivoted to its horizontal position to receive the next completed suture package. Alternatively, this particular, basically optional structure for removing the completed suture package from the support surface may be eliminated, if desired, and replaced by a manual suture package-removing operation.

From the chute 680, the suture packages may then be removed either through the intermediary of a further mechanism (not shown) or manually transported for additional processing; for example, such as sterilizing, and/or additional overwrapping, or the like.

The control process 900 for unloading suture packages at station 700 is illustrated in FIG. 4(*k*). The first step indicated as step 903 in FIG. 4(*k*) is the command to extend the package grippers 926 toward the package for gripping thereof. A continuous check is made at step 905 in FIG. 4(*k*) to determine whether the suture package grippers 926 have been extended. While the unload package gripper arm is extending to grasp the package for unloading, the system will perform a check at step 907 to determine whether a time-out flag has been generated by the control system 99 indicating a time-out error. If a time-out flag has not been generated, the check is made again to determine if the unload package gripper arm 673 has been fully extended (step 905). If the time-out flag is generated by the control system indicating a time-out error, then the cycle jam procedure will be implemented at step 775 shown in FIG. 4(*k*).

As shown in the pneumatic schematic diagram of FIGS. 50(*c*) and 50(*d*), supply line 701*a* supplies the pressurized air to pneumatically operate, i.e., extend and retract, the unload package gripper arm 673. The operation of the unload package gripper arm 673 is controlled by control lines 704*c,d* which operate the switch 707*u* under the timing and control of the control system 99.

As shown in FIG. 4(*k*), once the unload package gripper arm 673 has reached its extended position, the control system initiates a close gripper command at step 909 for enabling the gripper fingers 926 of the unload package gripper 673 to engage the package. While the pneumatic unload package gripper fingers 926 are closing, the system will perform a check at step 911 to determine whether a time-out flag has been generated by the control system indicating a time-out error. If a time-out flag has not been generated, a check is made again to determine if the unload package gripper fingers 926 have been closed (step 910). If the time-out flag is generated by the control system as a time-out error, then the cycle jam procedure will be implemented at step 775 shown in FIG. 4(*k*).

As shown in the pneumatic schematic diagram of FIGS. 50(*c*) and 50(*d*), supply line 701*a* supplies filtered air pneumatically operate unload package gripper fingers 926 for grasping each completed package for discharge from the suture wind and packaging dial. The operation of the gripper fingers 926 is controlled by switch 707*v* under the timing and control of the control system 99.

After the pneumatic unload package gripper fingers 926 have grasped the package, the unload package gripper arm 673 is retracted to a position away from the platform 542 as indicated at step 912 in FIG. 4(*k*). While the pneumatic unload package gripper arm 673 is retracting, the system will perform a check at step 914 to determine whether a time-out flag has been generated by the control system indicating a time-out error. If a time-out flag has not been generated, a check is made again to determine if the unload package gripper arm 673 has reached its retracted position (step 913). If the time-out flag is generated by the control system as a time-out error, then the cycle jam procedure will be implemented at step 775 shown in FIG. 4(*k*).

The next step of the unload package process 900 is to check whether the package cover 651 is present by checking for the package label by a suitable sensor means (not shown) as indicated at step 915 in FIG. 4(*l*). If it is determined at step 915 of FIG. 4(*l*) that the cover of the currently indexed package is not present, the control system will command the unload package gripper fingers 926 to release its grip on the package as indicated at step 918 in FIG. 4(*l*), and, in essence, reject the package. While the pneumatic unload package gripper fingers 926 are opening at step 919, the system will perform a check at step 920 to determine whether a time-out flag has been generated by the control system indicating a time-out error. If a time-out flag has not been generated, the package has been rejected (scrapped) as shown at step 921. If the time-out flag is generated by the control system as a time-out error, then the cycle jam procedure will be implemented at step 775 shown in FIG. 4(*l*).

If the cover is present as determined at step 915, then the package unload process 900 continues. The next step, indicated as step 922 in FIG. 4(*l*), is to remove the safe to unload light, and, at step 923, determine whether the package unload area is clear. If the package unload area is not clear, then the cycle jam procedure will be implemented at step 775 shown in FIG. 4(*l*). If the package unload area is clear, then the next step, indicated as step 931 in FIG. 4(*l*), is to rotate the unload package gripper arm to a vertical position to aid in unloading the package within chute 680. To accomplish this vertical rotation, rotary actuator 928 is enabled to rotate the package as indicated at step 931 in FIG. 4(*l*). While the rotary actuator 928 enables pneumatic unload package gripper arm 673 to rotate to a vertical position, the system will perform a check at step 932 to determine whether a time-out flag has been generated by the control system indicating a time-out error. If a time-out flag has not been generated, then the unload package gripper arm has fully rotated (step 933). If the time-out flag is generated by the control system as a time-out error, then the cycle jam procedure will be implemented at step 775 shown in FIG. 4(*l*). As shown in the pneumatic schematic diagram of FIGS. 50(*c*) and 50(*d*), supply line 701*a* supplies filtered, monitored, and pressurized air to the rotary actuator 928 which rotates the unload package gripper arm 673. The clockwise and counterclockwise operation of the rotary actuator 928, is controlled by control lines 704*c,d* which operate the switch 707*w* under the timing and control of the control system 99.

The next step of the package unload process 900, is to transfer the package from the fingers of the unload package gripper arm 673 into the vertically positioned chute 680. To accomplish the transfer, the cover gripper ram 682 of arm 673 is extended vertically to position the package within the chute as indicated at step 934 of FIG. 4(*l*). While the pneumatically operated gripper ram is extending as shown at step 935, the system will perform a check at step 936 to determine whether a time-out flag has been generated by the control system indicating a time-out error. If a time-out flag has not been generated, then the ram has fully extended as shown in step 935. If the time-out flag is generated by the control system as a time-out error, then the cycle jam procedure will be implemented at step 775 shown in FIG. 4(*l*).

As shown in FIG. 4(*m*), once the unload package gripper ram 628 has been extended to initiate the transfer of the package to the vertical chute 680, the control system initiates an open gripper finger command at step 938 for disengaging the gripper fingers 926 from the unloaded package. While the pneumatic unload package gripper fingers 926 are opening at step 939, the system will perform a check at step 941 to determine whether a time-out flag has been generated by the control system indicating a time-out error. If a time-out flag has not been generated, the process continues. If the time-out flag is generated by the control system as a time-out error, then the cycle jam procedure will be implemented at step 775 shown in FIG. 4(*m*).

After the pneumatic unload package gripper fingers 926 have disengaged the package, the unload package gripper ram 682 is retracted to a position away from the vertical chute 680 as indicated at step 942 in FIG. 4(*m*). While the pneumatic unload package gripper ram 682 is retracting at step 943, the system will perform a check at step 944 to determine whether a time-out flag has been generated by the control system indicating a time-out error. If a time-out flag has not been generated, then the unload package gripper ram has been fully retracted within pivot arm structure 673. If the time-out flag is generated by the control system as a time-out error, then the cycle jam procedure will be implemented at step 775 shown in FIG. 4(*m*).

At step 945 in FIG. 4(*m*), the safe to unload lamp (not shown) is turned on, indicating that it is safe to unload a package and that the unload area is clear.

At step 952 in FIG. 4(*m*), the control system 99 performs a check on the stack of completed packages (not shown) to ensure that the stack level is not too high. If it is determined that the number of completed packages in the stack is too high at step 954, then the control system will generate a warning signal at step 956 indicating that the stack level is too high and inform an operator to remove the stack. This warning will remain on for a duration of time corresponding to the unloading of fifteen (15) completed packages, (i.e., fifteen (15) rotations of the suture wind and package dial 500). The control system will decrement a counter (not shown) from fifteen (15) for each additional package inserted after the warning light is activated at step 957 in FIG. 4(*m*). If the counter for the insertion of completed packages in the stack reaches zero (0) before corrective action is taken, then the control system will generate an alarm signal at step 960 of FIG. 4(*m*) and the process will be terminated and the cycle jam procedure will be implemented at step 775 shown in FIG. 4(*m*). If corrective action is taken (by removing the stack of completed packages), then the command to initiate the rotation of the unload package gripper arm 673 to a horizontal position for receiving the next completed package, is generated at step 962. While the rotary actuator 928 enables pneumatic unload package gripper arm 673 to rotate to a horizontal position at step 963, the system will perform a check at step 965 to determine whether a time-out flag has been generated by the control system indicating a time-out error. If a time-out flag has not been generated, then the unload package gripper arm has fully rotated (step 963) and the package unload process 900 is completed. If the time-out flag is generated by the control system as a time-out error, then the cycle jam procedure will be implemented at step 775 shown in FIG. 4(*m*).

FIG. 4(*n*) illustrates the cycle jam procedure 775 indicating a time-out error whereby the dedicated procedure being performed could not be completed within the allotted time allowed for that particular procedure. When the cycle jam is initiated the first step 781 is to stop the current machine cycle. At step 782, a display is generated on a suitable display mechanism (not shown) instructing an operator to take appropriate remedial action, if possible. Thus, at step 783, an operator may manually investigate and correct the particular problem or error. When the operator is through correcting the problem, the control system will initiate a command to reset the system as shown at step 784 in FIG. 4(*n*). At step 785, the control system will make a determination of whether the particular error has cleared, or, whether the particular problem has been solved. If not, the display error message is again initiated at step 782. If the problem was solved, a determination is made at step 786 as to whether the doors of the machine housing (not shown) have been shut. If not, an appropriate display error message is again initiated at step 782. If the doors of the machine housing have been shut and the error solved, then the operator will be prompted to enable the start button to start the process again as shown at step 787 in FIG. 4(*n*).

As mentioned above at the needle-suture load to package station 600, the rotary dial 500 is indexed eight (8) times to hand-off eight armed needles to an empty package tray. The control system will verify that eight needles have been handed off at step 967 in FIG. 4(*a*). At step 967a, the set DONE bit that had been set at step 967 in FIG. 4(*a*) is cleared, thus indicating that a new package is ready to be indexed to the station needle-suture load to package station 600. Finally, at step 968 of FIG. 4(*a*), the suture wind and packaging dial 500 is rotated to index the next empty package to the needle-suture load to package station 600. A check is made at step 968a to verify when the packaging dial 500 has stopped indexing. The system will perform a check at step 968b to determine whether a time-out flag has been generated by the control system 99 indicating a time-out error. If a time-out flag has not been generated, the check is made again to determine if the large packaging dial has finished rotating (indexing) the rotary disk member 510 for approximately 45 degrees to the next successive workstation. If the time-out flag is generated by the control system 99 as a time-out error, the process will be terminated and prompted for reinitialization at step 959 in FIG. 4(*a*).

The reinitialization routine, shown in FIGS. 49(*a*) to 49(*e*) describe the steps necessary to ensure proper running of the automatic needle swaging and automatic packaging machines when reinitialization is called for during run-time. Additionally, an operator may perform this routine at start-up to initialize all system components.

As shown at step 970 of FIG. 49(*a*), the operator is prompted to thread the suture, i.e., wind the suture through the tensioner and around the plurality of pulleys located at the swaging tower as indicated at step 970a. Next, at step 972 all error flags that might have been set, are cleared. If all the errors are cleared, a start initialization message is displayed at step 973a of FIG. 49(*a*) that prompts the operator to enter the appropriate key (step 973b) to begin system initialization. Else, the operator is prompted to thread the suture again at step 972a, i.e., wind the suture through the tensioner and around the plurality of pulleys located at the swaging tower as indicated at steps 970 and 970a.

Figure 49A:
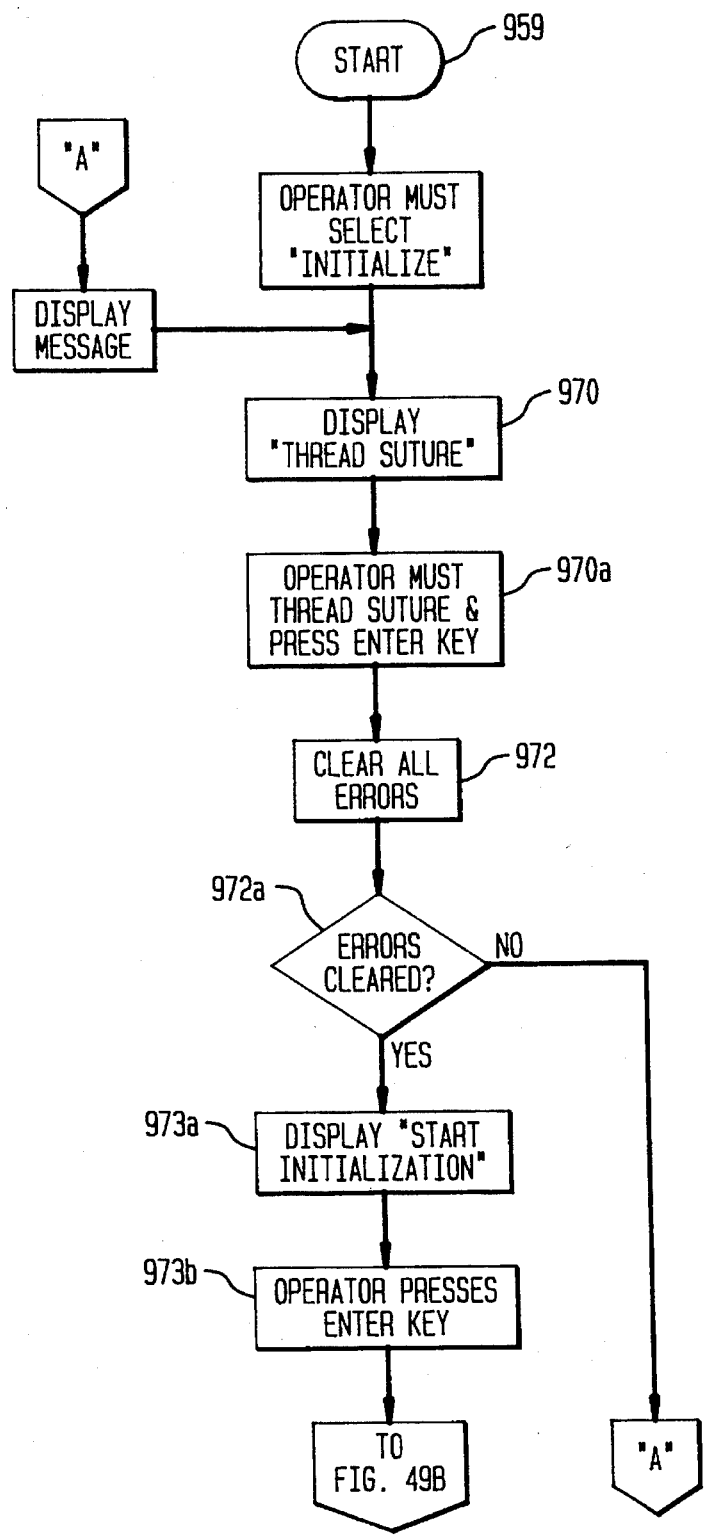
Figure 49B:
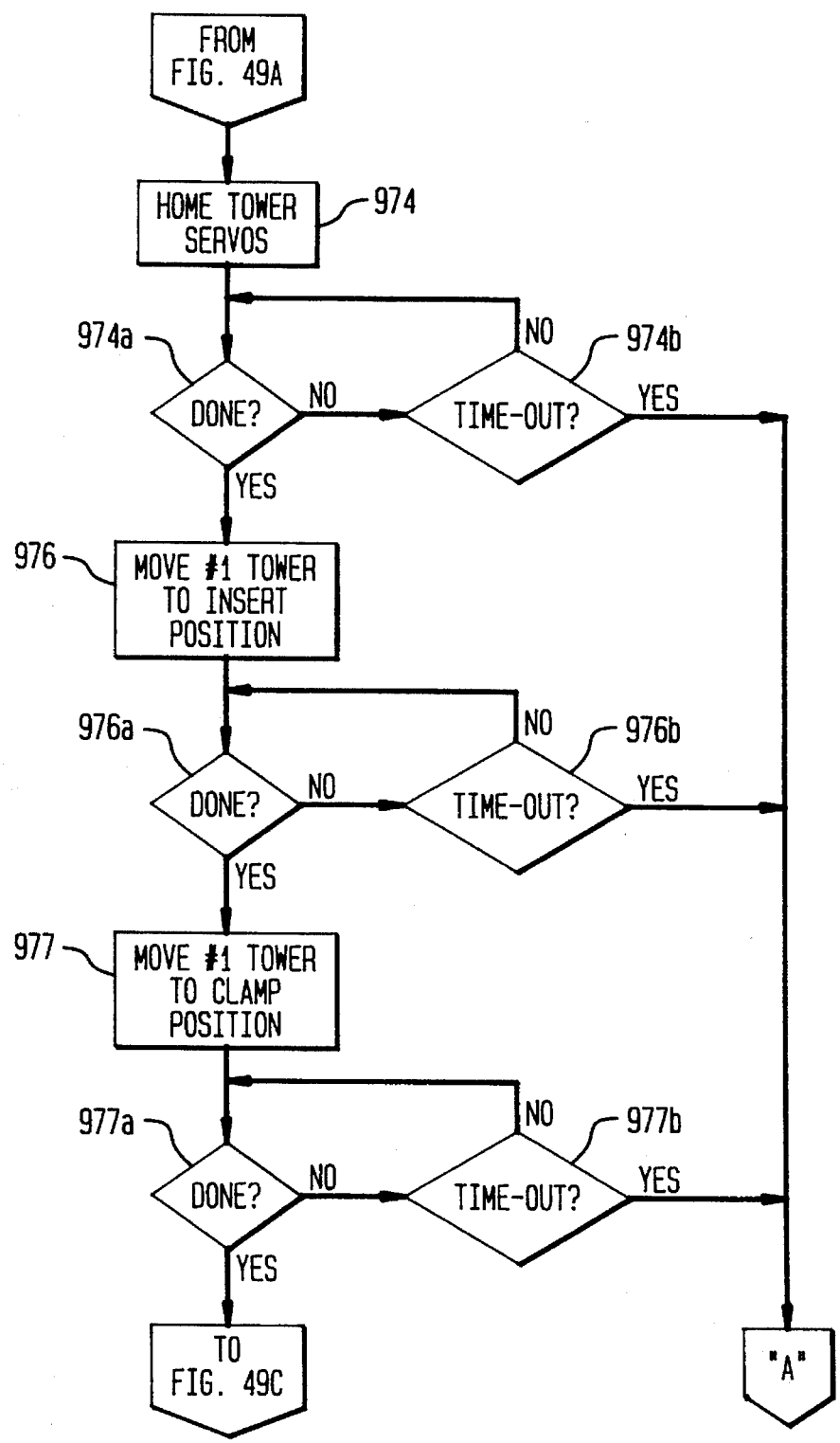

At step 974 in FIG. 49(b), the both left and right grippers are returned to their home positions. At steps 974a,b, a verification is made to ensure that each gripper is returned within the allotted time as programmed. If not, an appropriate message is displayed at step 971 of FIG. 49(a). The next step is to move the right or lead gripper to its suture insertion position along the suture tower as indicated at step 976 in FIG. 49(b). At steps 976a,b, a verification is made to ensure that the gripper is positioned within the allotted time as programmed. If not, an appropriate message is displayed at step 971 of FIG. 49(a). The gripper is then moved to its clamping position at step 977 in FIG. 49(a) and a verification is made at step 977a,b to ensure that the gripper is correctly positioned within the allotted time as programmed. If not, an appropriate message is displayed at step 971 of FIG. 49(a). At step 979 in FIG. 49(c), the lead gripper is closed so as to engage the threaded suture strand. Next, the cutter assembly is reciprocated from a retracted position to the cutting position as shown as step 980 and back to the retracted position as shown as step 981 in FIG. 49(c). The extended movement of the cutter assembly is verified at steps 980a,b to ensure that it is accomplished within the allotted time as programmed. Likewise, the retracted movement is verified at steps 981a,b to ensure that it is accomplished within the allotted time as programmed.

Figure 49C:
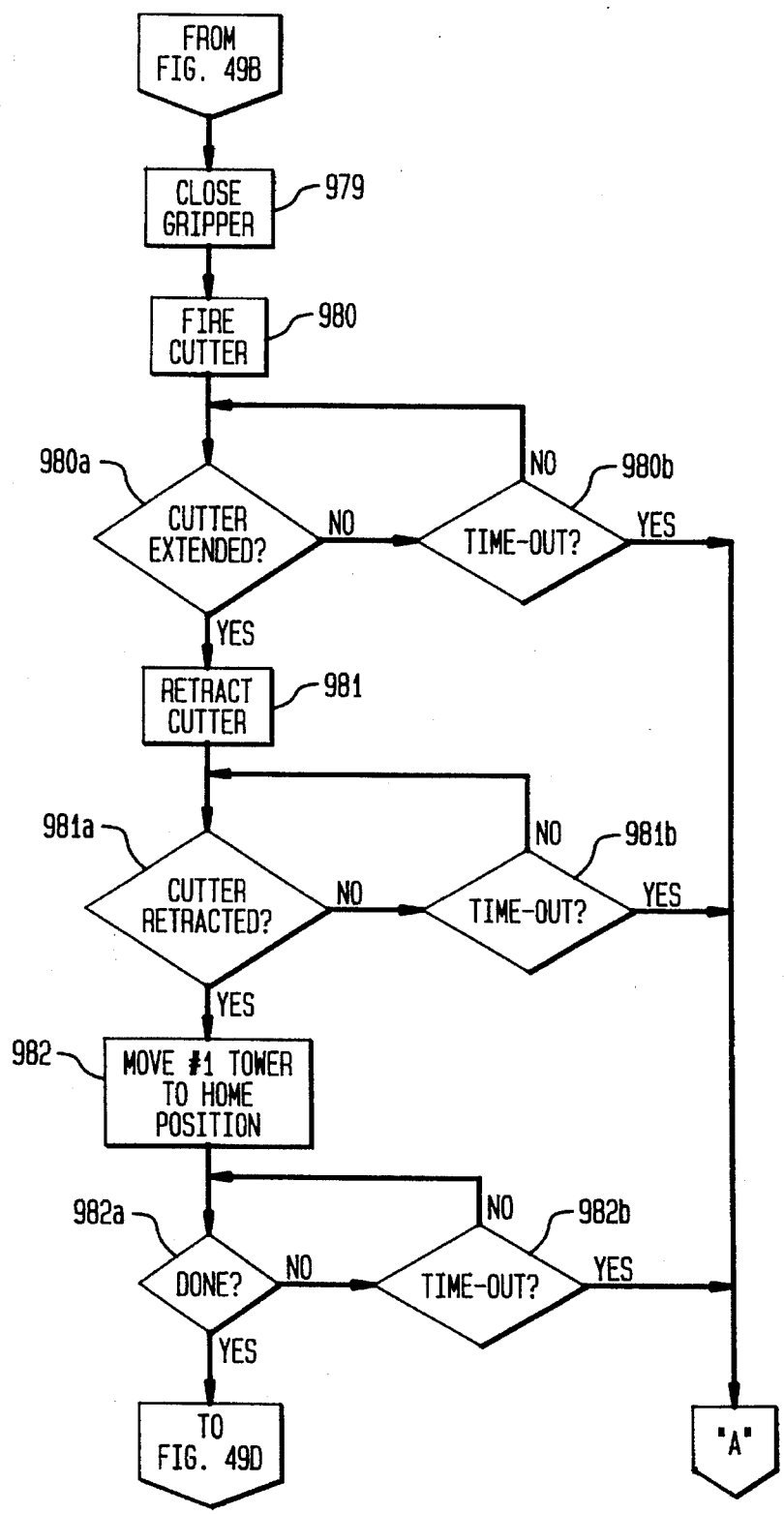

At steps 982, 982a, and 982b in FIG. 49(c), the check is again made to place the right or lead gripper at its home position along the tower. The right gripper is then positioned at the clamping position along the servo tower at step 983 in FIG. 49(d). The positioning of the second gripper is verified at steps 983a,b to ensure that it is accomplished within the allotted time as programmed.

Figure 49D:
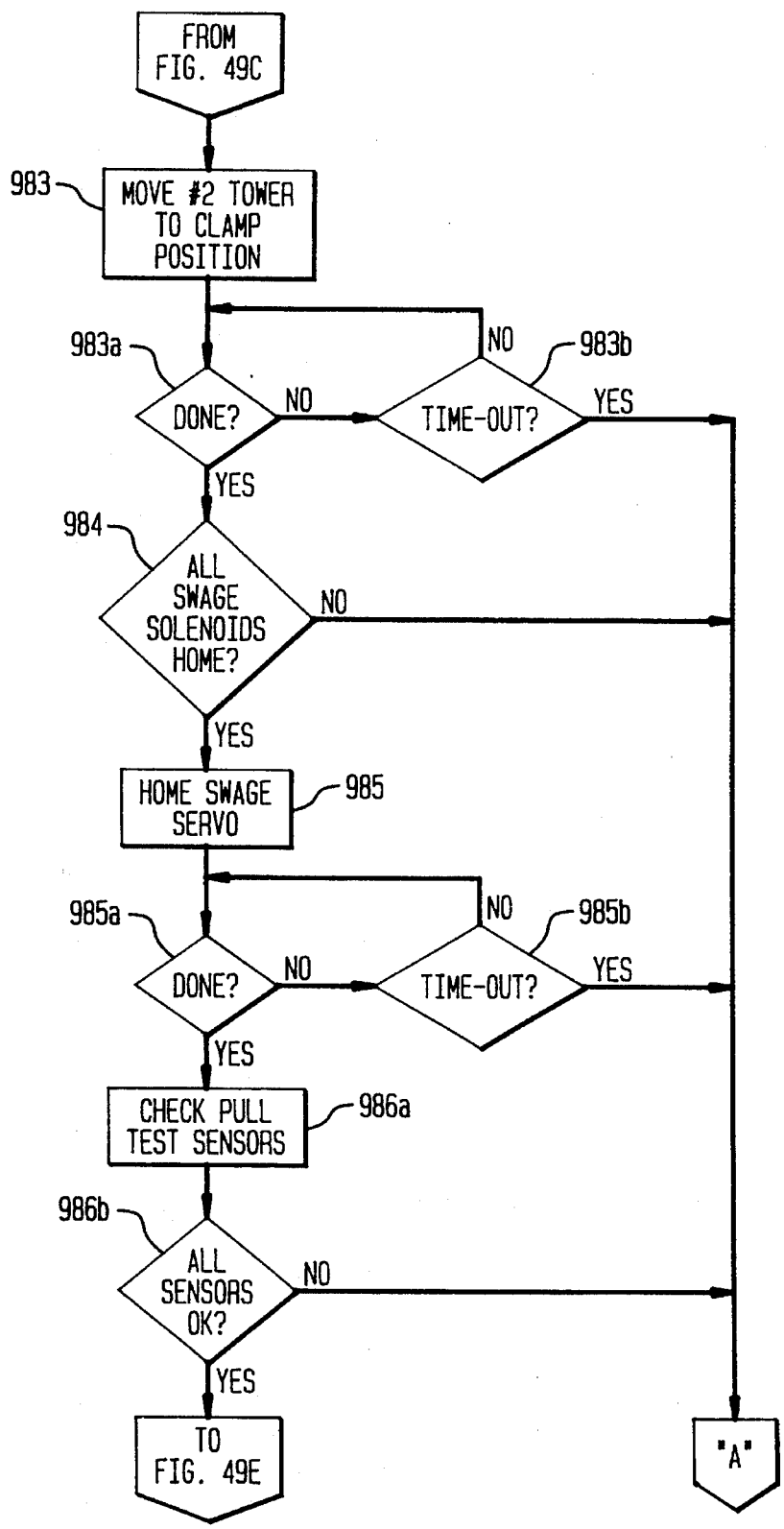

Next, as indicated at step 984 of FIG. 49(d), a determination is made concerning the status of the swage dies and swage cylinders. At step 985, the swage cylinder, specifically the movable swage die 369 is enabled to its normal, unbiased position and a verification is made at steps 985a,b to ensure that it is initialized within the allotted time.

The initialization routine 959 also includes a check of the status of the pull-test transducer located at the pull-test station, as indicated at steps 986a,b of FIG. 49(d).

Figure 49E:
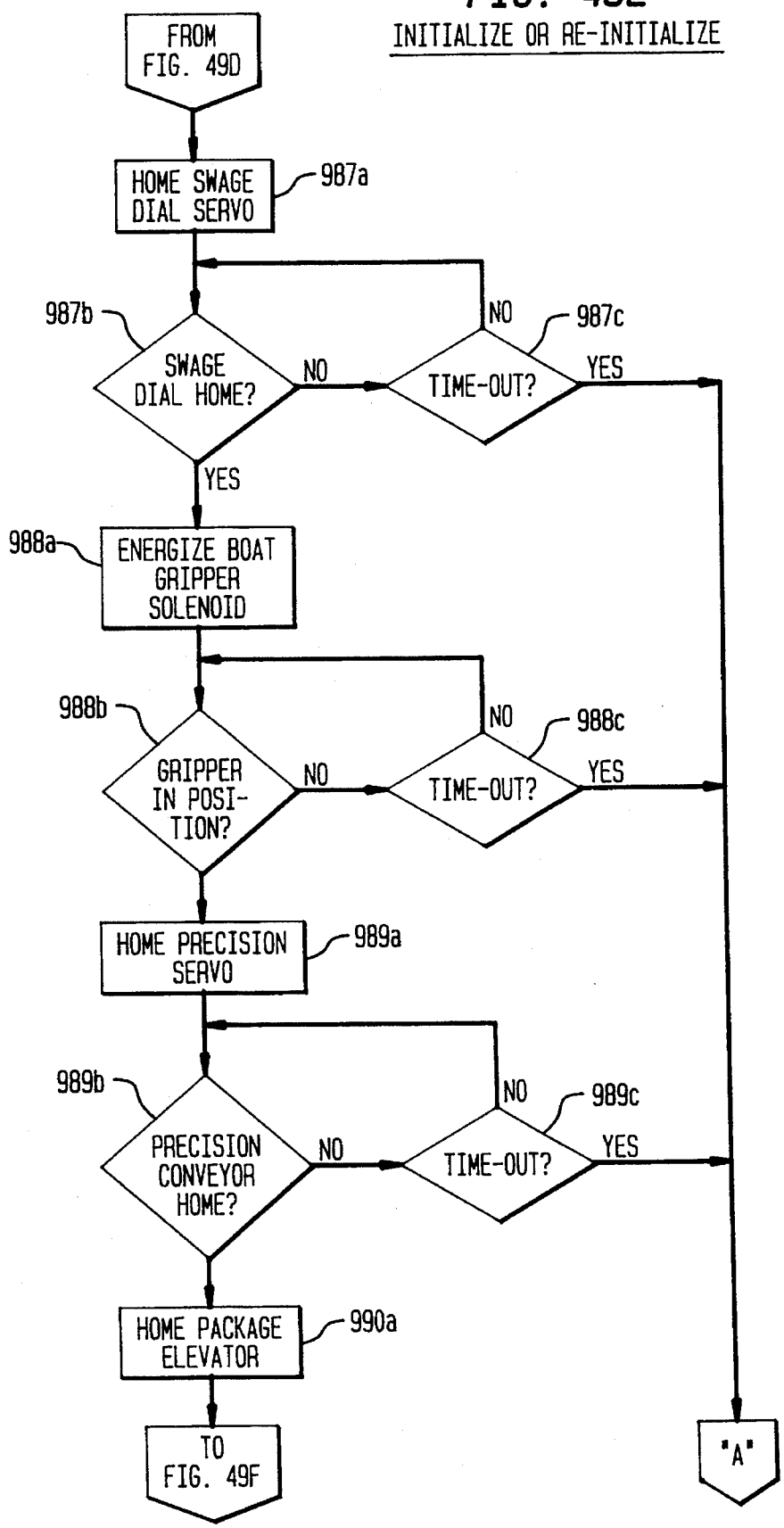

Next, as indicated at steps 987a of FIG. 49(e), the swage dial servomotor is activated to its home position, i.e., with the first multi-axis gripper facing the needle sorting station 100. A verification is made at steps 987b,c to ensure that the servomotor is indexed to a home position within the allotted time as programmed.

At step 988a the solenoid for enabling the engagement jaws of a precision conveyor boat 108 to retract to their open, non-engaging position is activated. A verification that the retraction of the engagement jaws is accomplished within the allotted time, is made at steps 988b,c in FIG. 49(e). At steps 989a,b,c a verification is made ensuring that the servomotor controlling the movement of precision conveyor 107 is placed in its initial position within the allotted time as programmed.

At step 990a in FIG. 49(e), the elevator assembly at the needle-load to package station 600 comprising servomotor 430 and elevator shaft 445 is activated to return to its home position. A verification is made at steps 990b,c to confirm that the elevator assembly is returned to its home position within the allotted time as programmed.

Figure 49F:
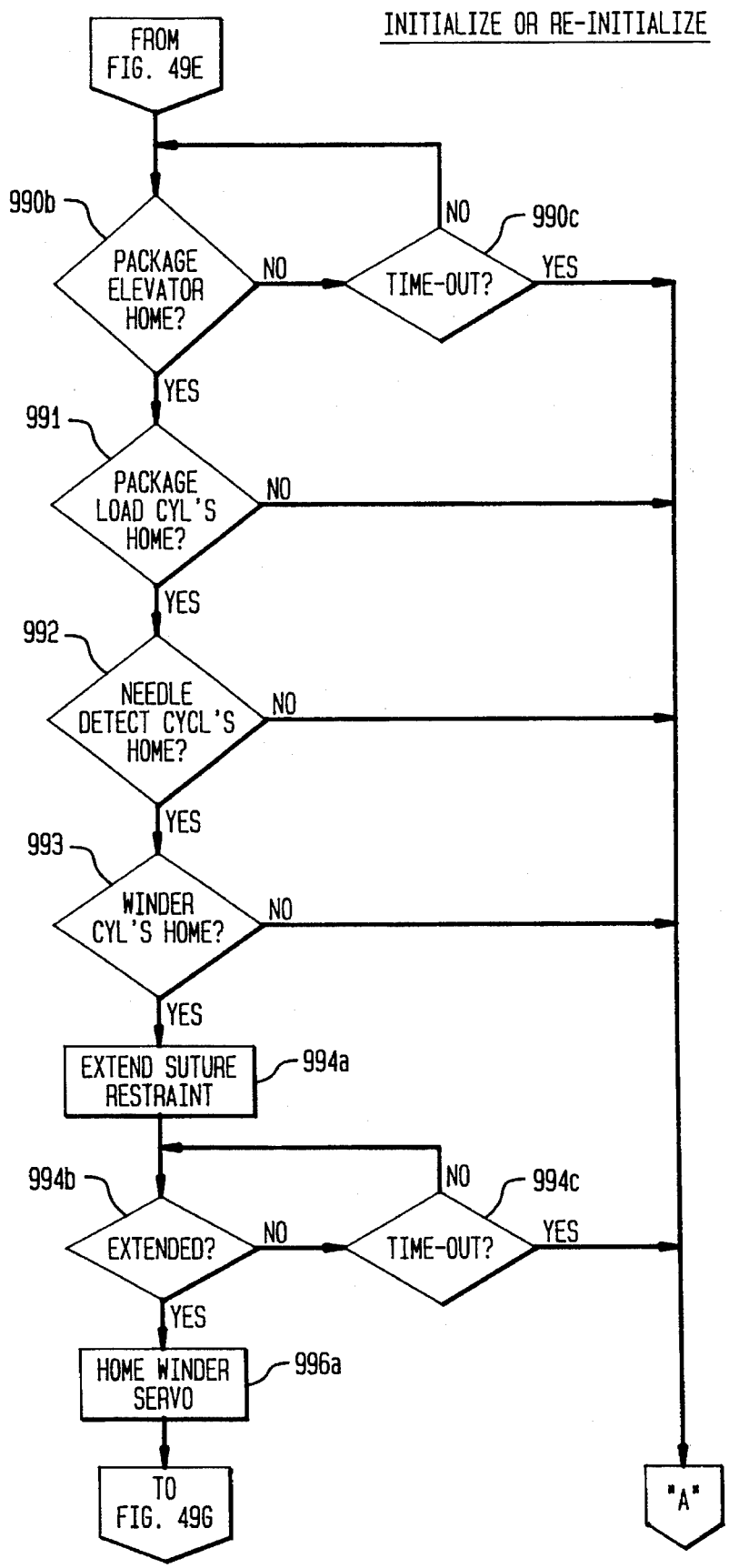

At steps 991 and 993 of FIG. 49(f), a verification is made to ensure that the respective pneumatically operated cylinders for controlling respectively, package load arm 758 and suture wind stylus slide 578, are in their initial home positions. A similar determination is made at step 992 to ensure that the operation of the needle detect unit 560 is at its home or retracted position.

Next, at steps 994a,b,c of FIG. 49(f), a verification that the pneumatically operated suture restraint plate 612 is retracted to its home position within the allotted time as programmed, is performed. Similarly, at step 996a the servomotor for controlling the rotation of the support platform and package tray and hence, the winding of the suture bundle, is activated to its home position and a verification is made at steps 996b,c of FIG. 49(g) that it is done in the allotted time as programmed.

At steps 998 and 999 of FIG. 49(g), a verification is made to ensure that the respective pneumatically operated cylinders for controlling respective cover load gripper arm 626, and unload package gripper arm 924, are retracted to their respective initial positions. At step 1001, a verification that the tilted cam 533 for tilting the support platform holding the package tray 420 at the needle-load to package station 600 is in its home position, is made.

Next, at step 1002a of FIG. 49(g), the suture wind and package dial servomotor is activated to its home position. A verification is made at steps 1002b,c to ensure that the servomotor is indexed to a home position within the allotted time as programmed.

Finally, if all the above initialization routines are verified, an electronic signal indicating that the system is ready to run, is set at step 1005 of FIG. 49(g). A message to the operator informing him to remove suture restraint plate is generated at step 1006 of FIG. 49(g). It should be noted that if time-out errors occur for any of the above initialization routines, the message prompting the operator to thread the suture (step 970) is again displayed and the corrective action must be taken.

While the invention has been particularly shown and described with respect to the preferred embodiments thereof, it will be understood by those skilled in the art that the foregoing and other changes in form and details may be made therein without departing from the spirit and scope of the invention, which should be limited only by the scope of the appended claims.

What is claimed:

1. A method of automatically swaging surgical needles to associated sutures, said method comprising:

(a) sequentially feeding a plurality of needles and a plurality of associated sutures between a pair of swaging dies, with a first of said pair being adjustably fixed;

(b) sequentially swaging each of said needles to an associated suture by driving the second of said pair of dies towards the adjustably fixed die to form a plurality of needle-suture assemblies;

(c) pull testing each nth needle-suture assembly to obtain an nth sample failure value;

(d) comparing said nth sample failure value with a low failure threshold value and generating a first signal if said nth sample failure value is below said low failure threshold value; and (e) incrementally adjusting the position of said adjustably fixed die in response to said first signal to move said adjustably fixed die an incremental distance towards the second die.

2. A method of automatically swaging surgical needles to associated sutures as claimed in claim 1 wherein said method also includes the steps of:

(a) comparing said nth sample failure value with a high failure threshold value and generating a second signal if said nth sample failure value is above said high threshold value;

(b) incrementally adjusting the position of said adjustably fixed die in response to said second signal to move said adjustably fixed die an incremental distance away from the second die.

3. The method of automatically swaging surgical needles to associated sutures as claimed in claim 2 wherein said first of said pair of swaging dies includes a wedge follower located at one end thereof and a wedge assembly positioned to move transverse to said wedge follower, wherein the step of incrementally adjusting the position of said adjustably fixed die further includes the steps of:

(a) inputting either of said first and second signals to a servomotor means for precisely rotating a swage adjust screw of a predetermined pitch in accordance with either of said first and second signals;

(b) translating said rotation of said swage adjust screw into linear motion of said wedge assembly, said wedge assembly moving transverse to said wedge follower of said first swaging die; and (c) moving said wedge follower of said first of said pair of swaging dies in incremental units correlating with said transverse linear motion of said wedge assembly.

4. The method of automatically swaging surgical needles to associated sutures as claimed in claim 1 further including the steps of:

(a) sequentially drawing a plurality of indefinite length suture strands to said pair of swaging dies;

(b) sequentially inserting free ends of said indefinite length suture strands into respective suture receiving openings formed in said plurality of needles prior to swaging thereof; and, (c) sequentially cutting said indefinite length suture strands to definite length after swaging said free ends to said needles, said strands being cut a predetermined distance from said free ends to form a plurality of needle-suture assemblies each having a said associated suture of definite length depending from said needle.

5. The method of automatically swaging surgical needles to associated sutures as claimed in claim 4 further including the steps of:

(a) mounting an empty package tray on a support structure;

(b) successively inserting said needle-suture assemblies onto predetermined needle-clamping locations in said tray to form an array of needles and attached sutures depending therefrom;

(c) gathering said depending suture portions into a bundle of strands and imparting axial tension thereto;

(d) rotating said package tray about an axis extending normal to the plane of said tray with a drive means; and (e) winding said bundle of strands into a peripheral channel formed in said package tray.

6. The method of automatically swaging surgical needles to associated sutures as claimed in claim 5 wherein the step of successively inserting said needle-suture assemblies into said package tray further includes the step of incrementally vertically displacing a package tray support structure with said package tray attached thereto so as to correlate the successive insertion of said needle-suture assemblies with said predetermined needle-clamping locations in said tray to form said needle array.

7. The method of automatically swaging surgical needles to associated sutures as claimed in claim 6 wherein the step of incrementally vertically displacing said support structure and said package tray further includes the step of grippingly engaging and conveying a specified quantity of needle-suture assemblies in successive sequence into said tray in synchronism with the incremental vertical displacement of said support structure and said package tray.

8. The method of automatically swaging surgical needles to associated sutures as claimed in claim 7 further including the step of applying a cover to said package tray to form a completed suture package containing said needles and attached wound sutures.

9. The method of automatically swaging surgical needles to associated sutures as claimed in claim 8 further including the step of disengaging said completed suture package from said support structure.

10. The method of automatically swaging surgical needles to associated sutures as claimed in claim 8 further including applying a cover to said package tray to form a completed suture package containing said needles and attached sutures, said cover being applied by a cover applying means, said cover applying means including a pivotable arm having grippers for gripping said covers, said method further including the steps of:

(a) successively obtaining individual covers from a supply of covers;

(b) pivoting said grippers into alignment with said tray on said support structure;

(c) extending said grippers to position a cover gripped thereby on said tray;

(d) releasing said cover; and, (e) withdrawing said grippers.

11. The method of automatically swaging surgical needles to associated sutures as claimed in claim 5 wherein the step of gathering said depending suture portions includes the step of imparting a subatmospheric pressure to said depending suture portions to cause said depending suture portions to be tensioned into said bundle of strands.

12. The method of automatically swaging surgical needles to associated sutures as claimed in claim 5 wherein the step of winding said bundle of strands includes the steps of:

(a) contacting said tensioned suture portions with an arm structure means; and (b) pivoting said arm structure means to bias said suture portions into an orientation facilitating winding of said suture portions into the tray channel.

13. The method of automatically swaging surgical needles to associated sutures as claimed in claim 12 wherein said winding step further includes the steps of:

(a) operatively contacting a stylus means with said tensioned and bundled suture strands;

(b) guiding said bundle of strands into said tray channel with said stylus means to facilitate winding of said sutures into said tray during rotation of said tray.

14. The method of automatically swaging surgical needles to associated sutures as claimed in claim 13 wherein said stylus means includes stylus legs for contacting said bundle of strands, a piston rod for mounting said stylus legs at one end thereof for axial movement, and, a stationary piston cylinder within which said piston rod is mounted, said method further including the step of exerting pressurized air against said piston rod within said stationary piston cylinder to provide reciprocatory motion thereof to enable said stylus legs to engage into and follow said peripheral tray channel during rotation of said tray.

15. The method of automatically swaging surgical needles to associated sutures as claimed in claim 14 wherein said package tray is supported on a support structure including a cam plate, and said stylus means further includes cam follower means mounted on said piston rod proximate said stylus legs, said method further comprising contacting a peripheral camming surface on said cam plate by said cam follower means in response to said pressure being exerted against said piston rod by pressurized air in said piston cylinder.

16. The method of automatically swaging surgical needles to associated sutures as claimed in claim 15 wherein said tray includes a plurality of resilient cantilevered fingers extending over said peripheral channel for protectively maintaining the sutures in said channel, said stylus legs engaging beneath successive of said fingers for raising said fingers during rotation of said tray to guide said bundle of strands therebeneath and bias said bundle of strands into and towards the bottom of said tray channel.

17. The method of automatically swaging surgical needles to associated sutures as claimed in claim 16 further including the step of inhibiting displacement of said package tray on said support structure by contacting said tray with a restraint means during rotation of said tray, wherein said restraint means is operatively connected to said drive means.

18. The method of automatically swaging surgical needles to associated sutures as claimed in claim 1 wherein step (c) of pull testing each nth needle-suture assembly further includes the steps of:

(a) supporting the needle of said nth needle-suture assembly;

(b) gripping said associated suture of said nth needle with a gripping means, said gripping means including a means for applying a force of predetermined value to said suture;

(c) applying said force of predetermined value to said suture while said suture is gripped by said gripping means; and, (d) measuring said force applied to obtain said nth sample failure value.

* * * * *

UNITED STATES PATENT AND TRADEMARK OFFICE
CERTIFICATE OF CORRECTION

PATENT NO. : 5,500,991            Page 1 of 2
DATED : March 26, 1996
INVENTOR(S) : David Demarest, et al.

It is certified that error appears in the above-indentified patent and that said Letters Patent is hereby corrected as shown below:

On the Title Page, Section [56], under "U.S. PATENT DOCUMENTS" "Vetake" should read --Uetake--

--invention.--

Column 11, line 8:  "65a" should read --265a--

Column 13, line 63: "sutures" should read --suture--

Column 19, line 62: "0,011" should read --0.011--

Column 24, line 10: "AS" should read --As--

Column 31, line 29: delete "5"

UNITED STATES PATENT AND TRADEMARK OFFICE
CERTIFICATE OF CORRECTION

PATENT NO. : 5,500,991
DATED : March 26, 1996
INVENTOR(S) : David Demarest, et al.

It is certified that error appears in the above-indentified patent and that said Letters Patent is hereby corrected as shown below:

Column 44, line 55: "enable" should read --enabled--
Column 44, lines 56 & 60, delete "degrees"
Column 45, line 49: delete "FIG. 50(c), supply line 701a supplies pressurized air"
Column 51, lines 3 & 13, "ram" should read --arm--

Signed and Sealed this

Third Day of December, 1996

Attest:

BRUCE LEHMAN

Attesting Officer

Commissioner of Patents and Trademarks